(12) United States Patent
Nishibu et al.

(10) Patent No.: US 10,794,899 B2
(45) Date of Patent: Oct. 6, 2020

(54) TIM PROTEIN-BOUND CARRIER, METHODS FOR OBTAINING, REMOVING AND DETECTING EXTRACELLULAR MEMBRANE VESICLES AND VIRUSES USING SAID CARRIER, AND KIT INCLUDING SAID CARRIER

(71) Applicants: FUJIFILM WAKO PURE CHEMICAL CORPORATION, Osaka-shi, Osaka (JP); OSAKA UNIVERSITY, Suita-shi, Osaka (JP)

(72) Inventors: Takahiro Nishibu, Amagasaki (JP); Naoko Imawaka, Amagasaki (JP); Ken Naruse, Amagasaki (JP); Rikinari Hanayama, Suita (JP)

(73) Assignees: FUJIFILM WAKO PURE CHEMICAL CORPORATION, Osaka (JP); OSAKA UNIVERSITY, Suita (JP)

(*) Notice: Subject to any disclaimer, the term of this patent is extended or adjusted under 35 U.S.C. 154(b) by 148 days.

(21) Appl. No.: 15/529,936

(22) PCT Filed: Nov. 27, 2015

(86) PCT No.: PCT/JP2015/083505
§ 371 (c)(1),
(2) Date: May 25, 2017

(87) PCT Pub. No.: WO2016/088689
PCT Pub. Date: Jun. 9, 2016

(65) Prior Publication Data
US 2018/0120299 A1     May 3, 2018

(30) Foreign Application Priority Data
Dec. 5, 2014   (JP) ................... 2014-246876

(51) Int. Cl.
| | | |
|---|---|---|
| *G01N 33/50* | (2006.01) | |
| *C07K 1/14* | (2006.01) | |
| *C07K 17/02* | (2006.01) | |
| *G01N 33/543* | (2006.01) | |
| *G01N 33/68* | (2006.01) | |
| *C12N 15/09* | (2006.01) | |
| *C07K 17/00* | (2006.01) | |
| *C12N 7/02* | (2006.01) | |
| *C07K 14/705* | (2006.01) | |
| *G01N 33/53* | (2006.01) | |
| *G01N 15/00* | (2006.01) | |

(Continued)

(52) U.S. Cl.
CPC .......... *G01N 33/5076* (2013.01); *C07K 1/14* (2013.01); *C07K 14/70503* (2013.01); *C07K 17/00* (2013.01); *C07K 17/02* (2013.01); *C12N 7/02* (2013.01); *C12N 15/09* (2013.01); *G01N 33/5432* (2013.01); *G01N 33/6842* (2013.01); *C07K 2319/40* (2013.01); *C12N 2760/16151* (2013.01); *C12N 2760/18551* (2013.01); *G01N 33/53* (2013.01); *G01N 2015/008* (2013.01); *G01N 2015/1006* (2013.01); *G01N 2015/149* (2013.01)

(58) Field of Classification Search
CPC .. C07K 14/70503; C07K 17/00; C07K 17/02; C07K 1/14; C07K 2319/40; C12N 15/09; C12N 2760/16151; C12N 2760/18551; C12N 7/02; G01N 2015/008; G01N 2015/1006; G01N 2015/149; G01N 33/5076; G01N 33/53; G01N 33/5432; G01N 33/6842
See application file for complete search history.

(56) References Cited

U.S. PATENT DOCUMENTS

2012/0009594 A1   1/2012   Yoneda
2013/0197206 A1   8/2013   Nishibu et al.

FOREIGN PATENT DOCUMENTS

JP    2011-132140 A     7/2011
WO    WO 2008/064031 A2  5/2008
(Continued)

OTHER PUBLICATIONS

Miyanishi et al., "Identification of Tim4 as a phosphatidylserine receptor," Nature, 2007, vol. 450, No. 7168, pp. 435-439 Supplementary Information.*

(Continued)

*Primary Examiner* — Galina M. Yakovleva
(74) *Attorney, Agent, or Firm* — Leydig, Voit & Mayer, Ltd.

(57) ABSTRACT

The invention provides a carrier and a method for obtaining, removing, or detecting extracellular membrane vesicle or virus present in a sample. In particular, the invention provides (a) a carrier (a Tim carrier) on which a protein (a Tim protein), selected from a T-cell immunoglobulin and mucin domain-containing molecule-4 (a Tim-4) protein, a Tim-3 protein, and a Tim-1 protein, is bound; (b) a method for obtaining the extracellular membrane vesicle or the virus in the sample; (c) a method for removing the extracellular membrane vesicle or the virus in the sample; (d) a method for detecting the extracellular membrane vesicle or the virus in the sample; (e) a kit for capturing the extracellular membrane vesicle or the virus, comprising the Tim carrier; and f) a kit for capturing the extracellular membrane vesicle or the virus, comprising a reagent containing the Tim protein and a reagent containing the carrier.

9 Claims, 12 Drawing Sheets
Specification includes a Sequence Listing.

(51) Int. Cl.
*G01N 15/10* (2006.01)
*G01N 15/14* (2006.01)

(56) References Cited

FOREIGN PATENT DOCUMENTS

| WO | WO 2010/107068 A1 | 9/2010 |
| WO | WO 2012/039395 A  | 3/2012 |
| WO | WO 2013/124327 A1 | 8/2013 |

OTHER PUBLICATIONS

Gieseler et al., "Using annexin V-coated magnetic beads to capture active tissue factor-bearing microparticles from body fluids," Cell Biol. Int., Feb. 2014, vol. 38, No. 2, pp. 277-281, doi: 10.1002/cbin.10216, Epub Nov. 27, 2013.*

Pasquet et al., "Microvesicle release is associated with extensive protein tyrosine dephosphorylation in platelets stimulated by A23187 or a mixture of thrombin and collagen," Biochem. J., 1998, vol. 333, pp. 591-599.*

Zimmermann et al., "Thiol-based, site-specific and covalent immobilization of biomolecules for single-molecule experiments," Nature Protocols, 2010, vol. 5, No. 6, pp. 975-985.*

Yoshida T., Ishidome T., Hanayama R., "High Purity Isolation and Sensitive Quantification of Extracellular Vesicles Using Affinity to TIM4," Curr. Protoc. Cell Biol., Dec. 11, 2017, Supplement 77, pp. 3.45.1-3.45.18.*

Nakai W., Yoshida T., Diez D., Miyatake Y., Nishibu T., Imawaka N., Naruse K., Sadamura Y., Hanayama R., "A novel affinity-based method for the isolation of highly purified extracellular vesicles," Sci. Rep., Sep. 23, 2016; 6:33935; pp. 1-11.*

Santiago et al., "Structures of T Cell Immunoglobulin Mucin Protein 4 Show a Metal-Ion-Dependent Ligand Binding Site where Phosphatidylserine Binds," *Immunity*, 27: 941-951 (2007).

Andree et al., *The Journal of Biological Chemistry*, 265(9): 4923-4928 (1990).

Chen et al., *Biotechnol. Prog.*, 25(6): 1669-1677 (2009).

Gerster et al., *Journal of Chromatography A*, 1290: 36-45 (2013).

Hanayama et al., *Nature*, 417: 182-187 (2002).

Jemielity et al., *PLOS Pathogens*, 9(3): e1003232 (2013).

Li et al., *PNAS*, 111(35): E3699-E3707 (2014).

Logozzi et al., *PLoS One*, 4(4): e5219 (2009).

Miyanishi et al., *Nature*, 450: 435-439 (2007).

Witwer et al., *Journal of Extracellular Vesicles*, 2: 20360 (2013).

Japanese Patent Office, International Search Report in International Patent Application No. PCT/JP2015/083505 (dated Jan. 12, 2016).

* cited by examiner

Fig.3
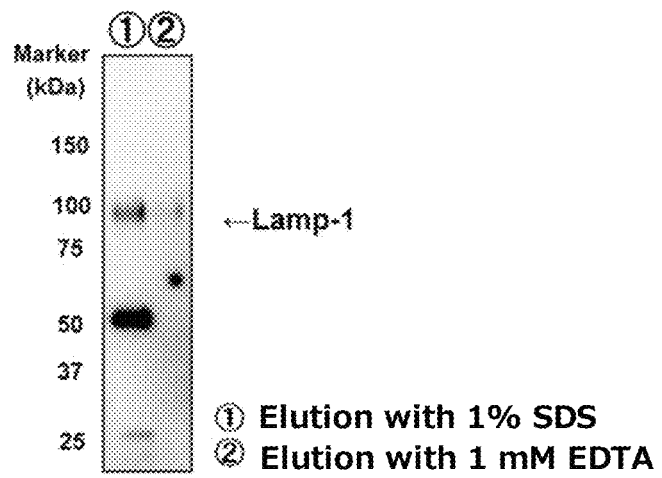
① Elution with 1% SDS
② Elution with 1 mM EDTA
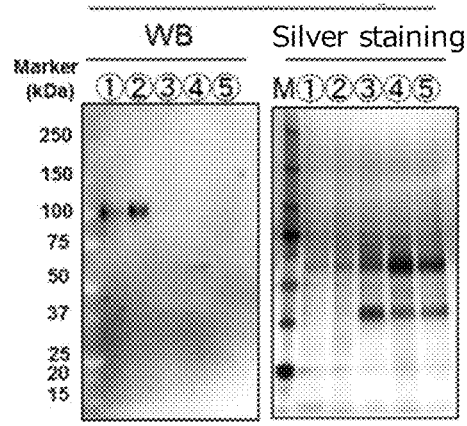
Fig.4-A   Fig.4-B 200nm ①③ Elution with 1% SDS
②④ Elution with 1 mM EDTA ①③⑤⑦ Elution with 1% SDS
②④⑥⑧ Elution with 1 mM EDTA ①③⑤ Elution with 1% SDS
②④⑥ Elution with 1 mM EDTA ①③⑤ Elution with 1% SDS
②④⑥ Elution with 1 mM EDTA ① Untreated
② Total Exosome Isolation

SEQUENCE LISTING

<160> NUMBER OF SEQ ID NOS: 34

<210> SEQ ID NO 1
<211> LENGTH: 114
<212> TYPE: PRT
<213> ORGANISM: Mus musculus

<400> SEQUENCE: 1

Ala Ala Ser Glu Asp Thr Ile Ile Gly Phe Leu Gly Gln Pro Val Thr
1               5                   10                  15

Leu Pro Cys His Tyr Leu Ser Trp Ser Gln Ser Arg Asn Ser Met Cys
            20                  25                  30

Trp Gly Lys Gly Ser Cys Pro Asn Ser Lys Cys Asn Ala Glu Leu Leu
        35                  40                  45

Arg Thr Asp Gly Thr Arg Ile Ile Ser Arg Lys Ser Thr Lys Tyr Thr
    50                  55                  60

Leu Leu Gly Lys Val Gln Phe Gly Glu Val Ser Leu Thr Ile Ser Asn
65                  70                  75                  80

Thr Asn Arg Gly Asp Ser Gly Val Tyr Cys Cys Arg Ile Glu Val Pro
                85                  90                  95

Gly Trp Phe Asn Asp Val Lys Lys Asn Val Arg Leu Glu Leu Arg Arg
            100                 105                 110

Ala Thr

<210> SEQ ID NO 2
<211> LENGTH: 113
<212> TYPE: PRT
<213> ORGANISM: Homo sapiens

<400> SEQUENCE: 2

Glu Thr Val Val Thr Glu Val Leu Gly His Arg Val Thr Leu Pro Cys
1               5                   10                  15

Leu Tyr Ser Ser Trp Ser His Asn Ser Asn Ser Met Cys Trp Gly Lys
            20                  25                  30

Asp Gln Cys Pro Tyr Ser Gly Cys Lys Glu Ala Leu Ile Arg Thr Asp
        35                  40                  45

Gly Met Arg Val Thr Ser Arg Lys Ser Ala Lys Tyr Arg Leu Gln Gly
    50                  55                  60

Thr Ile Pro Arg Gly Asp Val Ser Leu Thr Ile Leu Asn Pro Ser Glu
65                  70                  75                  80

Ser Asp Ser Gly Val Tyr Cys Cys Arg Ile Glu Val Pro Gly Trp Phe
                85                  90                  95

Asn Asp Val Lys Ile Asn Val Arg Leu Asn Leu Gln Arg Ala Ser Thr
            100                 105                 110

Thr

<210> SEQ ID NO 3
<211> LENGTH: 343
<212> TYPE: PRT
<213> ORGANISM: Mus musculus

<400> SEQUENCE: 3

Met Ser Lys Gly Leu Leu Leu Trp Leu Val Thr Glu Leu Trp Trp
1               5                   10                  15

Leu Tyr Leu Thr Pro Ala Ala Ser Glu Asp Thr Ile Ile Gly Phe Leu
            20                  25                  30

Gly Gln Pro Val Thr Leu Pro Cys His Tyr Leu Ser Trp Ser Gln Ser
        35                  40                  45

Arg Asn Ser Met Cys Trp Gly Lys Gly Ser Cys Pro Asn Ser Lys Cys
50                  55                  60

Asn Ala Glu Leu Leu Arg Thr Asp Gly Thr Arg Ile Ile Ser Arg Lys
65                  70                  75                  80

Ser Thr Lys Tyr Thr Leu Leu Gly Lys Val Gln Phe Gly Glu Val Ser
                85                  90                  95

Leu Thr Ile Ser Asn Thr Asn Arg Gly Asp Ser Gly Val Tyr Cys Cys
            100                 105                 110

Arg Ile Glu Val Pro Gly Trp Phe Asn Asp Val Lys Lys Asn Val Arg
        115                 120                 125

Leu Glu Leu Arg Arg Ala Thr Thr Thr Lys Lys Pro Thr Thr Thr Thr
130                 135                 140

Arg Pro Thr Thr Thr Pro Tyr Val Thr Thr Thr Pro Glu Leu Leu
145                 150                 155                 160

Pro Thr Thr Val Met Thr Thr Ser Val Leu Pro Thr Thr Pro Pro
                165                 170                 175

Gln Thr Leu Ala Thr Thr Ala Phe Ser Thr Ala Val Thr Thr Cys Pro
            180                 185                 190

Ser Thr Thr Pro Gly Ser Phe Ser Gln Glu Thr Thr Lys Gly Ser Ala
        195                 200                 205

Phe Thr Thr Glu Ser Glu Thr Leu Pro Ala Ser Asn His Ser Gln Arg
210                 215                 220

Ser Met Met Thr Ile Ser Thr Asp Ile Ala Val Leu Arg Pro Thr Gly
225                 230                 235                 240

Ser Asn Pro Gly Ile Leu Pro Ser Thr Ser Gln Leu Thr Thr Gln Lys
                245                 250                 255

Thr Thr Leu Thr Thr Ser Glu Ser Leu Gln Lys Thr Thr Lys Ser His
            260                 265                 270

Gln Ile Asn Ser Arg Gln Thr Ile Leu Ile Ile Ala Cys Cys Val Gly
        275                 280                 285

Phe Val Leu Met Val Leu Leu Phe Leu Ala Phe Leu Leu Arg Gly Lys
290                 295                 300

Val Thr Gly Ala Asn Cys Leu Gln Arg His Lys Arg Pro Asp Asn Thr
305                 310                 315                 320

Glu Asp Ser Asp Ser Val Leu Asn Asp Met Ser His Gly Arg Asp Asp
                325                 330                 335

Glu Asp Gly Ile Phe Thr Leu
            340

<210> SEQ ID NO 4
<211> LENGTH: 378
<212> TYPE: PRT
<213> ORGANISM: Homo sapiens

<400> SEQUENCE: 4

```
Met Ser Lys Glu Pro Leu Ile Leu Trp Leu Met Ile Glu Phe Trp Trp
1               5                   10                  15
Leu Tyr Leu Thr Pro Val Thr Ser Glu Thr Val Val Thr Glu Val Leu
            20                  25                  30
Gly His Arg Val Thr Leu Pro Cys Leu Tyr Ser Ser Trp Ser His Asn
        35                  40                  45
Ser Asn Ser Met Cys Trp Gly Lys Asp Gln Cys Pro Tyr Ser Gly Cys
    50                  55                  60
Lys Glu Ala Leu Ile Arg Thr Asp Gly Met Arg Val Thr Ser Arg Lys
65                  70                  75                  80
Ser Ala Lys Tyr Arg Leu Gln Gly Thr Ile Pro Arg Gly Asp Val Ser
                85                  90                  95
Leu Thr Ile Leu Asn Pro Ser Glu Ser Asp Ser Gly Val Tyr Cys Cys
            100                 105                 110
Arg Ile Glu Val Pro Gly Trp Phe Asn Asp Val Lys Ile Asn Val Arg
        115                 120                 125
Leu Asn Leu Gln Arg Ala Ser Thr Thr His Arg Thr Ala Thr Thr
130                 135                 140
Thr Thr Arg Arg Thr Thr Thr Ser Pro Thr Thr Arg Gln Met
145                 150                 155                 160
Thr Thr Thr Pro Ala Ala Leu Pro Thr Thr Val Val Thr Thr Pro Asp
                165                 170                 175
Leu Thr Thr Gly Thr Pro Leu Gln Met Thr Thr Ile Ala Val Phe Thr
            180                 185                 190
Thr Ala Asn Thr Cys Leu Ser Leu Thr Pro Ser Thr Leu Pro Glu Glu
        195                 200                 205
Ala Thr Gly Leu Leu Thr Pro Glu Pro Ser Lys Glu Gly Pro Ile Leu
    210                 215                 220
Thr Ala Glu Ser Glu Thr Val Leu Pro Ser Asp Ser Trp Ser Ser Val
225                 230                 235                 240
Glu Ser Thr Ser Ala Asp Thr Val Leu Leu Thr Ser Lys Glu Ser Lys
                245                 250                 255
Val Trp Asp Leu Pro Ser Thr Ser His Val Ser Met Trp Lys Thr Ser
            260                 265                 270
Asp Ser Val Ser Ser Pro Gln Pro Gly Ala Ser Asp Thr Ala Val Pro
        275                 280                 285
Glu Gln Asn Lys Thr Thr Lys Thr Gly Gln Met Asp Gly Ile Pro Met
    290                 295                 300
Ser Met Lys Asn Glu Met Pro Ile Ser Gln Leu Leu Met Ile Ile Ala
305                 310                 315                 320
Pro Ser Leu Gly Phe Val Leu Phe Ala Leu Phe Val Ala Phe Leu Leu
                325                 330                 335
Arg Gly Lys Leu Met Glu Thr Tyr Cys Ser Lys His Thr Arg Leu
            340                 345                 350
Asp Tyr Ile Gly Asp Ser Lys Asn Val Leu Asn Asp Val Gln His Gly
        355                 360                 365
Arg Glu Asp Glu Asp Gly Leu Phe Thr Leu
    370                 375
```

<210> SEQ ID NO 5
<211> LENGTH: 252
<212> TYPE: PRT

<213> ORGANISM: Mus musculus

<400> SEQUENCE: 5

Ala Ala Ser Glu Asp Thr Ile Ile Gly Phe Leu Gly Gln Pro Val Thr
1               5                   10                  15

Leu Pro Cys His Tyr Leu Ser Trp Ser Gln Ser Arg Asn Ser Met Cys
            20                  25                  30

Trp Gly Lys Gly Ser Cys Pro Asn Ser Lys Cys Asn Ala Glu Leu Leu
        35                  40                  45

Arg Thr Asp Gly Thr Arg Ile Ile Ser Arg Lys Ser Thr Lys Tyr Thr
    50                  55                  60

Leu Leu Gly Lys Val Gln Phe Gly Glu Val Ser Leu Thr Ile Ser Asn
65                  70                  75                  80

Thr Asn Arg Gly Asp Ser Gly Val Tyr Cys Cys Arg Ile Glu Val Pro
                85                  90                  95

Gly Trp Phe Asn Asp Val Lys Lys Asn Val Arg Leu Glu Leu Arg Arg
            100                 105                 110

Ala Thr Thr Thr Lys Lys Pro Thr Thr Thr Arg Pro Thr Thr Thr
        115                 120                 125

Pro Tyr Val Thr Thr Thr Pro Glu Leu Leu Pro Thr Thr Val Met
    130                 135                 140

Thr Thr Ser Val Leu Pro Thr Thr Thr Pro Pro Gln Thr Leu Ala Thr
145                 150                 155                 160

Thr Ala Phe Ser Thr Ala Val Thr Thr Cys Pro Ser Thr Thr Pro Gly
                165                 170                 175

Ser Phe Ser Gln Glu Thr Thr Lys Gly Ser Ala Phe Thr Thr Glu Ser
            180                 185                 190

Glu Thr Leu Pro Ala Ser Asn His Ser Gln Arg Ser Met Met Thr Ile
        195                 200                 205

Ser Thr Asp Ile Ala Val Leu Arg Pro Thr Gly Ser Asn Pro Gly Ile
    210                 215                 220

Leu Pro Ser Thr Ser Gln Leu Thr Thr Gln Lys Thr Thr Leu Thr Thr
225                 230                 235                 240

Ser Glu Ser Leu Gln Lys Thr Thr Lys Ser His Gln
                245                 250

<210> SEQ ID NO 6
<211> LENGTH: 258
<212> TYPE: PRT
<213> ORGANISM: Mus musculus

<400> SEQUENCE: 6

Ala Ala Ser Glu Asp Thr Ile Ile Gly Phe Leu Gly Gln Pro Val Thr
1               5                   10                  15

Leu Pro Cys His Tyr Leu Ser Trp Ser Gln Ser Arg Asn Ser Met Cys
            20                  25                  30

Trp Gly Lys Gly Ser Cys Pro Asn Ser Lys Cys Asn Ala Glu Leu Leu
        35                  40                  45

Arg Thr Asp Gly Thr Arg Ile Ile Ser Arg Lys Ser Thr Lys Tyr Thr
    50                  55                  60

Leu Leu Gly Lys Val Gln Phe Gly Glu Val Ser Leu Thr Ile Ser Asn
65                  70                  75                  80

Thr Asn Arg Gly Asp Ser Gly Val Tyr Cys Cys Arg Ile Glu Val Pro
                85                  90                  95

Gly Trp Phe Asn Asp Val Lys Lys Asn Val Arg Leu Glu Leu Arg Arg

```
                100             105             110
Ala Thr Thr Thr Lys Lys Pro Thr Thr Thr Arg Pro Thr Thr Thr
            115             120             125
Pro Tyr Val Thr Thr Thr Thr Pro Glu Leu Leu Pro Thr Thr Val Met
            130             135             140
Thr Thr Ser Val Leu Pro Thr Thr Thr Pro Pro Gln Thr Leu Ala Thr
145             150             155             160
Thr Ala Phe Ser Thr Ala Val Thr Thr Cys Pro Ser Thr Thr Pro Gly
            165             170             175
Ser Phe Ser Gln Glu Thr Thr Lys Gly Ser Ala Phe Thr Thr Glu Ser
            180             185             190
Glu Thr Leu Pro Ala Ser Asn His Ser Gln Arg Ser Met Met Thr Ile
            195             200             205
Ser Thr Asp Ile Ala Val Leu Arg Pro Thr Gly Ser Asn Pro Gly Ile
            210             215             220
Leu Pro Ser Thr Ser Gln Leu Thr Thr Gln Lys Thr Thr Leu Thr Thr
225             230             235             240
Ser Glu Ser Leu Gln Lys Thr Thr Lys Ser His Gln Ile Asn Ser Arg
            245             250             255
Gln Thr

<210> SEQ ID NO 7
<211> LENGTH: 291
<212> TYPE: PRT
<213> ORGANISM: Homo sapiens

<400> SEQUENCE: 7

Glu Thr Val Val Thr Glu Val Leu Gly His Arg Val Thr Leu Pro Cys
1               5               10              15
Leu Tyr Ser Ser Trp Ser His Asn Ser Asn Ser Met Cys Trp Gly Lys
            20              25              30
Asp Gln Cys Pro Tyr Ser Gly Cys Lys Glu Ala Leu Ile Arg Thr Asp
            35              40              45
Gly Met Arg Val Thr Ser Arg Lys Ser Ala Lys Tyr Arg Leu Gln Gly
        50              55              60
Thr Ile Pro Arg Gly Asp Val Ser Leu Thr Ile Leu Asn Pro Ser Glu
65              70              75              80
Ser Asp Ser Gly Val Tyr Cys Cys Arg Ile Glu Val Pro Gly Trp Phe
            85              90              95
Asn Asp Val Lys Ile Asn Val Arg Leu Asn Leu Gln Arg Ala Ser Thr
            100             105             110
Thr Thr His Arg Thr Ala Thr Thr Thr Arg Arg Thr Thr Thr Thr
            115             120             125
Ser Pro Thr Thr Thr Arg Gln Met Thr Thr Thr Pro Ala Ala Leu Pro
            130             135             140
Thr Thr Val Val Thr Thr Pro Asp Leu Thr Thr Gly Thr Pro Leu Gln
145             150             155             160
Met Thr Thr Ile Ala Val Phe Thr Thr Ala Asn Thr Cys Leu Ser Leu
            165             170             175
Thr Pro Ser Thr Leu Pro Glu Glu Ala Thr Gly Leu Leu Thr Pro Glu
            180             185             190
Pro Ser Lys Glu Gly Pro Ile Leu Thr Ala Glu Ser Glu Thr Val Leu
            195             200             205
Pro Ser Asp Ser Trp Ser Ser Val Glu Ser Thr Ser Ala Asp Thr Val
```

```
                210               215               220
Leu Leu Thr Ser Lys Glu Ser Lys Val Trp Asp Leu Pro Ser Thr Ser
225                 230                 235                 240

His Val Ser Met Trp Lys Thr Ser Asp Ser Val Ser Ser Pro Gln Pro
                245                 250                 255

Gly Ala Ser Asp Thr Ala Val Pro Glu Gln Asn Lys Thr Thr Lys Thr
            260                 265                 270

Gly Gln Met Asp Gly Ile Pro Met Ser Met Lys Asn Glu Met Pro Ile
        275                 280                 285

Ser Gln Leu
    290

<210> SEQ ID NO 8
<211> LENGTH: 110
<212> TYPE: PRT
<213> ORGANISM: Mus musculus

<400> SEQUENCE: 8

Tyr Val Glu Val Lys Gly Val Gly His Pro Val Thr Leu Pro Cys
1               5                   10                  15

Thr Tyr Ser Thr Tyr Arg Gly Ile Thr Thr Thr Cys Trp Gly Arg Gly
                20                  25                  30

Gln Cys Pro Ser Ser Ala Cys Gln Asn Thr Leu Ile Trp Thr Asn Gly
            35                  40                  45

His Arg Val Thr Tyr Gln Lys Ser Ser Arg Tyr Asn Leu Lys Gly His
        50                  55                  60

Ile Ser Glu Gly Asp Val Ser Leu Thr Ile Glu Asn Ser Val Glu Ser
65                  70                  75                  80

Asp Ser Gly Leu Tyr Cys Cys Arg Val Glu Ile Pro Gly Trp Phe Asn
                85                  90                  95

Asp Gln Lys Val Thr Phe Ser Leu Gln Val Lys Pro Glu Ile
                100                 105                 110

<210> SEQ ID NO 9
<211> LENGTH: 110
<212> TYPE: PRT
<213> ORGANISM: Homo sapiens

<400> SEQUENCE: 9

Ser Val Lys Val Gly Gly Glu Ala Gly Pro Ser Val Thr Leu Pro Cys
1               5                   10                  15

His Tyr Ser Gly Ala Val Thr Ser Met Cys Trp Asn Arg Gly Ser Cys
                20                  25                  30

Ser Leu Phe Thr Cys Gln Asn Gly Ile Val Trp Thr Asn Gly Thr His
            35                  40                  45

Val Thr Tyr Arg Lys Asp Thr Arg Tyr Lys Leu Leu Gly Asp Leu Ser
        50                  55                  60

Arg Arg Asp Val Ser Leu Thr Ile Glu Asn Thr Ala Val Ser Asp Ser
65                  70                  75                  80

Gly Val Tyr Cys Cys Arg Val Glu His Arg Gly Trp Phe Asn Asp Met
                85                  90                  95

Lys Ile Thr Val Ser Leu Glu Ile Val Pro Pro Lys Val Thr
                100                 105                 110

<210> SEQ ID NO 10
<211> LENGTH: 282
<212> TYPE: PRT
```

-continued

<213> ORGANISM: Mus musculus

<400> SEQUENCE: 10

Met Asn Gln Ile Gln Val Phe Ile Ser Gly Leu Ile Leu Leu Leu Pro
1               5                   10                  15

Gly Ala Val Asp Ser Tyr Val Glu Val Lys Gly Val Val Gly His Pro
            20                  25                  30

Val Thr Leu Pro Cys Thr Tyr Ser Thr Tyr Arg Gly Ile Thr Thr Thr
        35                  40                  45

Cys Trp Gly Arg Gly Gln Cys Pro Ser Ser Ala Cys Gln Asn Thr Leu
50                  55                  60

Ile Trp Thr Asn Gly His Arg Val Thr Tyr Gln Lys Ser Ser Arg Tyr
65                  70                  75                  80

Asn Leu Lys Gly His Ile Ser Glu Gly Asp Val Ser Leu Thr Ile Glu
                85                  90                  95

Asn Ser Val Glu Ser Asp Ser Gly Leu Tyr Cys Cys Arg Val Glu Ile
            100                 105                 110

Pro Gly Trp Phe Asn Asp Gln Lys Val Thr Phe Ser Leu Gln Val Lys
        115                 120                 125

Pro Glu Ile Pro Thr Arg Pro Pro Arg Arg Pro Thr Thr Thr Arg Pro
130                 135                 140

Thr Ala Thr Gly Arg Pro Thr Thr Ile Ser Thr Arg Ser Thr His Val
145                 150                 155                 160

Pro Thr Ser Thr Arg Val Ser Thr Ser Thr Pro Pro Thr Ser Thr His
                165                 170                 175

Thr Trp Thr His Lys Pro Asp Trp Asn Gly Thr Val Thr Ser Ser Gly
            180                 185                 190

Asp Thr Trp Ser Asn His Thr Glu Ala Ile Pro Pro Gly Lys Pro Gln
        195                 200                 205

Lys Asn Pro Thr Lys Gly Phe Tyr Val Gly Ile Cys Ile Ala Ala Leu
210                 215                 220

Leu Leu Leu Leu Leu Val Ser Thr Val Ala Ile Thr Arg Tyr Ile Leu
225                 230                 235                 240

Met Lys Arg Lys Ser Ala Ser Leu Ser Val Val Ala Phe Arg Val Ser
                245                 250                 255

Lys Ile Glu Ala Leu Gln Asn Ala Ala Val Val His Ser Arg Ala Glu
            260                 265                 270

Asp Asn Ile Tyr Ile Val Glu Asp Arg Pro
        275                 280

<210> SEQ ID NO 11
<211> LENGTH: 364
<212> TYPE: PRT
<213> ORGANISM: Homo sapiens

<400> SEQUENCE: 11

Met His Pro Gln Val Val Ile Leu Ser Leu Ile Leu His Leu Ala Asp
1               5                   10                  15

Ser Val Ala Gly Ser Val Lys Val Gly Gly Glu Ala Gly Pro Ser Val
            20                  25                  30

Thr Leu Pro Cys His Tyr Ser Gly Ala Val Thr Ser Met Cys Trp Asn
        35                  40                  45

Arg Gly Ser Cys Ser Leu Phe Thr Cys Gln Asn Gly Ile Val Trp Thr
50                  55                  60

Asn Gly Thr His Val Thr Tyr Arg Lys Asp Thr Arg Tyr Lys Leu Leu

```
                    65                  70                  75                  80
Gly Asp Leu Ser Arg Arg Asp Val Ser Leu Thr Ile Glu Asn Thr Ala
                    85                  90                  95

Val Ser Asp Ser Gly Val Tyr Cys Cys Arg Val Glu His Arg Gly Trp
                100                 105                 110

Phe Asn Asp Met Lys Ile Thr Val Ser Leu Glu Ile Val Pro Pro Lys
                115                 120                 125

Val Thr Thr Thr Pro Ile Val Thr Thr Val Pro Thr Val Thr Thr Val
130                 135                 140

Arg Thr Ser Thr Thr Val Pro Thr Thr Thr Val Pro Met Thr Thr
145                 150                 155                 160

Val Pro Thr Thr Thr Val Pro Thr Thr Met Ser Ile Pro Thr Thr Thr
                165                 170                 175

Thr Val Leu Thr Thr Met Thr Val Ser Thr Thr Ser Val Pro Thr
                180                 185                 190

Thr Thr Ser Ile Pro Thr Thr Ser Val Pro Val Thr Thr Thr Val
                195                 200                 205

Ser Thr Phe Val Pro Pro Met Pro Leu Pro Arg Gln Asn His Glu Pro
210                 215                 220

Val Ala Thr Ser Pro Ser Pro Gln Pro Ala Glu Thr His Pro Thr
225                 230                 235                 240

Thr Leu Gln Gly Ala Ile Arg Arg Glu Pro Thr Ser Ser Pro Leu Tyr
                245                 250                 255

Ser Tyr Thr Thr Asp Gly Asn Asp Thr Val Thr Glu Ser Ser Asp Gly
                260                 265                 270

Leu Trp Asn Asn Asn Gln Thr Gln Leu Phe Leu Glu His Ser Leu Leu
                275                 280                 285

Thr Ala Asn Thr Thr Lys Gly Ile Tyr Ala Gly Val Cys Ile Ser Val
                290                 295                 300

Leu Val Leu Leu Ala Leu Leu Gly Val Ile Ile Ala Lys Lys Tyr Phe
305                 310                 315                 320

Phe Lys Lys Glu Val Gln Gln Leu Ser Val Ser Phe Ser Ser Leu Gln
                325                 330                 335

Ile Lys Ala Leu Gln Asn Ala Val Glu Lys Glu Val Gln Ala Glu Asp
                340                 345                 350

Asn Ile Tyr Ile Glu Asn Ser Leu Tyr Ala Thr Asp
                355                 360

<210> SEQ ID NO 12
<211> LENGTH: 191
<212> TYPE: PRT
<213> ORGANISM: Mus musculus

<400> SEQUENCE: 12

Tyr Val Glu Val Lys Gly Val Val Gly His Pro Val Thr Leu Pro Cys
1               5                   10                  15

Thr Tyr Ser Thr Tyr Arg Gly Ile Thr Thr Thr Cys Trp Gly Arg Gly
                20                  25                  30

Gln Cys Pro Ser Ser Ala Cys Gln Asn Thr Leu Ile Trp Thr Asn Gly
            35                  40                  45

His Arg Val Thr Tyr Gln Lys Ser Ser Arg Tyr Asn Leu Lys Gly His
        50                  55                  60

Ile Ser Glu Gly Asp Val Ser Leu Thr Ile Glu Asn Ser Val Glu Ser
65                  70                  75                  80
```

```
Asp Ser Gly Leu Tyr Cys Cys Arg Val Glu Ile Pro Gly Trp Phe Asn
                 85                  90                  95

Asp Gln Lys Val Thr Phe Ser Leu Gln Val Lys Pro Glu Ile Pro Thr
            100                 105                 110

Arg Pro Pro Arg Pro Thr Thr Thr Arg Pro Thr Ala Thr Gly Arg
        115                 120                 125

Pro Thr Thr Ile Ser Thr Arg Ser Thr His Val Pro Thr Ser Thr Arg
        130                 135                 140

Val Ser Thr Ser Thr Pro Pro Thr Ser Thr His Thr Trp Thr His Lys
145                 150                 155                 160

Pro Asp Trp Asn Gly Thr Val Thr Ser Ser Gly Asp Thr Trp Ser Asn
                165                 170                 175

His Thr Glu Ala Ile Pro Pro Gly Lys Pro Gln Lys Asn Pro Thr
                180                 185                 190

<210> SEQ ID NO 13
<211> LENGTH: 275
<212> TYPE: PRT
<213> ORGANISM: Homo sapiens

<400> SEQUENCE: 13

Ser Val Lys Val Gly Gly Glu Ala Gly Pro Ser Val Thr Leu Pro Cys
1               5                   10                  15

His Tyr Ser Gly Ala Val Thr Ser Met Cys Trp Asn Arg Gly Ser Cys
                20                  25                  30

Ser Leu Phe Thr Cys Gln Asn Gly Ile Val Trp Thr Asn Gly Thr His
            35                  40                  45

Val Thr Tyr Arg Lys Asp Thr Arg Tyr Lys Leu Leu Gly Asp Leu Ser
50                  55                  60

Arg Arg Asp Val Ser Leu Thr Ile Glu Asn Thr Ala Val Ser Asp Ser
65                  70                  75                  80

Gly Val Tyr Cys Cys Arg Val Glu His Arg Gly Trp Phe Asn Asp Met
                85                  90                  95

Lys Ile Thr Val Ser Leu Glu Ile Val Pro Pro Lys Val Thr Thr Thr
            100                 105                 110

Pro Ile Val Thr Thr Val Pro Thr Val Thr Thr Val Arg Thr Ser Thr
        115                 120                 125

Thr Val Pro Thr Thr Thr Val Pro Met Thr Thr Val Pro Thr Thr
        130                 135                 140

Thr Val Pro Thr Met Ser Ile Pro Thr Thr Thr Val Leu Thr
145                 150                 155                 160

Thr Met Thr Val Ser Thr Thr Ser Val Pro Thr Thr Ser Ile
                165                 170                 175

Pro Thr Thr Thr Ser Val Pro Val Thr Thr Val Ser Thr Phe Val
                180                 185                 190

Pro Pro Met Pro Leu Pro Arg Gln Asn His Glu Pro Val Ala Thr Ser
            195                 200                 205

Pro Ser Ser Pro Gln Pro Ala Glu Thr His Pro Thr Thr Leu Gln Gly
        210                 215                 220

Ala Ile Arg Arg Glu Pro Thr Ser Ser Pro Leu Tyr Ser Tyr Thr Thr
225                 230                 235                 240

Asp Gly Asn Asp Thr Val Thr Glu Ser Ser Asp Gly Leu Trp Asn Asn
                245                 250                 255

Asn Gln Thr Gln Leu Phe Leu Glu His Ser Leu Leu Thr Ala Asn Thr
            260                 265                 270
```

Thr Lys Gly
        275

<210> SEQ ID NO 14
<211> LENGTH: 113
<212> TYPE: PRT
<213> ORGANISM: Mus musculus

<400> SEQUENCE: 14

Leu Glu Asn Ala Tyr Val Phe Glu Val Gly Lys Asn Ala Tyr Leu Pro
1               5                   10                  15

Cys Ser Tyr Thr Leu Ser Thr Pro Gly Ala Leu Val Pro Met Cys Trp
            20                  25                  30

Gly Lys Gly Phe Cys Pro Trp Ser Gln Cys Thr Asn Glu Leu Leu Arg
        35                  40                  45

Thr Asp Glu Arg Asn Val Thr Tyr Gln Lys Ser Ser Arg Tyr Gln Leu
    50                  55                  60

Lys Gly Asp Leu Asn Lys Gly Asp Val Ser Leu Ile Ile Lys Asn Val
65                  70                  75                  80

Thr Leu Asp Asp His Gly Thr Tyr Cys Cys Arg Ile Gln Phe Pro Gly
                85                  90                  95

Leu Met Asn Asp Lys Lys Leu Glu Leu Lys Leu Asp Ile Lys Ala Ala
                100                 105                 110

Lys

<210> SEQ ID NO 15
<211> LENGTH: 114
<212> TYPE: PRT
<213> ORGANISM: Homo sapiens

<400> SEQUENCE: 15

Ser Glu Val Glu Tyr Arg Ala Glu Val Gly Gln Asn Ala Tyr Leu Pro
1               5                   10                  15

Cys Phe Tyr Thr Pro Ala Ala Pro Gly Asn Leu Val Pro Val Cys Trp
            20                  25                  30

Gly Lys Gly Ala Cys Pro Val Phe Glu Cys Gly Asn Val Val Leu Arg
        35                  40                  45

Thr Asp Glu Arg Asp Val Asn Tyr Trp Thr Ser Arg Tyr Trp Leu Asn
    50                  55                  60

Gly Asp Phe Arg Lys Gly Asp Val Ser Leu Thr Ile Glu Asn Val Thr
65                  70                  75                  80

Leu Ala Asp Ser Gly Ile Tyr Cys Cys Arg Ile Gln Ile Pro Gly Ile
                85                  90                  95

Met Asn Asp Glu Lys Phe Asn Leu Lys Leu Val Ile Lys Pro Ala Lys
                100                 105                 110

Val Thr

<210> SEQ ID NO 16
<211> LENGTH: 281
<212> TYPE: PRT
<213> ORGANISM: Mus musculus

<400> SEQUENCE: 16

Met Phe Ser Gly Leu Thr Leu Asn Cys Val Leu Leu Leu Gln Leu
1               5                   10                  15

Leu Leu Ala Arg Ser Leu Glu Asn Ala Tyr Val Phe Glu Val Gly Lys
            20                  25                  30

Asn Ala Tyr Leu Pro Cys Ser Tyr Thr Leu Ser Thr Pro Gly Ala Leu
                35                  40                  45

Val Pro Met Cys Trp Gly Lys Gly Phe Cys Pro Trp Ser Gln Cys Thr
 50                  55                  60

Asn Glu Leu Leu Arg Thr Asp Glu Arg Asn Val Thr Tyr Gln Lys Ser
 65                  70                  75                  80

Ser Arg Tyr Gln Leu Lys Gly Asp Leu Asn Lys Gly Asp Val Ser Leu
                 85                  90                  95

Ile Ile Lys Asn Val Thr Leu Asp Asp His Gly Thr Tyr Cys Cys Arg
                100                 105                 110

Ile Gln Phe Pro Gly Leu Met Asn Asp Lys Lys Leu Glu Leu Lys Leu
                115                 120                 125

Asp Ile Lys Ala Ala Lys Val Thr Pro Ala Gln Thr Ala His Gly Asp
130                 135                 140

Ser Thr Thr Ala Ser Pro Arg Thr Leu Thr Thr Glu Arg Asn Gly Ser
145                 150                 155                 160

Glu Thr Gln Thr Leu Val Thr Leu His Asn Asn Gly Thr Lys Ile
                165                 170                 175

Ser Thr Trp Ala Asp Glu Ile Lys Asp Ser Gly Glu Thr Ile Arg Thr
                180                 185                 190

Ala Ile His Ile Gly Val Gly Val Ser Ala Gly Leu Thr Leu Ala Leu
                195                 200                 205

Ile Ile Gly Val Leu Ile Leu Lys Trp Tyr Ser Cys Lys Lys Lys
                210                 215                 220

Leu Ser Ser Leu Ser Leu Ile Thr Leu Ala Asn Leu Pro Pro Gly Gly
225                 230                 235                 240

Leu Ala Asn Ala Gly Ala Val Arg Ile Arg Ser Glu Glu Asn Ile Tyr
                245                 250                 255

Thr Ile Glu Glu Asn Val Tyr Glu Val Glu Asn Ser Asn Glu Tyr Tyr
                260                 265                 270

Cys Tyr Val Asn Ser Gln Gln Pro Ser
                275                 280

<210> SEQ ID NO 17
<211> LENGTH: 301
<212> TYPE: PRT
<213> ORGANISM: Homo sapiens

<400> SEQUENCE: 17

Met Phe Ser His Leu Pro Phe Asp Cys Val Leu Leu Leu Leu Leu
 1               5                  10                  15

Leu Leu Thr Arg Ser Ser Glu Val Glu Tyr Arg Ala Glu Val Gly Gln
                 20                  25                  30

Asn Ala Tyr Leu Pro Cys Phe Tyr Thr Pro Ala Ala Pro Gly Asn Leu
                 35                  40                  45

Val Pro Val Cys Trp Gly Lys Gly Ala Cys Pro Val Phe Glu Cys Gly
 50                  55                  60

Asn Val Val Leu Arg Thr Asp Glu Arg Asp Val Asn Tyr Trp Thr Ser
 65                  70                  75                  80

Arg Tyr Trp Leu Asn Gly Asp Phe Arg Lys Gly Asp Val Ser Leu Thr
                 85                  90                  95

Ile Glu Asn Val Thr Leu Ala Asp Ser Gly Ile Tyr Cys Cys Arg Ile
                100                 105                 110

Gln Ile Pro Gly Ile Met Asn Asp Glu Lys Phe Asn Leu Lys Leu Val

```
                    115                 120                 125
Ile Lys Pro Ala Lys Val Thr Pro Ala Pro Thr Arg Gln Arg Asp Phe
            130                 135                 140

Thr Ala Ala Phe Pro Arg Met Leu Thr Thr Arg Gly His Gly Pro Ala
145                 150                 155                 160

Glu Thr Gln Thr Leu Gly Ser Leu Pro Asp Ile Asn Leu Thr Gln Ile
                165                 170                 175

Ser Thr Leu Ala Asn Glu Leu Arg Asp Ser Arg Leu Ala Asn Asp Leu
            180                 185                 190

Arg Asp Ser Gly Ala Thr Ile Arg Ile Gly Ile Tyr Ile Gly Ala Gly
                195                 200                 205

Ile Cys Ala Gly Leu Ala Leu Ala Leu Ile Phe Gly Ala Leu Ile Phe
            210                 215                 220

Lys Trp Tyr Ser His Ser Lys Glu Lys Ile Gln Asn Leu Ser Leu Ile
225                 230                 235                 240

Ser Leu Ala Asn Leu Pro Pro Ser Gly Leu Ala Asn Ala Val Ala Glu
                245                 250                 255

Gly Ile Arg Ser Glu Glu Asn Ile Tyr Thr Ile Glu Glu Asn Val Tyr
            260                 265                 270

Glu Val Glu Glu Pro Asn Glu Tyr Tyr Cys Tyr Val Ser Ser Arg Gln
                275                 280                 285

Gln Pro Ser Gln Pro Leu Gly Cys Arg Phe Ala Met Pro
            290                 295                 300

<210> SEQ ID NO 18
<211> LENGTH: 168
<212> TYPE: PRT
<213> ORGANISM: Mus musculus

<400> SEQUENCE: 18

Leu Glu Asn Ala Tyr Val Phe Glu Val Gly Lys Asn Ala Tyr Leu Pro
1               5                   10                  15

Cys Ser Tyr Thr Leu Ser Thr Pro Gly Ala Leu Val Pro Met Cys Trp
                20                  25                  30

Gly Lys Gly Phe Cys Pro Trp Ser Gln Cys Thr Asn Glu Leu Leu Arg
            35                  40                  45

Thr Asp Glu Arg Asn Val Thr Tyr Gln Lys Ser Ser Arg Tyr Gln Leu
        50                  55                  60

Lys Gly Asp Leu Asn Lys Gly Asp Val Ser Leu Ile Ile Lys Asn Val
65                  70                  75                  80

Thr Leu Asp Asp His Gly Thr Tyr Cys Cys Arg Ile Gln Phe Pro Gly
                85                  90                  95

Leu Met Asn Asp Lys Lys Leu Glu Leu Lys Leu Asp Ile Lys Ala Ala
            100                 105                 110

Lys Val Thr Pro Ala Gln Thr Ala His Gly Asp Ser Thr Thr Ala Ser
        115                 120                 125

Pro Arg Thr Leu Thr Thr Glu Arg Asn Gly Ser Glu Thr Gln Thr Leu
    130                 135                 140

Val Thr Leu His Asn Asn Gly Thr Lys Ile Ser Thr Trp Ala Asp
145                 150                 155                 160

Glu Ile Lys Asp Ser Gly Glu Thr
                165

<210> SEQ ID NO 19
<211> LENGTH: 179
```

```
<212> TYPE: PRT
<213> ORGANISM: Homo sapiens

<400> SEQUENCE: 19

Ser Glu Val Glu Tyr Arg Ala Glu Val Gly Gln Asn Ala Tyr Leu Pro
1               5                   10                  15

Cys Phe Tyr Thr Pro Ala Ala Pro Gly Asn Leu Val Pro Val Cys Trp
            20                  25                  30

Gly Lys Gly Ala Cys Pro Val Phe Glu Cys Gly Asn Val Val Leu Arg
        35                  40                  45

Thr Asp Glu Arg Asp Val Asn Tyr Trp Thr Ser Arg Tyr Trp Leu Asn
    50                  55                  60

Gly Asp Phe Arg Lys Gly Asp Val Ser Leu Thr Ile Glu Asn Val Thr
65                  70                  75                  80

Leu Ala Asp Ser Gly Ile Tyr Cys Cys Arg Ile Gln Ile Pro Gly Ile
                85                  90                  95

Met Asn Asp Glu Lys Phe Asn Leu Lys Leu Val Ile Lys Pro Ala Lys
            100                 105                 110

Val Thr Pro Ala Pro Thr Arg Gln Arg Asp Phe Thr Ala Ala Phe Pro
        115                 120                 125

Arg Met Leu Thr Thr Arg Gly His Gly Pro Ala Glu Thr Gln Thr Leu
    130                 135                 140

Gly Ser Leu Pro Asp Ile Asn Leu Thr Gln Ile Ser Thr Leu Ala Asn
145                 150                 155                 160

Glu Leu Arg Asp Ser Arg Leu Ala Asn Asp Leu Arg Asp Ser Gly Ala
                165                 170                 175

Thr Ile Arg

<210> SEQ ID NO 20
<211> LENGTH: 1032
<212> TYPE: DNA
<213> ORGANISM: Mus musculus

<400> SEQUENCE: 20
atgtccaagg ggcttctcct cctctggctg gtgacggagc tctggtggct ttatctgaca      60
ccagctgcct cagaggatac aataataggg tttttgggcc agccggtgac tttgccttgt     120
cattacctct cgtggtccca gagccgcaac agtatgtgct ggggcaaagg ttcatgtccc     180
aattccaagt gcaatgcaga gcttctccgt acagatggaa caagaatcat ctccaggaag     240
tcaacaaaat atacttttt ggggaaggtc cagtttggtg aagtgtcctt gaccatctca      300
aacaccaatc gaggtgacag tggggtgtac tgctgccgta tagaggtgcc tggctggttc     360
aatgatgtca agaagaatgt gcgcttggag ctgaggagag ccacaacaac caaaaaacca     420
acaacaacca cccggccaac caccaccct tatgtgacca ccaccacccc agagctgctt      480
ccaacaacag tcatgaccac atctgttctc ccaaccacca caccccca gacactagcc       540
accactgcct tcagtacagc agtgaccacg tgcccctcaa caacacctgg ctccttctca     600
caagaaacca caaagggtc cgccttcact acagaatcag aaactctgcc tgcatccaat      660
cactctcaaa gaagcatgat gaccatatct cagacatag ccgtactcag gcccacaggc      720
tctaaccctg ggattctccc atccacttca cagctgacga cacagaaaac aacattaaca     780
acaagtgagt ctttgcagaa gacaactaaa tcacatcaga tcaacagcag acagaccatc     840
ttgatcattg cctgctgtgt gggatttgtg ctaatggtgt tattgtttct ggcgtttctc     900
cttcgaggga aagtcacagg agccaactgt ttgcagagac acaagaggcc agacaacact     960
```

```
gaagatagtg acagcgtcct caatgacatg tcacacggga gggatgatga agacgggatc   1020
ttcactctct ga                                                      1032

<210> SEQ ID NO 21
<211> LENGTH: 1137
<212> TYPE: DNA
<213> ORGANISM: Homo sapiens

<400> SEQUENCE: 21
atgtccaaag aacctctcat tctctggctg atgattgagt tttggtggct ttacctgaca     60
ccagtcactt cagagactgt tgtgacggag gttttgggtc accgggtgac tttgccctgt    120
ctgtactcat cctggtctca aacagcaac agcatgtgct gggggaaaga ccagtgcccc     180
tactccggtt gcaaggaggc gctcatccgc actgatggaa tgagggtgac ctcaagaaag    240
tcagcaaaat atagacttca ggggactatc ccgagaggtg atgtctcctt gaccatctta    300
aaccccagtg aaagtgacag cggtgtgtac tgctgccgca tagaagtgcc tggctggttc    360
aacgatgtaa agataaacgt gcgcctgaat ctacagagag cctcaacaac cacgcacaga    420
acagcaacca ccaccacacg cagaacaaca acaacaagcc ccaccaccac ccgacaaatg    480
acaacaaccc cagctgcact tccaacaaca gtcgtgacca cacccgatct cacaaccgga    540
acaccactcc agatgacaac cattgccgtc ttcacaacag caaacacgtg cctttcacta    600
accccaagca cccttccgga ggaagccaca ggtcttctga ctcccgagcc ttctaaggaa    660
gggcccatcc tcactgcaga atcagaaact gtcctcccca gtgattcctg gagtagtgtt    720
gagtctactt ctgctgacac tgtcctgctg acatccaaag agtccaaagt ttgggatctc    780
ccatcaacat cccacgtgtc aatgtggaaa acgagtgatt ctgtgtcttc tcctcagcct    840
ggagcatctg atacagcagt tcctgagcag aacaaaacaa caaaaacagg acagatggat    900 ggaatacccca tgtcaatgaa gaatgaaatg cccatctccc aactactgat gatcatcgcc    960
ccctccttgg gatttgtgct cttcgcattg tttgtggcgt ttctcctgag agggaaactc   1020
atggaaacct attgttcgca gaaacacaca aggctagact acattggaga tagtaaaaat   1080
gtcctcaatg acgtgcagca tggaagggaa gacgaagacg cctttttac cctctaa       1137

<210> SEQ ID NO 22
<211> LENGTH: 849
<212> TYPE: DNA
<213> ORGANISM: Mus musculus

<400> SEQUENCE: 22
atgaatcaga ttcaagtctt catttcaggc ctcatactgc ttctcccagg cgctgtggat     60
tcttatgtgg aagtaaaggg ggtggtgggt cacctgtca cacttccatg tacttactca     120
acatatcgtg gaatcacaac gacatgttgg ggccgagggc aatgcccatc ttctgcttgt    180
caaaatacac ttatttggac caatggacat cgtgtcacct atcagaagag cagtcggtac    240
aacttaaagg ggcatatttc agaaggagat gtgtccttga cgatagagaa ctctgttgag    300
agtgacagtg gtctgtattg ttgtcgagtg gagattcctg gatggtttaa tgatcagaaa    360
gtgacctttt cattgcaagt taaaccagag attcccacac gtcctccaag aagacccaca    420
actacaaggc ccacagctac aggaagaccc acgactattt caacaagatc cacacatgta    480
ccaacatcaa ccagagtctc tacctccact cctccaacat ctacacacac atggactcac    540
aaaccagact ggaatggcac tgtgcatatcc tcaggagata cctggagtaa tcacactgaa    600
```

```
gcaatccctc cagggaagcc gcagaaaaac cctactaagg gcttctatgt tggcatctgc     660
atcgcagccc tgctgctact gctccttgtg agcaccgtgg ctatcaccag gtacatactt     720
atgaaaagga agtcagcatc tctaagcgtg gttgccttcc gtgtctctaa gattgaagct     780
ttgcagaacg cagcggttgt gcattcccga gctgaagaca acatctacat tgttgaagat     840
agaccttga                                                             849
```

<210> SEQ ID NO 23
<211> LENGTH: 1095
<212> TYPE: DNA
<213> ORGANISM: Homo sapiens

<400> SEQUENCE: 23

```
atgcatcctc aagtggtcat cttaagcctc atcctacatc tggcagattc tgtagctggt      60
tctgtaaagg ttggtggaga ggcaggtcca tctgtcacac taccctgcca ctacagtgga     120
gctgtcacat ccatgtgctg gaatagaggc tcatgttctc tattcacatg ccaaaatggc     180
attgtctgga ccaatggaac ccacgtcacc tatcggaagg acacacgcta taagctattg     240
ggggaccttt caagaaggga tgtctctttg accatagaaa atacagctgt gtctgacagt     300
ggcgtatatt gttgccgtgt tgagcaccgt gggtggttca atgacatgaa aatcaccgta     360
tcattggaga ttgtgccacc caaggtcacg actactccaa ttgtcacaac tgttccaacc     420
gtcacgactg ttcgaacgag caccactgtt ccaacgacaa cgactgttcc aatgacgact     480
gttccaacga caactgttcc aacaacaatg agcattccaa cgacaacgac tgttctgacg     540
acaatgactg tttcaacgac aacgagcgtt ccaacgacaa cgagcattcc aacaacaaca     600
agtgttccag tgacaacaac tgtctctacc tttgttcctc caatgccttt gcccaggcag     660
aaccatgaac cagtagccac ttcaccatct tcacctcagc cagcagaaac ccaccctacg     720
acactgcagg gagcaataag gagagaaccc accagctcac cattgtactc ttacacaaca     780
gatgggaatg acaccgtgac agagtcttca gatggccttt ggaataacaa tcaaactcaa     840
ctgttcctag aacatagtct actgacggcc aataccacta aaggaatcta tgctggagtc     900
tgtatttctg tcttggtgct tcttgctctt tgggtgtca tcattgccaa aaagtatttc      960
ttcaaaaagg aggttcaaca actaagtgtt tcatttagca gccttcaaat taaagctttg    1020
caaaatgcag ttgaaaagga agtccaagca gaagacaata tctacattga gaatagtctt    1080
tatgccacgg actaa                                                     1095
```

<210> SEQ ID NO 24
<211> LENGTH: 846
<212> TYPE: DNA
<213> ORGANISM: Mus musculus

<400> SEQUENCE: 24

```
atgttttcag gtcttaccct caactgtgtc ctgctgctgc tgcaactact acttgcaagg      60
tcattggaaa atgcttatgt gtttgaggtt ggtaagaatg cctatctgcc ctgcagttac     120
actctatcta cacctggggc acttgtgcct atgtgctggg gcaagggatt ctgtccttgg     180
tcacagtgta ccaacgagtt gctcagaact gatgaaagaa atgtgacata tcagaaatcc     240
agcagatacc agctaaaggg cgatctcaac aaaggagacg tgtctctgat cataaagaat     300
gtgactctgg atgaccatgg gacctactgc tgcaggatac agttccctgg tcttatgaat     360
gataaaaaat tagaactgaa attagacatc aaagcagcca aggtcactcc agctcagact     420
gcccatgggg actctactac agcttctcca agaaccctaa ccacggagag aaatggttca     480
```

```
gagacacaga cactggtgac cctccataat aacaatggaa caaaaatttc cacatgggct    540
gatgaaatta aggactctgg agaaacgatc agaactgcta tccacattgg agtgggagtc    600
tctgctgggt tgaccctggc acttatcatt ggtgtcttaa tccttaaatg gtattcctgt    660
aagaaaaaga agttatcgag tttgagcctt attacactgg ccaacttgcc tccaggaggg    720
ttggcaaatg caggagcagt caggattcgc tctgaggaaa atatctacac catcgaggag    780
aacgtatatg aagtggagaa ttcaaatgag tactactgct acgtcaacag ccagcagcca    840
tcctga                                                              846
```

```
<210> SEQ ID NO 25
<211> LENGTH: 906
<212> TYPE: DNA
<213> ORGANISM: Homo sapiens

<400> SEQUENCE: 25
atgttttcac atcttcccatt tgactgtgtc ctgctgctgc tgctgctact acttacaagg     60
tcctcagaag tggaatacag agcggaggtc ggtcagaatg cctatctgcc ctgcttctac    120
accccagccg ccccagggaa cctcgtgccc gtctgctggg gcaaaggagc ctgtcctgtg    180
tttgaatgtg gcaacgtggt gctcaggact gatgaaaggg atgtgaatta ttggacatcc    240
agatactggc taaatgggga tttccgcaaa ggagatgtgt ccctgaccat agagaatgtg    300
actctagcag acagtgggat ctactgctgc cggatccaaa tcccaggcat aatgaatgat    360
gaaaaattta acctgaagtt ggtcatcaaa ccagccaagg tcacccctgc accgactcgg    420
cagagagact tcactgcagc cttccaagg atgcttacca ccaggggaca tggcccagca    480
gagacacaga cactggggag cctccctgat ataaatctaa cacaaatatc cacattggcc    540
aatgagttac gggactctag attggccaat gacttacggg actctggagc aaccatcaga    600
ataggcatct acatcggagc agggatctgt gctgggctgg ctctggctct tatcttcggc    660
gctttaattt tcaaatggta ttctcatagc aaagagaaga tacagaattt aagcctcatc    720
tctttggcca acctccctcc ctcaggattg gcaaatgcag tagcagaggg aattcgctca    780
gaagaaaaca tctataccat tgaagagaac gtatatgaag tggaggagcc caatgagtat    840
tattgctatg tcagcagcag gcagcaaccc tcacaacctt ggggttgtcg ctttgcaatg    900
ccatag                                                              906
```

```
<210> SEQ ID NO 26
<211> LENGTH: 822
<212> TYPE: DNA
<213> ORGANISM: Mus musculus

<400> SEQUENCE: 26
atgtccaagg ggcttctcct cctctggctg gtgacggagc tctggtggct ttatctgaca     60
ccagctgcct cagaggatac aataataggg tttttgggcc agccggtgac tttgccttgt    120
cattacctct cgtggtccca gagccgcaac agtatgtgct ggggcaaagg ttcatgtccc    180
aattccaagt gcaatgcaga gcttctccgt acagatggaa caagaatcat ctccaggaag    240
tcaacaaaat atacactttt ggggaaggtc cagtttggtg aagtgtcctt gaccatctca    300
aacaccaatc gaggtgacag tggggtgtac tgctgccgta tagaggtgcc tggctggttc    360
aatgatgtca agaagaatgt gcgcttggag ctgaggagag ccacaacaac caaaaaacca    420
acaacaacca cccggccaac caccaccccct tatgtgacca ccaccacccc agagctgctt    480
```

| | |
|---|---|
| ccaacaacag tcatgaccac atctgttctc ccaaccacca caccacccca gacactagcc | 540 |
| accactgcct tcagtacagc agtgaccacg tgcccctcaa caacacctgg ctccttctca | 600 |
| caagaaacca caaaagggtc cgccttcact acagaatcag aaactctgcc tgcatccaat | 660 |
| cactctcaaa gaagcatgat gaccatatct acagacatag ccgtactcag gcccacaggc | 720 |
| tctaaccctg ggattctccc atccacttca cagctgacga cacagaaaac aacattaaca | 780 |
| acaagtgagt ctttgcagaa gacaactaaa tcacatcagt ga | 822 |

<210> SEQ ID NO 27
<211> LENGTH: 840
<212> TYPE: DNA
<213> ORGANISM: Mus musculus

<400> SEQUENCE: 27

| | |
|---|---|
| atgtccaagg ggcttctcct cctctggctg gtgacggagc tctggtggct ttatctgaca | 60 |
| ccagctgcct cagaggatac aataataggg ttttttgggcc agccggtgac tttgccttgt | 120 |
| cattacctct cgtggtccca gagccgcaac agtatgtgct ggggcaaagg ttcatgtccc | 180 |
| aattccaagt gcaatgcaga gcttctccgt acagatggaa caagaatcat ctccaggaag | 240 |
| tcaacaaaat atacactttt ggggaaggtc cagtttggtg aagtgtcctt gaccatctca | 300 |
| aacaccaatc gaggtgacag tggggtgtac tgctgccgta tagaggtgcc tggctggttc | 360 |
| aatgatgtca agaagaatgt gcgcttggag ctgaggagag ccacaacaac caaaaaacca | 420 |
| acaacaacca cccggccaac caccaccccct tatgtgacca ccaccacccc agagctgctt | 480 |
| ccaacaacag tcatgaccac atctgttctc ccaaccacca caccacccca gacactagcc | 540 |
| accactgcct tcagtacagc agtgaccacg tgcccctcaa caacacctgg ctccttctca | 600 |
| caagaaacca caaaagggtc cgccttcact acagaatcag aaactctgcc tgcatccaat | 660 |
| cactctcaaa gaagcatgat gaccatatct acagacatag ccgtactcag gcccacaggc | 720 |
| tctaaccctg ggattctccc atccacttca cagctgacga cacagaaaac aacattaaca | 780 |
| acaagtgagt ctttgcagaa gacaactaaa tcacatcaga tcaacagcag acagacctga | 840 |

<210> SEQ ID NO 28
<211> LENGTH: 948
<212> TYPE: DNA
<213> ORGANISM: Homo sapiens

<400> SEQUENCE: 28

| | |
|---|---|
| atgtccaaag aacctctcat tctctggctg atgattgagt tttggtggct ttacctgaca | 60 |
| ccagtcactt cagagactgt tgtgacggag gttttgggtc accgggtgac tttgccctgt | 120 |
| ctgtactcat cctggtctca aacagcaac agcatgtgct gggggaaaga ccagtgcccc | 180 |
| tactccggtt gcaaggaggc gctcatccgc actgatggaa tgagggtgac ctcaagaaag | 240 |
| tcagcaaaat atagacttca ggggactatc ccgagaggtg atgtctcctt gaccatctta | 300 |
| aaccccagtg aaagtgacag cggtgtgtac tgctgccgca tagaagtgcc tggctggttc | 360 |
| aacgatgtaa agataaacgt gcgcctgaat ctacagagag cctcaacaac cacgcacaga | 420 |
| acagcaacca ccaccacacg cagaacaaca acaacaagcc ccaccaccac ccgacaaatg | 480 |
| acaacaaccc cagctgcact tccaacaaca gtcgtgacca cacccgatct cacaaccgga | 540 |
| acaccactcc agatgacaac cattgccgtc ttcacaacag caaacacgtg cctttcacta | 600 |
| accccaagca cccttccgga ggaagccaca ggtcttctga ctcccgagcc ttctaaggaa | 660 |
| gggcccatcc tcactgcaga atcagaaact gtcctcccca gtgattcctg gagtagtgtt | 720 |

```
gagtctactt ctgctgacac tgtcctgctg acatccaaag agtccaaagt ttgggatctc      780
ccatcaacat cccacgtgtc aatgtggaaa acgagtgatt ctgtgtcttc tcctcagcct      840
ggagcatctg atacagcagt tcctgagcag aacaaaacaa caaaaacagg acagatggat      900
ggaataccca tgtcaatgaa gaatgaaatg cccatctccc aactatga                   948

<210> SEQ ID NO 29
<211> LENGTH: 639
<212> TYPE: DNA
<213> ORGANISM: Mus musculus

<400> SEQUENCE: 29
atgaatcaga ttcaagtctt catttcaggc ctcatactgc ttctcccagg cgctgtggat       60
tcttatgtgg aagtaaaggg ggtggtgggt caccctgtca cacttccatg tacttactca      120
acatatcgtg aatcacaac gacatgttgg ggccgagggc aatgcccatc ttctgcttgt       180
caaaatacac ttatttggac caatggacat cgtgtcacct atcagaagag cagtcggtac      240
aacttaaagg ggcatatttc agaaggagat gtgtccttga cgatagagaa ctctgttgag      300
agtgacagtg gtctgtattg ttgtcgagtg gagattcctg gatggtttaa tgatcagaaa      360
gtgacctttt cattgcaagt taaaccagag attcccacac gtcctccaag aagacccaca      420
actacaaggc ccacagctac aggaagaccc acgactattt caacaagatc cacacatgta      480
ccaacatcaa ccagagtctc tacctccact cctccaacat ctacacacac atggactcac      540
aaaccagact ggaatggcac tgtgacatcc tcaggagata cctggagtaa tcacactgaa      600
gcaatccctc cagggaagcc gcagaaaaac cctacttga                            639

<210> SEQ ID NO 30
<211> LENGTH: 888
<212> TYPE: DNA
<213> ORGANISM: Homo sapiens

<400> SEQUENCE: 30
atgcatcctc aagtggtcat cttaagcctc atcctacatc tggcagattc tgtagctggt       60
tctgtaaagg ttggtggaga ggcaggtcca tctgtcacac taccctgcca ctacagtgga      120
gctgtcacat ccatgtgctg gaatagaggc tcatgttctc tattcacatg ccaaaatggc      180
attgtctgga ccaatggaac ccacgtcacc tatcggaagg acacacgcta taagctattg      240
ggggaccttt caagaaggga tgtctctttg accatagaaa atacagctgt gtctgacagt      300
ggcgtatatt gttgccgtgt tgagcaccgt gggtggttca atgacatgaa aatcaccgta      360
tcattggaga ttgtgccacc caaggtcacg actactccaa ttgtcacaac tgttccaacc      420
gtcacgactg ttcgaacgag caccactgtt ccaacgacaa cgactgttcc aatgacgact      480
gttccaacga caactgttcc aacaacaatg agcattccaa cgacaacgac tgttctgacg      540
acaatgactg tttcaacgac aacgagcgtt ccaacgacaa cgagcattcc aacaacaaca      600
agtgttccag tgacaacaac tgtctctacc tttgttcctc aatgcctttt gcccaggcag      660
aaccatgaac cagtagccac ttcaccatct tcacctcagc cagcagaaac ccaccctacg      720
acactgcagg gagcaataag gagagaaccc accagctcac cattgtactc ttacacaaca      780
gatgggaatg acaccgtgac agagtcttca gatggccttt ggaataacaa tcaaactcaa      840
ctgttcctag aacatagtct actgacggcc aataccacta aaggatga                  888

<210> SEQ ID NO 31
```

```
<211> LENGTH: 570
<212> TYPE: DNA
<213> ORGANISM: Mus musculus

<400> SEQUENCE: 31
atgttttcag gtcttaccct caactgtgtc ctgctgctgc tgcaactact acttgcaagg       60
tcattggaaa atgcttatgt gtttgaggtt ggtaagaatg cctatctgcc ctgcagttac      120
actctatcta cacctggggc acttgtgcct atgtgctggg gcaagggatt ctgtccttgg      180
tcacagtgta ccaacgagtt gctcagaact gatgaaagaa atgtgacata tcagaaatcc      240
agcagatacc agctaaaggg cgatctcaac aaaggagacg tgtctctgat cataaagaat      300
gtgactctgg atgaccatgg gacctactgc tgcaggatac agttccctgg tcttatgaat      360
gataaaaaat tagaactgaa attagacatc aaagcagcca aggtcactcc agctcagact      420
gcccatgggg actctactac agcttctcca agaaccctaa ccacggagag aaatggttca      480
gagacacaga cactggtgac cctccataat aacaatggaa caaaaattc cacatgggct      540 gatgaaatta aggactctgg agaaacgtga                                         570

<210> SEQ ID NO 32
<211> LENGTH: 603
<212> TYPE: DNA
<213> ORGANISM: Homo sapiens

<400> SEQUENCE: 32
atgttttcac atcttccctt tgactgtgtc ctgctgctgc tgctgctact acttacaagg       60
tcctcagaag tggaatacag agcggaggtc ggtcagaatg cctatctgcc ctgcttctac      120
accccagccg ccccagggaa cctcgtgccc gtctgctggg gcaaaggagc ctgtcctgtg      180
tttgaatgtg gcaacgtggt gctcaggact gatgaaaggg atgtgaatta ttggacatcc      240
agatactggc taaatgggga tttccgcaaa ggagatgtgt ccctgaccat agagaatgtg      300
actctagcag acagtgggat ctactgctgc cggatccaaa tcccaggcat aatgaatgat      360
gaaaaattta acctgaagtt ggtcatcaaa ccagccaagg tcaccctgc accgactcgg      420 cagagagact tcactgcagc ctttccaagg atgcttacca ccaggggaca tggcccagca      480
gagacacaga cactggggag cctccctgat ataaatctaa cacaaatatc cacattggcc      540
aatgagttac gggactctag attggccaat gacttacggg actctggagc aaccatcaga      600
tga                                                                    603

<210> SEQ ID NO 33
<211> LENGTH: 846
<212> TYPE: DNA
<213> ORGANISM: Mus musculus
<220> FEATURE:
<221> NAME/KEY: FLAG tag
<222> LOCATION: (820)..(843)

<400> SEQUENCE: 33
atgtccaagg ggcttctcct cctctggctg gtgacggagc tctggtggct ttatctgaca       60
ccagctgcct cagaggatac aataataggg ttttggggcc agccggtgac tttgccttgt      120
cattacctct cgtggtccca gagccgcaac agtatgtgct ggggcaaagg ttcatgtccc      180
aattccaagt gcaatgcaga gcttctccgt acagatggaa caagaatcat ctccaggaag      240
tcaacaaaat atacactttt ggggaaggtc cagtttggtg aagtgtcctt gaccatctca      300
aacaccaatc gaggtgacag tggggtgtac tgctgccgta tagaggtgcc tggctggttc      360
```

```
aatgatgtca agaagaatgt gcgcttggag ctgaggagag ccacaacaac caaaaaacca      420
acaacaacca cccggccaac caccacccct tatgtgacca ccaccacccc agagctgctt      480
ccaacaacag tcatgaccac atctgttctc ccaaccacca caccacccca gacactagcc      540
accactgcct tcagtacagc agtgaccacg tgcccctcaa caacacctgg ctccttctca      600
caagaaacca caaagggtc cgccttcact acagaatcag aaactctgcc tgcatccaat       660
cactctcaaa gaagcatgat gaccatatct acagacatag ccgtactcag gcccacaggc     720
tctaaccctg ggattctccc atccacttca cagctgacga cacagaaaac aacattaaca     780
acaagtgagt ctttgcagaa gacaactaaa tcacatcagg attacaagga tgacgacgat     840
aagtaa                                                                 846

<210> SEQ ID NO 34
<211> LENGTH: 840
<212> TYPE: DNA
<213> ORGANISM: Mus musculus
<220> FEATURE:
<221> NAME/KEY: His tag
<222> LOCATION: (820)..(837)

<400> SEQUENCE: 34
atgtccaagg ggcttctcct cctctggctg gtgacggagc tctggtggct ttatctgaca      60
ccagctgcct cagaggatac aataataggg tttttgggcc agccggtgac tttgccttgt    120
cattacctct cgtggtccca gagccgcaac agtatgtgct ggggcaaagg ttcatgtccc     180
aattccaagt gcaatgcaga gcttctccgt acagatggaa caagaatcat ctccaggaag     240
tcaacaaaat atacactttt ggggaaggtc cagtttggtg aagtgtcctt gaccatctca     300
aacaccaatc gaggtgacag tggggtgtac tgctgccgta tagaggtgcc tggctggttc    360
aatgatgtca agaagaatgt gcgcttggag ctgaggagag ccacaacaac caaaaaacca     420
acaacaacca cccggccaac caccacccct tatgtgacca ccaccacccc agagctgctt    480
ccaacaacag tcatgaccac atctgttctc ccaaccacca caccacccca gacactagcc    540
accactgcct tcagtacagc agtgaccacg tgcccctcaa caacacctgg ctccttctca    600
caagaaacca caaagggtc cgccttcact acagaatcag aaactctgcc tgcatccaat     660
cactctcaaa gaagcatgat gaccatatct acagacatag ccgtactcag gcccacaggc    720
tctaaccctg ggattctccc atccacttca cagctgacga cacagaaaac aacattaaca    780
acaagtgagt ctttgcagaa gacaactaaa tcacatcagc atcatcatca tcatcattga    840
```

TIM PROTEIN-BOUND CARRIER, METHODS FOR OBTAINING, REMOVING AND DETECTING EXTRACELLULAR MEMBRANE VESICLES AND VIRUSES USING SAID CARRIER, AND KIT INCLUDING SAID CARRIER

CROSS-REFERENCE TO RELATED APPLICATIONS

This patent application is the U.S. national phase of International Patent Application No. PCT/JP2015/083505, filed Nov. 27, 2015, which claims the benefit of Japanese Patent Application No. 2014-246876, filed on Dec. 5, 2014, which are incorporated by reference in their entireties herein.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 56,202 bytes ASCII (Text) file named "728241Replacement-SequenceListing.txt," created Sep. 12, 2017.

TECHNICAL FIELD

The present invention relates to a Tim protein-binding carrier, a method for obtaining, removing and detecting extracellular membrane vesicles and viruses using the carrier, as well as a kit comprising the carrier.

BACKGROUND ART

It has been known that the extracellular membrane vesicles contain proteins or nucleic acids, such as microRNAs, and the like, inside of the particles, and are responsible for transferring substances between cells. The extracellular membrane vesicles are secreted also into body fluids, such as blood, and the like, and proteins, microRNAs, and the like, in the extracellular membrane vesicles have been noticed as diagnostic markers for diseases. In addition, application of the extracellular membrane vesicles as a delivery tool of nucleic acid medicines has also been noticed.

In addition, there are many enveloped viruses covered with a membrane-like envelope on the surface of the viruses. Many enveloped viruses, such as influenza virus, human immunodeficiency virus, and the like, have been noticed as research subjects, since they cause diseases. In addition, the enveloped viruses are detoxified and utilized for vaccines, vectors, and the like, and they have been applied in prevention and treatment of diseases.

In this way, a process for obtaining the extracellular membrane vesicles or the enveloped viruses in high purity is indispensable, in the utilization of the extracellular membrane vesicles for diagnosis and medicines, in the utilization of the enveloped viruses as the vaccines and the vectors, and in carrying out basic research, or the like, of functional analysis, or the like, of the extracellular membrane vesicles or the enveloped viruses, and thus a means for obtaining the extracellular membrane vesicles or the enveloped viruses easily and conveniently, as well as in high purity has long been awaited. In addition, development of a method for efficiently removing the extracellular membrane vesicles or the enveloped viruses from materials derived from body fluid to be used has been expected, to prevent contamination of the extracellular membrane vesicles or the enveloped viruses derived from living organisms. Furthermore, a method for detecting the obtained extracellular membrane vesicles or the enveloped viruses, or the extracellular membrane vesicles or the enveloped viruses in a specimen in high sensitivity has also long been awaited.

As a method for obtaining the extracellular membrane vesicles, there has been known, as the most common method, a method in which a sample is subjected to ultra-centrifugal separation treatment to obtain the extracellular membrane vesicles as a precipitate fraction (NON-PATENT LITERATURE 1). However, with this method, it is difficult to obtain the highly pure extracellular membrane vesicles, because protein complexes or aggregates, lipoproteins, such as HDL, and the like, contained in a sample are also co-precipitated, other than the extracellular membrane vesicles. Although it is possible to separate the protein complexes or the aggregates by density fractionation of the precipitate fraction obtained by the ultracentrifugal separation treatment by a sucrose density gradient method, it is difficult to separate them from the HDL having the same density. In addition, it is difficult to process multiple samples at the same time, since this method requires ultracentrifugal separation treatment. In addition, expensive equipment is required for ultracentrifugal separation treatment.

In addition, there is also a method for obtaining the extracellular membrane vesicles, as a precipitated fraction, by centrifugal separation treatment by the addition of a commercial reagent, represented by ExoQuick (produced by System Biosciences Co., Ltd.) or Total Exosome Isolation Reagent (produced by Thermo Fisher Scientific Co., Ltd.) (NON-PATENT LITERATURE 1), however, there is a problem that purity of the resulting extracellular membrane vesicles is further lower as compared with a method by the ultra-centrifugal separation treatment.

In addition to these conventional methods, there are methods for obtaining the extracellular membrane vesicles by affinity of a surface antigenic protein and an antibody, using the antibody against the surface antigenic protein of the extracellular membrane vesicles (an anti-CD63 antibody immobilization method, Exosome-Human CD63 Isolation/Detection (produced by Thermo Fisher Scientific, Inc.), and the like.) (NON-PATENT LITERATURE 1). These methods have such problems that only the extracellular membrane vesicles having the surface antigenic protein for the antibody can be obtained; yield of the extracellular membrane vesicles is small; it is difficult to obtain the extracellular membrane vesicles in an intact state (that is, while maintaining an original state of function of the extracellular membrane vesicles) because it is necessary to use a surfactant, an acidic buffer, or the like, in order to elute the extracellular membrane vesicles from the antibody; and the like, although the high purity extracellular membrane vesicles can be obtained.

As a method for obtaining the viruses, there has been known, as the most general method, a method for subjecting a sample to ultracentrifugal separation treatment to obtain the viruses, as the precipitate fraction (NON-PATENT LITERATURE 1). However, in this method, it is difficult to obtain the high purity viruses, because the protein complexes and the aggregates, the lipoproteins, such as HDL, and the like, contained in the sample are co-precipitated other than the viruses. Although it is possible to separate the protein complexes or the aggregates by density fractionation of the precipitate fraction obtained by the ultracentrifugal separation treatment, by a sucrose density gradient method, it is difficult to separate them from the aggregates having the same density. In addition, there is also a problem that activity of the viruses is lowered by the ultracentrifugal separation treatment (NON-PATENT LITERATURE 2). In addition, this method is difficult to process multiple specimens at the same time, because it requires the ultracentrifugal separation treatment. In addition, an expensive machine is required for the ultracentrifugal separation treatment.

Other than these methods, there has been known a method for purifying the viruses by ion-exchange chromatography, (NON-PATENT LITERATURE 3). However, this method requires setting optimum condition for each of the viruses. In addition, condition setting may be difficult, in some cases, and thus it is difficult to apply it to purification of all viruses.

As a method for removing the extracellular membrane vesicles, there has been known, as the most general method, a method for subjecting the sample to the ultra-centrifugal separation treatment to precipitation fractionate the extracellular membrane vesicles to obtain the supernatant fraction as a removal sample. However, this method has difficulty in complete removal of the extracellular membrane vesicles, thus resulting in remaining of the extracellular membrane vesicles not completely removed, in the sample.

Furthermore, there is also a method for precipitation fractioning the extracellular membrane vesicles, by the centrifugal separation treatment and the addition of a commercial reagent, represented by ExoQuick (produced by System Biosciences Co., Ltd.) or Total Exosome Isolation Reagent (produced by Thermo Fisher Scientific Co., Ltd.) to obtain the supernatant fraction as the removal sample. However, in also this method, there was difficulty to completely remove the extracellular membrane vesicles, due to remaining of the extracellular membrane vesicles not completely removed, in the sample. In addition, there was the case of inducing a problem on bioactivity, or the like, of the extracellular membrane vesicles, by the reagent, because of contamination of the reagent added into the sample.

There has been known the same method also as a method for removing the viruses and there was the same problem as in the method for removing the extracellular membrane vesicles.

As a method for detecting the extracellular membrane vesicles, there has been known, as a general method, a sandwich ELISA using the antibody against the surface antigen of the extracellular membrane vesicles. However, the minimum detection sensitivity of the sandwich ELISA system using the antibody that detects an ordinary color development signal has been reported to be about 3 μg in purified exosomes, and sufficient sensitivity for measuring a body fluid sample, such as serum, has not been obtained (NON-PATENT LITERATURE 4). The same method has been known, also as the method for detecting the viruses, and sufficient sensitivity for detection of the viruses has also not been obtained.

In addition, as the other method for detecting the extracellular membrane vesicles, a flow cytometry method has been known. However, in the usual method for capturing the extracellular membrane vesicles using a carrier to which the antibody against the surface antigen of the extracellular membrane vesicles was immobilized, sufficient sensitivity has not been obtained; and thus direct detection from the sample, such as culture supernatant or body fluid, has been difficult, and the detection from the sample after concentrating or purifying the extracellular membrane vesicles has been required.

CITATION LIST

Non-Patent Literature

[NON-PATENT LITERATURE 1] Kenneth W. Witwer et al. Journal of Extracellular Vesicles, 2013 May 27; 2. doi: 10.3402

[NON-PATENT LITERATURE 2] G. Y. Chen et al. Biotechnol. Prog. 25 (2009), 1669

[NON-PATENT LITERATURE 3] Petra Gerster et al. Journal of Chromatography A, 1290 (2013), 36-45

[NON-PATENT LITERATURE 4] Mariantonia Logozzi et al. PLoS ONE 4 (2009), 5219

SUMMARY OF INVENTION

Technical Problem

As described above, the conventional methods for obtaining the extracellular membrane vesicles or the viruses have difficulty in obtaining the highly pure extracellular membrane vesicles or the viruses in an intact state, simply and conveniently, as well as efficiently. In addition, with the conventional methods for removing the extracellular membrane vesicles or the viruses, it is difficult to efficiently remove the extracellular membrane vesicles or the viruses in the sample. Furthermore, the conventional methods for detecting the extracellular membrane vesicles or the viruses have not achieved sufficient sensitivity.

Therefore, an object of the present invention is to obtain or remove the extracellular membrane vesicles or the viruses present in the sample in high purity, and in an intact state, simply and conveniently, as well as efficiently, and detect the extracellular membrane vesicles or the viruses in high sensitivity.

Solution to Problem

The present invention has been made to solve the problems, and has the following constitution:

1. A carrier (a Tim carrier) on which a protein (a Tim protein) selected from a T-cell immunoglobulin and mucin domain-containing molecule-4 (a Tim-4) protein, a T-cell immunoglobulin and mucin domain-containing molecule-3 (a Tim-3) protein, and a T-cell immunoglobulin and mucin domain-containing molecule-1 (a Tim-1) protein, is bound.

2. A method for obtaining an extracellular membrane vesicle or a virus in a sample, comprising the following steps:
(1) a step for forming a complex of the Tim protein bound to the carrier, and the extracellular membrane vesicle or the virus in the sample, in the presence of a calcium ion (complex formation step),
(2) a step for separating the complex from the sample (complex separation step),
(3) a step for separating the extracellular membrane vesicle or the virus from the complex to obtain the extracellular membrane vesicle or the virus (obtaining step).

3. A method for removing an extracellular membrane vesicle or a virus in a sample, comprising the following steps:
(1) a step for forming the complex of the Tim protein bound to the carrier, and the extracellular membrane vesicle or the virus in the sample in the presence of the calcium ion (complex formation step),
(2) a step for separating the complex and the sample (complex separation step).

4. A method for detecting an extracellular membrane vesicle or a virus in the sample, comprising the following steps:

(1) a step for forming the complex of the Tim protein bound to the carrier, and the extracellular membrane vesicle or the virus in the sample, in the presence of the calcium ion (complex formation step),
(2) a step for detecting the complex (detection step).
5. A kit for capturing an extracellular membrane vesicle or a virus comprising the Tim carrier.
6. A kit for capturing an extracellular membrane vesicle or a virus comprising a reagent containing the Tim protein and a reagent containing the carrier.

In view of the above circumstances, the present inventors have discovered, as a result of intensive studies, that the extracellular membrane vesicles or the viruses having phosphatidylserine on the surface can be obtained in high purity, that the extracellular membrane vesicles or the viruses can be obtained in an intact state, that the extracellular membrane vesicles or the viruses can be efficiently removed, and that they can be detected in high sensitivity, by using at least one kind of a protein selected from the Tim-1 protein, the Tim-3 protein and the Tim-4 protein, and have thus completed the present invention.

Phosphatidylserine, which is a phospholipid, is present (exposed) on the surface of the extracellular membrane vesicles. As a protein having binding capability to phosphatidylserine (hereinafter it may be abbreviated as "the phosphatidylserine-binding protein" or "the PS proteins", in some cases), there has been known, for example, Annexin V, MFG-E8, the Tim-1 (the T-cell immunoglobulin and mucin domain-containing molecule-1, the T-cell immunoglobulin-mucin-domain 1), the Tim-1 (the T-cell immunoglobulin and mucin domain-containing molecule-1, the T-cell immunoglobulin-mucin-domain-1) protein, the Tim-3 (the T-cell immunoglobulin and mucin domain-containing molecule-3, the T-cell immunoglobulin-mucin-domain-3) protein, the Tim-4 (the T-cell immunoglobulin and mucin domain-containing molecule-4, the T-cell immunoglobulin-mucin-domain-4) protein, or the like (The Journal of Biochemistry 265, 4923-4928 (25 Mar. 1990), Nature 417, 182-187 (9 May 2002), Nature 450, 435-439 (15 Nov. 2007).

However, it has been revealed that it is difficult to obtain, remove or detect the extracellular membrane vesicles or the viruses, when the PS proteins other than the Tim-1 protein, the Tim-3 protein and the Tim-4 protein are used, among these PS proteins.

Advantageous Effects of Invention

According to the present invention, the extracellular membrane vesicles or the viruses present in the sample can be obtained or removed in high purity, or in an intact state, simply and conveniently, as well as efficiently, and can be detected in high sensitivity.

BRIEF DESCRIPTION OF DRAWINGS

FIG. 3 is an electropherogram for confirming whether the extracellular membrane vesicles were obtained or not, by Western blotting, in Examples 17 to 18.

FIG. 4-A is an electropherogram for confirming whether the extracellular membrane vesicles were obtained or not, by Western blotting, in Examples 19 to 20, and Comparative Examples 1 to 3, and FIG. 4-B is an electropherogram for confirming whether the extracellular membrane vesicles were obtained or not, by silver staining, in Examples 19 to 20, and Comparative Examples 1 to 3.

DESCRIPTION OF EMBODIMENTS

Figure 1:
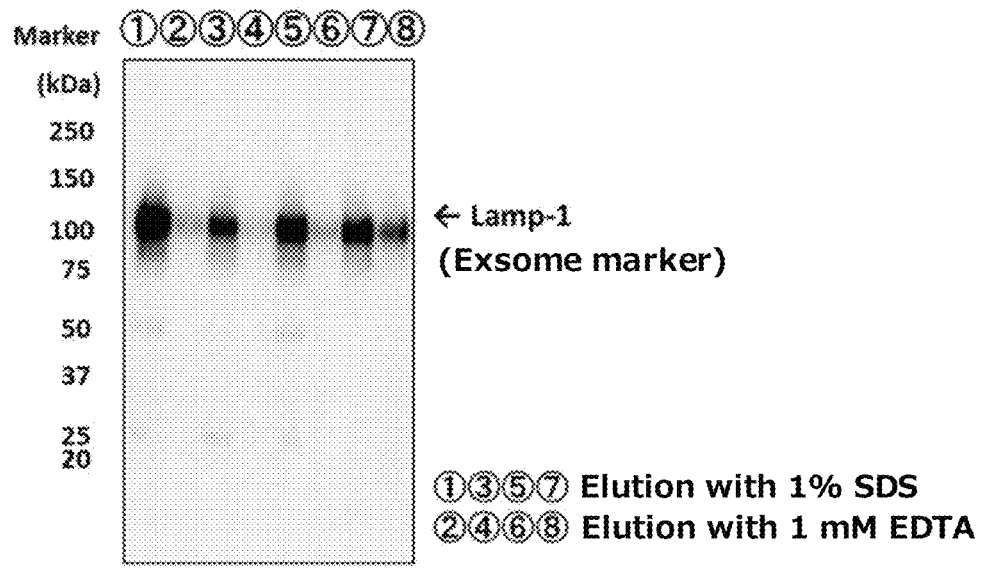
FIG. 1 is an electropherogram for confirming whether the extracellular membrane vesicles were obtained or not, by Western blotting, in Examples 1 to 8.

<1. Extracellular Membrane Vesicle Pertaining to the Present Invention>

The extracellular membrane vesicle pertaining to the present invention is the small-sized membrane vesicle secreted from in vivo cells or cultured cells, composed of a lipid bilayer membrane, and having phosphatidylserine on the membrane surface thereof. Diameter of the vesicle is usually 20 nm to 1000 nm, preferably 50 nm to 500 nm, and more preferably 50 nm to 200 nm.

The extracellular membrane vesicle pertaining to the present invention include those classified variously depending on origin of its generation and size of the small-sized membrane vesicle, and the like, as described in Nature Reviews Immunology 9, 581-593 (August, 2009), "Obesity Study" Vol. 13, No. 2, 2007, topics by Naoto Aoki et al. Specifically, there are included Exosomes, micro-vesicles, Ectosomes, Membrane particles, Exosome-like vesicles, Apoptotic vesicles, Adiposome, and the like.

Exosome is the small-sized membrane vesicle derived from late endosome composed of the lipid bilayer membrane, and having phosphatidylserine on the membrane surface thereof. Diameter of the vesicle is usually 50 nm to 200 nm, preferably 50 nm to 150 nm, and more preferably 50 nm to 100 nm. Exosome is known to contain proteins, such as tetraspanins, CD 63, CD 9, and the like, Alix, TSG 101, Lamp-1, Flotillin, and the like.

The micro-vesicle is the small-sized membrane vesicle derived from a cell membrane (plasma membrane), composed of the lipid bilayer membrane, and having phosphatidylserine on the membrane surface thereof. The micro-vesicle is usually 100 nm to 1000 nm, preferably 100 nm to 800 nm, and more preferably 100 nm to 500 nm. The micro-vesicle is known to contain proteins, such as integrin, selectin, CD40 ligands, and the like.

Ectosome is the small-sized membrane vesicle derived from the cell membrane (plasma membrane), composed of the lipid bilayer membrane, and having phosphatidylserine on the membrane surface thereof. Ectosome is usually 50 nm to 200 nm, preferably 50 nm to 150 nm, and more preferably 50 nm to 100 nm. Ectosome is known to contain CR1, a proteolytic enzyme, but does not contain CD63.

The membrane particle is the small-sized membrane vesicle derived from the cell membrane (plasma membrane), composed of the lipid bilayer membrane, and having phosphatidylserine on the membrane surface thereof. The membrane particle is usually 50 nm to 80 nm. It is known that the membrane particle contains CD133 but does not contain CD63.

The exosome-like vesicle is the small-sized membrane vesicle derived from the early endosome, composed of the lipid bilayer, and having phosphatidylserine on the membrane surface thereof. The exosome-like vesicle is usually 20 nm to 50 nm. The exosome-like vesicle is known to contain TNFRI.

The apoptotic vesicle is the small-sized membrane vesicle derived from the apoptotic cell, composed of the lipid bilayer, and having phosphatidylserine on the membrane surface thereof. The apoptotic vesicle is usually 50 nm to 500 nm, preferably 50 nm to 300 nm, and more preferably 50 nm to 200 nm. The apoptotic vesicle is known to contain histones.

Adiposome is the small-sized membrane vesicle derived from the adipocyte, composed of the lipid bilayer membrane, and having phosphatidylserine on the membrane surface thereof. The adiposome is usually 100 nm to 1000 nm, preferably 100 nm to 800 nm, and more preferably 100 nm to 500 nm. The adiposome is known to contain MFG-E8 (milk fat globule-EGF factor 8).

<2. Virus Pertaining to the Present Invention>

The virus pertaining to the present invention has an envelope composed of the lipid bilayer membrane derived from a cell membrane, a nuclear membrane, a Golgi apparatus, an endoplasmic reticulum, or the like, of a host cell as a capsid (outer shell) of the virus, and has phosphatidylserine on the surface of the envelope (hereinafter referred to as "the enveloped virus"). Diameter of the virus pertaining to the present invention is usually 20 nm to 320 nm. The enveloped virus pertaining to the present invention includes the virus having an envelope, belonging to a family described in the Biochemical Dictionary 2nd edition, Tokyo Kagaku Dojin, 1990, 1503p-1505p. Specifically, there are included Poxviridae, Baculoviridae, Rhabdoviridae, Bunyaviridae, Togaviridae, Herpesviridae, Paramyxoviridae, Orthomyxoviridae, Retroviridae, Arenaviridae, Coronaviridae, and the like.

<3. Tim Protein Pertaining to the Present Invention>

The Tim protein pertaining to the present invention is at least one kind of the Tim protein selected from the T-cell immunoglobulin and mucin domain-containing molecule-1 (the Tim-1) protein pertaining to the present invention (hereinafter it may be abbreviated as "the Tim-1 protein pertaining to the present invention", in some cases), the T-cell immunoglobulin and mucin domain-containing molecule-3 (the Tim-3) protein pertaining to the present invention (hereinafter it may be abbreviated as "the Tim-3 protein pertaining to the present invention", in some cases), and the T-cell immunoglobulin and mucin domain-containing molecule-4 (the Tim-4) protein pertaining to the present invention (hereinafter it may be abbreviated as "the Tim-4 protein pertaining to the present invention", in some cases).

The Tim-4 (the T-cell immunoglobulin and mucin domain-containing molecule-4) protein pertaining to the present invention may be any protein capable of binding to the extracellular membrane vesicles or the viruses pertaining to the present invention, and the Tim-4 protein derived from an animal is preferable. Among these, the Tim-4 protein of human or a mouse is preferable (hereinafter, the Tim-4 protein of human may be abbreviated as "the human-derived Tim-4 protein", and the Tim-4 protein of mouse may be abbreviated as "the mouse-derived Tim-4 protein", in some cases).

More specifically, it may be the one, as long as having at least an amino acid sequence of the binding domain (IgV domain) for phosphatidylserine, and it may be the one having a full-length amino acid sequence of the Tim-4 protein, or a part of the amino acid sequence of the Tim-4 protein.

The amino acid sequence of the binding domain (IgV domain) for phosphatidylserine includes, for example, SEQ ID NO: 1 (N-terminal 22 to 135 amino acid region (RefSeq NP_848874.3) of the mouse-derived Tim-4 protein), SEQ ID NO: 2 (N-terminal 25 to 137 amino acid region (RefSeq NP_612388.2) of the human-derived Tim-4 protein), or the like.

The full-length amino acid sequence of the Tim-4 protein includes SEQ ID NO: 3 (full-length sequence of the mouse-derived Tim-4 protein1 to 343 amino acid region (RefSeq NP_848874.3)), SEQ ID NO: 4 (full length sequence of the human-derived Tim-4 protein 1 to 378 amino acid region (RefSeq NP_612388.2)), or the like.

A part of the Tim-4 protein includes those having the amino acid sequence of the binding domain (IgV domain) for phosphatidylserine and the mucin domain, such as SEQ ID NO: 5 (N-terminal 22 to 273 amino acid region of the mouse-derived Tim-4 protein (RefSeq NP_848874.3)), SEQ ID NO: 6 (N-terminal 22 to 279 amino acid region of the mouse-derived Tim-4 protein (RefSeq NP_848874.3)), SEQ ID NO: 7 (N-terminal 25 to 315 amino acid region of the human-derived Tim-4 protein (RefSeq NP_612388.2)), or the like. These sequences may have a signal sequence, as needed.

The Tim-1 (the T-cell immunoglobulin and mucin domain-containing molecule-1) protein pertaining to the present invention may be any protein, as long as capable of binding to the extracellular membrane vesicles or the viruses pertaining to the present invention, and the Tim-1 protein derived from an animal is preferable. Among these, the Tim-1 protein of human or mouse is preferable (hereinafter, sometimes the Tim-1 protein of human is abbreviated as "the human-derived Tim-1 protein" and the Tim-1 protein of mouse is abbreviated as "the mouse-derived Tim-1 protein").

More specifically, it may be the one, as long as having at least the amino acid sequence of the binding domain (IgV domain) for phosphatidylserine, and it may be the one having a full-length amino acid sequence of the Tim-1 protein, or a part of the Tim-1 protein.

The amino acid sequence of the binding domain (IgV domain) for phosphatidylserine include, for example, SEQ ID NO: 8 (N-terminal 22 to 131 amino acid region (RefSeq NP_001160104.1) of the mouse-derived Tim-1 protein, SEQ ID NO: 9 (N-terminal 21 to 130 amino acid region (RefSeq NP_036338.2), or the like.

The full-length amino acid sequence of the Tim-1 protein includes SEQ ID NO: 10 (full-length sequence 1 to 282 amino acid region of the mouse-derived Tim-1 protein (RefSeq NP_001160104.1)), SEQ ID NO: 11 (full length sequence of the human-derived Tim-1 protein 1 to 364 amino acid region (RefSeq NP_036338.2)), or the like.

A part of the Tim-1 protein includes those having the amino acid sequence of the binding domain (IgV domain) for phosphatidylserine and the mucin domain, such as SEQ ID NO: 12 (N-terminal 22 to 212 amino acid region of the mouse-derived Tim-1 protein (RefSeq NP_001160104.1)), SEQ ID NO: 13 (N-terminal 21 to 295 amino acid region of the human-derived Tim-1 protein (RefSeq NP_612388.2), or the like. These sequences may have the signal sequence, as needed.

The Tim-3 (the T-cell immunoglobulin and mucin domain-containing molecule-3) protein pertaining to the present invention may be any protein, as long as capable of binding to the extracellular membrane vesicles or the viruses pertaining to the present invention, and the Tim-3 protein derived from an animal is preferable. Among these, the Tim-3 protein of human or mouse is preferable (hereinafter, the Tim-3 protein of human is abbreviated as "the human-derived Tim-3 protein", and the Tim-3 protein of mouse is abbreviated as "the mouse-derived Tim-3 protein", in some cases).

More specifically, it may be the one, as long as having at least the amino acid sequence of the binding domain (IgV domain) for phosphatidylserine, and it may be the one having a full-length amino acid sequence of the Tim-3 protein, or a part of the Tim-3 protein.

The amino acid sequence of the binding domain (IgV domain) for phosphatidylserine include, for example, SEQ ID NO: 14 (N-terminal 22 to 134 amino acid region (RefSeq NP_599011.2) of the mouse-derived Tim-3 protein), SEQ ID NO: 15 (N-terminal 22 to 135 amino acid region (RefSeq NP_116171.3) of the human-derived Tim-3 protein), or the like.

The full-length amino acid sequence of the Tim-3 protein includes SEQ ID NO: 16 (full-length sequence 1 to 281 amino acid region of the mouse-derived Tim-3 protein (RefSeq NP_599011.2)), SEQ ID NO: 17 (full length sequence of the human-derived Tim-3 protein 1 to 301 amino acid region (RefSeq NP_116171.3)), or the like.

A part of the Tim-3 protein includes those having the amino acid sequence of the binding domain (IgV domain) for phosphatidylserine and the mucin domain, such as SEQ ID NO: 18 (N-terminal 22 to 189 amino acid region of the mouse-derived Tim-3 protein (RefSeq NP_599011.2)), SEQ ID NO: 19 (N-terminal 22 to 200 amino acid region of the human-derived Tim-3 protein (RefSeq NP_116171.3), or the like. These sequences may have the signal sequence, as needed.

In addition, the Tim protein pertaining to the present invention may be a mutant of the above amino acid sequences, in which one or more amino acids are deleted, substituted, inserted and/or added, as long as it is capable of binding to the extracellular membrane vesicles or the viruses pertaining to the present invention.

The Tim protein pertaining to the present invention may be the one, as long as having properties as described above, and may be the one extracted from cells (for example, immune cells, such as macrophages) or tissues of living organisms having the Tim protein, such as animals including the mouse and the human, or plants, and the like, and the one prepared by genetic recombination technology based on this, or the like, and any of them can be used.

In using the Tim protein pertaining to the present invention prepared by genetic recombination technology, those having one or more affinity tags are preferable, from the viewpoint of simplicity of purification.

The affinity tags may be any tags, as long as being used in preparation of a protein by genetic recombination technology, and include the affinity tags, for example, Fc tag, FLAG tag, His tag, GST tag, MBP tag, HA tag, Myc tag, Strep (II) tag, PA tag, and the like.

The affinity tags are fused to the C-terminal side of the Tim protein pertaining to the present invention.

Therefore, the Tim protein pertaining to the present invention includes not only a protein consisting only of the amino acid sequence of the Tim protein (full length or partial sequence) but also a protein having the amino acid sequence (full length or partial sequence) of the Tim protein and the amino acid sequence of the affinity tag, as described above.

In addition, the affinity tag and the Tim protein may be bound directly to each other, or may be bound via a spacer as described in "Protein Expression using a cell-free protein synthesis reagent kit, Transdirect insect cell, derived from insect cultured cells", Toru Ezure, Takashi Suzuki, Masaaki Ito, Masamitu Shikata (Shimadzu Seisakusho, Analytical Measurement Division), publication date 2008 Jun. 9: Protein Science Foundation Archive, 1, e005 (2008)", or the like. Therefore, the Tim protein pertaining to the present invention also includes a protein having the amino acid sequence (full length or partial sequence) of the Tim protein, and the amino acid sequence of the affinity tag as described above, and the amino acid sequence of the spacer.

<4. Preparation Method for Tim Protein Pertaining to the Present Invention>

The Tim protein pertaining to the present invention can be produced by a general chemical production method, in accordance with the amino acid sequence thereof. The Tim protein pertaining to the present invention can be obtained by a usual chemical production method (chemical synthesis method), for example, a fluorenylmethyloxycarbonyl method (Fmoc method), a t-butyloxycarbonyl method (t-Boc method), or the like. In addition, it can be chemically synthesized also, using a commercially available peptide synthesizer.

Furthermore, the Tim protein pertaining to the present invention can also be obtained by a well-known method using the genetic recombination technique, such that a nucleic acid molecule encoding the Tim protein pertaining to the present invention is incorporated into an expression vector, such as an appropriate plasmid or phage, the host cell is transformed (transduced) using the recombinant expression vector, and the resulting host cell is proliferated to secrete the Tim protein inside of the cell or outside of the cell.

Explanation will be given below on the preparation method for the Tim protein pertaining to the present invention, for the case of preparation by the genetic recombination technology.

<Expression Vector Pertaining to the Present Invention>

The expression vector for expressing the Tim protein pertaining to the present invention (hereinafter, it is referred to as the expression vector pertaining to the present invention) may be any one, as long as it contains the nucleic acid sequence encoding the Tim protein pertaining to the present invention (hereinafter, it may be abbreviated as "Tim coding sequence pertaining to the present invention", in some cases).

Among the Tim coding sequences pertaining to the present invention, the nucleic acid sequence encoding the Tim-4 protein includes, for example, SEQ ID NO: 20 (the nucleotide sequence of cDNA encoding the full-length sequence 1 to 343 amino acid region of the mouse-derived Tim-4 protein (RefSeq No. NM_178759.4), and containing a stop codon (tga) at the terminal 3 nucleotides), SEQ ID NO: 21 (nucleotide sequence of cDNA encoding the full-length sequence 1 to 378 amino acid region of the human-derived Tim-4 protein (RefSeq No. NM_138379.2), and containing the stop codon (taa) at the terminal 3 nucleotides), or the like.

The nucleic acid sequence encoding the Tim-1 protein pertaining to the present invention includes, for example, SEQ ID NO: 22 (the nucleotide sequence of cDNA encoding the full-length sequence 1 to 282 amino acid region of the mouse-derived Tim-1 protein (RefSeq No. NM_001166632.1), containing the stop codon (tga) at the terminal 3 nucleotides), SEQ ID NO: 23 (the nucleotide sequence of cDNA encoding the full-length sequence 1 to 364 amino acid region of the human-derived Tim-1 protein (RefSeq No. NM_012206.3), containing the stop codon (taa) at the terminal 3 nucleotides), or the like.

The nucleic acid sequence encoding the Tim-3 protein pertaining to the present invention includes, for example, SEQ ID NO: 24 (the nucleotide sequence of cDNA encoding the full-length sequence 1 to 281 amino acid region of the mouse-derived Tim-3 protein (RefSeq No. NM_134250.2), containing the stop codon (tga) at the terminal 3 nucleotides), SEQ ID NO: 25 (the nucleotide sequence of cDNA encoding the full-length sequence 1 to 301 the amino acid region of the human derived Tim-3 protein (RefSeq No. NM_032782.4), containing the stop codon (tag) at the terminal 3 nucleotides), or the like.

For the expression vector pertaining to the present invention, the Tim-coding sequence pertaining to the present invention may be gene introduced into a commercially available vector, according to a conventional cloning method. The expression vector pertaining to the present invention includes, for example, an expression vector, such as a commercially available pCAG-Neo vector (produced by Wako Pure Chemical Industries, Ltd.), or the like, into which is incorporated SEQ ID NO: 26 (cDNA encoding the N-terminal 1 to 273 amino acid region of the mouse-derived Tim-4 protein, containing the stop codon (tga) at the terminal 3 nucleotides), SEQ ID NO: 27 (cDNA encoding the N-terminal 1 to 279 amino acid region of the mouse-derived Tim-4 protein, containing the stop codon (tga) at the terminal 3 nucleotides), SEQ ID NO: 28 (cDNA encoding the N-terminal 1 to 315 amino acid region of the human-derived Tim-4 protein, containing the stop codon (tga) at the terminal 3 nucleotides), SEQ ID NO: 29 (cDNA encoding the N terminal 1 to 212 amino acid region of the mouse-derived Tim-1 protein, containing the stop codon (tga) at the terminal 3 nucleotides), SEQ ID NO: 30 (cDNA encoding the N-terminal 1 to 295 amino acid region of the human-derived Tim-1 protein, containing the stop codon (tga) at the terminal 3 nucleotides), SEQ ID NO: 31 (cDNA encoding N-terminal 1 to 189 amino acid region of the mouse-derived Tim-3 protein, containing the stop codon (tga) at the terminal 3 nucleotides), or SEQ ID NO: 32 (cDNA encoding N-terminal 1 to 200 amino acid region of the human-derived Tim-3 protein, containing the stop codon (tga) at the terminal 3 nucleotides), in accordance with the conventional cloning technique. As the vector into which the Tim coding sequence is gene introduced, any vector may be used, as long as it has function of expressing and producing the Tim protein pertaining to the present invention in the host cell, and it is convenient to use commercially available vectors. The commercially available vectors used for this purpose include pCAG-Neo vector, pcDNA vector, and the like, when the host is an animal cell.

<Host>

As the host, anyone can be used, as long as it is capable of expressing the Tim protein pertaining to the present invention, and includes *Escherichia coli*, insect cells, mammalian cells, plant cells, yeast cells, or the like, and the mammalian cells are preferable. The mammalian cells include, for example, HEK 293T cell, COS-7 cell, CHO-K1 cell, CHO-S cell, and the like.

<Introduction of Gene into Host>

The expression vector pertaining to the present invention is gene introduced into the host, according to a usual method of the technique of gene introducing the vector into the host, described in "Protein expression protocol that can be selected depending on each purpose, Chapter 3, Protein expression protocol, ISBN 978-4-7581-0175-2, Yodosha Co., Ltd.", or the like.

<Culture of Host>

The host after carrying out gene introduction is cultured, according to a usual method for culturing the host. Culture condition varies depending on the host into which the gene has been introduced, but may be in accordance with a usual method for each host. For example, when it is an animal cell, the cell may be cultured for 1 day to 10 days, and preferably 3 days to 4 days, under conditions of usually 5 to 10% $CO_2$, preferably 5 to 8% $CO_2$, usually at 36° C. to 38° C., preferably at 36.5° C. to 37.5° C. It should be noted that, the Tim protein pertaining to the present invention is expressed and secreted in the culture supernatant, since it does not contain a transmembrane domain and an intracellular domain.

<Purification of Tim Protein Pertaining to the Present Invention>

A culture supernatant filtrate may be obtained by subsequently subjecting a culture solution of the resulting gene-introduced host to centrifugal separation treatment (usually at 200 to 400×G for 3 minutes to 10 minutes, and preferably at 300×G for 3 minutes to 6 minutes) to recover a culture supernatant, and subjecting, as needed, the recovered culture supernatant to (i) centrifugal separation treatment usually at 1000 to 2000×G for 20 minutes to 60 minutes, and preferably at 1200×G for 20 minutes to 40 minutes, and/or to (ii) filtration treatment to separate impurities.

Further, a concentrated culture supernatant filtrate may be obtained by concentration of the resulting culture supernatant filtrate usually 5 times to 20 times, and preferably 8 times to 12 times, according to a usual method, such as ultrafiltration, or the like, as needed.

Next, when the Tim protein pertaining to the present invention has the affinity tag, the Tim protein (a fusion protein of the Tim protein and the affinity tag) pertaining to the present invention may be purified from the resulting culture supernatant, from the resulting culture supernatant filtrate, or from the resulting concentrated solution of the culture supernatant filtrate, according to a usual method for protein purification utilizing the affinity tag (for example, a method for using a carrier on which a substance having affinity to the affinity tag is immobilized) for each tag, described in "Protein expression protocol that can be selected depending on each purpose, Chapter 3 Protein expression protocol, Section 6, Purification of protein purification by a tag, ISBN 978-4-7581-0175-2, Yodosha Co., Ltd.", or the like.

When the Tim protein pertaining to the present invention does not have the affinity tag, the Tim protein pertaining to the present invention may be purified by various kinds of chromatography, from the resulting culture supernatant, from the resulting culture supernatant filtrate, or from the resulting concentrated solution of the culture supernatant filtrate, according to a usual method of protein purification, described in "Protein expression protocol that can be selected depending on each purpose, Chapter 3, Protein expression protocol, Section 6, Purification of protein Purification by chromatography, ISBN 978-4-7581-0175-2, Yodosha Co., Ltd.", or the like.

Purification may be carried out by appropriately combining the above purification methods.

<Specific Preparation Method for Tim Protein Pertaining to the Present Invention>

As a specific preparation method for the Tim protein pertaining to the present invention, for example, when a Fc tag is used as the affinity tag, the following method is included. First, according to a usual method, the Tim coding sequence pertaining to the present invention is incorporated into a pEF-Fc vector or a commercially available vector to construct the expression vector pertaining to the present invention. Subsequently, the expression vector pertaining to the present invention is gene introduced into the host cell, according to a usual method to culture for 1 day to 10 days, and preferably 3 days to 4 days, under conditions of usually 5 to 10% $CO_2$, preferably 5 to 8% $CO_2$, at 36° C. to 38° C., preferably 36.5° C. to 37.5° C. The culture supernatant filtrate is obtained by subsequently subjecting the resulting culture solution of the gene-introduced host to a centrifugal separation treatment (usually at 200 to 400×G for 3 minutes to 10 minutes, and preferably at 300×G for 3 minutes to 6 minutes) to recover the culture supernatant, and by subjecting, as needed, the recovered culture supernatant to (i) centrifugal separation treatment usually at 1000 to 2000×G for 20 minutes to 60 minutes, and preferably at 1200×G for 20 minutes to 40 minutes, and/or to (ii) filtration treatment to separate impurities. Further, the concentrated solution of the culture supernatant filtrate is obtained by concentration, as needed, of the resulting culture supernatant filtrate usually 5 times to 20 times, and preferably 8 times to 12 times, according to a usual method, such as ultrafiltration, or the like. After that, when the Tim protein pertaining to the present invention has the affinity tag, the Tim protein pertaining to the present invention can be obtained by purifying the Tim protein pertaining to the present invention from the resulting culture supernatant, the resulting culture supernatant filtrate, or the resulting concentrated solution of the culture supernatant filtrate, in accordance with a usual method for purification utilizing affinity of respective affinity tags.

<5. Tim Carrier of the Present Invention>

A carrier on which the Tim protein of the present invention is bound (hereafter it may be abbreviated as "the Tim carrier of the present invention", in some cases) is the one where the Tim protein pertaining to the present invention is bound on the carrier pertaining to the present invention.

Specifically, the Tim carrier of the present invention includes a carrier on which the Tim-1 protein pertaining to the present invention is bound (hereafter it may be abbreviated as "the Tim-1 carrier of the present invention", in some cases), a carrier on which the Tim-3 protein pertaining to the present invention is bound (hereafter it may be abbreviated as "the Tim-3 carrier of the present invention", in some cases), a carrier on which the Tim-4 protein pertaining to the present invention is bound (hereafter it may be abbreviated as "the Tim-4 carrier of the present invention", in some cases), or the like. In addition, a carrier on which two or more kinds of proteins selected from the Tim-1 protein pertaining to the present invention, Tim-3 protein pertaining to the present invention, and Tim-4 protein pertaining to the present invention are bound is also encompassed in the Tim carrier of the present invention.

As the Tim carrier of the present invention, the Tim-4 carrier of the present invention is particularly preferable.

<Carrier Pertaining to the Present Invention>

As the carrier pertaining to the present invention, any carrier can be used as long as it is an insoluble carrier used in usual immunological assay, and includes an organic substance, such as, polystyrene, polyacrylic acid, polymethacrylic acid, polymethyl methacrylate, polyacryl amide, polyglycidyl methacrylate, polypropylene, polyolefin, polyimide, polyurethane, polyester, polyvinyl chloride, polyethylene, polychlorocarbonate, a silicone resin, silicone rubber, agarose, dextran, an ethylene-maleic anhydride copolymer, or the like; an inorganic substance, such as glass, silicon oxide, diatomaceous earth, porous glass, obscured glass, alumina, silica gel, a metal oxide, or the like; a magnetic substance, such as iron, cobalt, nickel, magnetite, chromite, or the like; and those prepared using alloys of these magnetic substances as raw materials. In addition, these carriers may be used in a wide variety of forms, such as a microplate, a tube, a disk-like piece, particles (the beads), and the like.

It should be noted that it is preferable to use as particles (the beads), when used in the obtaining method of the present invention, and the removing method of the present invention, to be described later, and particle size is not especially limited, however, there is included the one having usually 10 nm to 100 µm, and preferably 100 nm to 10 µm, according to objects and the applications.

In addition, the particles (the beads) or the microplate are preferable when used in the detection method of the present invention, to be described later, and particle size is not especially limited and includes the one having usually 10 nm to 100 µm, and preferably 100 nm to 10 µm, according to the objects and the applications. In addition, number and size of a well of the microplate are not especially limited, and include the one having usually 12 holes to 1536 holes, and preferably 96 holes to 384 holes, according to the objects and the applications.

<Binding Method for Tim Protein Pertaining to the Present Invention and Carrier Pertaining to the Present Invention>

The binding method for the Tim protein pertaining to the present invention and the carrier pertaining to the present invention may be in accordance with a method known per se for binding a protein to a carrier, and the method includes, for example, a binding method by affinity binding; a binding method by chemical binding (for example, a method described in JP No. 3269554, WO 2012/039395); a binding method by physical adsorption (for example, a method described in JP-B-05-41946), or the like, and the binding method by affinity binding and the binding method by physical adsorption are preferable.

It should be noted that the binding method by affinity binding is preferable, when used in the obtaining method and the removing method of the present invention to be described later. In addition, the binding method by the affinity binding, or physical adsorption is preferable, when used in the detection method of the present invention, to be described later.

<Binding Form of Tim Protein Pertaining to the Present Invention and Carrier Pertaining to the Present Invention>

Binding form of the Tim protein pertaining to the present invention and the carrier pertaining to the present invention is not limited, as long as the carrier pertaining to the present invention and the Tim protein pertaining to the present invention are bound, however, the one in which the carrier pertaining to the present invention binds to an SH group of the Tim protein pertaining to the present invention is preferable. In addition, the Tim protein pertaining to the present invention and the carrier pertaining to the present invention may be bound either by direct binding, or indirect binding via a chemical linker, an affinity substance [for example, a substance having affinity to an affinity-tag (to be described later), an antibody against the Tim protein pertaining to the present invention, biotins (to be described later), avidins (to be described later), an antibody, or the like], or the like.

<Method for Binding by Affinity Binding>

The method for binding by affinity binding may be any one, as long as it is a method for binding by utilization of affinity binding (affinity) between substances, and includes, for example, the following (a) to (c):

(a) Method for Binding by Affinity Binding of Biotins and Avidins.

The Tim protein pertaining to the present invention and the carrier pertaining to the present invention can be bound, via the affinity substances, by using two or more kinds of substances (affinity substances) having affinity each other, comprising a combination of, for example, biotins (biotin, iminobiotin, desthiobiotin, biocytin, biotin sulfoxide, and the like) and avidins (avidin, tamavidin, tamavidin 2, and the like), and the like.

It should be noted that either one of the affinity substances may be bound to the Tim protein pertaining to the present invention, and the remaining one may be bound to the carrier pertaining to the present invention, however, it is general, for example, that the avidins are bound to the carrier pertaining to the present invention, and biotins are bound to the Tim protein pertaining to the present invention, when biotins and avidins are used.

(b) Method for Binding by Affinity Binding of the Affinity Tag and a Substance Having Affinity to the Affinity Tag.

The Tim protein pertaining to the present invention and the carrier pertaining to the present invention can be bound, via the affinity substance by using the substance having affinity to the Tim protein pertaining to the present invention (the affinity substance), for example, the substance having affinity to the affinity tag (Protein A, Protein G, or the like).

It should be noted that the affinity substance is generally bound to the carrier pertaining to the present invention.

(c) Method for Binding by Affinity Binding of the Antibody Against the Tim Protein of the Present Invention and the Tim Protein of the Present Invention.

The Tim protein pertaining to the present invention and the carrier pertaining to the present invention can be bound, via the affinity substance, by using the substance which has affinity to the Tim protein pertaining to the present invention (the affinity substance), for example, an antibody against the Tim protein pertaining to the present invention (an antibody against the affinity tag, such as an anti-FLAG tag antibody, an anti-His tag antibody, an anti-HA tag antibody, an anti-Myc tag antibody, an anti-MBP tag antibody, an anti-GST tag antibody, an anti-Strep (II) tag antibody, or the like; and an anti-Tim 4 antibody (clone RMT 4-54) (produced by LifeSpan Biosciences Inc.), or the like), or the like.

It should be noted that the affinity substance is generally bound to the carrier pertaining to the present invention.

It should be noted that also as for a method for binding the Tim protein pertaining to the present invention and/or the carrier pertaining to the present invention, and the affinity substance, in the above method, a method for binding by physical adsorption, or a method for binding by chemical bonding, known per se, can be used, and the binding may be carried out directly or indirectly via a linker, or the like.

<Amount of Tim Protein Pertaining to the Present Invention to be Bound on Carrier Pertaining to the Present Invention>

Amount of the Tim protein pertaining to the present invention to be bound on the carrier pertaining to the present invention is, for example, when the carrier pertaining to the present invention is the beads, usually 0.1 µg to 50 µg, preferably 0.5 µg to 30 µg, and more preferably 1.0 µg to 20 µg, relative to 1 mg of the carrier.

In addition, when the carrier pertaining to the present invention is the microplate, it is usually 0.1 µg to 10 µg, preferably 0.2 µg to 5 µg, and more preferably 0.5 µg to 2 µg, relative to 1 well.

<Specific Preparation Methods for Tim Carrier of the Present Invention>

Explanation will be given below on specific preparation methods for the Tim carrier of the present invention, taking the cases of preparation of the Tim carrier of the present invention, by the methods (a) to (c), as examples.

<(a) Method for Binding by Affinity Binding of Biotins and Avidins>

First of all, in the method (a), the Tim protein pertaining to the present invention is prepared, according to the preparation method for the Tim protein pertaining to the present invention. Next, the Tim protein pertaining to the present invention-biotins complex is formed by binding the Tim protein pertaining to the present invention and biotins (hereinafter, it may be abbreviated as "biotin labelling" or "biotinylation", in some cases). On the other hand, the carrier pertaining to the present invention-avidins complex is formed, by binding avidins to the carrier pertaining to the present invention (hereinafter, it may be abbreviated as "the carrier pertaining to the present invention bound with avidins", in some cases). The Tim carrier of the present invention is obtained, by bringing into contacted the resulting Tim protein pertaining to the present invention-biotins complex, and the carrier pertaining to the present invention-avidins complex, to bind biotins in the Tim protein pertaining to the present invention-biotins complex, and avidins in the carrier pertaining to the present invention-avidins complex. —Binding of Tim Protein Pertaining to the Present Invention and Biotins (Biotin Labelling)—

In the method (a), binding of the Tim protein pertaining to the present invention and biotins may be carried out by using a commercially available biotin labelling-kit, or according to a usual method of biotin labelling of a protein, by appropriately adjusting reagents required. A method for using the commercially available biotin labelling-kit of the protein (Biotinylation kit) may be in accordance with a method described in a protocol attached to Biotin Labeling Kit-SH (manufactured by Dojindo Molecular Technologies, Inc.), or Biotin Labeling Kit-NH$_2$ (manufactured by Dojindo Molecular Technologies, Inc.).

Amount of biotins to be bound with 1 μg of the Tim protein pertaining to the present invention is usually 10 ng to 1.0 μg, preferably 20 ng to 200 ng, and more preferably 30 ng to 150 ng.

A site for binding biotins to the Tim protein pertaining to the present invention is preferably an SH group of the Tim protein pertaining to the present invention.

—Carrier Pertaining to the Present Invention-Avidins Complex (Carrier of the Present Invention Bound with Avidins)—

As the carrier pertaining to the present invention-avidins complex (the carrier pertaining to the present invention bound with avidins), in the method (a), commercially available one may be used, or it may be prepared in accordance with a usual method by appropriately adjusting reagents required. The carrier pertaining to the present invention-avidins complex includes, for example, the beads or the microplate bound with avidin; the beads or the microplate bound with tamavidin; the beads or the microplate bound with tamavidin 2; the beads or the microplate bound with streptavidin, or the like; and the commercially available one includes Dynabeads M-270 Streptavidin C1 (manufactured by Thermo Fisher Scientific, Inc.), FGbeads Streptavidin (manufactured by Tamagawa Seiki Co., Ltd.), Avidin plate (manufactured by Sumitom Bakelite Co., Ltd.), or the like.

Amount of avidins to be brought into contacted with 1 mg of the carrier pertaining to the present invention is usually 5.0 to 150 μg, preferably 10 to 100 μg, and more preferably 20 to 50 μg, when the carrier pertaining to the present invention is, for example, the beads, in binding of the carrier pertaining to the present invention and avidins. Amount of avidins to be brought into contacted to 1 well is usually 0.1 μg to 10 μg, preferably 0.2 μg to 5 μg, and more preferably 0.5 μg to 2 μg, when the carrier pertaining to the present invention is, for example, the microplate. —Binding of Carrier Pertaining to the Present Invention-Avidins Complex, and Tim Protein Pertaining to the Present Invention-Biotins Complex—

To obtain the Tim carrier of the present invention (by binding the carrier pertaining to the present invention-avidins complex, and the Tim protein pertaining to the present invention-biotins complex), in the method (a), usually 0.1 mg to 10 mg, preferably 0.3 mg to 5.0 mg, and more preferably 0.5 to 3.0 mg of the carrier pertaining to the present invention-avidins complex, and usually 1.0 to 50 μg, preferably 1.0 to 30 μg, and more preferably 1.0 to 20 μg of the Tim protein pertaining to the present invention-biotins complex, relative to 1 mg of the carrier pertaining to the present invention-avidins complex, may be brought into contacted, when the carrier pertaining to the present invention is, for example, the beads; in addition, the carrier pertaining to the present invention-avidins complex, relative to 1 well, and usually 1.0 to 10 μg, preferably 1.0 to 5.0 μg, and more preferably 1.0 to 2.0 μg of the Tim protein pertaining to the present invention-biotins complex may be brought into contacted, when the carrier pertaining to the present invention is the microplate, and then subjected to a reaction at usually 4.0° C. to 37° C., preferably 11° C. to 30° C., and more preferably 20° C. to 25° C., for usually 0.5 hour to 24 hours, preferably 0.5 hour to 8.0 hours, and more preferably 0.5 hour to 2.0 hours to bind avidins and biotins. In this way, the carrier pertaining to the present invention-avidins complex, and the Tim protein pertaining to the present invention-biotins complex are bound to obtain the Tim carrier of the present invention.

It should be noted that contact of the carrier pertaining to the present invention-avidins complex, and the Tim protein pertaining to the present invention-avidins complex is generally carried out by bringing into contacted a solution containing the Tim protein pertaining to the present invention-biotins complex, and the carrier pertaining to the present invention-avidins complex.

The solution for containing the Tim protein pertaining to the present invention-biotins complex may be any solution, as long as it is capable of dissolving the Tim protein pertaining to the present invention-biotins complex in a stable state, and includes for example, purified water, a buffer solution which has buffer action, for example, at pH 7.0 to 8.0, and preferably 7.2 to 7.6 (for example, PBS, TBS, HBS or the like). In addition, buffer agent concentration in these buffer solutions is appropriately selected from a range of usually 5.0 to 50 mM, and preferably 10 to 30 mM, and NaCl concentration is appropriately selected from a range of usually 100 to 200 mM, and preferably 140 to 160 mM. In addition, for example, saccharides, salts, such as NaCl, and the like, a surfactant, a preservative, a protein, or the like, may be contained in this solution, as long as in such an amount that does not inhibit binding of the carrier pertaining to the present invention-avidins complex, and the Tim protein pertaining to the present invention-biotins complex, after contacting the carrier pertaining to the present invention-avidins complex, and the solution containing the Tim protein pertaining to the present invention-biotins complex. The surfactant includes, for example, Tween 20, or the like, and surfactant concentration in the solution for containing the Tim protein pertaining to the present invention-biotins complex is usually 0.00001 to 0.2%, and preferably 0.0005 to 0.1%. It should be noted that the solution dissolving the Tim protein pertaining to the present invention-biotins complex in these solvents may be abbreviated as "the Tim protein pertaining to the present invention-biotins complex-containing solution", in some cases.

—Specific Preparation Method for Tim Carrier of the Present Invention by Method (a)—

A specific preparation method for the Tim carrier of the present invention by the method (a) may be carried out, for example, by the following method.

First of all, the Tim protein pertaining to the present invention is prepared, according to the preparation method for the Tim protein pertaining to the present invention. Next, the Tim protein pertaining to the present invention-biotins complex is formed by binding biotins to the Tim protein pertaining to the present invention, according to an attached protocol in the Biotin Labeling Kit-SH (manufactured by Dojindo Molecular Technologies, Inc.), the Biotin Labeling Kit-NH$_2$ (manufactured by Dojindo Molecular Technologies, Inc.), or a usual method in biotin labelling of the protein.

After that, when the carrier pertaining to the present invention is the beads, the Tim carrier of the present invention is obtained, by bringing into contacted usually 0.1 mg to 10 mg, preferably 0.3 mg to 5.0 mg, and more preferably 0.5 to 3.0 mg of the carrier pertaining to the present invention-avidins complex, and usually 50 µL to 1500 µL, preferably 100 µL to 1000 µL, and more preferably 200 µL to 500 µL of a solution containing usually 1.0 to 50 µg, preferably 1.0 to 30 µg, and more preferably 1.0 to 20 µg of the Tim protein pertaining to the present invention-biotins complex (a solution containing the Tim protein pertaining to the present invention-biotins complex, for example, in purified water, or in buffer solution, or the like, which has buffer action at pH 7.0 to 8.0, and preferably 7.2 to 7.6), relative to 1 mg of the carrier pertaining to the present invention-avidins complex, and then subjecting them to a reaction at usually 4.0° C. to 37° C., preferably 11° C. to 30° C., and more preferably 20° C. to 25° C., for usually 0.5 hour to 24 hours, preferably 0.5 hour to 8.0 hours, and more preferably 0.5 hour to 2.0 hours, to bind avidins in the carrier pertaining to the present invention-avidins complex, and biotins in the Tim protein pertaining to the present invention-biotins complex.

When the carrier pertaining to the present invention is the microplate, the Tim carrier of the present invention is obtained by bringing into contacted the carrier pertaining to the present invention-avidins complex, relative to 1 well, and usually 50 µL to 300 µL, preferably 50 µL to 200 µL, more preferably 100 µL to 200 µL of a solution containing usually 1.0 to 10 µg, preferably 1.0 to 5.0 µg, and more preferably 1.0 to 2.0 µg of the Tim protein pertaining to the present invention-biotins complex (a solution containing the Tim protein pertaining to the present invention-biotins complex, for example, in purified water, or in a buffer solution, or the like, which has buffer action at pH 7.0 to 8.0, and preferably 7.2 to 7.6), and then subjecting them to a reaction at usually 4.0° C. to 37° C., preferably 11° C. to 30° C., and more preferably 20° C. to 25° C., usually for 0.5 hour to 24 hours, preferably 0.5 hour to 8.0 hours, and more preferably 0.5 hour to 2.0 hours, to bind avidins in the carrier pertaining to the present invention-avidins complex, and biotins in the Tim protein pertaining to the present invention-biotins complex.

<(b) Method for Binding by Affinity Binding of Affinity-Tag, and Substance Having Affinity to Affinity-Tag>

In the method of (b), first of all, the Tim protein pertaining to the present invention having the affinity-tag is prepared, according to the preparation method for the Tim protein pertaining to the present invention. On the other hand, the carrier pertaining to the present invention-the affinity substance complex (hereinafter, it may be abbreviated as "the carrier pertaining to the present invention bound with the affinity substance", in some cases) is formed, by binding the substance having affinity to the affinity-tag (the affinity substance) to the carrier pertaining to the present invention. The Tim carrier of the present invention is obtained by bringing into contacted the resulting carrier pertaining to the present invention-affinity substance complex, and the Tim protein pertaining to the present invention having the affinity-tag to bind the affinity substance in the carrier pertaining to the present invention-the affinity substance complex, and the affinity-tag in the Tim protein pertaining to the present invention having the affinity-tag, and to bind the carrier pertaining to the present invention-affinity substance complex, and the Tim protein pertaining to the present invention having the affinity-tag.

—Carrier Pertaining to the Present Invention-Affinity Substance Complex—

As the carrier pertaining to the present invention-the affinity substance complex in the method (b), the commercially available one may be used, or it may be prepared, according to a usual method by appropriately adjusting reagents required. The carrier pertaining to the present invention-the affinity substance complex includes, for example, the beads or the microplate bound with Protein G, the beads or the microplate bound with Protein A, or the like, and the commercially available one includes, Dynabeads Protein G (manufactured by Thermo Fisher Scientific Co.), Dynabeads Protein A (manufactured by Thermo Fisher Scientific Co.), FG beads Protein G (manufactured by Tamagawaseiki Co. Ltd.), FG beads Protein A (manufactured by Tamagawaseiki Co. Ltd.), or the like.

Amount of the affinity substance to be brought into contacted with 1 mg of the carrier pertaining to the present invention, in binding of the carrier pertaining to the present invention and the affinity substance, is usually 5.0 to 50 µg, preferably 10 to 50 µg, and more preferably 20 to 50 µg, when the carrier pertaining to the present invention is the beads. Amount of the affinity substance to be brought into contacted with 1 well is usually 0.1 µg to 10 µg, preferably 0.2 µg to 5 µg, and more preferably 0.5 µg to 2 µg, when the carrier pertaining to the present invention is the microplate.

—Binding of Carrier Pertaining to the Present Invention-Affinity Substance Complex, and Tim Protein Pertaining to the Present Invention Having Affinity-Tag—

In the method (b), for example, the following method may be carried out to obtain the Tim carrier of the present invention (by binding the carrier pertaining to the present invention-affinity substance complex, and the Tim protein pertaining to the present invention having the affinity-tag). The Tim carrier of the present invention is obtained by bringing into contacted usually 0.1 mg to 10 mg, preferably 0.3 mg to 5.0 mg, and more preferably 0.5 to 3.0 mg of the carrier pertaining to the present invention-affinity substance complex, and usually 1.0 to 50 µg, preferably 1.0 to 30 µg, and more preferably 1.0 to 20 µg of the Tim protein pertaining to the present invention having the affinity-tag, relative to 1 mg of the carrier pertaining to the present invention-affinity substance complex, when the carrier pertaining to the present invention is the beads; and by bringing into contacted the carrier pertaining to the present invention-affinity substance complex, relative to 1 well, and usually 1.0 to 10 µg, preferably, 1.0 to 5.0 µg, and more preferably 1.0 to 2.0 µg of the Tim protein pertaining to the present invention having the affinity-tag, when the carrier pertaining to the present invention is the microplate, and by subjecting them to a reaction at usually 4.0° C. to 37° C., preferably 11° C. to 30° C., more preferably 20° C. to 25° C., for usually 0.5 hour to 24 hours, preferably 0.5 hour to 8.0 hours, more preferably 0.5 hour to 2.0 hours, to bind the carrier pertaining to the present invention-affinity substance complex, and the Tim protein pertaining to the present invention having the affinity-tag.

It should be noted that contact of the carrier pertaining to the present invention-the affinity substance complex, and the Tim protein pertaining to the present invention having the affinity-tag, in the method (b), is generally carried out by bringing into contacted the carrier pertaining to the present invention-the affinity substance complex, and a solution containing the Tim protein pertaining to the present invention having the affinity-tag.

The solution for containing the Tim protein pertaining to the present invention having the affinity tag may be any solution, as long as capable of dissolving the Tim protein pertaining to the present invention having the affinity-tag, in a stable state, and includes for example, purified water, or a buffer solution which has buffer action, for example, at pH 7.0 to 8.0, and preferably 7.2 to 7.6 (for example, PBS, TBS, HBS or the like). In addition, buffer agent concentration in these buffer solutions is appropriately selected from a range of usually 5.0 to 50 mM, and preferably 10 to 30 mM, and NaCl concentration is appropriately selected from a range of usually 100 to 200 mM, and preferably 140 to 160 mM.

In addition, for example, saccharides, salts, such as NaCl, and the like, a surfactant, a preservative, a protein, or the like, may be contained in this solution, as long as in such an amount that does not inhibit binding of the Tim protein pertaining to the present invention having the affinity-tag, and the carrier pertaining to the present invention-the affinity-substance complex, after contacting the solution containing the Tim protein pertaining to the present invention having the affinity-tag, and the carrier pertaining to the present invention-the affinity substance complex. The surfactant includes, for example, Tween 20, or the like, and surfactant concentration in the solution for containing the Tim protein pertaining to the present invention having the affinity-tag, is usually 0.00001 to 0.2%, and preferably 0.0005 to 0.1%. It should be noted that the solution dissolving the Tim protein pertaining to the present invention having the affinity-tag, in these solutions, may be abbreviated as "the Tim protein pertaining to the present invention having the affinity-tag-containing solution", in some cases.

—Specific Preparation Method for Tim Carrier of the Present Invention by Method (b)—

A specific preparation method for the Tim carrier of the present invention in the method (b) may be carried out, for example, by the following method.

First of all, the Tim protein pertaining to the present invention having the affinity-tag is prepared, according to the preparation method for the Tim protein pertaining to the present invention.

Next, when the carrier pertaining to the present invention is the beads, the Tim carrier of the present invention is obtained by bringing into contacted usually 0.1 mg to 10 mg, preferably 0.3 mg to 5.0 mg, and more preferably 0.5 to 3.0 mg of the carrier pertaining to the present invention-the affinity substance complex, and usually 50 μL to 1500 μL, preferably 100 μL to 1000 μL, and more preferably 200 μL to 500 μL of the solution containing usually 1.0 to 50 μg, preferably 1.0 to 30 μg, and more preferably 1.0 to 20 μg of the Tim protein pertaining to the present invention having the affinity-tag (the solution containing the Tim protein pertaining to the present invention having the affinity-tag, for example, in purified water, or in the buffer solution at pH 7.0 to 8.0, or the like), relative to 1 mg of the carrier pertaining to the present invention-the affinity substance complex, and are subjected them to a reaction at usually 4.0° C. to 37° C., preferably 11° C. to 30° C., and more preferably 20° C. to 25° C., for usually 0.5 hour to 24 hours, preferably 0.5 hour to 8.0 hours, and more preferably 0.5 hour to 2.0 hours, to bind the affinity substance in the carrier pertaining to the present invention-the affinity substance complex, and the affinity-tag in the Tim protein pertaining to the present invention having the affinity-tag.

When the carrier pertaining to the present invention is the microplate, the Tim carrier of the present invention is obtained by bringing into contacted the carrier pertaining to the present invention-the affinity substance complex, relative to 1 well, and usually 50 μL to 300 μL, preferably 50 μL to 200 μL, and more preferably 100 μL to 200 μL of the solution containing 1.0 to 10 μg, preferably 1.0 to 5.0 μg, and more preferably 1.0 to 2.0 μg of the Tim protein pertaining to the present invention having the affinity-tag pertaining to the present invention (the solution containing the Tim protein pertaining to the present invention-biotins complex, for example, in purified water, or the buffer solution, or the like, which has buffer action at pH 7.0 to 8.0, and preferably 7.2 to 7.6), and are subjected them to a reaction at usually 4.0° C. to 37° C., preferably 11° C. to 30° C., and more preferably 20° C. to 25° C., for usually 0.5 hour to 24 hours, preferably 0.5 hour to 8.0 hours, and more preferably 0.5 hour to 2.0 hours, to bind the affinity substance in the carrier pertaining to the present invention-the affinity substance complex, and the affinity-tag in the Tim protein pertaining to the present invention having the affinity-tag.

<(C) Method for Binding by Affinity Binding of Antibody Against Tim Protein of the Present Invention and Tim Protein of the Present Invention>

First of all, the Tim protein pertaining to the present invention is prepared, according to the preparation method for the Tim protein pertaining to the present invention. On the other hand, an antibody against the Tim protein pertaining to the present invention (hereinafter it may be abbreviated as "the anti-Tim antibody", in some cases) is bound to the carrier pertaining to the present invention to form a carrier pertaining to the present invention-anti-Tim antibody complex. The Tim carrier of the present invention is obtained by bringing into contacted the resulting carrier pertaining to the present invention-anti-Tim antibody complex, and the Tim protein pertaining to the present invention to bind the antibody against the Tim protein in the carrier pertaining to the present invention-anti-Tim antibody complex, and the Tim protein pertaining to the present invention.

It should be noted that, in the above description, when the Tim protein having the affinity tag (a protein having the amino acid sequence of the Tim protein and the amino acid sequence of the affinity tag) is used as the Tim protein pertaining to the present invention, as the anti-Tim antibody, either an antibody recognizing the Tim protein (an antibody recognizing a protein portion, based on the amino acid sequence of the Tim protein), or an antibody recognizing the affinity tag (an antibody recognizing a protein portion, based on the amino acid sequence of the affinity tag) may be used. In addition, when the Tim protein not having the affinity tag (a protein consisting only of the amino acid sequence of the Tim protein) is used as the Tim protein pertaining to the present invention, as the anti-Tim antibody, an antibody that recognizes the Tim protein (an antibody that recognizes a protein portion, based on the amino acid sequence of the Tim protein) may be used.

—Carrier Pertaining to the Present Invention-Anti-Tim Antibody Complex (the Carrier Pertaining to the Present Invention to which Antibody is Bound)—

In the method (c), as the carrier pertaining to the present invention-anti-Tim antibody complex, a commercially available one may be used, or it may be prepared, according to a usual method by arranging necessary reagents appropriately. The carrier pertaining to the present invention-anti-Tim antibody complex includes, for example, the beads or the microplates to which an anti-Fc tag antibody is bound, the beads or the microplates to which an anti-FLAG tag antibody is bound, the beads or the microplates to which an anti-His tag antibody is bound, the beads or the microplates to which an anti-GST tag is bound, the beads or the microplates to which an anti-MBP tag is bound, the beads or the microplates to which an anti-HA tag is bound, the beads or the microplates to which an anti-Myc tag is bound, the beads or the microplates to which an anti-Strep (II) tag is bound, the beads or the microplates to which an antibody against an anti-Tim protein is bound, or the like, and as a commercially available one, the anti-DYKDDDDK tag antibody magnetic beads (produced by Wako Pure Chemical Industries, Ltd.), or the like, is included.

The origin of the anti-Tim antibody is not especially limited. In addition, either polyclonal antibodies or monoclonal antibodies may be used, and the monoclonal antibodies are preferable. In addition, as the anti-Tim antibody, a commercially available one may be used, or it may be prepared according to a usual method by arranging necessary reagents appropriately. Specific examples of the anti-Tim antibody are as described above.

Amount of the antibody, relative to the Tim protein pertaining to the present invention, to be brought into contacted with 1 mg of the carrier pertaining to the present invention, is usually 5.0 to 50 μg, preferably 10 to 50 μg, and more preferably 20 μg to 50 μg, when the obtaining method of the present invention and the removing method of the present invention are used, when the carrier pertaining to the present invention is the beads, in binding of the carrier pertaining to the present invention and the anti-Tim antibody. When the carrier pertaining to the present invention is the microplate, it is usually 0.1 μg to 10 μg, preferably 0.2 μg to 5 μg, and more preferably 0.5 μg to 2 μg, relative to 1 well.

—Binding of Carrier Pertaining to the Present Invention-Anti-Tim Antibody Complex and Tim Protein Pertaining to the Present Invention A method for obtaining the Tim carrier of the present invention, by binding of the carrier pertaining to the present invention-the anti-Tim antibody complex, and the Tim protein pertaining to the present invention, in the method (c), includes, for example, the following methods. That is, when the carrier pertaining to the present invention is the beads, the Tim carrier of the present invention is obtained by bringing into contacted usually 0.1 mg to 10 mg, preferably 0.3 mg to 5.0 mg, and more preferably 0.5 to 3.0 mg of the carrier pertaining to the present invention-the anti-Tim antibody complex, and usually 1.0 to 50 μg, preferably 1.0 to 30 μg, and more preferably 1.0 to 20 μg of the Tim protein pertaining to the present invention, relative to 1 mg of the carrier pertaining to the present invention-the anti-Tim antibody complex; and when the carrier pertaining to the present invention is the microplate, by bringing into contacted the carrier pertaining to the present invention-the anti-Tim antibody complex, relative to 1 well, and usually 1.0 to 10 μg, preferably 1.0 to 5.0 μg, and more preferably 1.0 to 2.0 μg of the Tim protein pertaining to the present invention, and by subjecting them to a reaction at usually 4.0° C. to 37° C., preferably 11° C. to 30° C., and more preferably 20° C. to 25° C., for usually 0.5 hour to 24 hours, preferably 0.5 hour to 8.0 hours, and more preferably 0.5 hour to 2.0 hours to bind the anti-Tim antibody in the carrier pertaining to the present invention-the anti-Tim antibody complex, and the Tim protein pertaining to the present invention.

It should be noted that contact between the carrier pertaining to the present invention-the anti-Tim antibody complex, and the Tim protein pertaining to the present invention, in the method (c), is carried out generally by bringing into contacted the carrier pertaining to the present invention-the anti-Tim antibody complex, and a solution containing the Tim protein pertaining to the present invention.

The solution for containing the Tim protein pertaining to the present invention may be any one, as long as it dissolves the Tim protein pertaining to the present invention in a stable state, and includes, for example, purified water, or the buffer solution which has buffer action, for example, at pH 7.0 to 8.0, and preferably 7.2 to 7.6 (for example, PBS, TBS, HBC or the like). In addition, buffer agent concentration in these buffer solutions is appropriately selected from a range of usually 5 to 50 mM, and preferably 10 to 30 mM, and NaCl concentration is appropriately selected from a range of usually 100 to 200 mM, and preferably 140 to 160 mM. In addition, for example, saccharides, salts, such as NaCl, and the like, a surfactant, a preservative, a protein, or the like, may be contained in this solution, as long as in such an amount that does not inhibit binding of the Tim protein pertaining to the present invention and the carrier pertaining to the present invention-the anti-Tim antibody complex, after contacting the solution containing to Tim protein pertaining to the present invention, and the carrier pertaining to the present invention-the anti-Tim antibody complex. The surfactant includes, for example, Tween 20, or the like, and surfactant concentration in the solution containing the Tim protein pertaining to the present invention is usually 0.00001 to 0.2%, and preferably 0.0005 to 0.1%. It should be noted that the solution dissolving the Tim protein pertaining to the present invention in these solutions may be abbreviated as "the Tim protein pertaining to the present invention-containing solution", in some cases.

—Specific Preparation Method for Tim Carrier of the Present Invention by Method (c)—

A specific preparation method for the Tim carrier of the present invention in the method (c) may be carried out, for example, by the following method.

First of all, the Tim protein pertaining to the present invention is prepared, according to the preparation method for the Tim protein pertaining to the present invention. Next, when the carrier pertaining to the present invention is the beads, the Tim carrier of the present invention is obtained, by bringing into contacted usually 0.1 mg to 10 mg, preferably 0.3 mg to 5.0 mg, and more preferably 0.5 mg to 3.0 mg of the carrier pertaining to the present invention-the anti-Tim antibody complex, and usually 100 to 1000 μL, and preferably 200 to 500 μL of the solution containing usually 1.0 to 50 μg, preferably 1.0 to 30 μg, and more preferably 1.0 to 20 μg of the Tim protein pertaining to the present invention, relative to 1 mg of the carrier pertaining to the present invention-anti-Tim antibody complex (for example, the solution containing the Tim protein pertaining to the present invention, for example, in purified water, or the buffer solution, for example, at pH 7.0 to 8.0), and by subjecting them to a reaction at usually 4° C. to 37° C., preferably 11° C. to 30° C., and more preferably 20° C. to 25° C., for usually 0.5 hour to 24 hours, preferably 0.5 hour to 8.0 hours, and more preferably 0.5 hour to 2.0 hours to bind the antibody against the Tim protein pertaining to the present invention in the carrier pertaining to the present invention-the anti-Tim antibody complex, and the Tim protein pertaining to the present invention. When the carrier pertaining to the present invention is the microplate, the Tim carrier of the present invention is obtained by bringing into contacted the carrier pertaining to the present invention-the anti-Tim antibody complex, relative to 1 well, and usually 50 μL to 300 μL, preferably 50 μL to 200 μL, and more preferably 100 μL to 200 μL of the solution containing 1.0 to 10 μg, preferably 1.0 to 5.0 μg, and more preferably 1.0 to 2.0 μg of the Tim protein pertaining to the present invention (the solution containing the Tim protein pertaining to the present invention-biotins complex, for example, in purified water, or the buffer solution having buffer action at pH 7.0 to 8.0, and preferably 7.2 to 7.6), and by subjecting them to a reaction at usually 4.0° C. to 37° C., preferably 11° C. to 30° C., and more preferably 20° C. to 25° C., for usually 0.5 hour to 24 hours, preferably 0.5 hour to 8.0 hours, and more preferably 0.5 hour to 2.0 hours to bind the affinity substance in the carrier pertaining to the present invention-the affinity substance complex, and the affinity-tag in the Tim protein pertaining to the present invention having the affinity-tag.

<Method for Binding by Physical Adsorption>

As the method for binding the Tim protein pertaining to the present invention and the carrier pertaining to the present invention by physical adsorption, the Tim protein pertaining to the present invention and the carrier pertaining to the present invention may be brought into contacted under condition where the Tim protein pertaining to the present invention and the carrier pertaining to the present invention bind, according to a known method per se.

Reaction temperature of the Tim protein pertaining to the present invention and the carrier pertaining to the present invention is usually 2° C. to 37° C., and preferably 4° C. to 11° C.

Reaction time of the Tim protein pertaining to the present invention and the carrier pertaining to the present invention is usually 4 hours to 48 hours, and preferably 12 hours to 24 hours.

Amount of the Tim protein pertaining to the present invention to be brought into contacted with 1 mg of the carrier pertaining to the present invention is usually 5.0 to 50 μg, preferably 10 to 50 μg, and more preferably 20 to 50 μg, when the carrier pertaining to the present invention is the beads. Amount of the Tim protein pertaining to the present invention to be brought into contacted with 1 well is usually 0.1 μg to 10 μg, preferably 0.2 μg to 5 μg, and more preferably 0.5 μg to 2 μg, when the carrier pertaining to the present invention is the microplate.

It should be noted that physical adsorption of the Tim protein pertaining to the present invention and the carrier pertaining to the present invention may be carried out generally by bringing into contacted the solution containing the Tim protein pertaining to the present invention, and the carrier pertaining to the present invention.

The solution for containing the Tim protein pertaining to the present invention may be any solution, as long as being capable of dissolving the Tim protein pertaining to the present invention in a stable state, and includes for example, purified water, or a buffer solution which has buffer action, for example, at pH 6.0 to 9.5, and preferably 7.0 to 8.0 (for example, a Good's buffer solution, such as MOPS, or the like, a carbonate buffer solution, PBS, TBS, HBS or the like). In addition, buffer agent concentration in these buffer solutions is appropriately selected from a range of usually 5 to 100 mM, and preferably 10 to 50 mM, and NaCl concentration, if added, is appropriately selected from a range of usually 100 to 200 mM, and preferably 140 to 160 mM. In addition, for example, saccharides, salts, such as NaCl, and the like, a surfactant, a preservative, a protein, or the like, may be contained in this solution, as long as in such an amount that does not inhibit binding of the carrier of the present invention and the extracellular membrane vesicles or the viruses, after contacting the solution containing the Tim protein pertaining to the present invention, and the carrier pertaining to the present invention. It should be noted that the solution dissolving the Tim protein pertaining to the present invention in these solutions may be abbreviated as "the Tim protein pertaining to the present invention-containing solution", in some cases.

Specific examples of the binding method by physical adsorption, in the binding method for the Tim protein pertaining to the present invention and the carrier pertaining to the present invention, include, for example, the following methods.

First of all, the Tim protein pertaining to the present invention is prepared, according to a preparation method for the Tim protein pertaining to the present invention. Next, the Tim carrier of the present invention is obtained by bringing into contacted usually 50 μL to 300 μL, preferably 50 μL to 200 μL, and more preferably 50 μL to 100 μL of the solution containing usually 5.0 to 50 μg, preferably 10 to 50 μg, and more preferably 20 to 50 μg of the Tim protein (the solution containing the Tim protein pertaining to the present invention, for example, in purified water, or in a buffer solution of, for example, pH 7.0 to 8.0, or the like), to 1 mg of the carrier pertaining to the present invention when the carrier pertaining to the present invention is the beads; or by bringing into contacted usually 50 μL to 300 μL, preferably 50 μL to 200 μL, and more preferably 50 μL to 100 μL of a solution containing usually 0.1 μg to 10 μg, preferably 0.2 μg to 5 μg, and more preferably 0.5 μg to 2 μg of the Tim protein (the solution containing the Tim protein pertaining to the present invention, for example, in purified water, or in a buffer solution of, for example, pH 7.0 to 8.0, or the like), to 1 well when the carrier pertaining to the present invention is the microplate; and by subjecting them to a reaction at usually 2° C. to 37° C., and preferably 4° C. to 11° C., for usually 4 hours to 48 hours, and preferably 12 hours to 24 hours to bind the carrier pertaining to the present invention and the Tim protein pertaining to the present invention.

<Treatment of Tim Carrier of the Present Invention>

The resulting Tim carrier of the present invention as above may be subjected to blocking treatment usually carried out in this field.

The resulting Tim carrier of the present invention as above may be subjected to purification treatment usually carried out in this field, as needed. Purification treatment is not especially limited, as long as impurities adhered on the carrier surface can be removed, and includes, for example, a method for washing the Tim carrier of the present invention with a washing solution (hereafter it may be abbreviated as "washing operation", in some cases).

Explanation will be given on an example by taking the case of using the magnetic particles, as the carrier pertaining to the present invention.

First of all, a container, containing the solution containing the resulting Tim carrier of the present invention as described above, is installed in a magnet stand, to collect the Tim carrier of the present invention on a tube wall using magnetic force, and the solution in the container is discarded. Next, the washing solution is added in the container, and stirred. After that, the container is installed in the magnet stand, the same as the above, to collect the Tim carrier of the present invention on the tube wall by using magnetic force, and the solution in the container is discarded. The washing operation may be repeated several times, as necessary. The washing solution to be used in the washing operation may be any solution, as long as it does not affect binding of the Tim protein pertaining to the present invention in the Tim carrier of the present invention, and the carrier of the present invention, and includes, for example, purified water or the buffer solution which has buffer action, for example, at pH 7.0 to 8.0, and preferably 7.2 to 7.6 (for example, PBS, TBS, HBC, or the like). In addition, buffer agent concentration in these solutions is appropriately selected from a range of usually 5 to 50 mM, and preferably 10 to 30 mM, and NaCl concentration is appropriately selected from a range of usually 100 to 200 mM, and preferably 140 to 160 mM. This solution may contain, for example, saccharides, salts, such as NaCl, and the like, a surfactant, a preservative, a protein, or the like, as long as in such an amount that does not inhibit binding of the Tim protein pertaining to the present invention and the carrier pertaining to the present invention.

The surfactant includes, for example, Tween 20, or the like, and surfactant concentration in the washing solution is usually 0.00001 to 0.2%, and preferably 0.0005 to 0.1%.

The extracellular membrane vesicles or the viruses can be obtained efficiently, and the extracellular membrane vesicles or the viruses in the sample can be obtained in high purity, by using the Tim carrier of the present invention. In addition, the extracellular membrane vesicles or the viruses in the sample can also be removed efficiently. Further, the extracellular membrane vesicles or the viruses in the sample can also be detected in high sensitivity.

<6. Obtaining Method for Extracellular Membrane Vesicles or the Viruses in Sample>

A method for obtaining the extracellular membrane vesicle or the virus of the present invention (hereafter it may be abbreviated as "the obtaining method of the present invention", in some cases) is characterized by comprising the following steps:
(1) A step for forming a complex of the Tim protein bound to the carrier, and the extracellular membrane vesicle or the virus in the sample, in the presence of the calcium ion (hereafter it may be abbreviated as "the complex formation step", in some cases).
(2) A step for separating the complex and the sample (hereafter it may be abbreviated as "the complex separation step", in some cases).
(3) A step for separating the extracellular membrane vesicle or the virus from the complex to obtain the extracellular membrane vesicles or the viruses (hereafter it may be abbreviated as "the obtaining step", in some cases).

<6-1. Complex Formation Step>

The complex formation step is a step for forming the complex of the Tim protein, the carrier, and the extracellular membrane vesicle or the virus in the sample, in the presence of the calcium ion.

<Sample Pertaining to the Present Invention>

The sample pertaining to the present invention may be either of the one containing the extracellular membrane vesicle or the virus pertaining to the present invention in liquid, or the one possibly containing the extracellular membrane vesicle or the virus pertaining to the present invention. The sample pertaining to the present invention may be either of the one derived from a living organism or may be the one where the extracellular membrane vesicle or the virus pertaining to the present invention is dissolved or suspended in a solution, such as a medium or a buffer solution, or the like. Specific examples of the sample pertaining to the present invention include body fluids, such as blood, saliva, urine, milk, amniotic fluid, ascites, and the like, cell culture supernatant, and the like.

The solution for containing (dissolving or suspending) the extracellular membrane vesicle or the virus pertaining to the present invention may be any one, as long as it dissolves or suspends the extracellular membrane vesicle or the virus pertaining to the present invention in a stable state, and does not inhibit binding of the complex of the Tim protein bound to the carrier, and the extracellular membrane vesicle or the virus in the sample, and includes, for example, water, a buffer solution having buffering action at pH 7.0 to pH 8.0, and preferably pH 7.2 to pH 7.6 (for example, TBS, HBS, or the like), or the like. It should be noted that, a phosphate buffer is not preferable because it binds with calcium and causes precipitation. In addition, concentration of the buffering agents in these buffer solutions is appropriately selected usually from a range of 5 to 50 mM, and preferably 10 to 30 mM, and NaCl concentration is appropriately selected from a range of usually 100 to 200 mM, and preferably 140 to 160 mM.

This solution may contain, for example, saccharides, salts, such as NaCl, and the like, a surfactant, an antiseptic agent, a protein, or the like, as long as in such an amount that does not inhibit binding of the complex of the Tim protein bound to the carrier and the extracellular membrane vesicle or the virus in the sample. Examples of the surfactant include Tween 20, or the like, and concentration of the surfactant in the solution, for containing the extracellular membrane vesicles or the viruses pertaining to the present invention, is usually 0.00001 to 0.2%, and preferably it is usually 0.0005 to 0.1%.

<Calcium Ion Concentration and Origin of Calcium Ion>

In the present invention, the calcium ion is present in formation of the complex of the Tim protein pertaining to the present invention, the carrier, and the extracellular membrane vesicle or the virus in the sample. More specifically, the calcium ion is present in bringing into contacted the Tim protein pertaining to the present invention, and the extracellular membrane vesicle or the virus in the sample.

Calcium ion concentration, in bringing into contacted the Tim protein pertaining to the present invention, and the extracellular membrane vesicle or the virus in the sample pertaining to the present invention, is usually 0.5 to 100 mM, preferably 1.0 to 10 mM, and more preferably 2.0 to 5.0 mM. It should be noted that it is not without saying that the calcium ion of the concentration as above is necessary, in the solution containing the complex, until the complex of the Tim protein pertaining to the present invention, and the extracellular membrane vesicle or the virus in the sample pertaining to the present invention is formed, and up to carrying out the obtaining step, that is, until the complex is subjected to the separation step.

In addition, source of the calcium ion is not especially limited, and includes, for example, calcium chloride, calcium hydroxide, calcium hydrogen carbonate, calcium iodide, calcium bromide, calcium acetate, or the like; preferably calcium chloride, calcium hydrogen carbonate, and calcium iodide; and more preferably calcium chloride, and calcium hydrogen carbonate.

It should be noted that, as the method for the calcium ion to be present, when the Tim protein pertaining to the present invention, and the extracellular membrane vesicle or the virus in the sample is brought into contacted, generally, the calcium ion as described above may be contained in the solution containing the Tim carrier of the present invention, the solution containing the sample and the solution containing the Tim protein pertaining to the present invention, and/or the solution containing the carrier pertaining to the present invention, in such an amount that attains calcium ion concentration in a range described above, when the Tim protein pertaining to the present invention, the carrier pertaining to the present invention, and the extracellular membrane vesicle or the virus in the sample is brought into contacted. In addition, using a solution containing the calcium ion, in such an amount that attains calcium ion concentration in a range described above, when the Tim protein pertaining to the present invention, the carrier pertaining to the present invention, and the extracellular membrane vesicle or the virus in the sample is brought into contacted, this solution, the solution containing the Tim protein of the present invention, the solution containing the sample and the solution containing the Tim protein pertaining to the present invention, and/or the carrier pertaining to the present invention may be mixed.

The solution for containing the calcium ion is the same as the solution for containing (dissolving or suspending) the extracellular membrane vesicle or the virus pertaining to the present invention, and specific examples, and the like, are also the same.

<Amount of Sample>

Amount of the sample to be brought into contacted with 1 µg of the Tim protein of the present invention, in the complex formation step, is usually 0.1 to 100 mL, preferably 0.1 to 10 mL, and more preferably 0.1 to 1.0 mL.

<Temperature>

Temperature in bringing into contacted the Tim protein of the present invention, with the extracellular membrane vesicles or the viruses in the sample, in the complex formation step, is usually 4° to 37° C., preferably 4 to 25° C., and more preferably 4 to 11° C.

<Time>

Contacting time of the Tim protein pertaining to the present invention and the sample, in the complex formation step, is usually 0.5 to 24 hours, preferably 0.5 to 8 hours, and more preferably 0.5 to 4 hours.

The complex formation step is classified into two cases of (1-A) where the Tim carrier of the present invention, prepared in advance, is used (that is, the case where the carrier on which the Tim protein pertaining to the present invention is bound is used), and (1-B) where the Tim protein pertaining to the present invention and the carrier pertaining to the present invention are used separately.

<(1-A)>

(1-A) is a method for forming the complex of the Tim protein bound to the carrier pertaining to the present invention, and the extracellular membrane vesicle or the virus in the sample (hereafter it may be abbreviated as "the complex pertaining to the present invention", in some cases), by bringing into contacted the Tim carrier of the present invention, and the extracellular membrane vesicle or the virus in the sample, in the presence of the calcium ion. In (1-A), the calcium ion may be present, when the Tim carrier of the present invention and the extracellular membrane vesicle or the virus in the sample is brought into contacted. Specifically, the solution containing the carrier on which the Tim protein pertaining to the present invention is bound and containing the calcium ion and/or the solution containing the sample and the calcium ion may be used, or the solution containing the carrier on which the Tim protein pertaining to the present invention is bound, and the solution containing the sample and the calcium ion may be used.

—Amount of Sample Pertaining to the Present Invention—

Amount of the sample to be brought into contacted with 1 mg of the Tim carrier of the present invention, in (1-A), is usually 0.1 to 100 mL, preferably 0.1 to 10 mL, and more preferably 0.1 to 1.0 mL.

—Contacting Temperature—

Temperature when the Tim carrier of the present invention, and the sample are brought into contacted, in (1-A), is usually 4.0 to 37° C., preferably 4.0 to 25° C., and more preferably 4.0 to 11° C.

—Contacting Time—

Contacting time of the Tim carrier of the present invention, and the sample (the extracellular membrane vesicles or the viruses), in (1-A), is usually 0.5 to 24 hours, preferably 0.5 to 8.0 hours, and more preferably 0.5 to 4.0 hours.

—Amount of Tim Carrier of the Present Invention—

Amount of the Tim carrier of the present invention, in (1-A), is usually 0.1 to 20 mg, preferably 0.3 to 10 mg, and more preferably 0.5 to 6.0 mg, relative to 1 mL of the solution in forming the complex pertaining to the present invention.

Specific Example of 1-A (1-A) may be carried out, for example, by the following method. That is, the complex of the Tim protein bound to the carrier pertaining to the present invention, and the extracellular membrane vesicles or the viruses in the sample is formed by bringing into contacted usually 0.1 to 20 mg, preferably 0.3 to 10 mg, and more preferably 0.5 to 6.0 mg of the Tim carrier of the present invention, relative to 1 mL of the solution after mixing of the Tim carrier of the present invention, and the solution containing the sample and the solution containing the calcium ion (the solution in forming the complex pertaining to the present invention), with the solution containing the calcium ion, in an amount to attain a calcium ion concentration of usually 0.5 to 100 mM, preferably 1.0 to 10 mM, and more preferably 2.0 to 5.0 mM, in the solution in forming the complex pertaining to the present invention, and usually 0.1 to 100 mL, preferably 0.1 to 10 mL, and more preferably 0.1 to 1.0 mL of the sample, relative to 1 mg of the Tim carrier of the present invention, at usually 4.0 to 37° C., preferably 4.0 to 25° C., and more preferably 4.0 to 11° C., for usually 0.5 to 24 hours, preferably 0.5 to 8.0 hours, and more preferably 0.5 to 4.0 hours.

<(1-B)>

(1-B) is a method for using the Tim protein of the present invention, and the carrier pertaining to the present invention separately. For example, when the Tim protein pertaining to the present invention and the carrier pertaining to the present invention are bound, utilizing affinity binding, it may be carried out as the following (1-B-i), (1-B-ii), or (1-B-iii).

(1-B-i)

The complex pertaining to the present invention is formed by bringing into contacted the Tim protein of the present invention, the carrier pertaining to the present invention, and the extracellular membrane vesicle or the virus in the sample, at the same time, in the presence of the calcium ion.

(1-B-ii)

The complex pertaining to the present invention is formed by forming the complex of the Tim protein of the present invention, and the extracellular membrane vesicle or the virus by bringing into contacted the Tim protein of the present invention, and the extracellular membrane vesicle or the virus in the sample, in the presence of the calcium ion, and then by further bringing into contacted the complex and the carrier pertaining to the present invention.

(1-B-iii)

The complex pertaining to the present invention is formed by bringing into contacted the carrier of the present invention, and the extracellular membrane vesicle or the virus in the sample, and then by further bringing into contacted the Tim protein of the present invention, in the presence of the calcium ion.

—(1-B-i)—

(1-B-i) is a method for forming the complex pertaining to the present invention composed of [the extracellular membrane vesicle or the virus-(the Tim protein pertaining to the present invention)-the affinity substance-(the carrier pertaining to the present invention)], by bringing into contacted the Tim protein pertaining to the present invention, the carrier pertaining to the present invention, and the extracellular membrane vesicle or the virus in the sample, at the same time, in the presence of the calcium ion.

Specifically, for example, in using two or more kinds of substances having affinity each other, as the affinity substance, the complex pertaining to the present invention composed of [the extracellular membrane vesicle or the virus in the sample-(the Tim protein pertaining to the present invention)-the affinity substance-(the carrier pertaining to the present invention)] is formed by bringing into contacted the Tim protein pertaining to the present invention bound with either of the affinity substances (the affinity substance-binding Tim protein), and the carrier bound with the remaining affinity substances (the affinity substance-binding carrier), and the extracellular membrane vesicle or the virus in the sample, at the same time, in the presence of the calcium ion, to bind the Tim protein pertaining to the present invention in the affinity substance-binding Tim protein, and the extracellular membrane vesicle or the virus, as well as to bind the affinity substance in the affinity substance-binding Tim protein, and the affinity substance in the affinity substance-binding carrier.

In (1-B-i), the calcium ion may be present in bringing into contacted the Tim protein pertaining to the present invention, the carrier pertaining to the present invention, and the extracellular membrane vesicle or the virus in the sample, at the same time. Specifically, it may be carried out either by using the solution containing the Tim protein pertaining to the present invention, the solution containing the carrier pertaining to the present invention, and the sample, which the calcium ion contained in at least one more kinds of the solutions, or by bringing into contacted the solution containing the Tim protein pertaining to the present invention, the solution containing the carrier pertaining to the present invention, and the solution containing the sample and the calcium ion.

—Amount of Sample Pertaining to the Present Invention—

In (1-B-i), an amount of the sample to be brought into contacted with 1 μg of the Tim protein pertaining to the present invention is usually 0.1 to 100 mL, preferably 0.1 to 10 mL, and more preferably 0.1 to 1.0 mL.

—Amount of Tim Protein Pertaining to the Present Invention—

In (1-B-i), an amount of the Tim protein pertaining to the present invention is usually 0.01 to 200 μg, preferably 0.15 to 50 μg, and more preferably 0.5 to 24 μg, relative to 1 mL of the solution in forming the complex pertaining to the present invention.

—Amount of Carrier Pertaining to the Present Invention—

In (1-B-i), an amount of the carrier pertaining to the present invention is usually 1 to 20 mg, preferably 0.3 to 10 mg, and more preferably 0.5 to 6.0 mg, relative to 1 mL of the solution in forming the complex pertaining to the present invention.

—Contacting Temperature—

In (1-B-i), temperature in bringing into contacted the Tim protein of the present invention, the carrier pertaining to the present invention, and the extracellular membrane vesicle or the virus in the sample, is usually 4 to 37° C., preferably 4 to 25° C., and more preferably 4 to 11° C.

—Contacting Time—

Contacting time in bringing into contacted the Tim protein of the present invention, the carrier pertaining to the present invention, and the extracellular membrane vesicle or the virus in the sample, is usually 0.5 to 24 hours, preferably 0.5 to 8.0 hours, and more preferably 0.5 to 4.0 hours.

It should be noted that contact of the Tim protein of the present invention, the carrier pertaining to the present invention, and the extracellular membrane vesicle or the virus in the sample is carried out usually by bringing into contacted the solution containing the Tim protein of the present invention, the carrier pertaining to the present invention, the extracellular membrane vesicle or the virus in the sample, and the solution containing the calcium ion.

The solution for containing the Tim protein pertaining to the present invention may be any solution which is capable of dissolving the Tim protein pertaining to the present invention in a stable state, and does not inhibit binding of the Tim protein pertaining to the present invention, the carrier pertaining to the present invention and the extracellular membrane vesicle or the virus, and includes for example, purified water, or a buffer solution which has buffer action, for example, at pH 7.0 to 8.0, and preferably 7.2 to 7.6 (for example, PBS, TBS, HBS or the like). In addition, buffer agent concentration in these buffer solutions is appropriately selected from a range of usually 5 to 50 mM, and preferably 10 to 30 mM, and NaCl concentration is appropriately selected from a range of usually 100 to 200 mM, and preferably 140 to 160 mM. For example, saccharides, salts, such as NaCl, and the like, a surfactant, a preservative, a protein, or the like, may be contained in this solution, as long as in such an amount that dissolves the Tim protein pertaining to the present invention in a stable state, and does not inhibit binding of the Tim protein pertaining to the present invention, the carrier pertaining to the present invention and the extracellular membrane vesicle or the virus. The surfactant includes, for example, Tween 20, or the like, and surfactant concentration in the solution for containing the Tim protein pertaining to the present invention is usually 0.00001 to 0.2%, and preferably 0.0005 to 0.1%.

The solution for containing the calcium ion is the same as the solution for containing (dissolving or suspending) the extracellular membrane vesicle or the virus pertaining to the present invention, and the specific example, or the like, is also the same.

The solution containing the calcium ion is the solution containing such amount of the calcium ion that attains a calcium ion concentration of usually 0.5 to 100 mM, preferably 1 to 10 mM, and more preferably 2 to 5 mM in the solution in forming the complex pertaining to the present invention, among the solutions containing the calcium ion.

Specific Example of (1-B-i)

(1-B-i) may be carried out, for example, by the following method. That is, the complex pertaining to the present invention is formed by bringing into contacted usually 0.5 µL to 1 ml, preferably 0.5 µL to 100 µL, and more preferably 0.5 µL to 10 µL of the solution containing usually 0.01 to 200 µg, preferably 0.15 to 50 µg, and more preferably 0.5 to 24 µg of the Tim protein pertaining to the present invention (for example, the solution containing the Tim protein of the present invention, for example, in purified water or, in the buffer solution which has buffer action at pH 7.0 to 8.0, and preferably 7.2 to 7.6), relative to 1 mL of the solution in forming the complex pertaining to the present invention; usually 0.1 to 100 ml, preferably 0.1 to 10 ml, and more preferably 0.1 to 1 ml of the sample, relative to 1 µg of the Tim protein pertaining to the present invention; the solution containing the calcium ion in such an amount that attains a concentration of the calcium ion of usually 0.5 to 100 mM, preferably 1 to 10 mM, and more preferably 2 to 5 mM, in the solution in forming the complex pertaining to the present invention; and usually 0.1 to 20 mg, preferably 0.3 to 10 mg, and more preferably 0.5 to 6 mg of the carrier pertaining to the present invention, relative to 1 mL of a solution after mixing the solution containing the Tim protein pertaining to the present invention, the solution containing the sample and the calcium ion, and the solution containing the carrier pertaining to the present invention (the solution in forming the complex pertaining to the present invention), for usually 0.5 to 24 hours, preferably 0.5 to 8 hours, and more preferably 0.5 to 4 hours.

—(1-B-ii)—

(1-B-ii) is a method for forming the complex of the Tim protein of the present invention, and the extracellular membrane vesicle or the virus, by bringing into contacted the Tim protein of the present invention, and the extracellular membrane vesicle or the virus in the sample, in the presence of the calcium ion, and further by bringing into contacted the complex and the carrier pertaining to the present invention to form the complex composed of [the extracellular membrane vesicle or the virus-(the Tim protein pertaining to the present invention)-the affinity substance-(the carrier pertaining to the present invention)].

Specifically, for example, in using two or more kinds of substances having affinity each other, as the affinity substances, the complex of [the extracellular membrane vesicle or the virus-(the Tim protein pertaining to the present invention)-the affinity substance] is formed by bringing into contacted the Tim protein bound with either of the affinity substances (the affinity substance-binding Tim protein), and the extracellular membrane vesicle or the virus in the sample, in the presence of the calcium ion to bind the Tim protein in the affinity substance-binding Tim protein, and the extracellular membrane vesicle. Next, [the extracellular membrane vesicle or the virus-(the Tim protein pertaining to the present invention-the affinity substance)-(the affinity substance-the carrier pertaining to the present invention)] is formed by bringing into contacted the [the extracellular membrane vesicle-(the Tim protein pertaining to the present invention-the affinity substance)] complex, and the carrier bound with the other affinity substance (the affinity substance-binding carrier) to bind the affinity substance in [the extracellular membrane vesicle or the virus-(the Tim protein pertaining to the present invention-the affinity substance)] complex, and the affinity substance in the affinity substance-binding carrier.

In addition, for example, in using a substance having affinity to an affinity tag or an anti-Tim antibody, as the affinity substance, [the extracellular membrane vesicle or the virus-the Tim protein pertaining to the present invention] complex is formed, by bringing into contacted the Tim protein pertaining to the present invention and the extracellular membrane vesicle or the virus in the sample, in the presence of the calcium ion to bind the Tim protein pertaining to the present invention and the extracellular membrane vesicle or the virus. Next, [the extracellular membrane vesicle or the virus-the Tim protein pertaining to the present invention-(the affinity substance-the carrier pertaining to the present invention)] complex is formed, by bringing into contacted [the extracellular membrane vesicle or the virus-the Tim protein pertaining to the present invention] complex, and the carrier bound with the affinity substance (the affinity substance-binding carrier) to bind the Tim protein pertaining to the present invention in [the extracellular membrane vesicle or the virus-the Tim protein pertaining to the present invention] complex, and the affinity substance in the affinity substance-binding carrier.

In (1-B-ii), the calcium ion may be present in bringing into contacted the Tim protein pertaining to the present invention, and the extracellular membrane vesicle or the virus in the sample. Specifically, the solution containing the Tim protein pertaining to the present invention and/or the sample, which is containing the calcium ion may be used, or the solution containing the Tim protein pertaining to the present invention, the sample, and the solution containing the calcium ion may be used.

—Amount of Sample Pertaining to the Present Invention—

An amount of the sample to be brought into contacted with 1 µg of the Tim protein pertaining to the present invention in (1-B-ii), is usually 0.1 to 100 ml, preferably 0.1 to 10 ml, and more preferably 0.1 to 1.0 ml.

—Amount of Tim Protein Pertaining to the Present Invention—

An amount of the Tim protein pertaining to the present invention in (1-B-ii) is usually 0.01 to 200 µg, preferably 0.15 to 50 µg, and more preferably 0.5 to 24 µg, relative to 1 mL of the solution in forming the complex pertaining to the present invention.

—Amount of Carrier Pertaining to the Present Invention—

An amount of the carrier pertaining to the present invention in (1-B-ii) is usually 0.1 to 20 mg, preferably 0.3 to 10 mg, and more preferably 0.5 to 6 mg, relative to 1 mL of the solution in forming the complex pertaining to the present invention.

—Contacting Temperature—

Temperature in bringing into contacted the Tim protein of the present invention, and the extracellular membrane vesicles or the viruses in the sample in (1-B-ii), is usually 4 to 37° C., preferably 4 to 25° C., and more preferably 4 to 11° C.

After forming the complex of the Tim protein of the present invention and extracellular membrane vesicle or the virus in (1-B-ii), temperature in further bringing into contacted the complex and the carrier pertaining to the present invention is usually 4 to 37° C., preferably 4 to 25° C., and more preferably 4 to 11° C.

—Contacting Time—

Contacting time of the Tim protein of the present invention, the carrier pertaining to the present invention, and the extracellular membrane vesicle or the virus in the sample pertaining to present invention in (1-B-ii), is usually 0.5 to 24 hours, preferably 0.5 to 8 hours, and more preferably 0.5 to 4 hours.

After forming the complex of the Tim protein of the present invention and extracellular membrane vesicle or the virus in (1-B-ii), time for further bringing into contacted the complex and the carrier pertaining to the present invention is usually 0.5 to 24 hours, preferably 0.5 to 8 hours, and more preferably 0.5 to 4 hours.

It should be noted that contact of the Tim protein pertaining to the present invention and the extracellular membrane vesicle or the virus in the sample is usually carried out by bringing into contacted the solution containing the Tim protein pertaining to the present invention, the sample and the solution containing the calcium ion.

The solution for containing the Tim protein pertaining to the present invention may be any solution, as long as it is capable of dissolving the Tim protein pertaining to the present invention in a stable state, and dose not inhibit binding of the Tim protein pertaining to the present invention, the carrier pertaining to the present invention and the extracellular membrane vesicle or the virus pertaining to the present invention, and includes for example, purified water, or a buffer solution which has buffer action, for example, at pH 7.0 to 8.0, and preferably 7.2 to 7.6 (for example, TBS, HBS or the like). In addition, buffer agent concentration in these buffer solutions is appropriately selected from a range of usually 5 to 50 mM, and preferably 10 to 30 mM, and NaCl concentration is appropriately selected from a range of usually 100 to 200 mM, and preferably 140 to 160 mM. For example, saccharides, salts, such as NaCl, and the like, a surfactant, a preservative, a protein, or the like, may be contained in this solution, as long as in such an amount that dissolves the Tim protein pertaining to the present invention in a stable state, and dose not inhibit binding of the Tim protein pertaining to the present invention, the carrier pertaining to the present invention, and the extracellular membrane vesicle or the virus. The surfactant includes, for example, Tween 20, or the like, and surfactant concentration in the solution for containing the Tim protein pertaining to the present invention is usually 0.00001 to 0.2%, and preferably 0.0005 to 0.1%.

The solution for containing the calcium ion is the same as the solution for containing (dissolving or suspending) the extracellular membrane vesicle or the virus pertaining to the present invention. The specific example, or the like, is also the same.

The solution containing the calcium ion is the solution containing such an amount of the calcium ion that attains a calcium ion concentration of usually 0.5 to 100 mM, preferably 1 to 10 mM, and more preferably 2 to 5 mM, in the solution in forming the complex pertaining to the present invention.

Specific Example of (1-B-ii)

(1-B-ii) may be carried out, for example, by the following method. That is, the complex of the Tim protein of the present invention and the extracellular membrane vesicles or the viruses is formed, by bringing into contacted usually 0.5 μL to 1 mL, preferably 0.5 μL to 100 μL, and more preferably 0.5 μL to 10 μL of the solution containing usually 0.01 to 200 μg, preferably 0.15 to 50 μg, and more preferably 0.5 to 24 μg of the Tim protein pertaining to the present invention (the solution containing the Tim protein pertaining to the present invention, for example, in purified water, or in the buffer solution, having buffering action, for example, at pH 7.0 to 8.0, and preferably 7.2 to 7.6), relative to 1 mL of the solution in forming the complex pertaining to the present invention; usually 0.1 to 100 mL, preferably 0.1 to 10 mL, and more preferably 0.1 to 1 mL of the sample, relative to 1 μg of the Tim protein pertaining to the present invention; and the solution containing the calcium ion, in such an amount that attains a calcium ion concentration of usually 0.5 to 100 mM, preferably 1 to 10 mM, and more preferably 2 to 5 mM, in a solution mixed with the sample, the solution containing the calcium ion, and the solution containing the Tim protein pertaining to the present invention, and further in a solution after bringing into contacted the mixed solution and the carrier pertaining to the present invention; at usually 4 to 37° C., preferably 4 to 25° C., and more preferably 4 to 11° C., for usually 0.5 to 24 hours, preferably 0.5 to 8 hours, and more preferably 0.5 to 4 hours, and after that, the complex pertaining to the present invention is formed, by the further addition of usually 0.1 to 20 mg, preferably 0.3 to 10 mg, and more preferably 0.5 to 6 mg of the carrier pertaining to the present invention, relative to 1 mL of the solution in formation of the complex pertaining to the present invention, and by bringing into contacted the resulting complex of the Tim protein of the present invention and the extracellular membrane vesicles or the viruses, and the carrier pertaining to the present invention, at usually 4 to 37° C., preferably 4 to 25° C., and more preferably 4 to 11° C., for usually 0.5 to 24 hours, preferably 0.5 to 8 hours, and more preferably 0.5 to 4 hours.

—(1-B-iii)—

(1-B-iii) is a method for forming the complex pertaining to the present invention composed of [the extracellular membrane vesicle or the virus-(the Tim protein pertaining to the present invention)-the affinity substance-(the carrier pertaining to the present invention)], by bringing into contacted the carrier of the present invention, and the extracellular membrane vesicle or the virus in the sample, and after that by further bringing into contacted the Tim protein of the present invention, in the presence of the calcium ion.

Specifically, for example, in using two or more kinds of substances having affinity each other as the affinity substance, [the extracellular membrane vesicle or the virus-(the Tim protein pertaining to the present invention-the affinity substance)-(the affinity substance-the carrier pertaining to the present invention)] complex is formed by bringing into contacted the carrier bound with either of the affinity substances (the affinity substance-binding carrier), and the extracellular membrane vesicle or the virus in the sample, and next by bringing into contacted with the Tim protein bound with the other affinity substance (the affinity substance-binding Tim protein), at the same time, in the presence of the calcium ion to bind the Tim protein in the affinity substance-binding Tim protein, and the extracellular membrane vesicle or the virus, as well as to bind the affinity substance in the affinity substance-binding Tim protein, and the affinity substance in the affinity substance-binding carrier.

In addition, in using, for example, a substance having affinity to the affinity tag or an anti-Tim antibody, as the affinity substance, [the extracellular membrane vesicle or the virus-the Tim protein pertaining to the present invention-(the affinity substance-the carrier pertaining to the present invention)] complex is formed, by bringing into contacted the carrier bound with the affinity substance (the affinity substance-binding carrier), and the extracellular membrane vesicle or the virus in the sample, and next by bringing into contacted with the Tim protein pertaining to the present invention, at the same time, in the presence of the calcium ion to bind the Tim protein pertaining to the present invention and the extracellular membrane vesicle or the virus, as well as to bind the Tim protein pertaining to the present invention, and the affinity substance in the affinity substance-binding carrier.

In (1-B-iii), the calcium ion may be present in bringing into contacted the Tim protein pertaining to the present invention, and the extracellular membrane vesicle or the virus in the sample. Specifically, either the solution containing the Tim protein pertaining to the present invention, and/or the solution containing the calcium ion in the extracellular membrane vesicle or the virus in the sample may be used, or the solution containing the Tim-4 protein pertaining to the present invention, and the solution containing the extracellular membrane vesicle or the virus in the sample and the calcium ion may be used.

—Amount of Sample Pertaining to the Present Invention—

An amount of the sample to be brought into contacted with 1 µg of the Tim protein pertaining to the present invention in (1-B-iii), is usually 0.1 to 100 ml, preferably 0.1 to 10 ml, and more preferably 0.1 to 1 ml.

—Amount of Tim Protein Pertaining to the Present Invention—

An amount of the Tim protein pertaining to the present invention in (1-B-iii) is usually 0.01 to 200 µg, preferably 0.15 to 50 µg, and more preferably 0.5 to 24 µg, relative to 1 mL of the solution in forming the complex pertaining to the present invention.

—Amount of Carrier Pertaining to the Present Invention—

An amount of the carrier pertaining to the present invention in (1-B-iii) is usually 0.1 to 20 mg, preferably 0.3 to 10 mg, and more preferably 0.5 to 6 mg, relative to 1 mL of the solution in forming the complex pertaining to the present invention.

—Contacting Temperature—

Temperature in bringing into contacted the carrier pertaining to the present invention and the extracellular membrane vesicle or the virus in the sample in (1-B-iii), is usually 4 to 37° C., preferably 4 to 25° C., and more preferably 4 to 11° C.

Temperature in further bringing into contacted the Tim protein of the present invention, after bringing into contacted the carrier of the present invention, and the extracellular membrane vesicle or the virus in the sample, in (1-B-iii), is usually 4 to 37° C., preferably 4 to 25° C., and more preferably 4 to 11° C.

—Contacting Time—

Contacting time in bringing into contacted the carrier pertaining to the present invention and the sample in (1-B-iii), is usually 0.5 to 24 hours, preferably 0.5 to 8 hours, and more preferably 0.5 to 4 hours.

Contacting time in further bringing into contacted the Tim protein pertaining to the present invention, after bringing into contacted the carrier of the present invention and the extracellular membrane vesicle or the virus in the sample in (1-B-iii), is usually 0.5 to 24 hours, preferably 0.5 to 8 hours, and more preferably 0.5 to 4 hours.

It should be noted that further contact with the Tim protein pertaining to the present invention, after bringing into contacted the carrier of the present invention, and the extracellular membrane vesicle or the virus in the sample, is generally carried out by using the solution containing the Tim protein pertaining to the present invention, and the solution containing the calcium ion.

The solution for containing the Tim protein pertaining to the present invention may be any solution, as long as it is capable of dissolving the Tim protein pertaining to the present invention in a stable state, and dose not inhibit binding of the Tim protein pertaining to the present invention, the carrier pertaining to the present invention and the extracellular membrane vesicle or the virus, and includes for example, purified water, or the buffer solution which has buffer action, for example, at pH 7.0 to 8.0, and preferably 7.2 to 7.6 (for example, PBS, TBS, HBS or the like). In addition, buffer agent concentration in these buffer solutions is appropriately selected from a range of usually 5 to 50 mM, and preferably 10 to 30 mM, and NaCl concentration is appropriately selected from a range of usually 100 to 200 mM, and preferably 140 to 160 mM. For example, saccharides, salts, such as NaCl, and the like, a surfactant, a preservative, a protein, or the like, may be contained in this solution, as long as in such an amount that dissolves the Tim-4 protein pertaining to the present invention in a stable state, and dose not inhibit binding of the Tim protein pertaining to the present invention, the carrier pertaining to the present invention and the extracellular membrane vesicle or the virus. The surfactant includes, for example, Tween 20, or the like, and surfactant concentration in the solution for containing the Tim protein pertaining to the present invention is usually 0.00001 to 0.2%, and preferably 0.0005 to 0.1%.

The solution for containing the calcium ion is the same as the solution for containing (dissolving or suspending) the extracellular membrane vesicle or the virus pertaining to the present invention, and the specific examples are also the same.

The solution containing the calcium ion is the solution having such an amount of the calcium ion that attains a calcium ion concentration of usually 0.5 to 100 mM, preferably 1 to 10 mM, and more preferably 2 to 5 mM, in the solution in forming the complex pertaining to the present invention.

Specific Example of (1-B-iii)

(1-B-iii) may be carried out, for example, by the following method. That is, the complex pertaining to the present invention is formed by bringing into contacted usually 0.1 to 100 ml, preferably 0.1 to 10 ml, and more preferably 0.1 to 1 ml of the sample pertaining to the present invention, relative to 1 µg of the Tim protein pertaining to the present invention, and usually 0.1 to 20 mg, preferably 0.3 to 10 mg, and more preferably 0.5 to 6 mg of the carrier pertaining to the present invention, relative to 1 mL of the solution in forming the complex pertaining to the present invention, at usually 4 to 37° C., preferably 4 to 25° C., and more preferably 4 to 11° C., for usually 0.5 to 24 hours, preferably 0.5 to 8 hours, and more preferably 0.5 to 4 hours, and after that, by the addition of the solution containing such amount of the calcium ion that attains a calcium ion concentration of usually 0.5 to 100 mM, preferably 1.0 to 10 mM, and more preferably 2 to 5 mM, in the solution obtained by bringing into contacted the solution containing the sample pertaining to the present invention and the calcium ion, and the carrier pertaining to the present invention, and further by bringing into contacted the solution containing the Tim protein pertaining to the present invention; and usually 0.5 µL to 1 mL, preferably 0.5 µL to 100 µL, and more preferably 0.5 µL to 10 µL of the solution containing usually 0.01 to 200 µg, preferably 0.15 to 50 µg, and more preferably 0.5 to 24 µg of the Tim protein pertaining to the present invention (the solution containing the Tim protein pertaining to the present invention, for example, in purified water or in the buffer solution, which has buffer action, for example, at pH 7.0 to 8.0, and preferably 7.2 to 7.6), relative to 1 mL of the solution in forming the complex pertaining to the present invention, to bring into contacted at usually 4 to 37° C., preferably 4 to 25° C., and more preferably 4 to 11° C., for usually 0.5 to 24 hours, preferably 0.5 to 8 hours, and more preferably 0.5 to 4 hours.

<6-2. Complex Separation Step>

The complex separation step in the obtaining method of the present invention is an obtaining step of the separated complex pertaining to the present invention, after the complex formation step, by separation of the complex of the Tim protein bound to the resulting carrier pertaining to the present invention (the Tim carrier of the present invention), and the extracellular membrane vesicle or the virus in the sample (the complex pertaining to the present invention), and the sample.

The complex separation step in the obtaining method of the present invention may be any method, as long as it is capable of obtaining the complex pertaining to the present invention, by separation of the complex pertaining to the present invention, and the sample, and includes, for example, the following methods.

(1) When a magnetic carrier is used as the carrier pertaining to the present invention, a method for installing a container, used in the complex formation step, in the magnet stand as needed, collecting the complex pertaining to the present invention on the tube wall by using magnetic force and removing the supernatant sample to separate them.
(2) When the carrier of the present invention is beads-like, a method for subjecting the container, used in the complex formation step, to centrifugal separation treatment to collect the complex pertaining to the present invention as precipitate, and to remove the supernatant sample to separate them.
(3) When the carrier of the present invention in a form of a non-beads-like plate, or the like, is used, a method for separating these by removing only the sample.
(4) A method for separating the complex pertaining to the present invention, and the sample by filtration.

After separation of the complex of the present invention and the sample, in this way, the separated complex of the present invention may be obtained (recovered) by a method known per se.

Specific Example of Complex Separation Step

When the magnetic carrier is used as the carrier pertaining to the present invention, the container used in the complex formation step is installed in the magnet stand, as needed, and the complex pertaining to the present invention is collected on the tube wall by using magnetic force to remove the supernatant sample.

<6-3. Washing Operation>

After the complex formation step and the complex separation step, the resulting complex pertaining to the present invention may be washed, as needed, using the calcium ion-containing washing solution (hereinafter, it may be optionally abbreviated as "washing operation"). Impurities in the sample pertaining to the present invention, such as components originated from the cell attached on the surface of the carrier pertaining to the present invention, and the like, can be removed by the washing operation. A washing method usually practiced in this field can be used, except for using the washing solution containing the calcium ion, as described above, as the washing method. The calcium ion-containing washing solution, to be used in the washing operation, may be any solution, as long as it contains usually 0.5 to 100 mM, preferably 1 to 10 mM, and more preferably 2 to 5 mM of the calcium ion, and does not influence binding of the extracellular membrane vesicle or the virus pertaining to the present invention in the complex, the Tim-4 protein pertaining to the present invention, and the carrier of the present invention, and includes, for example, the buffer solution containing usually 0.5 to 100 mM, preferably 1 to 10 mM, and more preferably 2 to 5 mM of the calcium ion, and having buffer action at pH 7.0 to 8.0, and preferably 7.2 to 7.6, and not precipitating calcium (for example, TBS, HBS). It should be noted that the phosphate buffer is not preferable, because it precipitates by binding with calcium. In addition, buffer agent concentration in these buffer solutions is selected from a range of usually 5 to 50 mM, and preferably 10 to 30 mM, and NaCl concentration is selected from a range of usually 100 to 200 mM, and preferably 140 to 160 mM. This solution may contain, for example, saccharides, salts, such as NaCl, and the like, a surfactant, a preservative, a protein, or the like, as long as in such an amount that does not inhibit binding of the extracellular membrane vesicle or the virus pertaining to the present invention in the complex, the Tim protein pertaining to the present invention, and the carrier of the present invention. The surfactant includes, for example, Tween 20 (produced by Wako Pure Chemical Industries Co.), or the like, and surfactant concentration in the washing solution is usually 0.00001 to 0.2%, and preferably 0.0005 to 0.1%.

Explanation will be given on an example by taking the case of using the magnetic particles, as the carrier pertaining to the present invention. First of all, the calcium ion-containing washing solution is added in the container containing the resulting complex pertaining to the present invention by the complex separation step, and is stirred. After that, the container is installed in the magnet stand, to collect the complex on the tube wall by using magnetic force, and the solution in the container is discarded. The washing operation may be repeated several times, as needed.

Specific Example of Washing Operation

First of all, the calcium ion-containing washing solution (for example, the buffer solution containing usually 0.5 to 100 mM, preferably 1 to 10 mM, and more preferably 2 to 5 mM of the calcium ion, having buffer action at pH 7.0 to 8.0, and preferably 7.2 to 7.6, and not precipitation calcium. However, the phosphate buffer is not preferable because it precipitates by binding with calcium) is added into the container containing the resulting complex pertaining to the present invention by the complex separation step, and is stirred. After that, the container is installed in the magnet stand, to collect the complex on the tube wall by using magnetic force, and solution in the container is discarded. The washing operation may be repeated several times, as needed.

<6-4. Obtaining Step>

The obtaining step is a step for obtaining the extracellular membrane vesicle or the virus pertaining to the present invention, after carrying out the complex formation step, the complex separation step, and carrying out the washing step (washing operation), as needed, to separate the extracellular membrane vesicle or the virus from the complex of the Tim protein bound to the resulting carrier pertaining to the present invention, and the extracellular membrane vesicle or the virus in the sample.

In this way, the extracellular membrane vesicle or the virus pertaining to the present invention can be obtained in high purity.

Specific examples of the obtaining step include, for example, the following
(2-A) and (2-B).
(2-A) A method for using a protein denaturing agent.
(2-B) A method for decreasing calcium ion concentration.

<(2-A): Method for Using Protein Denaturing Agent>

(2-A) is a step for separating the extracellular membrane vesicle or the virus from the complex pertaining to the present invention, after carrying out the complex formation step, the complex separation step, and carrying out the washing operation, as needed, to make acting the protein denaturing agent on the resulting complex pertaining to the present invention, to denature the Tim protein pertaining to the present invention in the complex pertaining to the present invention. In this way, the extracellular membrane vesicle or the virus pertaining to the present invention can be obtained in high purity.

—Protein Denaturing Agent—

The protein denaturing agent to be used in (2-A) may be any one, as long as it is generally used in this field, as a compound to denature the protein, and includes an anionic surfactant, for example, SDS (sodium dodecyl sulfate), N-lauroyl sarcosine, or the like; an amphoteric surfactant, such as CHAPS (3-(3-cholamidepropyl)dimethylamino-1-propane sulfonate salt), Zwittergent 3-12 (N-dodecyl-N,N-dimethyl-3-ammonio-1-propane sulfonate), or the like; a non-ionic surfactant, such as Brij 35 (produced by Takara Bio Inc.), dodecyl-β-D-maltoside(n-dodecyl-β-D-maltoside), Nonidet P-40, octyl-β-D-glucoside (octyl-β-D-glcoside), Triton X-100 (polyoxyethylene (10) octylphenol), Tween 20 (polyoxyethylene (20) sorbitan monolaurate), or the like; a chautropic agent, such as urea, formamide, guanidine, or the like, and the anionic surfactant is preferable, and SDS is particularly preferable.

Action of these protein denaturing agents on the complex pertaining to the present invention, in (2-A), is generally carried out by bringing into contacted the solution containing the protein denaturing agent (hereinafter, it may be abbreviated as "the protein denaturing agent-containing solution", in some cases), and the complex of the Tim protein bound to the carrier pertaining to the present invention, and the extracellular membrane vesicle or the virus in the sample to make acted the protein denaturing agent-containing solution on the complex pertaining to the present invention.

It should be noted that the contacting of the protein denaturing agent-containing solution and the complex pertaining to the present invention can be carried out, for example, by a method for suspending the complex in the solution (when the carrier is the beads, and the like); a method for dipping the complex into the solution (when the carrier is a disc-like piece, a tube, or the like); a method for the addition of the solution to the complex (the carrier), (when the carrier is the microplate, the tube, or the like).

—Solution for Containing Protein Denaturing Agent—

The solution for containing the protein denaturing agent, in (2-A), includes purified water, the buffer solution which is capable of dissolving the protein denaturing agent, or the like. The buffer solution includes the buffer solution having buffer action at usually pH 6 to 9, preferably 7 to 8 (for example, Tris, HEPES, or the like). In addition, buffer agent concentration in these solutions is appropriately selected from a range of usually 5 to 100 mM, and preferably 10 to 50 mM.

—Protein Denaturing Agent-Containing Solution—

The protein denaturing agent-containing solution has a pH of usually 6.0 to 9.0, and preferably 7.0 to 8.0, in (2-A). Concentration of the protein denaturing agent in the protein denaturing agent-containing solution is different depending on kind of the protein denaturing agent, and generally, may be within a concentration range to be used in this field, and for example, when using SOS, it is usually 0.1 to 10%, preferably 0.3 to 4%, and more preferably 0.5 to 2%. In addition, the protein denaturing agent-containing solution may contain, for example, saccharides, salts, such as NaCl, and the like, a preservative, a protein, or the like. Usually 10 μL to 500 μL, preferably 20 μL to 200 μL, and more preferably 50 μL to 100 μL of the protein denaturing agent-containing solution, relative to 1 mg of the Tim carrier of the present invention is used, in (2-A).

—Action (Contact) Condition—

Temperature or time for bringing into acted (contacted) the protein denaturing agent on the complex, in (2-A), is at usually 4.0 to 37° C., preferably 10 to 30° C., and more preferably 20 to 30° C., for usually 5.0 to 60 seconds, preferably 10 to 30 seconds, and more preferably 10 to 20 seconds.

—Tim Protein—

As the Tim protein pertaining to the present invention in obtaining the extracellular membrane vesicle, in bringing into acted (contacted) the protein denaturing agent (that is, in the (2-A)), any one may be used, as long as it is the Tim protein pertaining to the present invention, and, the Tim-4 protein pertaining to the present invention and the Tim-1 protein pertaining to the present invention are preferable, and the Tim-4 protein pertaining to the present invention is particularly preferable, and in obtaining the virus, the Tim-4 protein pertaining to the present invention and the Tim-3 protein pertaining to the present invention are particularly preferable.

Specific Example of (2-A)

(2-A) may be carried out, for example, by the following method. That is, the extracellular membrane vesicles or the viruses are separated from the complex pertaining to the present invention, after carrying out the complex formation step, the complex separation step, and carrying out the washing operation, as needed, by the addition of usually 10 μL to 500 μL, preferably 20 μL to 200 μL, and more preferably 50 μL to 100 μL, relative to 1 mg of the Tim carrier of the present invention, of the solution containing usually 0.1 to 10%, preferably 0.3 to 4.0%, and more preferably 0.5 to 2.0% of the protein denaturing agent (the solution containing the protein denaturing agent in purified water, or the buffer solution which has buffer action at usually pH 6 to 9, and preferably 7 to 8), to the resulting complex pertaining to the present invention, and by subjecting them to a reaction at usually 4 to 37° C., preferably 10 to 30° C., and more preferably 20 to 30° C., for usually 5 to 60 seconds, preferably 10 to 30 seconds, and more preferably 10 to 20 seconds, while stirring by using a vortex mixer, or the like, so as to make acted by bringing into contacted the Tim protein pertaining to the present invention in the complex pertaining to the present invention, and the protein denaturing agent.

<(2-B): Method for Decreasing Calcium Ion Concentration>

(2-B) is a method for separating the extracellular membrane vesicle or the virus pertaining to the present invention from the complex pertaining to the present invention, by decreasing calcium ion concentration bound to the resulting complex pertaining to the present invention, and the calcium ion in the solution containing the complex, after carrying out the complex formation step, the complex separation step, and carrying out the washing operation, as needed.

In this way, the extracellular membrane vesicle or the virus pertaining to the present invention can be obtained in high purity and in an intact state.

By the way, it has been known that the calcium ion is intermediated in binding of the Tim protein and phosphatidyl serine (Immunity 2007 December; 27 (6): 941-951). Co-presence of the calcium ion is required also for the resulting complex pertaining to the present invention, after carrying out the complex formation step, and the complex separation step, and the washing operation, as needed, to maintain binding of the Tim protein pertaining to the present invention in the complex pertaining to the present invention, and the extracellular membrane vesicle or the virus in the sample. It is necessary to maintain 0.5 mM or more of the calcium ion in the solution of the complex pertaining to the present invention, for example, when the complex pertaining to the present invention is made co-present in the solution. Here, a pellet state carrier, after carrying out the complex formation step, the complex separation step, and the washing operation, as needed, is also encompassed, when the complex pertaining to the present invention is made co-present in the solution.

It should be noted that the calcium ion never elutes from the complex unless the obtaining step is carried out, even if the complex pertaining to the present invention is dried, after carrying out the complex formation step, the complex separation step, and the washing operation, as needed, and thus binding of the carrier of the present invention and the extracellular membrane vesicle or the virus is maintained.

It is possible, in (2-B), to separate the extracellular membrane vesicle or the virus pertaining to the present invention from the complex pertaining to the present invention, by decreasing concentration of the calcium ion, entrained from the calcium ion bound to the complex pertaining to the present invention, to lower than required concentration (effective concentration) to maintain binding of the Tim protein pertaining to the present invention and the extracellular membrane vesicle or the virus, as described above.

Specifically, calcium ion concentration in the solution containing the complex pertaining to the present invention may be set usually lower than 0.5 mM, preferably lower than 0.4 mM, and more preferably lower than 0.2 mM.

The method for decreasing (effective) concentration of the calcium ion includes, for example, the following (2-B-i), (2-B-ii), or the like.
(2-B-i) Method for using calcium ion chelating agent.
(2-B-ii) Method for using solution not containing calcium ion.
—(2-B-i) Method for Using Calcium Ion Chelating Agent.—

(2-B-i) is a method for separating the extracellular membrane vesicle or the virus from the complex pertaining to the present invention, after carrying out the complex formation step, the complex separation step, and the washing operation, as needed, and after making acted the calcium ion chelating agent on the calcium ion bound to the resulting complex pertaining to the present invention, and the calcium ion entrained from the solution containing the complex, by decreasing (effective) concentration of the calcium ion bound to the complex pertaining to the present invention, and the calcium ion entrained from the solution containing the complex.

In this way, the extracellular membrane vesicle or the virus pertaining to the present invention can be obtained in high purity and in an intact state.
—Calcium Ion Chelating Agent—

The calcium ion chelating agent may be any compound, as long as it is capable of chelating the calcium ion, and includes, for example, EDTA (ethylenediamine tetraacetate), NTA (nitrilotriacetate), DTPA (diethylenetriamine pentaacetate), GLDA (L-glutamic acid diacetate), HEDTA (hydroxyethylethylenediamine triacetate), GEDTA (ethyleneglycol bis(β-aminoethyl ether)-N,N,N,N-tetraacetate), TTHA (triethylenetetramine-N,N, N',N'',N''',N'''-hexaacetate), HIDA (2-hydroxyethyliminodiacetic acid), DHEG (N,N-bis(2-hydroxtethyl)glycin), CyDTA (trans-1,2-diaminocyclohexane-N,N,N',N'-tetraacetic acid monohydrate), or the like, and EDTA, GEDTA, and CyDTA are preferable. The solution containing the calcium ion chelating agents (hereinafter it may be abbreviated as "the calcium ion chelating agent-containing solution", in some cases) is generally brought into contacted with the pellet-like complex pertaining to the present invention, then the calcium ion bound to the complex pertaining to the present invention, and the calcium ion chelating agent in the calcium ion chelating agent-containing solution are subjected to a reaction, to make acted these calcium ion chelating agents to the calcium ion bound to the complex pertaining to the present invention.

It should be noted that contacting of the calcium ion chelating agent-containing solution and the complex pertaining to the present invention can be carried out, for example, by a method for suspending the complex in the solution (when the carrier is the beads, and the like); a method for dipping the complex in the solution (when the carrier is disc-like piece, a tube, or the like); a method for the addition of the solution to the complex (carrier) (when the carrier is the microplate, the tube, or the like), or the like.
—Calcium Ion Chelating Agent-Containing Solution—

The solution for containing the calcium ion chelating agent, in (2-B-i), may be any one, as long as it dissolves the calcium ion chelating agent, and includes for example, purified water, a buffer solution, or the like. As the buffer solution, the one which has buffer action at usually pH 7.0 to 8.0, preferably 7.2 to 7.6 (for example, PBS, TBS, HBS or the like) is preferable. In addition, buffer agent concentration in these buffer solutions is appropriately selected from a range of usually 5 to 50 mM, and preferably 10 to 30 mM, and NaCl concentration is appropriately selected from a range of usually 100 to 200 mM, and preferably 140 to 160 mM. For example, saccharides, salts, such as NaCl, and the like, a surfactant, a preservative, a protein, or the like, may be contained in the calcium ion chelating agent-containing solution.

Concentration of the calcium ion chelating agent in the calcium ion chelating agent-containing solution, in (2-B-i), is usually 0.5 to 500 mM, preferably 0.5 to 100 mM, and more preferably 0.5 to 50 mM.

The calcium ion chelating agent-containing solution, in (2-B-i), has a pH of usually 6.0 to 9.0, preferably 7.0 to 8.0, and more preferably 7.2 to 7.6.

Amount of the calcium ion chelating agent-containing solution to be mixed in the reaction solution, in (2-B-i), may be such amount that concentration of the calcium ion in the reaction solution attains lower than effective concentration, and the extracellular membrane vesicle or the virus can be separated from the complex pertaining to the present invention.
—Acting (Contacting) Condition—

Temperature or time of bringing into acted (contacted) the calcium ion chelating agent on the complex, in (2-B-i), is usually 4.0 to 37° C., preferably 10 to 30° C., more preferably 20 to 30° C., and usually 5 to 60 seconds, preferably 10 to 30 seconds, and more preferably 10 to 20 seconds.

—Tim Carrier—

Binding form of the Tim protein pertaining to the present invention and the carrier pertaining to the present invention, in (2-B-i), is not limited, as long as the carrier pertaining to the present invention and the Tim protein pertaining to the present invention are bound. The one in which the carrier pertaining to the present invention binds to the SH group of the Tim protein pertaining to the present invention is preferable, and the one in which the carrier pertaining to the present invention binds to the SH group of the Tim-4 protein pertaining to the present invention is particularly preferable, when the extracellular membrane vesicle or the virus is eluted by using the calcium ion chelating agent (that is, in (2-B-i)), because many extracellular membrane vesicle or virus can be obtained.

Specific Example of (2-B-i)

(2-B-i) may be carried out, for example, by the following method. That is, the extracellular membrane vesicle or the virus is separated from the complex pertaining to the present invention, after carrying out the complex formation step, the complex separation step, and carrying out the washing operation, as needed, by the addition of usually 10 µL to 500 µL, preferably 20 µL to 200 µL, and more preferably 50 µL to 100 µL of the solution containing usually 0.5 to 500 mM, preferably 0.5 to 100 mM, and more preferably 0.5 to 50 mM of the calcium ion chelating agent (a solution containing the calcium ion chelating agent, in purified water, or the buffer solution which has buffer action at usually pH 7.0 to 8.0, preferably 7.2 to 7.6), to the resulting complex pertaining to the present invention, relative to 1 mg of the Tim carrier of the present invention, and by subjecting them to a reaction at usually 4.0 to 37° C., preferably 10 to 30° C., and more preferably 20 to 30° C., for usually 5 to 60 seconds, preferably 10 to 30 seconds, and more preferably 10 to 20 seconds, while stirring by using a vortex mixer, or the like.

—(2-B-ii) Method for Using Solution not Containing Calcium Ion—

(2-B-ii) is a method for separating the extracellular membrane vesicle or the virus from the complex pertaining to the present invention, after carrying out the complex formation step, the complex separation step, and the washing operation, as needed, by bringing into contacted the resulting complex pertaining to the present invention to the solution not containing the calcium ion to decrease (dilute) (effective) concentration of the calcium ion bound to the complex pertaining to the present invention.

That is, the extracellular membrane vesicle can be separated from the complex pertaining to the present invention, by decreasing (diluting) (effective) concentration of the calcium ion, which is required to maintain binding of the Tim protein pertaining to the present invention in the complex pertaining to the present invention, and the extracellular membrane vesicle or the virus in the sample, by bringing into contacted the solution not containing the calcium ion to the complex pertaining to the present invention.

It should be noted that contact of the solution not containing the calcium ion and the complex pertaining to the present invention can be carried out, for example, by a method for suspending the complex in the solution (when the carrier is the beads, or the like); a method for dipping the complex in the solution (when the carrier is a disc-like piece, a tube, or the like); a method for the addition of the solution to the complex (carrier) (when the carrier is the microplate, the tube, or the like), or the like.

—Solution not Containing Calcium Ion—

The solution not containing the calcium ion to be added to the resulting complex pertaining to the present invention, in (2-B-ii), may be any one, as long as not denaturing the extracellular membrane vesicle or the virus, and includes for example, purified water, the buffer solution, or the like. As the buffer solution, the one which has buffer action at usually pH 7.0 to 8.0, preferably 7.2 to 7.6 (for example, PBS, TBS, HBS or the like) is preferable. In addition, buffer agent concentration in these buffer solutions is appropriately selected from a range of usually 5 to 50 mM, and preferably 10 to 30 mM, and NaCl concentration is appropriately selected from a range of usually 100 to 200 mM, and preferably 140 to 160 mM. For example, saccharides, salts, such as NaCl, and the like, a surfactant, a preservative, a protein, or the like, may be contained in the solvent not containing the calcium ion.

Amount of the solution not containing the calcium ion to be added to the resulting complex pertaining to the present invention, in (2-B-ii), may be any amount, as long as it is capable of making calcium ion concentration lower than the effective concentration.

Specific Example of (2-B-ii)

(2-B-ii) is carried out by the addition of the solution not containing the calcium ion to the resulting complex pertaining to the present invention, after carrying out the complex formation step, the complex separation step, and as needed, after carrying out the washing operation, in such an amount that attains a calcium ion concentration of usually lower than 0.5 mM, preferably lower than 0.1 mM, more preferably lower than 0.01 mM, in the solution containing the complex pertaining to the present invention.

It should be noted that, the solution containing the calcium ion may be replaced to the solution not containing the calcium ion and/or diluted by the solution not containing the calcium ion, after carrying out the complex formation step, the complex separation step, and after carrying out the washing operation, as needed, so as to attain the final concentration of the calcium ion to lower than the effective concentration, when the resulting complex pertaining to the present invention is present in the solution containing the calcium ion (for example, a reaction solution after carrying out the complex formation step, or a calcium ion-containing washing solution).

(2-B-i) is preferable, because amount (volume increase) of the solution containing the resulting extracellular membrane vesicle by the obtaining step is more in (2-B-ii) than in (2-B-i).

In the above description, the solution brought into contacted and interacted with the complex (the protein denaturing agent-containing solution, the calcium ion chelating agent-containing solution, the solution not containing the calcium ion) results in to contain the carrier and extracellular membrane vesicle or the virus separated (released) from the carrier (complex). Therefore, the solution containing the extracellular membrane vesicle or the virus can be obtained by removing the carrier from the solution, and recovering only the solution.

The extracellular membrane vesicle or the virus can be efficiently removed from the sample, therefore, the sample with less contaminants can be obtained by using the Tim carrier of the present invention.

The removing method of the present invention is capable of removing the extracellular membrane vesicle or the virus in the sample in good precision and efficiently, which cannot be removed completely by conventional methods, such as ultracentrifugal separation method, polymer sedimentation treatment, and the like.

<7. Removing Method of Extracellular Membrane Vesicle or the Virus in Sample>

The method for obtaining the extracellular membrane vesicle or the virus of the present invention (hereinafter it may be abbreviated as "the removing method of the present invention", in some cases) is characterized by including the following steps.

(1) The step for forming the complex of the Tim protein bound to the carrier, and the extracellular membrane vesicle or the virus in the sample, in the presence of the calcium ion (hereinafter, it may be abbreviated as "the complex formation step", in some cases).

(2) The step for separating the complex and the sample (hereinafter, it may be abbreviated as "the complex separation step", in some cases).

<7-1. Complex Formation Step>

The complex formation step in the removing method of the present invention is the same as the complex formation step in the obtaining step of the present invention, and various kinds of preferable conditions are also the same.

<7-2. Complex Separation Step>

The complex separation step in the removing method of the present invention is a step for separating the resulting complex of the Tim protein bound to the carrier pertaining to the present invention (the Tim carrier of the present invention), and the extracellular membrane vesicle or the virus in the sample (the complex pertaining to the present invention), and the sample, after carrying out the complex formation step, to obtain the separated sample.

By carrying out this step, the sample from where the extracellular membrane vesicle or the virus is removed can be obtained.

The complex separation step in the removing method of the present invention may be any method, as long as it is capable of removing the complex pertaining to the present invention from the sample, and includes the same method as the complex separation step in the obtaining method of the present invention. After separating the complex of the present invention and the sample in this way, the separated sample may be obtained (recovered) by a method known per se.

In this way, the extracellular membrane vesicle or the virus in the sample can be removed in good precision and efficiently, which cannot be removed completely by a conventional method, such as the ultracentrifugal separation method or a polymer precipitation treatment, or the like.

In addition, removal of the extracellular membrane vesicle or the virus from the sample can be carried out more efficiently, by repeating the complex formation step and the complex separation step multiple times. Either a new carrier may be used, or a carrier after use may also be re-utilized, in carrying out the complex formation step and the complex separation step repeatedly. In re-utilization of the carrier, the complex pertaining to the present invention, which was removed at the complex separation step in the removing method of the present invention, may be subjected to the same treatment as the obtaining step of the obtaining method of the present invention ((2-B) a method for decreasing calcium ion concentration) using the solution containing the calcium ion chelating agent, or the solution not containing the calcium ion. In this way, the Tim carrier of the present invention and the extracellular membrane vesicle or the virus can be separated from the complex pertaining to the present invention. That is, removal of the extracellular membrane vesicle or the virus in the sample can be carried out in good precision and efficiently, by re-utilization of the Tim carrier of the present invention, because the Tim carrier of the present invention can be used again in the removing method of the present invention.

The extracellular membrane vesicle or the virus in the sample can be detected in good precision and in high sensitivity, by using the Tim carrier of the present invention.

<8. Method for Detecting Extracellular Membrane Vesicle or the Virus in Sample>

A method for detecting the extracellular membrane vesicle or the virus of the present invention (hereafter it may be abbreviated as "the detection method of the present invention", in some cases) is characterized by comprising the following steps:

(1) A step for forming the complex of the Tim protein bound to the carrier, and the extracellular membrane vesicle or the virus in the sample, in the presence of the calcium ion (complex formation step).

(2) A step for detecting the complex (detection step).

<8-1. Complex Formation Step>

The complex formation step in the detection method of the present invention is a step for forming the complex of the Tim carrier of the present invention, and the extracellular membrane vesicle or the virus in the sample, in the presence of the calcium ion.

—Sample Pertaining to the Present Invention—

The sample pertaining to the present invention is the same as the sample in the obtaining method of the present invention.

—Calcium Ion Concentration and Origin of Calcium Ion—

In the detection method of the present invention, the calcium ion is present in forming the complex of the Tim carrier pertaining to the present invention, and the extracellular membrane vesicle or the virus in the sample (the complex pertaining to the present invention).

In the detection method of the present invention, calcium ion concentration, in bringing into contacted the Tim carrier pertaining to the present invention, and the extracellular membrane vesicle or the virus in the sample pertaining to the present invention, is usually 0.5 to 100 mM, preferably 1 to 10 mM, and more preferably 2 to 5 mM. It should be noted that it is not without saying that the calcium ion of such concentration as described above is necessary in the solution containing the complex, until the complex of the Tim carrier pertaining to the present invention, and the extracellular membrane vesicle or the virus in the sample pertaining to the present invention is formed and the detection step is carried out, that is, until the complex is subjected to the detection step.

In addition, origin of the calcium ion is not especially limited, and includes the same as specific example as origin of the calcium ion in the obtaining method of the present invention.

It should be noted that as a method for the calcium ion to be present in bringing into contacted the Tim carrier of the present invention, and the extracellular membrane vesicle or the virus in the sample, generally the calcium ion as described above may be contained in the sample, in such an amount that attains a calcium ion concentration of the above range, in bringing into contacted the Tim carrier of the present invention, and the extracellular membrane vesicle or the virus in the sample.

The solution for containing the calcium ion is the same as the solution for containing (dissolving or suspending) the extracellular membrane vesicle or the virus pertaining to the present invention, and specific examples, and the like, are also the same.

—Amount of Sample—

Amount of the sample, in the complex formation step of the detection method of the present invention, is usually 0.1 to 1000 mL, preferably 0.1 to 500 mL, and more preferably 0.1 to 100 mL, relative to 1 mg of the Tim carrier of the present invention, in using the beads as the carrier pertaining to the present invention, and is usually 50 μL to 300 μL, and preferably 100 μL to 200 μL, relative to 1 well, in using the microplate as the carrier pertaining to the present invention.

—Temperature—

In the complex formation step of the detection method of the present invention, temperature in bringing into contacted the Tim carrier of the present invention, and the extracellular membrane vesicle or the virus in the sample, is usually 2 to 37° C., and preferably 2 to 30° C.

—Time—

In the complex formation step of the detection method of the present invention, contacting time of the Tim protein pertaining to the present invention and the sample is usually 0.5 to 24 hours, preferably 1 to 20 hours, and more preferably 1 to 12 hours.

—Tim Protein—

As the Tim protein pertaining to the present invention in the detection method of the present invention, any one may be used, as long as being the Tim protein pertaining to the present invention, however, the Tim-4 protein pertaining to the present invention is particularly preferable.

—Tim Carrier—

Binding form of the Tim protein pertaining to the present invention and the carrier pertaining to the present invention is not especially limited, as long as the carrier pertaining to the present invention and the Tim protein pertaining to the present invention are bound, and, the one where the carrier pertaining to the present invention is bound to the SH group of the Tim protein pertaining to the present invention is preferable, and the one where the carrier pertaining to the present invention is bound to the SH group of the Tim-4 protein pertaining to the present invention is particularly preferable, because they are capable of detecting the extracellular membrane vesicles or the viruses in high sensitivity.

Specific Example of Complex Formation Step in Detection Method of the Present Invention The complex formation step in the detection method of the present invention may be carried out, for example, by the following method.

That is, in using the beads as the carrier pertaining to the present invention, the complex of the Tim protein bound to the carrier pertaining to the present invention, and the extracellular membrane vesicles or the viruses in the sample is formed, by bringing into contacted usually 0.001 to 20 mg, preferably 0.005 to 10 mg, and more preferably 0.01 to 6.0 mg of the Tim carrier of the present invention, relative to 1 mL of the solution after mixing the Tim carrier of the present invention, and the solution containing the sample and the calcium ion (the solution in forming the complex pertaining to the present invention); the solution containing the calcium ion, in such an amount that attains a concentration of the calcium ion of usually 0.5 to 100 mM, preferably 1.0 to 10 mM, and more preferably 2.0 to 5.0 mM, in the solution in forming the complex pertaining to the present invention; and usually 0.1 to 1000 mL, preferably 0.1 to 500 mL, and more preferably 0.1 to 100 mL of the sample, relative to 1 mg of the Tim carrier of the present invention; at usually 2 to 37° C., and preferably 2 to 30° C., for usually 0.5 to 24 hours, preferably 1 to 20 hours, and more preferably 1 to 12 hours.

In using the microplate as the carrier pertaining to the present invention, the complex of the Tim carrier of the present invention, and the extracellular membrane vesicles or the viruses in the sample (the complex pertaining to the present invention) is formed by the addition of the solution containing the calcium ion, in such an amount that attains a calcium ion concentration of usually 0.5 to 100 mM, preferably 1.0 to 10 mM, and more preferably 2.0 to 5.0 mM, in the solution in forming the complex pertaining to the present invention, and usually 50 μL to 300 μL, and preferably 100 μL to 200 μL of the sample pertaining to the present invention, relative to 1 well, to each well of the microplate on which the Tim protein is immobilized (the Tim carrier of the present invention) to be subjected to a reaction at usually 2° C. to 37° C., and preferably 2° C. to 30° C., for usually 0.5 hour to 24 hours, preferably 1 hour to 20 hours, and more preferably 1 to 12 hours.

<8-2. Detection Step in Detection Method of the Present Invention>

The detection step in the detection method of the present invention is a step for detecting the complex of the Tim carrier of the present invention, and the extracellular membrane vesicle or the virus in the sample (the complex pertaining to the present invention), by carrying out the complex separation step of the sample, as needed, after carrying out the complex formation step, and after carrying out the washing operation, as needed.

—Complex Separation Step—

The complex separation step in the detection method of the present invention is, after the complex formation step, a step for removing the sample from the resulting complex of the Tim protein bound to the carrier pertaining to the present invention (the Tim carrier of the present invention), and the extracellular membrane vesicle or the virus in the sample (the complex pertaining to the present invention), as needed.

The complex separation step in the detection method of the present invention may be any method, as long as it is capable of separating the complex pertaining to the present invention and the sample, in other words, is capable of what is called B/F separation, and the B/F separation method usually used in this field can be used. Such a method includes the same one as the complex separation step in the obtaining method of the present invention.

Specific Example of Complex Separation Step

The complex separation step in the detection method of the present invention may be carried out, according to a usual method in this field, and, in using the magnetic beads as the carrier pertaining to the present invention, for example, a container used in the complex formation step is placed on a magnet stand, as needed, to collect the complex pertaining to the present invention on the tube wall using magnetic force, to remove the sample of the supernatant.

In using the microplate as the carrier pertaining to the present invention, the sample is removed using a micropipette or a plate washer, as need, for example, from the microplate after carrying out the complex formation step.

<8.3. Washing Operation>

After the complex formation step, and carrying out the complex separation step, as needed, the resulting complex pertaining to the present invention may be washed further using a washing solution containing the calcium ion (hereafter it may be abbreviated as "washing operation", in some cases), as needed. Impurities in the sample pertaining to the present invention, such as cell-derived components, and the like, adhered at the carrier surface pertaining to the present invention can be removed by the washing operation. Various conditions of the washing method, and the like, are the same as those in the washing operation in the obtaining method of the present invention.

Specific Example of Washing Operation

In carrying out the washing operation in a tube having a volume of 1.5 mL, using the magnetic beads as the carrier pertaining to the present invention, firstly, usually 100 μL to 1500 μL, and preferably 200 μL to 1000 μL of the washing solution containing the calcium ion (a buffer solution, containing, for example, usually 0.5 to 100 mM, preferably 1 to 10 mM, and more preferably 2 to 5 mM of the calcium ion, and having buffering action at pH 7.0 to 8.0, and preferably 7.2 to 7.6, and not precipitating calcium. However, the phosphate buffer is not preferable because it precipitates by binding with calcium.) is added into a container containing the resulting complex pertaining to the present invention by the complex separation step, and stirred. After that, the container is placed at the magnet stand to collect the complex on the tube wall, using magnetic force, and the solution in the container is discarded. The washing operation may be carried out repeatedly several times, as needed.

In using the microplate as the carrier pertaining to the present invention, firstly, usually 100 μL to 300 μL, and preferably 200 μL to 300 μL of the calcium ion-containing washing solution (for example, the buffer solution containing usually 0.5 to 100 mM, preferably 1 to 10 mM, and more preferably 2.0 to 5.0 mM of the calcium ion, and having buffering action at pH 7.0 to 8.0, and preferably 7.2 to 7.6, and not precipitating calcium. However, the phosphate buffer is not preferable because it precipitates by binding with calcium.) is added in a well containing the resulting complex pertaining to the present invention by the complex separation step, and then the added washing solution is removed. The washing operation may be carried out repeatedly several times, as needed.

<8-4. Detection Step>

The detection step in the detection method of the present invention may be any method, as long as it is a method capable of detecting presence or absence and/or amount of the complex pertaining to the present invention, and any method known per se to be used for immunological measurement can be used.

The detection step of the present invention is not especially limited, except for using the Tim carrier of the present invention prepared by the method as described above. Such an immunological measurement method includes all of, for example, a measurement method utilizing an agglutination reaction, such as a reversed passive agglutination reaction method ("(sequel) Biochemical Experimental Course 5, Immuno-biochemical Research Method" p. 36-37, Tokyo Kagaku Dojin Co., Ltd.; "Kanai's Manual of Clinical Laboratory Medicine", 30th edition, p. 844-845, Kanehara Publishing Co., Ltd., or the like.), for example, an optical measurement method applying the agglutination reaction, such as nephelometry ("Kanai's Manual of Clinical Laboratory Medicine", 30th edition, p. 851-853, Kanehara Publishing Co., Ltd., or the like.), immunoturbidimetry ("Kanai's Manual of Clinical Laboratory Medicine", 30th edition, p. 853-854, Kanehara Publishing Co., Ltd., or the like.), radioimmunoassay (RIA) ("(sequel) Biochemical Experimental Course 5, Immuno-biochemical Research Method" p. 57-61, Tokyo Kagaku Dojin Co., Ltd.; "Kanai's Manual of Clinical Laboratory Medicine", 30th edition, p. 856-862, Kanehara Publishing Co., Ltd., or the like.), immune-radiometric assay (IRMA) ("Kanai's Manual of Clinical Laboratory Medicine", 30th edition, p. 856-862, Kanehara Publishing Co., Ltd., or the like.), enzyme immunoassay (EIA) ("(sequel) Biochemical Experimental Course 5 Immuno-biochemical Research Method" p. 62-65, Tokyo Kagaku Dojin Co., Ltd.; "Kanai's Manual of Clinical Laboratory Medicine", 30th edition, p. 862-865, Kanehara Publishing Co., Ltd.; JP-A-56-106154; JP-A-58-23796, or the like.), solid phase enzyme immunoassay (ELISA) ("Kanai's Manual of Clinical Laboratory Medicine", 30th edition, p. 1145-1149, Kanehara Publishing Co., Ltd., or the like.), fluorescence/luminescence immunoassay ("Kanai's Manual of Clinical Laboratory Medicine", 30th edition, p. 865-867, Kanehara Publishing Co., Ltd., or the like.), the flow cytometry method, or the like, and the solid phase enzyme immunoassay (ELISA) or the flow cytometry is preferable.

When the detection step of the present invention is carried out by the solid phase enzyme immunoassay (ELISA) or the flow cytometry, it may be carried out, according to a method known per se, as long as the complex pertaining to the present invention is a detection object. There is included, for example, a method for using a labeled primary antibody which is a primary antibody labeled with a labelling substance, such as an anti-extracellular membrane vesicle antibody or an anti-virus antibody capable of binding with the extracellular membrane vesicle or the virus, or a method for using the primary antibody and a labeled secondary antibody that binds to the primary antibody. Any labeled primary antibody and labeled secondary antibody may be used, as long as they are used for a labeled antibody of the ELISA method or the flow cytometry method, and includes, for example, a fluorescent labeled antibody labeled with a fluorescent substance, such as Cy3, Cy5, FITC, rhodamine, PE or the like, an enzyme labeled antibody labeled with an enzyme, such as a peroxidase, an alkaline phosphatase, or the like, the magnetic beads labeled antibody, an infrared labeled antibody, or the like. Fluorescence, or the like, pertaining to these labeled antibodies may be measured by a method known per se, corresponding to the labeling method (labeling substance) of the labeled antibody.

—Diluent of Labelled Antibody—

A diluent of the labelled primary antibody, or the primary antibody and the labelled secondary antibody to be subjected to a reaction with the complex pertaining to the present invention, in the detection method of the present invention, may be any one, as long as it does not inhibit binding of the complex of the Tim protein and the extracellular membrane vesicle or the virus in the sample, and the antibody, except for containing the calcium ion, and includes, for example, water, or the buffer solution which has buffer action at pH 7.0 to 8.0, and preferably 7.2 to 7.6 (for example, TBS, HBS or the like), or the like. It should be noted that the phosphate buffer is not preferable, because it precipitates by binding with calcium. In addition, buffer concentration in theses buffer solutions is appropriately selected from a range of usually 5 to 50 mM, and preferably 10 to 30 mM, and NaCl concentration is appropriately selected from a range of usually 100 to 200 mM, and preferably 140 to 160 mM. For example, saccharides, salts such as NaCl, and the like, a surfactant, a preservative, a protein, or the like, may be contained in these solutions, as long as in such amount that does not inhibit binding of the complex of the Tim carrier pertaining to the present invention and the extracellular membrane vesicle or the virus in the sample. The surfactant includes, for example, Tween 20, and surfactant concentration in the solution for containing the extracellular membrane vesicle or the virus relevant to the present invention is usually 0.00001% to 0.2%, and preferably 0.0005% to 0.1%. In addition, concentration of the calcium ion contained in the diluent is usually 0.5 to 100 mM, preferably 1 to 10 mM, and more preferably 2 to 5 mM.

In the detection method of the present invention, dilution degree of the labeled primary antibody or the primary antibody and the labeled secondary antibody to be subjected to a reaction with the complex pertaining to the present invention, is different depending on activity or concentration of the antibody, however, it is usually 10-fold to 1000000-fold, and preferably 1000-fold to 100000-fold.

In the detection method of the present invention, amount of the diluent of the labeled primary antibody, or the primary antibody and the labeled secondary antibody to be subjected to a reaction with the complex pertaining to the present invention, is usually 0.1 mL to 1000 mL, preferably 0.1 mL to 500 mL, and more preferably 0.1 mL to 100 mL, relative to 1 mg of the carrier pertaining to the present invention, when the carrier pertaining to the present invention is the beads; and it is usually 50 μL to 300 μL, preferably 50 μL to 200 μL, and more preferably 50 μL to 100 μL, relative to 1 well, when the carrier pertaining to the present invention is the microplate.

—Reaction (Contacting) Temperature—

In the detection method of the present invention, reaction temperature of the complex pertaining to the present invention, and the labelled primary antibody, or the primary antibody and the labelled secondary antibody, is usually 2 to 37° C., preferably 11 to 337° C., and more preferably 20 to 30° C.

—Reaction (Contacting) Time—

In the detection method of the present invention, reaction time of the complex pertaining to the present invention and the labelled primary antibody, or the primary antibody and the labelled secondary antibody, is usually 0.5 to 12 hours, preferably 1 to 4 hours, and more preferably 1 to 2 hours.

It is possible to remove the unreacted labelled primary antibody, by the washing operation after subjecting the complex pertaining to the present invention and labelled primary antibody to a reaction, when the labelled primary antibody is used in the detection operation of the detection step in the detection method of the present invention. In addition, it is possible to remove the unreacted primary antibody and the labelled secondary antibody, by the washing operation after subjecting the complex pertaining to the present invention and the primary antibody to a reaction, or after subjecting the complex pertaining to the present invention and the complex of primary antibody and the labelled secondary antibody to a reaction, when the primary antibody and the labelled secondary antibody are used. As the washing method, a washing method usually used in this field can be used, except for using the washing solution containing the calcium ion, as described above. The washing solution containing the calcium ion, to be used in the washing operation, may be any solution, as long as it contains usually 0.5 to 100 mM, preferably 1 to 10 mM, and more preferably 2 to 5 mM of the calcium ion, and does not inhibit binding of the extracellular membrane vesicles or the viruses pertaining to the present invention in the complex, the Tim protein pertaining to the present invention, and the carrier of the present invention, and includes for example, a buffer solution containing usually 0.5 to 100 mM, preferably 1 to 10 mM, and more preferably 2 to 5 mM of the calcium ion, and having buffer action at pH 7.0 to 8.0, and preferably 7.2 to 7.6, and not precipitating calcium (for example, TBS, HBS). It should be noted that the phosphate buffer is not preferable, because it precipitates by binding with calcium. In addition, buffer agent concentration in these buffer solutions is appropriately selected from a range of usually 5 to 50 mM, and preferably 10 to 30 mM, and NaCl concentration is appropriately selected from a range of usually 100 to 200 mM, and preferably 140 to 160 mM. This solution may contain, for example, saccharides, salts such as NaCl, and the like, a surfactant, a preservative, a protein, or the like, as long as in such an amount that does not inhibit binding of the extracellular membrane vesicles or the viruses pertaining to the present invention in the complex, the Tim protein pertaining to the present invention and the carrier of the present invention. The surfactant includes, for example, Tween 20 (produced by Wako Pure Chemical Industries Co.), or the like, and surfactant concentration in the washing solution is usually 0.00001 to 0.2%, and preferably 0.0005 to 0.1%. When the carrier pertaining to the present invention is the beads, it is usually 0.1 mL to 1000 mL, and preferably 0.1 mL to 500 mL, and more preferably 0.1 mL to 100 mL, relative to 1 mg of the carrier pertaining to the present invention. Amount of the washing solution to be used in 1 well is usually 100 μL to 300 μL, and preferably 200 μL to 300 μL, and the washing solution is removed after the addition, when the carrier pertaining to the present invention is the microplate. The washing operation may be repeated plural times, as needed.

—Detection—

The labelled substance of the labelled primary antibody or the labelled secondary antibody includes peroxidase, alkali phosphatase, or the like, when the detection step in the detection method of the present invention is chromogenic detection. These labelled substances may be detected, according to the known method per se, in response to each labelled substance.

The chromogenic substrate solution in the chromogenic detection may be any one, as long as it is a chromogenic substrate solution usually used in this field, and includes, when peroxidase is used as the labelled substance, for example, a TMB (tetramethyl benzidine) solution or an OPD (o-phenylene diaime) solution, and preferably includes the TMB solution.

Amount of the chromogenic substrate in the chromogenic detection is usually 0.1 mL to 1000 mL, preferably 0.1 mL to 500 mL, and more preferably 0.1 mL to 100 mL, relative to 1 mg of the carrier pertaining to the present invention, when the carrier pertaining to the present invention is the beads, and it is usually 50 μL to 300 μL, preferably 50 μL to 200 μL, and more preferably 50 μL to 100 μL, relative to 1 well, when the carrier pertaining to the present invention is the microplate.

Reaction time with the chromogenic substance is usually 5 minutes to 60 minutes, and preferably 10 minutes to 40 minutes, when the detection step in the detection method of the present invention is the chromogenic detection.

Temperature of a reaction with the chromogenic substrate solution is usually 2° C. to 37° C., and preferably 20° C. to 30° C., when the detection step in the detection method of the present invention is the chromogenic detection.

As a reaction stopping solution to stop the chromogenic reaction, a strong acid, such as usually 1 mol/L of hydrochloric acid, or 1 mol/L of sulfuric acid, or the like, is added in the same amount as the chromogenic substrate solution to stop the chromogenic reaction, when the detection step in the detection method of the present invention is the chromogenic detection.

Fluorescence is measured by the addition of a fluorescence measurement solution to the complex of the complex pertaining to the present invention and the labelled primary antibody, or the complex of the complex pertaining to the present invention and the primary antibody and the labelled secondary antibody, when the detection step in the detection method of the present invention is fluorescence detection, and a fluorescence substance is used as the labelled substance of labelled primary antibody or the labelled secondary antibody. Any of the fluorescence measurement solution usually used in this field (hereinafter, it may be abbreviated as "measuring solution", in some cases) may be used, except for using the calcium ion containing-fluorescence measurement solution, as the fluorescence measurement solution. The calcium ion-containing measurement solution to be used in the fluorescence measurement solution may be any one, as long as it contains usually 0.5 to 100 mM, preferably 1 to 10 mM, and more preferably usually 2 to 5 mM of the calcium ion, and does not affect binding of the extracellular membrane vesicle or the virus pertaining to the present invention in the complex, the Tim protein pertaining to the present invention, and the carrier of the present invention, and includes, for example, the buffer solution containing usually 0.5 to 100 mM, preferably 1 to 10 mM, and more preferably 2 to 5 mM of the calcium ion, and having buffer action at pH 7.0 to 8.0, and preferably 7.2 to 7.6, and not precipitating calcium (for example, TBS, HBS). It should be noted that the phosphate buffer is not preferable because it precipitates by binding with calcium. In addition, buffer agent concentration in these buffer solutions is appropriately selected from a range of usually 5 to 50 mM, preferably 10 to 30 mM, and NaCl concentration is appropriately selected from a range of usually 100 to 200 mM, preferably 140 to 160 mM. This solution may contain, for example, saccharides, salts, such as NaCl, and the like, a surfactant, a preservative, a protein, such as BSA, as long as in such an amount that does not inhibit binding of the extracellular membrane vesicle or the virus pertaining to the present invention in the complex, the Tim protein pertaining to the present invention, and the carrier of the present invention. The surfactant includes, for example, Tween 20 (produced by Wako Pure Chemical Industries Co.), or the like, and surfactant concentration in the washing solution is usually 0.00001 to 0.2%, and preferably 0.0005 to 0.1%. Amount of the fluorescence measurement solution to be used, in 1 well, in the detection method of the present invention is usually 50 µL to 300 µL, and preferably 50 µL to 200 µL, when the detection method of the present invention is the ELISA method, and the carrier pertaining to the present invention is the microplate. It is usually 0.1 mL to 1000 mL, preferably 0.1 mL to 500 mL, more preferably 0.1 mL to 100 mL, relative to 1 mg of the carrier pertaining to the present invention, when the detection method pertaining to the present invention is the flow cytometry method, and the carrier pertaining to the present invention is the beads.

Specific Example of Detection Step in Detection Method of the Present Invention

When the detection step is carried out by the ELISA method, using, for example, the microplate, as the carrier pertaining to the present invention, after the complex formation step, and the complex separation step, as needed, and further after carrying out the washing operation, as needed, to each well of the microplate, on which the resulting Tim protein pertaining to the present invention is immobilized, usually 50 µL to 300 µL, preferably 50 µL to 200 µL, and more preferably 50 µL to 100 µL of a diluted solution, which was obtained by diluting a peroxidase labeled primary antibody or a unlabeled primary antibody, against the extracellular membrane vesicles or the viruses, using usually 10 times to 1000000 times, and preferably 1000 times to 100000 times of a diluent containing usually 0.5 to 100 mM, preferably 1 to 10 mM, and more preferably 2 to 5 mM of the calcium ion, is added relative to 1 well, and subjected to a reaction at usually 2 to 37° C., and preferably 11 to 37° C., for usually 0.5 to 12 hours, and preferably 1 to 4 hours, and next each well is washed using a washing buffer containing the calcium ion (a solution which contains usually 0.5 to 100 mM, preferably 1 to 10 mM, and more preferably 2 to 5 mM of the calcium ion, and does not influence binding of the extracellular membrane vesicles or the viruses pertaining the present invention in the complex, the Tim protein pertaining to the present invention, and the carrier of the present invention). In using the unlabeled primary antibody, each well is washed using usually 100 µL to 300 µL, and preferably 200 µL to 300 µL of the washing buffer containing the calcium ion (the solution which contains usually 0.5 to 100 mM, preferably 1 to 10 mM, and more preferably 2 to 5 mM of the calcium ion, and does not influence binding of the extracellular membrane vesicles or the viruses pertaining to the present invention in the complex, the Tim protein pertaining to the present invention, and the carrier of the present invention), after further subjecting the peroxidase labeled second antibody to a reaction with the primary antibody by the same method. Next, usually 50 µL to 300 µL, preferably 50 µL to 200 µL, and preferably 50 µL to 100 µL of a chromogenic substrate solution, such as a TMB solution, an OPD solution, or the like, relative to 1 well, is added to each well and subjected them to a reaction at usually 2° C. to 37° C., and preferably 20° C. to 30° C., for usually 5 minutes to 60 hours, and preferably 10 minutes to 40 hours. After that, a reaction termination solution such as 1 mol/L hydrochloric acid or 1 mol/L sulfuric acid, or the like, is added in the same amount as the chromogenic substrate solution to terminate a color reaction, and measure absorbance using a microplate reader.

When the detection step is carried out by the flow cytometry method using, for example, the beads, as the carrier pertaining to the present invention, after the complex formation step, and the complex separation step, as needed, and further after carrying out the washing operation, as needed, to the beads, on which the resulting Tim protein pertaining to the present invention is immobilized, usually 0.1 mL to 1000 mL, preferably 0.1 mL to 500 mL, and more preferably 0.1 mL to 100 mL of the diluted solution, which was obtained by diluting a fluorescent labelled primary antibody, or a unlabeled primary antibody, using usually 10 times to 1000000 times, and preferably 1000 times to 100000 times of the diluent containing usually 0.5 to 100 mM, preferably 1 to 10 mM, and more preferably 2 to 5 mM of the calcium ion, is added, relative to 1 mg of the carrier pertaining to the present invention, and subjected them to a reaction at usually 2 to 37° C., and preferably 11 to 37° C., for usually 0.5 to 12 hours, and preferably 1 to 4 hours, and next the beads are washed using the washing buffer containing the calcium ion (the solution which contains usually 0.5 to 100 mM, preferably 1 to 10 mM, and more preferably 2 to 5 mM of the calcium ion, and does not influence binding of the extracellular membrane vesicles or the viruses pertaining to the present invention in the complex, the Tim protein pertaining to the present invention, and the carrier of the present invention). In using the unlabeled primary antibody, the beads are washed using the washing buffer containing the calcium ion (the solution which contains usually 0.5 to 100 mM, preferably 1 to 10 mM, and more preferably 2 to 5 mM of the calcium ion, and does not influence binding of the extracellular membrane vesicles or the viruses pertaining to the present invention in the complex, the Tim protein pertaining to the present invention, and the carrier of the present invention), after further subjecting a fluorescent labelled second antibody to a reaction with the primary antibody by the same method. Next, after suspending the beads by the addition of usually 0.1 mL to 1000 mL, preferably 0.1 mL to 500 mL, and preferably 0.1 mL to 100 mL of a fluorescence measurement solution, relative to 1 mg of the carrier pertaining to the present invention, fluorescence intensity is measured using a flow cytometer.

Affinity of antibodies for antigens is generally said to have Kd at a level of 10 nM to 100 pM. On the other hand, binding strength of the Tim-4 protein and phosphatidylserine has been reported to be Kd=about 2 nM (Nature (Impact Factor: 41.46). December 2007; 450 (7168): 435-9. DOI: 10.1038/nature 06307). It was surprising that sensitivity of the detection method of the present invention for detecting the extracellular membrane vesicle or the virus, and the like, using the Tim protein pertaining to the present invention is higher as compared with a conventional method for detecting the extracellular membrane vesicle or the virus using the antibodies, although affinity of antibodies against surface antigens of the extracellular membrane vesicle or the virus envelope membranes, and their surface antigens is comparable degree to affinity between phosphatidylserine on the surface of the extracellular membrane vesicle or the virus envelope membrane and the Tim protein of the present invention.

The extracellular membrane vesicle or the virus obtained by the method of the present invention can be used for analyzing proteins and nucleic acids, such as microRNAs, which are present on the surface or inside of the particle, and for basic research of functional analysis of the extracellular membrane vesicle or the virus, or the like. In addition, it can also be utilized for diagnostic drugs, medicines, vaccines, or the like.

<9. Kit for Capturing Extracellular Membrane Vesicle or the Virus of the Present Invention>

The Kit for capturing the extracellular membrane vesicle or the virus of the present invention comprises, as components:
1. a reagent comprising the Tim protein pertaining to the present invention, and a reagent comprising the carrier pertaining to the present invention, or 2. a reagent comprising the Tim carrier of the present invention.

These kits may further contain at least one kind selected from the calcium ion-containing washing solution, the protein denaturing agent-containing solution, and the calcium ion chelating agent-containing solution. Specific examples of each component, preferable aspects, and the like, are as described above.

In addition, in the reagents contained in these kits, there may be contained reagents usually used in this field, for example, the buffer agent, a sensitizer, a surfactant, a preservative (for example, sodium azide, salicylic acid, benzoic acid, or the like), a stabilizer (for example, albumin, globulin, water-soluble gelatin, the surfactant, saccharides, or the like), an activator, an effect avoidance agent of co-present substances, and the one usually used in this field, which does not inhibit stability with co-present reagents, and does not inhibit a reaction or binding of the Tim protein and the carrier pertaining to the present invention, the Tim protein pertaining to the present invention bound to the carrier pertaining to the present invention and the extracellular membrane vesicle in the sample. In addition, concentration ranges, and the like, of these reagents, and the like, may be used, according to appropriate selection of the usually used concentration ranges, and the like, to exert effect each of the reagents has.

Furthermore, the kit of the present invention may contain description of the obtaining method of the present invention, the removing method of the present invention, the detection method of the present invention, or the like. The "description" means an instruction manual, a package insert, a pamphlet (leaflet), or the like, of the kit, in which features, principles, operation procedures, determination procedures, and the like, of the method are substantially described by documents or figures.

Explanation will be given below on the present invention in more detail with reference to Experimental Examples, Examples and Comparative Examples, however, the present invention should not be limited at all by them.

It should be noted that the Tim protein of the present invention, and the T-cell immunoglobulin and mucin domain-containing molecule-2 (Tim-2) protein (hereinafter it may be abbreviated as "the Tim-2 protein", in some cases) together may be abbreviated as "the Tim family protein", in some cases.

EXAMPLES

Experimental Example 1. Preparation of Fc Tag Fusion Type Tim-4 Protein

The Fc tag fusion type Tim-4 protein was prepared by the following method.
<(1) Vector Construction and Culture Conditions>

First, a vector was constructed for expression of the Fc tag fusion type Tim-4 protein in which a cDNA (SEQ ID NO: 26) encoding the N-terminal 1 to 273 amino acid region of a mouse-derived Tim-4 protein was incorporated into the SalI-EcoRV site of a pEF-Fc vector (hereinafter it may be abbreviated as "the pEF-Tim-4-Fc", in some cases).

On the other hand, 293 T cells (RIKEN BRC) were each cultured for 1 day using 25 sheets of 150 mm dishes for cell culture, using 20 mL of DMEM (produced by Nacalai Tesque, Inc.) containing 10% FBS (produced by BioWest Co., Ltd.). Thereafter, for each dish, 25 mL of DMEM containing 10% FBS was replaced with 25 mL of FBS-free DMEM.

Thereafter, 20 μg of the pEF-Tim-4-Fc was transfected into each of 293 T cells, using Polyethylenimine "MAX" (produced by Polysciences Inc.), according to a usual method. After transfection, the 293 T cells after transfection were each cultured for 4 days under condition at 37° C., and 5% $CO_2$.
<(2) Purification>

The resulting culture of the transfected 293T cells was each subjected to centrifugal separation treatment (800×G, for 5 minutes) to recover and pool each culture supernatant. The resulting culture supernatant was subjected to filtration treatment using a Rapid Flow 0.2 μm filter unit (manufactured by Thermo Fisher Scientific Inc.) to separate impurities and obtain a culture supernatant filtrate.

Subsequently, 500 mL of the resulting culture supernatant filtrate was added to a poly prep column (manufactured by Bio-Rad Laboratories, Inc.) packed with 700 μL of a nProtein A Sepharose 4 Fast Flow (produced by GE Healthcare Japan; Protein A has affinity for the Fc tag) washed with 20 mL of PBS, and the Fc tag fusion type Tim-4 protein in the culture supernatant filtrate was bound on the nProtein A Sepharose 4 Fast Flow. Then, the nProtein A Sepharose 4 Fast Flow was washed with 20 mL of PBS. Thereafter, using each 600 µL of a 0.1 M glycine hydrochloride buffer solution (pH 3.0), elution was carried out 5 times, in 100 µL of a 1 M Tris buffer solution (pH 8.0), as a neutralizing solution, to obtain each 600 µL of five eluate fractions.

Absorbance at 280 nm was measured for each of the resulting five eluate fractions to determine presence or absence of a protein. Fractions containing the protein were mixed into one portion, and concentrated by ultrafiltration using an Amicon Ultra-0.5 mL, 10K centrifugal filter column (manufactured by Millipore Corp.), and then the solvent was replaced with 40 µL of PBS using the same column. Then, amount of the protein in the eluate replaced with PBS was quantitated by a BCA method, then concentration of the protein was adjusted to 88 µg/mL using PBS to obtain the PBS solution containing the Fc tag fusion type mouse-derived Tim-4 protein (it may be abbreviated as "the Fc tag fusion type mTim-4 protein", in some cases) (the solution may be abbreviated as "the Fc tag fusion type mTim-4 protein-containing PBS solution", in some cases).

Experimental Example 2. Preparation of FLAG Tag Fusion Type Tim-4 Protein

The FLAG tag fusion type Tim-4 protein was prepared by the following method.
<(1) Vector Construction and Culture Conditions>

First, a FLAG tag fusion type mouse-derived Tim-4 protein cDNA (a cDNA encoding an amino acid sequence fused with 1×FLAG at the C-terminal of the N-terminal 1 to 273 amino acid region of the mouse-derived Tim-4 protein, SEQ ID NO: 33 (containing a stop codon (taa) and a nucleotide sequence encoding 1×FLAG, in this regard, however, excluding the restriction enzyme site), produced by Fasmac Co., Ltd.), was incorporated in an XhoI/BamHI site of a pCAG-Neo vector (produced by Wako Pure Chemical Industries, Ltd.) to construct a vector for expressing the FLAG tag fusion type Tim-4 protein (hereinafter it may be abbreviated as "the pCAG-Tim-4-FLAG", in some cases).

On the other hand, the 293 T cells (RIKEN BRC) were cultured for 1 day using 50 mL DMEM (produced by Wako Pure Chemical Industries, Ltd.) containing 10% FBS (produced by Biosera) in a 225 cm$^2$ flask by seeding, so that the cells grow to 70% to 90% at the time of transfection. Thereafter, 60 µg of the pCAG-Tim-4-FLAG was transfected into the 293 T cells cultured for 1 day using a Lipofectamine 2000 (produced by Thermo Fisher Scientific Inc.), according to a usual method. After transfection, the 293 T cells transfected were cultured for 1 day under condition at 37° C. and 5% $CO_2$. Thereafter, the whole amount of the culture solution was removed, the transfected 293 T cells were washed twice with 10 mL of PBS, and the culture solution was exchanged with 50 mL of an Opti-MEM (produced by Thermo Fisher Scientific Inc.) to culture for 3 days under condition at 37° C. and 5% $CO_2$.
<(2) Purification>

The culture solution of the 293 T cells transfected, after three days of culture, was subjected to centrifugal separation treatment (300×G, for 5 minutes) to recover the culture supernatant. The recovered culture supernatant was further subjected to centrifugal separation treatment three times (first time: 300×G, for 3 minutes, second time: 1200×G, for 20 minutes, and third time: 10000×G, for 20 minutes) to obtain a supernatant, where impurities were separated. The resulting supernatant was subjected to ultrafiltration using a Vivaspin (cut off molecular weight of 30,000, manufactured by GE Healthcare) to concentrate 10 times to obtain a concentrated culture supernatant solution. An ANTI-FLAG M2 affinity gel (500 µL, ¹/₁₀ volume of the concentrated culture supernatant solution, produced by Sigma-Aldrich Co., Ltd.) washed with PBS was added to 5 mL of the resulting concentrated culture supernatant solution and mixed with inversion for 3 hours, and the FLAG tag fusion type Tim-4 protein in the concentrated culture supernatant solution and the ANTI-FLAG M2 affinity gel were subjected to a reaction to bind the FLAG tag fused Tim-4 protein to the ANTI-FLAG M2 affinity gel. Then, the ANTI-FLAG M2 affinity gel was washed three times with 5 µL of PBS.

After that, 250 µL (half volume of the ANTI-FLAG M2 affinity gel used) of a 200 µg/mL FLAG peptide solution (a solution of a DYKDDDDK peptide (produced by Wako Pure Chemical Industries, Ltd.) diluted with PBS) was added to the ANTI-FLAG M2 affinity Gel, and mixed with inversion at 4° C. for 30 minutes, and after centrifugal separation treatment (at 4° C., at 8000×G, for 1 minute), the supernatant (eluate) was recovered. In order to remove the FLAG peptide in the recovered supernatant (eluate), 20 mL of PBS was added to the supernatant (eluate) and subjected to ultrafiltration to obtain a concentrated solution. PBS was added to the resulting concentrated solution, and volume of the solution was adjusted to 500 µL to obtain the PBS solution containing the FLAG tag fusion type mouse-derived Tim-4 protein (it may be abbreviated as "the FLAG tag fusion type mTim-4 protein", in some cases) (the solution may be abbreviated as "the FLAG tag fusion type mTim-4 protein-containing PBS solution", in some cases) (Experimental Example 2).

Experimental Example 3. Preparation of His Tag Fusion Type Tim-4 Protein

The His tag fusion type Tim-4 protein was prepared by the following method.
<(1) Vector Construction and Culture Conditions>

The His tag fusion type mouse-derived Tim-4 protein cDNA (a cDNA encoding an amino acid sequence fused with 6×His tag at the C-terminal of the N-terminal 1 to 273 amino acid region of the mouse-derived Tim-4 protein, SEQ ID NO: 34 (containing the stop codon (tga) and a cDNA encoding 6×His tag) was incorporated in the XhoI/BamHI site of the pCAG-Neo vector (produced by Wako Pure Chemical Industries, Ltd.) to construct a vector for expressing the His tag fusion type Tim-4 protein (hereinafter it may be abbreviated as "the pCAG-Tim-4-His", in some cases).

On the other hand, the 293 T cells (RIKEN BRC) were cultured for 1 day using 50 mL of DMEM (manufactured by Wako Pure Chemical Industries, Ltd.) containing 10% FBS (produced by Biosera) in a 225 cm$^2$ flask. Thereafter, 60 µg of the pCAG-Tim-4-His was transfected into the 293 T cells using Lipofectamine 2000 (produced by Thermo Fisher Scientific Inc.), according to a usual method. After transfection, the 293 T cells transfected were cultured for 1 day under condition at 37° C. and 5% $CO_2$. Thereafter, the whole amount of the culture solution was removed, the transfected 293 T cells were washed twice with 10 mL of PBS, and the culture solution was exchanged with 50 mL of the Opti-MEM (manufactured by Thermo Fisher Scientific Inc.) and cultured for 3 days under condition at 37° C. and 5% $CO_2$.

<(2) Purification>

The culture solution of the 293 T cells transfected after three days of culture was subjected to centrifugal separation treatment (300×G, for 5 minutes) to recover the culture supernatant. The recovered culture supernatant was further subjected to centrifugal separation treatment three times (the first time: 300×G, for 3 min, the second time: 1200×G, for 20 min, and the third time: 10000×G, for 20 min) to separate impurities, and obtain the supernatant. The resulting supernatant was subjected to ultrafiltration using the Vivaspin (cut off molecular weight 30,000, manufactured by GE Healthcare) and concentrated 10 times to obtain a concentrated culture supernatant solution.

Ni Sepharose 6 Fast Flow (2.7 mL, produced by GE Healthcare) was prepared according to a protocol attached to the Ni Sepharose 6 Fast Flow, and transferred to a column. A binding buffer (50 mM Tris-HCl, 500 mM NaCl, 20 mM imidazole) was added to the column at a flow rate of about 1 mL/min, while measuring an OD 280 nm until absorbance at 280 nm was stabilized. After the addition of 5 mL of the resulting concentrated culture supernatant solution to the column, the binding buffer was sufficiently added and washed until the absorbance was stabilized. Subsequently, an elution buffer (50 mM Tris-HCl, 500 mM NaCl, 300 mM imidazole) was added to the column, and each 1 mL of the eluate fractions was recovered by 10 fractions.

<(3) Electrophoresis and Silver Staining>

Each 15 μL aliquot of the eluted fractions was fractionated and mixed with 5 μL of 4×sample buffer solution (produced by Wako Pure Chemical Industries, Ltd.), and incubated at 98° C. for 5 minutes to obtain each 20 μL of a sample for electrophoresis. Each 15 μL of the sample for electrophoresis was loaded on a Super Sep Ace 5-20% gel (produced by Wako Pure Chemical Industries, Ltd.), and subjected to electrophoresis at 25 mA for 65 minutes.

The gel was stained with Silver Stain II Kit Wako (manufactured by Wako Pure Chemical Industries, Ltd.) to select and pool (put together) five fractions containing a target protein. Then, to remove imidazole contained in the eluate, 20 mL of PBS was added and ultrafiltration was carried out using the Vivaspin (cut off molecular weight 30,000, produced by GE Healthcare) to obtain a concentrated solution. PBS was added to the resulting concentrated solution, and volume of the solution was adjusted to 500 μL to obtain the PBS solution containing the His tag fusion type mouse-derived Tim-4 protein (it may be abbreviated as "the His tag fusion type mTim-4 protein", in some cases) (the solution may be abbreviated as "the His tag fusion type mTim-4 protein-containing PBS solution", in some cases).

Examples 1 to 8. Obtaining of Extracellular Membrane Vesicles Using Tim-4 Carrier of the Present Invention (Obtaining Method of the Present Invention)

The Tim-4 carrier of the present invention was prepared as follows, and the extracellular membrane vesicles pertaining to the present invention were obtained using this.

<(1) Preparation of Calcium Ion-Containing Culture Supernatant Sample>

A human chronic myelogenous leukemia cell strain K562, $1×10^7$ cells, secreting the extracellular membrane vesicle, was cultured for 3 days under condition at 37° C. and 5% $CO_2$, using 80 mL of the X-VIVO 15 medium (produced by Lonza AG). Then the cells were subjected to centrifugal separation treatment (300×G, for 5 minutes) to precipitate the cells, and remove the supernatant. The precipitated cells were suspended in 60 mL of the X-VIVO 15 medium containing 10 μM monensin sodium (produced by MP Biomedicals Co., Ltd.) and cultured for 24 hours under condition at 37° C. and 5% $CO_2$.

Thereafter, the culture solution was subjected to centrifugal separation treatment (300×G, for 5 minutes) to recover the culture supernatant. The recovered culture supernatant (60 mL) was further subjected to centrifugal separation treatment three times (the first time, 300×G, for 3 minutes, the second time, 1200×G, for 20 minutes, and the third time, 10000×G, for 20 minutes) to separate impurities and obtain the supernatant. The resulting supernatant was subjected to ultrafiltration using the Vivaspin (cut off molecular weight 30,000, produced by GE Healthcare) until volume attained 6 mL or less to obtain the concentrated solution. The X-VIVO 15 medium containing 10 μM monensin sodium (manufactured by MP Biomedicals Co., Ltd.) was added to the resulting concentrated solution to adjust liquid volume to 6 mL to obtain the 10 times concentrated K562 cell culture concentrated solution sample (hereinafter it may be abbreviated as "the culture supernatant sample", in some cases).

In addition, $CaCl_2$ was added to the resulting culture supernatant sample, so as to attain the final concentration of 2 mM to obtain the K562 cell culture supernatant concentrated sample containing 2 mM $CaCl_2$ (hereinafter it may be abbreviated as "the calcium ion-containing culture supernatant sample", in some cases).

<(2) Biotin Labeling of Fc Tag Fusion Type Mouse-Derived Tim-4 Protein>

For 114 μL of the PBS solution containing the Fc tag fusion type mTim-4 protein (containing 10 μg of the Fc tag fusion type mTim-4 protein) prepared by the same method as in Experimental Example 1, the $NH_2$-group of the Fc tag fusion type mTim-4 protein was labeled with biotin, using the Biotin Labeling Kit-$NH_2$ (manufactured by Dojindo Molecular Technologies, Inc.), according to a protocol attached to the kit to obtain 100 μL of the PBS solution containing 3.8 μg of the $NH_2$-group biotin-labeled Fc tag fusion type mouse-derived Tim-4 protein (it may be abbreviated as "the $NH_2$-group biotin-labeled Fc tag fusion type mTim-4 protein", in some cases) (the solution may be abbreviated as "the $NH_2$-group biotin-labeled Fc tag fusion type mTim-4 protein-containing PBS solution", in some cases).

In addition, for 114 μL of the Fc tag fusion type mTim-4 protein-containing PBS solution (containing 10 μg of the Fc tag fusion type mouse-derived Tim-4 protein) prepared by the same method as in Experimental Example 1, the SH-group of the Fc tag fusion type mouse-derived Tim-4 protein was labeled with biotin, using a Biotin Labeling Kit-SH manufactured by Dojindo Molecular Technologies, Inc.), according to a protocol attached to the kit to obtain 100 μL of the PBS solution containing 5.9 μg of the SH-group biotin-labeled Fc tag fusion type mouse-derived Tim-4 protein (it may be abbreviated as "the SH-group biotin-labeled Fc tag fusion type mTim-4 protein", in some cases) (the solution may be abbreviated as "the SH-group biotin-labeled Fc tag fusion type mTim-4 protein-containing PBS solution", in some cases).

<(3) Dilution of Fc Tag Fusion Type Mouse-Derived Tim-4 Protein-Containing PBS Solution>

The Fc tag fusion type mTim-4 protein-containing PBS solution (11.4 μL), prepared by the same method as in Experimental Example 1, was mixed with 188.6 μL of PBS to obtain 200 μL of the PBS solution containing 1 μg of the biotin-unlabeled Fc tag fusion type mTim-4 protein.

The NH$_2$-group biotin-labeled Fc tag fusion type mTim-4 protein-containing PBS solution (26.3 μL) prepared above (containing 1 μg of the NH$_2$-group biotin-labeled Fc tag fusion type mTim-4 protein) was mixed with 173.7 μL of PBS to obtain 200 μL of the PBS solution containing 1 μg of the NH$_2$-group biotin-labeled Fc tag fusion type mTim-4 protein.

In addition, 16.9 μL of the SH-group biotin-labeled Fc tag fusion type mTim-4 protein-containing PBS solution prepared above (containing 1 μg of the SH-group biotin-labeled Fc tag fusion type mTim-4 protein) was mixed with 183.1 μL of PBS to obtain 200 μL of the PBS solution containing 1 μg of the SH-group biotin-labeled Fc tag fusion type mTim-4 protein.

<(4) Washing of Beads>

A PBS-T solution (20 μL) containing a 30 μg/μL Dynabeads Protein G (produced by Thermo Fisher Scientific Inc.) (containing 0.6 mg of the Dynabeads Protein G) was dispensed into each of three 1.5 mL tubes (manufactured by BM Equipment Co., Ltd.). Next, 500 μL of PBS was added to each of the 1.5 mL tubes, and after stirring, each of the 1.5 mL tubes were loaded on a magnet stand, and the Dynabeads Protein G was collected on the tube wall using magnetic force, and the solution in the 1.5 mL tube was discarded with a pipette (hereinafter it may be abbreviated as "the washing operation", in some cases).

In addition, 60 μL of the PBS solution containing a 10 μg/μL Dynabeads M-270 Streptavidin C1 (produced by Thermo Fisher Scientific Inc.) (containing 0.6 mg of the Dynabeads M-270 Streptavidin C1) was dispensed into the 1.5 mL tube (manufactured by BM Instruments co., Ltd), and the washing operation was carried out in the same method as above using 500 μL of PBS.

<(5) Immobilization of Fc Tag Fusion Type Mouse-Derived Tim-4 Protein on Beads>

For one of the three 1.5 mL tubes containing the Dynabeads Protein G (0.6 mg), 200 μL of the PBS solution containing 1 μg of the biotin-unlabeled Fc tag fusion type mTim-4 protein prepared above was added in its entirety, and subjected to a reaction at 8° C. for 1 hour to obtain 200 μL of the PBS solution containing the carrier on which the biotin-unlabeled Fc tag fusion type mTim-4 protein was bound (mTim-4 carrier).

For one of the remaining two 1.5 mL tubes containing the Dynabeads Protein G (0.6 mg), 200 μL of the PBS solution containing 1 μg of the NH$_2$-group biotin-labeled Fc tag fusion type mTim-4 protein prepared above was added in its entirety, and subjected to a reaction at 8° C. for 1 hour to obtain 200 μL of the PBS solution containing the carrier on which the NH$_2$-group biotin-labeled Fc tag fusion type mTim-4 protein was bound (mTim-4 carrier).

In addition, for one tube, 200 μL of the PBS solution containing 1 μg of the SH-group biotin-labeled Fc tag fusion type mTim-4 protein prepared above was added in its entirety, and subjected to a reaction at 8° C. for 1 hour to obtain 200 μL of the PBS solution containing the carrier on which the SH-group biotin-labeled Fc tag fusion type mTim-4 protein was bound (mTim-4 carrier).

For one of 1.5 mL tube containing the Dynabeads M-270 Streptavidin C1, 200 μL of the PBS solution containing 1 μg of the SH-group biotin-labeled Fc tag fusion type mTim-4 protein prepared by the same method as above was added, and subjected to a reaction at 8° C. for 1 hour to obtain 200 μL of the PBS solution containing the carrier on which the SH-group biotin-labeled Fc tag fusion type mTim-4 protein was bound (mTim-4 carrier).

In this way, 200 μL of the PBS solution containing 0.6 mg of each of the four types of the mTim-4 carriers shown in the following Table 1 was obtained.

TABLE 1

|  | 1 | 2 | 3 | 4 |
|---|---|---|---|---|
| Mouse-derived Tim-4 carrier | Fc tag fusion type mouse-derived Tim-4 protein Carrier | Unlabeled | Biotin labeled (NH$_2$-group) Protein G beads | Biotin labeled (SH-group) Protein G beads | Biotin labeled (SH-group) Streptavidin beads |

<(6) Obtaining of Extracellular Membrane Vesicles by Obtaining Method of the Present Invention>

The resulting 0.6 mg of the four types of the mTim-4 carriers above, described in Table 1, was subjected to the washing operation each three times with 500 μL of PBS, and then 200 μL of the calcium ion-containing culture supernatant sample prepared in the (1) was added to each of the mTim-4 carriers in a pellet state and subjected them to a reaction at 8° C. for 3 hours.

The mTim-4 carrier after the reaction was subjected to the washing operation 3 times with 500 μL each of TBS-T containing 2 mM CaCl$_2$ (Tris buffer, 0.05% Tween 20, 2 mM CaCl$_2$). At the third time of the washing operation, each 250 μL of the 4 types of the mTim-4 carriers was dispensed into two 1.5 mL tubes.

Each 20 μL of the 1% SDS aqueous solution or the 1 mM EDTA aqueous solution was added, as the eluent, to each 0.3 mg of the four types of the mTim-4 carriers in a pellet state, and then they were mixed at room temperature for 10 seconds using a vortex mixer and spun down. Each 1.5 mL tube was loaded on a magnet stand, and the mTim-4 carrier was collected on the tube wall using magnetic force to recover the supernatant (eluate).

It should be noted that, the types of the mTim-4 proteins, the carriers and the eluents used to obtain the extracellular membrane vesicles from the mTim-4 carrier, used in each Example, and the lane numbers in Western blotting to be described later are shown in the following Table 2.

TABLE 2

|  |  | Example 1 | Example 2 | Example 3 | Example 4 | Example 5 | Example 6 | Example 7 | Example 8 |
|---|---|---|---|---|---|---|---|---|---|
| Mouse-derived Tim-4 carrier | Fc tag fusion type mouse-derived Tim-4 protein Carrier | Unlabeled | | Biotin labeled (NH$_2$-group) | | Biotin labeled (SH-group) | | | |
|  |  | Protein G beads | | | | Streptavidin beads | | | |
| Eluent |  | 1% SDS | 1 mM EDTA | 1% SDS | 1 mM EDTA | 1% SDS | 1 mM EDTA | 1% SDS | 1 mM EDTA |
| Lane number in FIG. 1 |  | 1 | 2 | 3 | 4 | 5 | 6 | 7 | 8 |

<(7) Western Blotting>

To each 7.5 μL of the supernatants (eluates) obtained in Examples 1 to 8, 2.5 μL of the 4×sample buffer (produced by Wako Pure Chemical Industries, Ltd.) was added and incubated at 98° C. for 5 minutes to obtain each sample for Western blotting. Each 10 μL of the sample for Western blotting was loaded on the Super Sep Ace 5-20% gel (produced by Wako Pure Chemical Industries, Ltd.), and subjected to electrophoresis at 25 mA for 65 minutes. The resulting electrophoresis gel was transcribed onto a PVDF membrane (produced by Millipore Corporation) under 1 mA/cm$^2$ for 60 minutes using a semi-dry blotter and a discontinuous buffer (Anode buffer 1: 0.3 M Tris/20% methanol, Anode buffer 2: 0.025 M Tris/20% methanol, Cathode buffer: 0.025 M Tris/0.04 M aminocaproic acid/ 20% methanol).

To the PVDF membrane, 3% skimmed milk diluted with PBS-T (the PBS buffer, 0.1% Tween 20) was added and subjected to a reaction at room temperature for 1 hour for blocking, and 2 mL of an anti-human Lamp-1 mouse monoclonal antibody diluted 250-fold with PBS-T (produced by BD Biosciences, hereinafter it may be abbreviated as "the anti-human Lamp-1 antibody", in some cases) was subjected to a reaction at 8° C. overnight.

After that, the PVDF membrane after the reaction was washed three times with PBS-T, and then subjected to a reaction with a secondary antibody {anti-mouse IgG (H+L), rabbit, IgG fraction, peroxidase-conjugated antibody} (produced by Wako Pure Chemical Industries, Ltd.) diluted 10,000-fold with PBS-T at room temperature for 1 hour. After washing it 5 times with PBS-T, ImmunoStar Zeta (produced by Wako Pure Chemical Industries, Ltd.) was added to detect a luminescent signal using LAS-4000 (manufactured by General Electric Company). It should be noted that the anti-human Lamp-1 antibody is an antibody against Lamp-1 which is one of the marker proteins of exosome.

<Results>

The results of Western blotting obtained are shown in FIG. 1. In FIG. 1, each lane is as follows:

Lane 1: Results of Example 1 (results of the case of using the mTim-4 carrier in which the biotin-unlabeled Fc tag fusion type mTim-4 protein was bound on the Protein G beads, and using the 1% SDS aqueous solution as the eluent);

Lane 2: Results of Example 2 (the results of the case of using the mTim-4 carrier in which the biotin-unlabeled Fc tag fusion type mTim-4 protein was bound on the Protein G beads, and using the 1 mM EDTA solution as the eluent);

Lane 3: Results of Example 3 (the results of the case of using the mTim-4 carrier in which the NH$_2$-group biotin-labeled Fc tag fusion type mTim-4 protein was bound on the Protein G beads, and using the 1% SDS aqueous solution as the eluent);

Lane 4: Results of Example 4 (the results of the case of using the mTim-4 carrier in which the NH$_2$-group biotin-labeled Fc tag fusion type mTim-4 protein was bound on the Protein G beads, and using the 1 mM EDTA solution as the eluent);

Lane 5: Results of Example 5 (the results of the case of using the mTim-4 carrier in which the SH-group biotin-labeled Fc tag fusion type mTim-4 protein was bound on the Protein G beads, and using the 1% SDS aqueous solution as the eluent);

Lane 6: Results of Example 6 (the results of the case of using the mTim-4 carrier in which the SH-group biotin-labeled Fc tag fusion type mTim-4 protein was bound on the Protein G beads, and using the 1 mM EDTA solution as the eluent);

Lane 7: Results of Example 7 (the results of the case of using the mTim-4 carrier in which the SH-group biotin-labeled Fc tag fusion type mTim-4 protein was bound to the streptavidin beads, and using the 1% SDS aqueous solution as the eluent);

Lane 8: Results of Example 8 (the results of the case of using the mTim-4 carrier in which the SH-group biotin-labeled Fc tag fusion type mTim-4 protein was bound to the streptavidin beads, and using the 1 mM EDTA solution as the eluent).

From FIG. 1, it has been revealed that the extracellular membrane vesicles including exosome can be obtained, according to the obtaining method of the present invention, from the fact that a band of Lamp-1, which is an exosome marker, was recognized at the vicinity of 100 kDa in any of Examples 1 to 8

Examples 1 to 8: The Lanes 1 to 8

In particular, from comparison among Examples 2, 4, 6, and 8, it has been revealed that, when the calcium ion chelating agent is used as the eluent, the one in which the Tim-4 protein and the carrier are bound via the SH-group of the Tim-4 protein (Example 8: the lane 8) is possible to obtain more extracellular membrane vesicles, as compared with the one bound via the NH$_2$-group (Example 4: the lane 4) or those bound via the affinity tag (Example 2: lane 2, Example 6: the lane 6) (Example 2: lane 2, Example 4: lane 4, Example 6: lane 6, Example 8: the lane 8).

Examples 9 to 16. Obtaining of Extracellular Membrane Vesicles Using Tim-4 Carrier of the Present Invention (Obtaining Method of the Present Invention)

The Tim-4 carrier of the present invention was prepared as follows, and the extracellular membrane vesicles pertaining to the present invention were obtained using the same.

<(1) Preparation of Culture Supernatant Sample>

Preparation of the culture supernatant sample was carried out in the same method as in "(1) preparation of culture supernatant sample" of Examples 1 to 8.

<(2) Biotin Labeling of Fc Tag Fusion Type Mouse-Derived Tim-4 Protein>

For 114 μL of the PBS solution containing the Fc tag fusion type mTim-4 protein (containing 10 μg of the Fc tag fusion type mTim-4 protein), prepared by the same method as in "(2) Biotin labeling of Fc tag fusion type mouse-derived Tim-4 protein" of Experimental Example 1, the SH-group of the Fc tag fusion type mTim-4 protein was labeled with biotin by the same method as in Example 1 to obtain 100 μL of the PBS solution containing 3.9 μg of the SH-group biotin-labeled Fc tag fusion type mTim-4 protein (hereinafter it may be abbreviated as "the SH-group biotin-labeled Fc tag fusion type mTim-4 protein-containing PBS solution", in some cases).

<(3) Biotin Labeling of FLAG Tag Fusion Type Mouse-Derived Tim-4 Protein>

For 99 μL of the PBS solution containing the FLAG tag fusion type mTim-4 protein prepared by the same method as in Experimental Example 2 (containing 10 μg of the FLAG tag fusion type mTim-4 protein), the SH-group of the FLAG tag fusion type mTim-4 protein was labeled with biotin using the Biotin Labeling Kit-SH (manufactured by Dojindo Molecular Technologies, Inc.), according to a protocol attached to the kit to obtain 100 μL of the PBS solution containing 4.6 μg of the SH-group biotin-labeled FLAG tag fusion type mTim-4 protein (hereinafter it may be abbreviated as "the PBS solution containing the SH-group biotin-labeled FLAG tag fusion type mTim-4 protein", in some cases).

<(4) Biotin Labeling of his Tag Fusion Type Mouse-Derived Tim-4 Protein>

For 54 μL of the PBS solution containing the His tag fusion type mTim-4 protein prepared by the same method as in Experiment Example 3 (containing 10 μg of the His tag fusion type mTim-4 protein), the SH-group of the His tag fusion type mTim-4 protein was labeled with biotin using the Biotin Labeling Kit-SH (manufactured by Dojindo Molecular Technologies, Inc.), according to a protocol attached to the kit to obtain 100 μL of the PBS solution containing 7.2 μg of the SH-group biotin-labeled His tag fusion type mTim-4 protein (hereinafter it may be abbreviated as "the PBS solution containing the SH-group biotin-labeled His tag fusion type mTim-4 protein", in some cases).

<(5) Dilution of Tag Fusion Type Mouse-Derived Tim-4 Protein>

The Fc tag fusion type mTim-4 protein-containing PBS solution (11.4 μL), prepared by the same method as in Experimental Example 1 (containing 1 μg of the Fc tag fusion type mouse-derived Tim-4 protein), was mixed with 188.6 μL of PBS to obtain 200 μL of the PBS solution containing 1 μg of biotin-unlabeled Fc tag fusion type mouse-derived Tim-4 protein.

The SH-group biotin-labeled Fc tag fusion type mTim-4 protein-containing PBS solution (16.9 μL), prepared in the (2) (containing 1 μg of the SH-group biotin-labeled Fc tag fusion type mTim-4 protein), was mixed with 183.1 μL of PBS to obtain 200 μL of the PBS solution containing 1 μg of the SH-group biotin-labeled Fc tag fusion type mTim-4 protein.

In addition, 21.6 μL of the SH-group biotin-labeled FLAG tag fusion type mTim-4 protein-containing PBS solution, prepared in the (3) (containing 1 μg of the SH-group biotin-labeled FLAG tag fusion type mTim-4 protein), was mixed with 178.4 μL of PBS to obtain 200 μL of the PBS solution containing 1 μg of the SH-group biotin-labeled FLAG tag fusion type mTim-4 protein.

The SH-group biotin-labeled His tag fusion type mTim-4 protein-containing PBS solution (13.9 μL), prepared in the (4) (containing 1 μg of the SH-group biotin-labeled His tag fusion type mTim-4 protein), was mixed with 186.1 μL of PBS to obtain 200 μL of the PBS solution containing 1 μg of the SH-group biotin-labeled His tag fusion type mTim-4 protein.

<(6) Washing of Beads>

The PBS-T solution (20 μL) containing 30 μg/μL of the Dynabeads Protein G (produced by Thermo Fisher Scientific, Inc.) (containing 0.6 mg of the Dynabeads Protein G) was dispensed into one 1.5 mL tube (manufactured by BM Equipment Co., Ltd.), and the washing operation was carried out using 500 μL of PBS in the same method as in "(4) washing of beads" in Examples 1 to 8.

In addition, 60 μL of the PBS solution containing the 10 μg/μL Dynabeads M-270 Streptavidin (produced by Thermo Fisher Scientific Inc.) (containing 0.6 mg of the Dynabeads M-270 Streptavidin) was dispensed into each of the three 1.5 mL tubes (manufactured by BM Equipment Co., Ltd.), and the washing operation was carried out using each 500 μL of PBS in the same method as in "(4) washing of beads" in Examples 1 to 8.

<(7) Immobilization of Tag-Fused Mouse-Derived Tim-4 Protein on Beads>

Subsequently, 200 μL of the PBS solution containing 1 μg of the biotin-unlabeled Fc tag fusion type mTim-4 protein was added in its entirety to the 1.5 mL tube containing 0.6 mg of the Dynabeads Protein G in a pellet state, after the washing operation, and subjected to a reaction at 8° C. for 1 hour to obtain 200 μL of the PBS solution containing the carrier on which the biotin-unlabeled Fc tag fusion type mTim-4 protein was bound (the mTim-4 carrier).

Furthermore, for one of the three 1.5 mL tubes containing 0.6 mg of the Dynabeads M-270 Streptavidin in a pellet state, after the washing operation, 200 μL of the PBS solution containing 1 μg of the SH-group biotin-labeled Fc tag fusion type mTim-4 protein prepared above was added in its entirety and subjected to a reaction at 8° C. for 1 hour to obtain 200 μL of the PBS solution containing the carrier on which the SH-group biotin-labeled Fc tag fusion type mTim-4 protein was bound (the mTim-4 carrier).

For one of the remaining two 1.5 mL tubes containing 0.6 mg of the Dynabeads M-270 Streptavidin in a pellet state, after the washing operation, 200 μL of the PBS solution containing 1 μg of the SH-group biotin-labeled FLAG tag fusion type mTim-4 protein prepared above was added in its entirety, and subjected to a reaction at 8° C. for 1 hour to obtain 200 μL of the PBS solution containing the carrier on which the SH-group biotin-labeled FLAG tag fusion type mTim-4 protein was bound (the mTim-4 carrier).

In addition, for one tube, 200 μL of the PBS solution containing 1 μg of the SH-group biotin-labeled His tag fusion type mTim-4 protein prepared above was added in its entirety, and subjected to a reaction at 8° C. for 1 hour to obtain 200 μL of the PBS solution containing the carrier on which the SH-group biotin-labeled His tag fusion type mTim-4 protein was bound (the mTim-4 carrier).

In this way, 200 μL of the PBS solutions containing 0.6 mg of each of the four types of mTim-4 carriers shown in the following Table 3 were obtained.

TABLE 3

| | 1 | 2 | 3 | 4 |
|---|---|---|---|---|
| Mouse-derived Tim-4 carrier | Type of tag | Fc tag | FLAG tag | His tag |
| | Tag fusion type mouse-derived Tim-4 protein | Unlabeled | Biotin labeled (SH-group) | |
| | Carrier | Protein G beads | Streptavidin beads | |

<(8) Obtaining of Extracellular Membrane Vesicles by Obtaining Method of the Present Invention>

Each supernatant (eluate) was obtained by carrying out the same method as in "(6) Obtaining of extracellular membrane vesicles by obtaining method of the present invention" of Examples 1 to 8, except for using "0.6 mg of the four kinds of the mTim-4 carriers shown in Table 3" instead of "0.6 mg of the four kinds of the mTim-4 carrier shown in Table 1". It should be noted that the type of the mTim-4 proteins, the carriers, and the eluents used to obtain the extracellular membrane vesicles from the mTim-4 carrier, used in each Example, and the lane numbers in Western blotting to be described later are shown in the following Table 4.

TABLE 4

Figure 2:
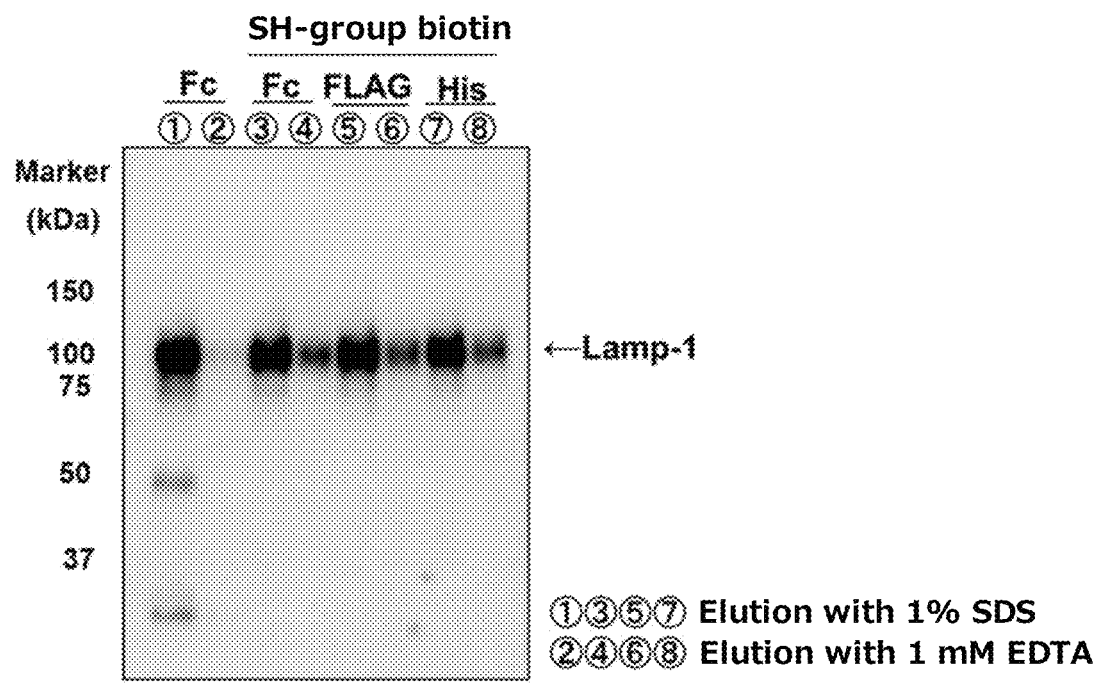
FIG. 2 is an electropherogram for confirming whether the extracellular membrane vesicles were obtained or not, by Western blotting, in Examples 9 to 16.

| | | Example 9 | Example 10 | Example 11 | Example 12 | Example 13 | Example 14 | Example 15 | Example 16 |
|---|---|---|---|---|---|---|---|---|---|
| Mouse-derived Tim-4 carrier | Type of tag | | | Fc tag | | | FLAG tag | | His tag |
| | Tag fusion type mouse-derived Tim-4 protein | Unlabeled | | | | Biotin labeled (SH-group) | | | |
| | Carrier | Protein G beads | | | | Streptavidin beads | | | |
| Eluent | | 1% SDS | 1 mM EDTA | 1% SDS | 1 mM EDTA | 1% SDS | 1 mM EDTA | 1% SDS | 1 mM EDTA |
| Lane number in FIG. 2 | | 1 | 2 | 3 | 4 | 5 | 6 | 7 | 8 |

<(7) Western Blotting>

Western blotting was carried out by the same method as in "(7) Western blotting" of Examples 1 to 8, except for using "7.5 µL of each supernatant (eluate) obtained in Examples 9 to 16 (above (8)), instead of "7.5 µL of each supernatant (eluate) obtained in Examples 1 to 8".

<Results>

The results of Western blotting obtained are shown in FIG. 2. In FIG. 2, each lane is as follows:

Lane 1: Results of Example 9 (the results of the case of using the mTim-4 carrier in which the biotin-unlabeled Fc tag fusion type mTim-4 protein was bound on the Protein G beads, and using the 1% SDS aqueous solution as the eluent);

Lane 2: Result of Example 10 (the results of the case of using the mTim-4 carrier in which the biotin-unlabeled Fc tag fusion type mTim-4 protein was bound on the Protein G beads, and using the 1 mM EDTA solution as the eluent);

Lane 3: Results of Example 11 (the results of the case of using the mTim-4 carrier in which the SH-group biotin-labeled Fc tag fusion type mTim-4 protein was bound on the streptavidin beads, and using the 1% SDS aqueous solution as the eluent);

Lane 4: Results of Example 12 (the results of the case of using the mTim-4 carrier in which the SH-group biotin-labeled Fc tag fusion type mTim-4 protein was bound on the streptavidin beads, and using the 1 mM EDTA solution as the eluent);

Lane 5: Results of Example 13 (the results of the case of using the mTim-4 carrier in which the SH-group biotin-labeled FLAG tag fusion type mTim-4 protein was bound on the streptavidin beads, and using the 1% SDS aqueous solution as the eluent);

Lane 6: Results of Example 14 (the results of the case of using the mTim-4 carrier in which the SH-group biotin-labeled FLAG tag fusion type mTim-4 protein was bound on the streptavidin beads, and using the 1 mM EDTA solution as the eluent);

Lane 7: Results of Example 15 (the results of the case of using the mTim-4 carrier in which the SH-group biotin-labeled His tag fusion type mTim-4 protein was bound on the streptavidin beads, and using the 1% SDS aqueous solution as the eluent);

Lane 8: The results of Example 16 (the results of the case of using the mTim-4 carrier in which the SH-group biotin-labeled His tag fusion type mTim-4 protein was bound on the streptavidin beads, and using the 1 mM EDTA solution as the eluent).

From FIG. 2, it has been revealed that the extracellular membrane vesicles including exosome can be obtained, by using the obtaining method of the present invention, because of the fact that a band of Lamp-1, which is a marker protein of exosome, was detected at the vicinity of 100 kDa, in any of Examples 9 to 16 (Example 9 to 16: the lanes 1 to 8).

In addition, it has been revealed that the extracellular membrane vesicles can be obtained by using the Tim-4 carrier of the present invention, irrespective of the type, length, and presence or absence of the tags (Examples 9 to 16: the lanes 1 to 8).

From comparison among Examples 10, 12, 14, and 16, it has been revealed that when EDTA, which is the calcium ion chelating agent, is used as the eluent, those on which the Tim-4 protein and the carrier are bound via the SH-group of the Tim-4 protein (Example 12: the lane 4, Example 14: the lane 6, Example 16: the lane 8) are possible to obtain more extracellular membrane vesicles as compared with the one bound via the affinity tag (Example 10: the lane 2).

Examples 17 to 18. Obtaining of Extracellular Membrane Vesicles Using Tim-4 Carrier of the Present Invention (Obtaining Method of the Present Invention)

The Tim-4 carrier of the present invention was prepared as follows, and the extracellular membrane vesicles pertaining to the present invention were obtained using the same.

<(1) Preparation of Culture Supernatant Sample>

Preparation of culture supernatant sample was carried out in the same method as in "(1) Preparation of culture supernatant sample" of Examples 1 to 8.

<(2) Dilution of Biotin-Unlabeled FLAG Tag Fusion Type Mouse-Derived Tim-4 Protein>

The PBS solution (47 µL) containing 5 µg of the biotin-unlabeled FLAG tag fusion type mTim-4 protein, prepared by the same method as in Experimental Example 2 (the biotin-unlabeled FLAG tag fusion type mTim-4 protein-containing PBS solution) was mixed with 153 µL of PBS to obtain 200 µL of the PBS solution containing 5 µg of the biotin-unlabeled FLAG tag fusion type mTim-4 protein.

<(3) Washing of Beads>

A 50% glycerol TBS solution (50 µL) containing 10 µg/µL of anti-DYKDDDDK tag antibody magnetic beads (containing 0.5 mg of the anti-DYKDDDDK tag antibody magnetic beads) (produced by Wako Pure Chemical Industries, Ltd.) was dispensed into the 1.5 mL tube (manufactured by BM Equipment Co., Ltd.), and the washing operation was carried out using 500 µL of PBS.

<(4) Immobilization of FLAG Tag Fusion Type Mouse-Derived Tim-4 Protein on Carrier>

Subsequently, 200 µL of the PBS solution containing 5 µg of the FLAG tag fusion type mTim-4 protein was added in its entirety to the anti-DYKDDDDK tag antibody magnetic beads in a pelleted state, after the washing operation, and subjected to a reaction at 8° C. for 1 hour to obtain 200 µL of the PBS solution containing the mTim-4 carrier.

In this way, 200 µL of the PBS solution containing 0.5 mg of the mTim-4 carrier shown in the following Table 5 was obtained.

TABLE 5

| | | 1 | |
|---|---|---|---|
| Mouse-derived Tim-4 carrier | Type of tag Tag fusion type mouse-derived Tim-4 protein Carrier | FLAG tag Biotin-unlabeled Anti-DYKDDDDK tag antibody beads | |

<(5) Obtaining of Extracellular Membrane Vesicles by Obtaining Method of the Present Invention>

Each supernatant (eluate) was obtained by carrying out the same method as in "(6) Obtaining of extracellular membrane vesicles by the obtaining method of the present invention" of Examples 1 to 8, except for using "0.5 mg of the mTim-4 carrier described in Table 5", instead of "0.6 mg of the four kinds of the mTim-4 carrier described in Table 1".

It should be noted that the types of the mTim-4 protein, the carrier and the eluent used to obtain the extracellular membrane vesicles from the mTim-4 carrier, used in each Example, and the lane numbers in Western blotting to be described later are shown in the following Table 6.

TABLE 6

| | | Example 17 | Example 18 |
|---|---|---|---|
| Mouse-derived Tim-4 carrier | Type of tag Tag fusion type mouse-derived Tim-4 protein Carrier | FLAG tag Biotin-unlabeled Anti-DYKDDDDK tag antibody beads | |
| Eluent | | 1% SDS | 1 mM EDTA |
| Lane number in FIG. 3 | | 1 | 2 |

<(6) Western Blotting>

Western blotting was carried out by the same method as in "(7) Western blotting" of Examples 1 to 8, except for using "7.5 μL of each supernatant (eluate) obtained in Examples 17 to 18 (above (5)) instead of "7.5 μL of each supernatant (eluate) obtained in Examples 1 to 8".

<Results>

The results of Western blotting obtained are shown in FIG. 3. In FIG. 3, each lane is as follows:

Lane 1: Results of Example 17 (the results of the case of using the mTim-4 carrier in which the biotin-unlabeled FLAG tag fusion type mTim-4 protein was bound on the anti-DYKDDDDK antibody beads, and using the 1% SDS aqueous solution as the eluent);

Lane 2: Result of Example 18 (the results of the case of using the mTim-4 carrier in which the biotin-unlabeled FLAG tag fusion type mTim-4 protein was bound on the anti-DYKDDDDK antibody beads, and using the 1 mM EDTA solution as the eluent).

From FIG. 3, it has been revealed that the extracellular membrane vesicles including exosome can be obtained, according to the obtaining method of the present invention, when the carrier on which the Tim-4 protein is immobilized via the anti-tag antibody, from the fact that a band of Lamp-1, which is an exosome marker, was observed at the vicinity of 100 kDa, in any case of Examples 17 to 18 (Examples 17 to 18: the lanes 1 to 2).

Examples 19 to 20 and Comparative Examples 1 to 3. Comparison of Purity of Extracellular Membrane Vesicles Obtained by the Obtaining Method of the Present Invention and Conventional Method As described below, comparison was carried out on purity of the extracellular membrane vesicles obtained by each of the obtaining method of the present invention by SDS elution (Example 19), the obtaining method of the present invention by EDTA elution (Example 20), the ultracentrifugal separation method (Comparative Example 1), Exo Quick (Comparative Example 2), and Total Exosome Isolation (Comparative Example 3).

<Obtaining of Extracellular Membrane Vesicles by the Obtaining Method of the Present Invention (Examples 19 and 20)>

The mTim-4 protein where the SH-group biotin-labeled FLAG tag fusion type mTim-4 protein was bound to the Dynabeads M-270 Streptavidin C1 (produced by Thermo Fisher Scientific Inc.) and the extracellular membrane vesicles in the calcium ion-containing culture supernatant sample were subjected to a reaction by the same method as in Examples 13 to 14, and the extracellular membrane vesicles were each eluted with the 1% SDS aqueous solution or 1 mM EDTA aqueous solution, as the eluent, to obtain each of the supernatants (eluates) except for using "500 μL of the calcium ion-containing culture supernatant sample", instead of "200 μL of the calcium ion-containing culture supernatant sample", "50 μL of the 1% SDS aqueous solution", instead of "20 μL of the 1% SDS aqueous solution" as an eluent, and using "50 μL of the 1 mM EDTA aqueous solution", instead of "20 μL of the 1 mM EDTA aqueous solution.

Each of the resulting supernatants (eluates) was defined as Sample 1 (when eluted with the 1% SDS aqueous solution), and Sample 2 (when eluted with the 1 mM EDTA aqueous solution).

It should be noted that the type of the mTim-4 protein, the carrier and the eluents used to obtain the extracellular membrane vesicles from the mTim-4 carrier, used in Examples 19 and 20, are shown in the following Table 7.

TABLE 7

| | | Example 19 | Example 20 |
|---|---|---|---|
| Mouse-derived Tim-4 carrier | Type of tag Tag fusion type mouse-derived Tim-4 protein Carrier | FLAG tag Biotin-labeled (SH-group) Streptavidin beads | |
| Eluent | | 1% SDS | 1 mM EDTA |

Obtaining of Extracellular Membrane Vesicles by Ultracentrifugal Separation Method (Comparative Example 1)

The culture supernatant sample (1 mL), prepared by the same method as in Example 1, was subjected to centrifugal separation treatment (20,000×G, for 30 minutes) to separate impurities and obtain the supernatant. Then, 1 mL of the resulting supernatant was subjected to ultracentrifugal separation treatment (110,000×G, for 70 minutes) to obtain a precipitate fraction. Thereafter, the resulting precipitate fraction was suspended in 1 mL of PBS. The suspension of the precipitate fraction was subjected to ultracentrifugal separation treatment again (110,000×G, for 70 minutes), and then the resulting precipitate fraction was suspended in 50 μL of PBS. The resulting suspension was referred to as Sample 3 (Comparative Example 1).

Obtaining of Extracellular Membrane Vesicles by Centrifugal Separation Method Using Commercially Available Reagent (Obtaining of Extracellular Membrane Vesicles by ExoQuick) (Comparative Example 2)

The culture supernatant sample (1 mL), prepared by the same method as in Example 1, was subjected to centrifugal separation treatment (20,000×G, for 30 minutes) to separate impurities and obtain the supernatant. Then, 1 mL of the resulting supernatant was mixed with 0.2 mL of the Exo-Quick-TC Reagent (produced by System Biosciences, Inc.) and the mixture solution was allowed to stand overnight at 8° C. Thereafter, the mixture solution that had been allowed to stand overnight was subjected to centrifugal separation treatment (1,500×G, for 30 minutes), and the resulting precipitate fraction was suspended in 100 μL of PBS. The resulting suspension solution was referred to as Sample 4 (Comparative Example 2).

Obtaining of Extracellular Membrane Vesicles by Centrifugal Separation Method Using Commercially Available Reagent (Obtaining of Extracellular Membrane Vesicles by Total Exosome Isolation) (Comparative Example 3)

The K562 cell culture supernatant concentrated solution sample (1 mL), prepared by the same method as in Example 1, was subjected to centrifugal separation treatment (20,000×G, for 30 minutes) to separate impurities and obtain the supernatant. Subsequently, 1 mL of the resulting supernatant was mixed with 0.5 mL of the Total Exosome Isolation Reagent (produced by Thermo Fisher Scientific Inc.) and allowed to stand at 8° C. for 1 day. The precipitate fraction obtained by centrifugal separation treatment (10,000×G, for 1 hour) of the mixed solution was suspended in 100 μL of PBS. The resulting suspension solution was referred to as Sample 5 (Comparative Example 3).

It should be noted that the methods used in each Example and Comparative Example, the resulting samples, and the lane numbers in Western blotting and silver staining to be described later are shown in the following Table 8.

Ace 5-20% gel (produced by Wako Pure Chemical Industries, Ltd.), and subjected to electrophoresis at 25 mA for 60 minutes. One of the resulting two sheets of the gels was transcribed onto the PVDF membrane (produced by Millipore Corporation) at 1 mA/cm$^2$ for 60 minutes, using the semi-dry blotter and the discontinuous buffer (Anode Buffer 1: 0.3 M Tris/20% Methanol, Anode Buffer 2: 0.025 M Tris/20% Methanol, Cathode Buffer: 0.025 M Tris/0.04 M aminocaproic acid/20% methanol). The 3% skimmed milk, diluted with PBS-T, was added to the PVDF membrane and subjected to a reaction at room temperature for 1 hour for blocking, and then 2 mL of the anti-human Lamp-1 mouse monoclonal antibody (produced by BD Biosciences), diluted 250-fold with PBS-T, was subjected to a reaction at room temperature for 1 hour. After washing 3 times with PBS-T, the membrane was subjected to a reaction with the secondary antibody {anti-mouse IgG (H+L), rabbit, the IgG fraction, the peroxidase-conjugated antibody (produced by Wako Pure Chemical Industries, Ltd.)}, diluted 10,000-fold with PBS-T, at room temperature for 1 hour. After washing five times with PBS-T, an ECL prime (produced by General Electric Company) was added, and each luminescent signal was detected using the LAS-4000 (manufactured by General Electric Company).

In addition, the other one gel was silver stained using a Silver staining II kit Wako (manufactured by Wako Pure Chemical Industries, Ltd.).

<Results>

The results of Western blotting obtained, and the results of silver staining are shown in FIG. 4-A and FIG. 4-B, respectively. In FIG. 4-A and FIG. 4-B, each lane is as follows:

Lane 1: Results of Example 19 (the results of the case where the method of the present invention was carried out using the mTim-4 carrier where the SH-group biotin-labeled FLAG tag fusion type mTim-4 protein was bound on the streptavidin beads, and using the 1% SDS aqueous solution as the eluent);

Lane 2: Results of Example 20 (the results of the case where the method of the present invention was carried out using the mTim-4 carrier where the SH-group biotin-labeled

TABLE 8

|  | Example 19 | Example 20 | Comparative Example 1 | Comparative Example 2 | Comparative Example 3 |
| --- | --- | --- | --- | --- | --- |
| Method | Method of the present invention (elution by 1% SDS) | Method of the present invention (elution by 1 mM EDTA) | Ultra-centrifugation method | Exo Quick | Total Exosome Isolation |
| Sample number | Sample 1 | Sample 2 | Sample 3 | Sample 4 | Sample 5 |
| Lane number in FIG. 4 | 1 | 2 | 3 | 4 | 5 |

<Western Blotting>

Amounts of the proteins in the resulting Samples 1 to 5 by each method were measured by the BCA method, and based on the measurement result, and using the amounts of the proteins as standard amounts of electrophoresis, Western blotting was carried out. That is, 37.5 μL of the PBS solution containing 0.25 μg of each of the proteins in Samples 1 to 5, and 12.5 μL of the 4×sample buffer solution (produced by Wako Pure Chemical Industries, Ltd.) were mixed, and incubated at 98° C. for 5 minutes to obtain 50 μL of each sample for Western blotting.

Subsequently, each 20 μL of the resulting sample for Western blotting was loaded on two sheets of the Super Sep FLAG tag fusion type mTim-4 protein was bound on the streptavidin beads, and using the 1 mM EDTA solution as the eluent);

Lane 3: Results of Comparative Example 1 (the results of the case where obtaining of the extracellular membrane vesicles was carried out by the ultracentrifugal separation method);

Lane 4: Results of Comparative Example 2 (the results of the case where obtaining of the extracellular membrane vesicles was carried out by ExoQuick);

Lane 5: Results of Comparative Example 3 (the results of the case where obtaining of the extracellular membrane vesicles was carried out by Total Exosome Isolation).

From FIG. 4-A, it has been revealed that the extracellular membrane vesicles including exosome can be obtained, according to the obtaining method of the present invention, from the fact that a band of Lamp-1, which is an exosome marker, was observed at the vicinity of 100 kDa in any of Examples 19 and 20, which are the obtaining method of the present invention (Examples 19 to 20: the lanes 1 to 2).

On the other hand, from FIG. 4-A, a band of Lamp-1, which is an exosome marker, was only slightly observed in any of the conventional methods (the ultracentrifugal separation method (Comparative Example 1), Exo Quick (Comparative Example 2) and Total Exosome Isolation (Comparative Example 3)) (Comparative Examples 1 to 3: the lanes 3 to 5).

In addition, from FIG. 4-B, the bands derived from contaminating proteins and the like were found fewer in the obtaining method of the present invention (Examples 19 and 20), as compared with in any of the conventional methods (ultracentrifugal separation method (Comparative Example 1), Exo Quick (Comparative Example 2), and Total Exosome Isolation (Comparative Example 3)), (Examples 19 and 20: lanes 1 and 2, Comparative Examples 1 to 3: lanes 3 to 5).

From the above results, it has been revealed that the extracellular membrane vesicles can be obtained in good purity, by the obtaining method of the present invention (Examples 19 and 20), as compared with any of the conventional methods (the ultracentrifugal separation method (Comparative Example 1), Exo Quick (Comparative Example 2), and Total Exosome Isolation 3)) (the lanes 1 to 5).

Example 21. Electron Microscopic Observation of Extracellular Membrane Vesicles Obtained by Obtaining Method of the Present Invention In order to investigate states of the extracellular membrane vesicles obtained by the obtaining method of the present invention, observation was carried out with an electron microscope.

<(1) Preparation of Mouse Macrophage Culture Supernatant Sample>

In order to obtain peritoneal macrophage, 2 mL of a 3% thioglycolate solution (produced by Fluka) was injected intraperitoneally to 6 female C57BL/6J mice, 8 weeks old (purchased from Japan SLC, Inc.). After 3 days, macrophages were recovered from the peritoneal cavity, and the recovered macrophages were cultured for 2 days in 4 pieces of 150 mm dishes for cell culture, using 80 mL of DMEM (produced by Nacalai Tesque, Inc.) containing 10% FBS (produced by BioWest Co., Ltd.), then the culture supernatant was recovered to obtain the mouse macrophage culture supernatant sample.

<(2) Preparation of Tim-4 Carrier>

The mTim-4 carrier, where the SH-group biotin-labeled Fc tag fusion type mTim-4 protein is bound on the Dynabeads MyOne Streptavidin C1, was prepared by the same method as in Examples 11 to 12, except for using 1 mg of the Dynabeads MyOne Streptavidin C1 (produced by Thermo Fisher Scientific Inc.), instead of 0.6 mg of the Dynabeads MyOne Streptavidin C1 (produced by Thermo Fisher Scientific Inc.), using 100 µL of the PBS solution containing 100 µg of the SH-group biotin labeled Fc tag fusion type mTim-4 protein, instead of 200 µL of the PBS solution containing 1 µg of the SH-group biotin labeled Fc tag fusion type mTim-4 protein, and setting reaction time of the PBS solution containing the Dynabeads and the SH-group biotin labeled Fc tag fusion type mTim-4 protein to 2 hours instead of 1 hour.

<(3) Obtaining of Extracellular Membrane Vesicles Using Tim-4 Carrier>

The mouse macrophage culture supernatant sample (32 mL) was subjected to centrifugal separation treatment (first time: 800×G, for 10 minutes, second time: 12,000×G, for 30 minutes) to obtain the supernatant. After $CaCl_2$ was added to the resulting supernatant, so as to attain the final concentration of 2 mM, 1 mg of the mTim-4 carrier prepared above was added, and mixed while stirring at room temperature for 1 hour. Subsequently, the mTim-4 carrier, mixed under stirring at room temperature for 1 hour, was recovered, then subjected to the washing operation three times with 5 mL of TBS-T containing 2 mM $CaCl_2$ as the final concentration, and further subjected to the washing operation twice with 1 mL thereof, and then eluted three times with 100 µL of TBS containing 1 mM EDTA to obtain 300 µL of the extracellular membrane vesicles fraction.

Subsequently, in order to surely recover the extracellular membrane vesicles in the mouse macrophage culture supernatant sample, the extracellular membrane vesicles were recovered again by the following method, from the mouse macrophage culture supernatant sample after eluting three times with 100 µL of TBS containing 1 mM EDTA to obtain 300 µL of the extracellular membrane vesicles fraction. That is, $CaCl_2$ was added to the mouse macrophage culture supernatant sample, after three times of the elutions with 100 µL of TBS containing 1 mM EDTA, so as to attain the final concentration of 2 mM, then 1 mg of the mTim-4 carrier, after the elution of three times with 100 µL of TBS containing 1 mM EDTA, was added and mixed while stirring at room temperature for 1 hour. Subsequently, the mTim-4 carrier, mixed under stirring at room temperature for 1 hour, was recovered, and subjected to the washing operation three times with 5 mL of TBS-T containing 2 mM $CaCl_2$ at the final concentration, and further subjected to the washing operation twice with 1 mL thereof, and then eluted three times with 100 µL of TBS containing 1 mM EDTA to obtain 300 µL of the extracellular membrane vesicles fraction.

Thereafter, in order to more surely recover the extracellular membrane vesicles in the mouse macrophage culture supernatant sample, the above operation was carried out again, and the extracellular membrane vesicles were recovered from the mouse macrophage culture supernatant sample, after the elution of six times in total with 100 µL of TBS containing 1 mM EDTA to obtain 300 µL of the extracellular membrane vesicles fraction.

Total 900 µL of the extracellular membrane vesicles, obtained by nine times of the elution operations, was concentrated to 60 µL using an Amicon Ultra-0.5 mL 10K centrifugal filter column to obtain a sample for observation with an electron microscope.

<(4) Observation of Extracellular Membrane Vesicles Obtained by Obtaining Method of the Present Invention, with Electron Microscope>

The sample (10 µL) for observation with the electron microscope was adsorbed on a grid, and the excessive sample for observation with the electron microscope was suctioned with a filter paper. Subsequently, the grid was washed with water, and stained twice with a uranium acetate aqueous solution, and then observation by a negative staining method was carried out with a transmission electron microscope.

It should be noted that the type of the mTim-4 protein, the carrier, and the eluent used for obtaining the extracellular membrane vesicles from the mTim-4 carrier, used in Example 21, are shown in the following Table 9.

TABLE 9

|  |  | Example 21 |
| --- | --- | --- |
| Mouse-derived Tim-4 carrier | Type of tag | Fc tag |
|  | Tag fusion type mouse-derived Tim-4 protein | Biotin-labeled (SH-group) |
|  | Carrier | Streptavidin beads |
| Eluent |  | TBS containing 1 mM EDTA |

<Results>

Figure 5:
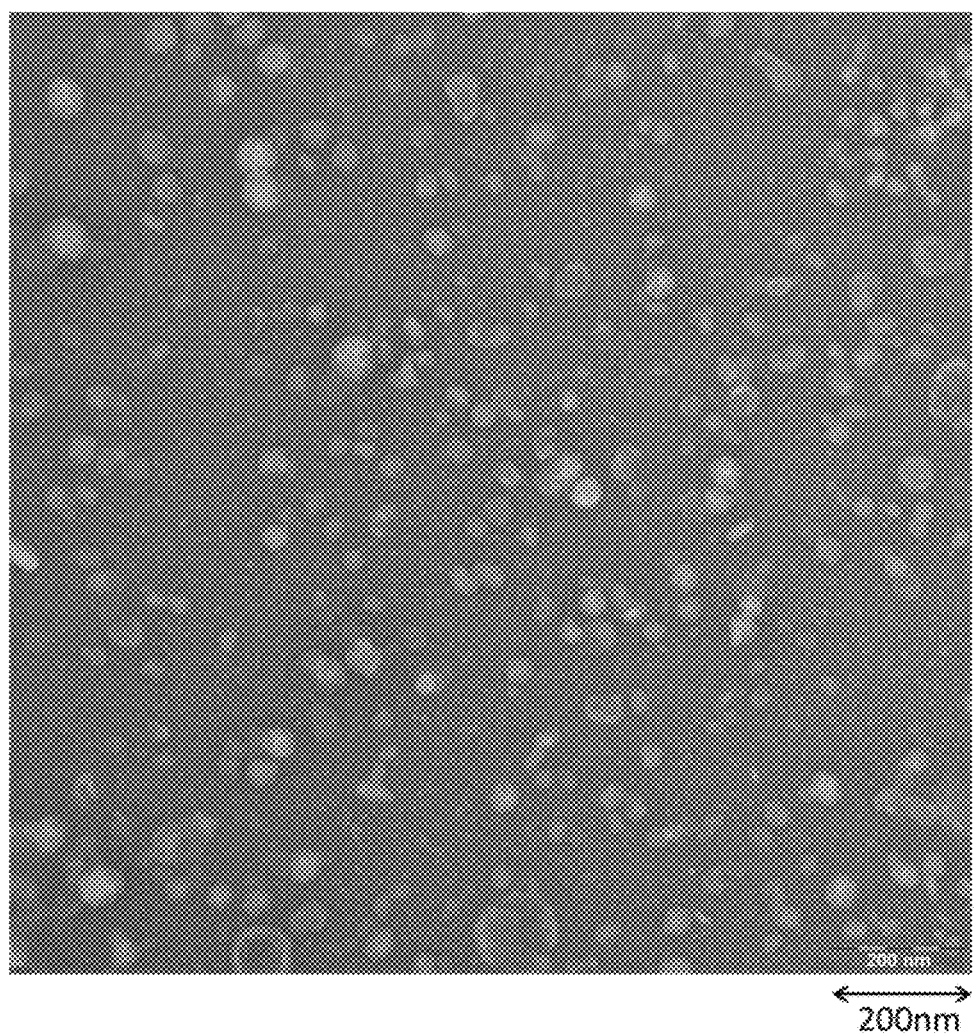
FIG. 5 is a drawing where the extracellular membrane vesicles, obtained by the method of the present invention, were observed using an electron microscope, in Example 21.

The resulting observation image with the electron microscope is shown in FIG. 5. From FIG. 5, it has been revealed that the extracellular membrane vesicles, having a diameter of about 50 to 150 nm, can be obtained, while maintaining a spherical shape, according to the obtaining method of the present invention.

From the above, it has been revealed that the extracellular membrane vesicles can be obtained in an intact state, according to the obtaining method of the present invention.

Examples 22 to 25. Obtaining of Extracellular Membrane Vesicles by Tim-4 Carrier of the Present Invention (Obtaining Method of the Present Invention)

The extracellular membrane vesicles pertaining to the present invention was obtained using the carrier where the human-derived Tim-4 protein was immobilized on the beads (hereinafter it may be abbreviated as "the hTim-4 carrier", in some cases), and the mTim-4 carrier.

<(1) Preparation of Culture Supernatant Sample>

Preparation of the culture supernatant sample was carried out in the same method as in "(1) preparation of culture supernatant sample" of Examples 1 to 8.

<(2) Dilution of Fc Tag Fusion Type Tim-4 Protein>

The PBS solution containing 100 µg/mL of the biotin-unlabeled Fc tag fusion type human-derivedTim-4 protein was prepared by dissolving, in 1 mL of PBS, 100 µg of a freeze-dried product of the biotin-unlabeled Fc tag fusion type human-derived Tim-4 protein (produced by Wako Pure Chemical Industries, Ltd., SEQ ID NO: 7 (the human-derived Tim-4 protein in which Fc tag was fused to the N-terminal 25 to 315 amino acid region of the human-derived Tim-4 protein (GenBank NP_612388.2)). The PBS solution (200 µL) containing 1 µg of the biotin-unlabeled Fc tag fusion type hTim-4 protein was obtained by mixing 10 µL of the PBS solution containing the biotin-unlabeled Fc tag fusion type hTim-4 protein, and 190 µL of PBS.

In addition, the PBS solution containing 100 µg/mL of the biotin-unlabeled Fc tag fusion type mTim-4 protein was prepared by dissolving, in 1 mL of PBS, 100 µg of the freeze-dried product of the biotin-unlabeled Fc tag fusion type mouse-derived Tim-4 protein (produced by Wako Pure Chemical Industries, Ltd., SEQ ID NO: 6 (the mTim-4 protein in which the Fc tag was fused to N-terminal 22 to 279 amino acid region of the mouse-derived Tim-4 protein (GenBank NP_848874.3)). The PBS solution (200 µL) containing 1 µg of the biotin-unlabeled Fc tag fusion type mTim-4 protein was obtained by mixing 10 µL of the PBS solution containing the biotin-unlabeled Fc tag fusion type mTim-4 protein, and 190 µL of PBS.

<(3) Washing of Beads>

The PBS-T solution (20 µL) containing the 30 µg/µL Dynabeads Protein G (produced by Thermo Fisher Scientific Inc.) (containing 0.6 mg of the Dynabeads Protein G) was dispensed into each of two 1.5 mL tubes (manufactured by BM Equipment Co., Ltd.) to carry out the washing operation using 500 µL of PBS.

<(4) Immobilization of Biotin-Unlabeled Fc Tag Fusion Type Tim-4 Protein on Beads>

For one of two 1.5 mL tubes containing the Dynabeads Protein G (0.6 mg), 200 µL of the PBS solution containing 1 µg of the biotin-unlabeled Fc tag fusion type hTim-4 protein, prepared above, was added in its entirety, and subjected to a reaction at 8° C. for 1 hour to obtain 200 µL of the PBS solution containing the carrier on which the biotin-unlabeled Fc tag fusion type hTim-4 protein was bound (the hTim-4 carrier).

For remaining one 1.5 mL tube containing the Dynabeads Protein G (0.6 mg), 200 µL of the PBS solution containing 1 µg of the biotin-unlabeled Fc tag fusion type mTim-4 protein prepared above was added in its entirety, and subjected to a reaction at 8° C. for 1 hour to obtain 200 µL of the PBS solution containing the carrier on which the biotin-unlabeled Fc tag fusion type mTim-4 protein was bound (mTim-4 carrier).

<(5) Obtaining of Extracellular Membrane Vesicles by Obtaining Method of the Present Invention>

After subjecting each 0.6 mg of the resulting hTim-4 carrier and the mTim-4 carrier above to the washing operation with 500 µL of PBS three times, 200 µL of the calcium ion-containing culture supernatant sample was added to each of the hTim-4 carrier and the mTim-4 carrier, in a pellet state, and subjected to a reaction each at 8° C. for 3 hours. Thereafter, the hTim-4 carrier and the mTim-4 carrier after the reaction were each subjected to the washing operation three times with 500 µL of 2 mM $CaCl_2$-containing TBS-T.

At the third time of washing, the hTim-4 carrier and the mTim-4 carrier each 250 µL, (0.3 mg of the carrier) were dispensed into two 1.5 mL tubes. To each 0.3 mg of the mTim-4 carrier and the hTim-4 carrier, in a pellet state, 20 µL of the 1% SDS aqueous solution, or the 1 mM EDTA aqueous solution was added, as the eluent, and then they were mixed at room temperature for 10 seconds using a vortex mixer and spun down. The 1.5 mL tubes were each loaded on a magnet stand, and the hTim-4 carrier and the mTim-4 carrier were collected on the tube wall by magnetic force to recover each supernatant (eluate).

It should be noted that the types of the Tim-4 proteins, the carrier used, and the eluates used for obtaining the extracellular membrane vesicles from the Tim-4 carrier, in Examples 22 to 25, and the lane numbers in Western blotting to be described later are shown in the following Table 10.

TABLE 10

|  | Example 22 | Example 23 | Example 24 | Example 25 |
| --- | --- | --- | --- | --- |
| Mouse-derived Tim-4 carrier or | Tim-4 protein | Fc tag fusion type human-derived | | Fc tag fusion type mouse-derived |

TABLE 10-continued

Figure 6:
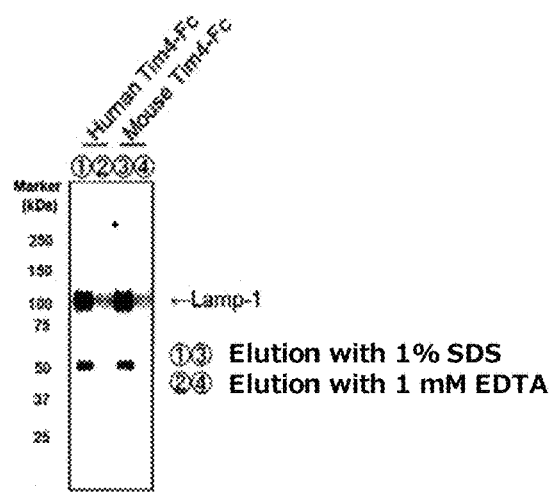
FIG. 6 is an electropherogram for confirming whether the extracellular membrane vesicles were obtained or not, by Western blotting, in Examples 22 to 25.

|  |  | Example 22 | Example 23 | Example 24 | Example 25 |
|---|---|---|---|---|---|
| Human-derived Tim-4 carrier | | Tim-4 protein (Biotin-unlabeled) | | Tim-4 protein (Biotin-unlabeled) | |
| | Carrier | Dynabeads | | Protein G beads | |
| Eluent | | 1% SDS | 1 mM EDTA | 1% SDS | 1 mM EDTA |
| Lane number in FIG. 6 | | 1 | 2 | 3 | 4 |

<(6) Western Blotting>

Western blotting was carried out by the same method as in "(7) Western blotting" of Examples 1 to 8, except for using "7.5 μL of each supernatant (eluate) obtained in Examples 22 to 25 (above (5))", instead of "7.5 μL of each supernatant (eluate) obtained in Examples 1 to 8".

<Results>

The results of Western blotting obtained are shown in FIG. 6. In FIG. 6, each lane is as follows:

Lane 1: Results of Example 22 (the results of the case of using the hTim-4 carrier where the biotin-unlabeled Fc tag fusion type hTim-4 protein was bound on the Protein G beads, and using the 1% SDS aqueous solution as the eluent);

Lane 2: Results of Example 23 (the results of the case of using the hTim-4 carrier where the biotin-unlabeled Fc tag fusion type hTim-4 protein was bound on the Protein G beads, and using the 1 mM EDTA aqueous solution as the eluent);

Lane 3: Results of Example 24 (the results of the case of using the mTim-4 carrier where the biotin-unlabeled Fc tag fusion type mTim-4 protein was bound on the Protein G beads, and using the 1% SDS aqueous solution as the eluent);

Lane 4: Results of Example 25 (the results of the case of using the mTim-4 carrier where the biotin-unlabeled Fc tag fusion type mTim-4 protein was bound on the Protein G beads, and using the 1 mM EDTA aqueous solution as the eluent).

From FIG. 6, it has been revealed that the extracellular membrane vesicles including exosome can be obtained, according to the obtaining method of the present invention, from the fact that a band of Lamp-1, which is an exosome marker, was observed at the vicinity of 100 kDa in any case of Examples 22 to 25 (Example 22 to 25: the lanes 1 to 4).

In addition, it has been revealed that the Tim-4 protein can be used for the Tim-4 carrier of the present invention and the obtaining method of the present invention, regardless of organism species of origin.

Examples 26 to 27 and Comparative Examples 4 to 9. Comparison of Obtained Amount of Extracellular Membrane Vesicles by Tim-4 Carrier and Carrier on which PS Protein was Immobilized Obtaining of the extracellular membrane vesicles pertaining to the present invention was carried out using the Tim-4 carrier and the carrier where PS proteins (human origin Annexin V, human MFG-E8, and mouse derived MFG-E8) were each immobilized on the beads.

<(1) Dilution of PS Protein-Containing PBS Solution>

The His tag fusion type human-derived Annexin V (20 μg, produced by Creative BioMart Co., Ltd., it may be abbreviated as "the His tag fusion type hAnnexin V", in some cases) was dissolved in 100 μL of PBS, so as to attain 200 μg/mL to prepare the His tag fusion type hAnnexin V-containing PBS solution. Then, 5 μL of the PBS solution containing 1 μg of the His tag fusion type hAnnexin V protein and 195 μL of PBS were mixed for dilution.

The His tag fusion type human-derived MFG-E8 (50 μg, produced by R & D Systems Co., Ltd., it may be abbreviated as "the His tag fusion type hMFG-E8") was dissolved in 500 μL of PBS, so as to attain 100 μg/mL to prepare the His tag fusion type hMFG-E8-containing PBS solution. Then, 10 μL of the PBS solution containing 1 μg of the His tag fusion type hMFG-E8 protein, and 190 μL of PBS were mixed for dilution. The His tag fusion type mouse-derived MFG-E8 (50 μg, produced by R & D Systems Co., Ltd., it may be abbreviated as "the His tag fusion type mMFG-E8") was dissolved in 500 μL of PBS, so as to attain 100 μg/mL to prepare the His tag fusion type mMFG-E8-containing PBS solution. Then, 10 μL of the PBS solution containing 1 μg of the His tag fusion type mouse-derived MFG-E8 protein, and 190 μL of PBS were mixed for dilution.

<(2) Preparation of Anti-his Tag Antibody-Immobilized Beads>

A solution (100 μL) containing 30 μg/μL Dynabeads M-270 Carboxylic Acid (produced by Thermo Fisher Scientific Inc.) (containing 3 mg of the Dynabeads M-270 Carboxylic Acid) was dispensed into the 1.5 mL tube (manufactured by BM Equipment Co., Ltd.), and the washing operation was carried out using a reaction buffer (0.1 M MES, pH 5.0).

Subsequently, 60 μL of a solution of a 6× His antibody (produced by Wako Pure Chemical Industries, Ltd.) (containing 60 μg of the 6× His antibody), diluted with 490 μL of the reaction buffer, was added and mixed with inversion at room temperature for 30 minutes, then 50 μL of 6 mg/mL WSC (produced by Dojindo Molecular Technologies, Inc.) was added and mixed with inversion at room temperature for 4 hours. The Dynabeads M-270 Carboxylic Acid after mixing by inversion was subjected to the washing operation with TBS-T, and diluted with 100 μL of PBS to obtain 3 mg of the anti-His tag antibody-immobilized beads.

<(3) Preparation of Tim-4 Carrier and Carrier on which Various PS Proteins were Immobilized>

Subsequently, 100 μL of the PBS solution containing the resulting anti-His tag antibody-immobilized beads (containing 3 mg of the anti-His tag antibody-immobilized beads) was dispensed into each of four 1.5 mL tubes (manufactured by BM Equipment Co., Ltd.) in an amount of each 20 μL (containing 0.6 mg of the anti-His tag antibody-immobilized beads), and the washing operation was each carried out with 500 μL PBS.

After that, for one of the four 1.5 mL tubes containing 0.6 mg of the anti-His tag antibody-immobilized beads in a pellet state, after the washing operation, 200 μL of the His tag fusion type mTim-4 protein-containing PBS solution prepared above (containing 1 μg of the His tag fusion type mTim-4 protein) was added and subjected to a reaction at 8° C. for 1 hour.

Further, for one tube, 200 μL of the His tag fusion type hAnnexin V-containing PBS solution prepared above (containing 1 μg of the His tag fusion type hAnnexin V) was added and subjected to a reaction at 8° C. for 1 hour.

For one tube, 200 μL of the His tag fusion type hMFG-E8-containing PBS solution prepared above (containing 1 μg of the His tag fusion type hMFG-E8) was added and subjected to a reaction at 8° C. for 1 hour.

For one tube, 200 μL of the His tag fusion type mMFG-E8-containing PBS solution prepared above (containing 1 μg of the His tag fusion type mMFG-E8) was added and subjected to a reaction at 8° C. for 1 hour.

In this way, 200 μL of the PBS solutions each containing 0.6 mg of each of the four types of the carriers shown in the following Table 11 were obtained.

TABLE 11

| | | 1 | 2 | 3 | 4 |
|---|---|---|---|---|---|
| Mouse-derived Tim-4 carrier or Phosphatidylserine bound protein-immobilized carrier | Phosphatidylserine bound protein Carrier | His tag fusion type mouse-derived Tim-4 protein | His tag fusion type human-derived Annexin V | His tag fusion type human-derived MFG-E8 | His tag fusion type mouse-derived MFG-E8 |
| | | | Anti-Histag antibody-immobilized beads | | |

<(4) Obtaining of Extracellular Membrane Vesicles>

The PBS solution (200 μL) each containing 0.6 mg of each of the resulting 4 types of carriers above was subjected to the washing operation three times with 500 μL of PBS, then 200 μL of the calcium ion-containing culture supernatant sample, prepared by the same method as in Examples 1 to 8, was added to each of 5 types of the carriers in a pellet state, and subjected to a reaction at 8° C. for 3 hours.

Thereafter, 4 types of the carriers, which were subjected to a reaction with the calcium ion-containing culture supernatant sample, were subjected to the washing operation three times each with 500 μL of TBS-T containing 2 mM $CaCl_2$.

At the third time of washing, each 250 μL of 4 types of the carriers was dispensed into two 1.5 mL tubes. The 1% SDS aqueous solution or the 1 mM EDTA aqueous solution (each 20 μL) was added, as the eluent, to each 0.3 mg of 4 types of the carriers in a pellet state, and then spun down using a vortex mixer at room temperature for 10 seconds. Each 1.5 mL of the tube was loaded on a magnet stand, and the resulting 4 types of the carriers were collected on the tube wall using magnetic force to recover the supernatant (eluate).

It should be noted that types of the PS proteins, the carriers, and the eluates used for obtaining the extracellular membrane vesicles from the carriers, used in each Example, and the lane numbers in Western blotting to be described later are shown in the following Table 12.

<(5) Western Blotting>

Western blotting was carried out by the same method as in "(7) Western blotting" of Examples 1 to 8, except for using "7.5 μL of each supernatant (eluate) obtained in Examples 26 to 27, Comparative Examples 4 to 9 (above (4))", instead of "7.5 μL of each supernatant (eluate) obtained in Examples 1 to 8".

<Results>

Figure 7:
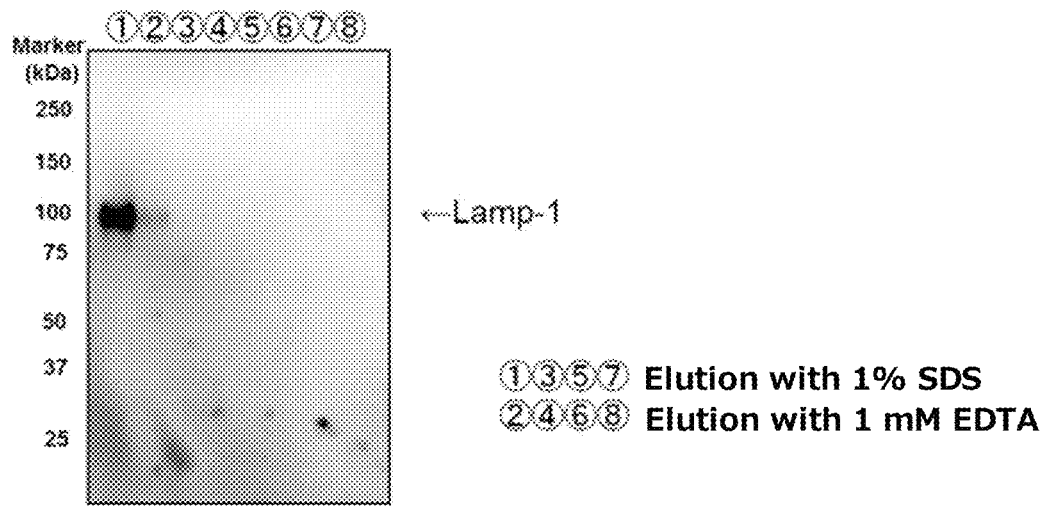
FIG. 7 is an electropherogram for confirming whether the extracellular membrane vesicles were obtained or not, by silver staining, in Examples 26 to 27, and Comparative Examples 4 to 9.

The results of Western blotting obtained are shown in FIG. 7. In FIG. 7, each lane is as follows:

Lane 1: Results of Example 26 (the results of the case of using the carrier where the His tag fusion type mTim-4 protein was bound on the anti-His tag antibody-immobilized beads, and using the 1% SDS aqueous solution as the eluent);

Lane 2: Results of Example 27 (the results of the case of using the carrier where the His tag fusion type mTim-4 protein was bound on the anti-His tag antibody-immobilized beads, and using the 1 mM EDTA aqueous solution as the eluent);

Lane 3: Results of Comparative Example 4 (the results of the case of using the carrier where the His tag fusion type hAnnexin V was bound on the anti-His tag antibody-immobilized beads, and using the 1% SDS aqueous solution as the eluent);

Lane 4: Results of Comparative Example 5 (Results in a case of using the carrier where the His tag fusion type hAnnexin V was bound on the anti-His tag antibody-immobilized beads, and using the 1 mM EDTA aqueous solution as the eluent);

Lane 5: Results of Comparative Example 6 (the results of the case of using the carrier where the His tag fusion type hMFG-E8 was bound on the anti-His tag antibody-immobilized beads, and using the 1% SDS aqueous solution as the eluent);

Lane 6: Results of Comparative Example 7 (the results of the case of using the carrier where the His tag fusion type hMFG-E8 was bound on the anti-His tag antibody-immobilized beads, and using the 1 mM EDTA aqueous solution as the eluent);

Lane 7: Results of Comparative Example 8 (the results of the case of using the carrier where the His tag fusion type

TABLE 12

| | | Example 26 | Example 27 | Comparative Example 4 | Comparative Example 5 | Comparative Example 6 | Comparative Example 7 | Comparative Example 8 | Comparative Example 9 |
|---|---|---|---|---|---|---|---|---|---|
| Mouse-derived Tim-4 carrier or PS protein-immobilized carrier | PS protein Carrier | His tag fusion type mouse-derived Tim-4 protein | | His tag fusion type human-derived Annexin V | | His tag fusion type human-derived MFG-E8 | | His tag fusion type mouse-derived MFG-E8 | |
| | | | | Anti-His tag antibody-immobilized beads | | | | | |
| Eluent | | 1% SDS | 1 mM EDTA | 1% SDS | 1 mM EDTA | 1% SDS | 1 mM EDTA | 1% SDS | 1 mM EDTA |
| Lane number in FIG. 7 | | 1 | 2 | 3 | 4 | 5 | 6 | 7 | 8 | mMFG-E8 was bound on the anti-His tag antibody-immobilized beads and using the 1% SDS aqueous solution as the eluent);

Lane 8: Results of Comparative Example 9 (the results of the case of using the carrier where the His tag fusion type mMFG-E8 was bound on the anti-His tag antibody-immobilized beads, and using the 1 mM EDTA aqueous solution as the eluent).

From FIG. 7, it has been revealed that the extracellular membrane vesicles including exosome can be obtained, according to the obtaining method of the present invention, from the fact that a band of Lamp-1, which is an exosome marker, was observed at the vicinity of 100 kDa in any case of Examples 26 to 27 (Example 26 to 27: the lanes 1 to 2).

On the other hand, from FIG. 7, it has been revealed that the extracellular membrane vesicles including exosome cannot be obtained by the carriers on which the PS proteins other than the Tim-4 protein (Annexin V, MFG-E8) were immobilized, from the fact that the band of Lamp-1 was not observed at the vicinity of 100 kDa in any case of Comparative Examples 4 to 9 (Comparative Example 4 to 9: the lanes 3 to 8).

Examples 28 to 33. Obtaining of Extracellular Membrane Vesicles by Obtaining Method of the Present Invention (Examination of Complex Formation Step)

The extracellular membrane vesicles were obtained by each of the obtaining methods of the present invention as described below.

In Examples 28 to 29, after the SH-group biotin-labeled FLAG tag fusion type mouse-derived Tim-4 protein, prepared by the same method as in Examples 13 to 14, was subjected to a reaction with the carrier pertaining to the present invention, the sample was further added thereto to obtain the extracellular membrane vesicles pertaining to the present invention.

In Examples 30 to 31, after the SH-group biotin-labeled FLAG tag fusion type mouse-derived Tim-4 protein, prepared by the same method as in Examples 13 to 14, was subjected to a reaction with the sample, the carrier pertaining to the present invention was further added thereto to obtain the extracellular membrane vesicles pertaining to the present invention.

In Examples 32 to 33, the SH-group biotin-labeled FLAG tag fusion type mouse-derived Tim-4 protein, prepared by the same method as in Examples 13 to 14, the sample, and the carrier pertaining to the present invention were added at the same time to obtain the extracellular membrane vesicles pertaining to the present invention.

<Washing of Beads>

Each 60 µL of the PBS solution containing the 10 µg/µL Dynabeads M-270 Streptavidin C1 (produced by Thermo Fisher Scientific Inc.) (containing 0.6 mg of the Dynabeads M-270 Streptavidin C1) was dispensed into three 1.5 mL tubes (manufactured by BM Equipment Co., Ltd.), and the washing operation was carried out each using 500 µL of PBS.

The His tag fusion type mTim-4 protein-containing PBS solution (270 µL) (containing 50 µg of the His tag fusion type mTim-4 protein) was labeled with biotin by the same method as in Examples 13 to 14 to obtain 200 µL of the PBS solution containing 39.2 µg of the SH-group biotin-labeled FLAG tag fusion type mTim-4 protein. Into 5.1 µL of the PBS solution containing 1 µg of the resulting SH-group biotin-labeled FLAG tag fusion type mTim-4 protein, 194.9 µL of the PBS solution was added to obtain 200 µL of the PBS solution containing 1 µg of the SH-group biotin-labeled FLAG tag fusion type mTim-4 protein.

<The Case of Subjecting the SH-Group Biotin-Labeled FLAG Tag Fusion Type mTim-4 Protein and the Carrier Pertaining to the Present Invention to a Reaction, Followed by Further Subjecting the Extracellular Membrane Vesicles in the Sample Pertaining to the Present Invention to a Reaction (Examples 28 to 29)>

The PBS solution (200 µL) containing 1 µg of the SH-group biotin-labeled FLAG tag fusion type mTim-4 protein was added to the 1.5 mL tube containing 0.6 mg of the pellet-like Dynabeads M-270 Streptavidin C1 which had been subjected to the washing operation, and the Dynabeads M-270 Streptavidin C1, and the SH-group biotin-labeled FLAG tag fusion type mTim-4 protein were brought into contacted and subjected to a reaction at 8° C. for 1 hour to obtain the mTim-4 carrier. Subsequently, the resulting mTim-4 carrier was subjected to the washing operation three times with 500 µL of PBS, and 200 µL of the calcium ion-containing culture supernatant sample, prepared by the same method as in Example 1, was added to the 1.5 mL tube containing 0.6 mg of the mTim-4 carrier after washing, and subjected to a reaction at 8° C. for 3 hours. After that, the mTim-4 carrier which had been subjected to a reaction with the calcium ion-containing culture supernatant sample was subjected to the washing operation three times with 500 µL of TBS-T added with 2 mM $CaCl_2$ as the final concentration. At the third time of washing, each 250 µL of the mTim-4 carrier was dispensed into two 1.5 mL tubes. After the addition of 20 µL of the 1% SDS aqueous solution or the 1 mM EDTA aqueous solution, as the eluent, to each 0.3 mg of the mTim-4 carrier in a pellet state, they were mixed at room temperature for 10 seconds using a vortex mixer and spun down. Each of the 1.5 mL tubes was loaded on a magnet stand, and the mTim-4 carrier was collected on the tube wall using magnetic force to recover each supernatant (eluate).

<The Case of Subjecting SH-Group Biotin-Labeled FLAG Tag Fusion Type mTim-4 Protein and Sample Pertaining to the Present Invention to a Reaction, Followed by Further Subjecting the Carrier Pertaining to the Present Invention to a Reaction Examples 30-31>

The calcium ion-containing culture supernatant sample (200 µL) prepared by the same method as in Example 1 was dispensed into the 1.5 mL tube, and 5.1 µL of the PBS solution containing 1 µg of the SH-group biotin-labeled FLAG tag fusion type mTim-4 protein was added, and the extracellular membrane vesicles in the calcium ion-containing culture supernatant sample, and the SH-group biotin-labeled FLAG tag fusion type mTim-4 protein were brought into contacted and subjected to a reaction at 8° C. for 3 hours.

The complex of the extracellular membrane vesicles and the mTim-4 carrier was obtained by the addition of the solution after subjecting the extracellular membrane vesicles in the calcium ion-containing culture supernatant sample, and the SH-group biotin-labeled FLAG tag fusion type mTim-4 protein to a reaction at 8° C. for 3 hours, to the 1.5 mL tube containing 0.6 mg of the pellet-like Dynabeads M-270 Streptavidin C1 after the washing operation, and subjecting them to a reaction at 8° C. for 1 hour. Thereafter, the resulting complex of the extracellular membrane vesicles and the mTim-4 carrier was subjected to the washing operation three times with 500 µL of TBS-T added with 2 mM $CaCl_2$ as the final concentration. At the third time of washing, each 250 µL of the complex with the mTim-4 carrier was dispensed into the two 1.5 mL tubes. After the addition of 20 μL of the 1% SDS aqueous solution or the 1 mM EDTA aqueous solution, as the eluent, to each 0.3 mg of the complex with the mTim-4 carrier in a pellet state, they were mixed using a vortex mixer at room temperature for 10 seconds and spun down. Each of the 1.5 mL tubes was loaded on a magnet stand, and the mTim-4 carrier was collected on the tube wall using magnetic force to recover each supernatant (eluate).

<The Case of Subjecting the SH-Group Biotin-Labeled FLAG Tag Fusion Type mTim-4 Protein, Sample Pertaining to the Present Invention, and Carrier Pertaining to the Present Invention to Reaction Simultaneously (Examples 32 to 33)>

The calcium ion-containing culture supernatant sample (200 μL) prepared by the same method as in Example 1, and 5.1 μL of the PBS solution containing 1 μg of the SH-group biotin-labeled FLAG tag fusion type mTim-4 protein were added to the 1.5 mL tube containing 0.6 mg of the pellet-like Dynabeads M-270 Streptavidin C1 after the washing operation, and subjected to a reaction at 8° C. for 4 hours. The Dynabeads M-270 Streptavidin C1 in a pellet state after the reaction was subjected to the washing operation three times with 500 μL of TBS-T containing 2 mM $CaCl_2$ as the final concentration. At the third time of washing, each 250 μL of the mTim-4 carrier was dispensed into the two 1.5 mL tubes, and 20 μL of the 1% SDS aqueous solution or the 1 mM EDTA aqueous solution was added, as the eluate, to each 0.3 mg of the mTim-4 carrier, and then they were mixed using a vortex mixer at room temperature for 10 seconds and spun down. Each of the 1.5 mL tubes was loaded on a magnet stand, and the Dynabeads M-270 Streptavidin C1 was collected on the tube wall using magnetic force to recover each supernatant (eluate).

It should be noted that, the order of bringing into contacted the carrier, the mTim-4 protein, and the calcium ion-containing culture supernatant sample, and the types of the eluents used for obtaining the extracellular membrane vesicles from the carrier, in each Example, are shown in the following Table 13.

TABLE 13

| | Order of contact | Eluent |
|---|---|---|
| Example 28 | (1) Contacting carrier with mouse-derived Tim-4 protein | 1% SDS |
| Example 29 | (2) Further contacting with calcium ion-containing cell culture supernatant sample | 1% EDTA |
| Example 30 | (1) Contacting mouse-derived Tim-4 protein with calcium ion-containing cell culture supernatant sample | 1% SDS |
| Example 31 | (2) Further contacting with carrier | 1% EDTA |
| Example 32 | (1) Contacting carrier, calcium ion-containing cell culture supernatant sample, and | 1% SDS |
| Example 33 | mouse-derived Tim-4 protein at the same time | 1% EDTA |

<Western Blotting>

Western blotting was carried out by the same method as in "(7) Western blotting" of Examples 1 to 8, except for using "7.5 μL of each supernatant (eluate) obtained in Examples 28 to 33 (above (5))", instead of "7.5 μL of each supernatant (eluate) obtained in Examples 1 to 8".

<Results>

Figure 8:
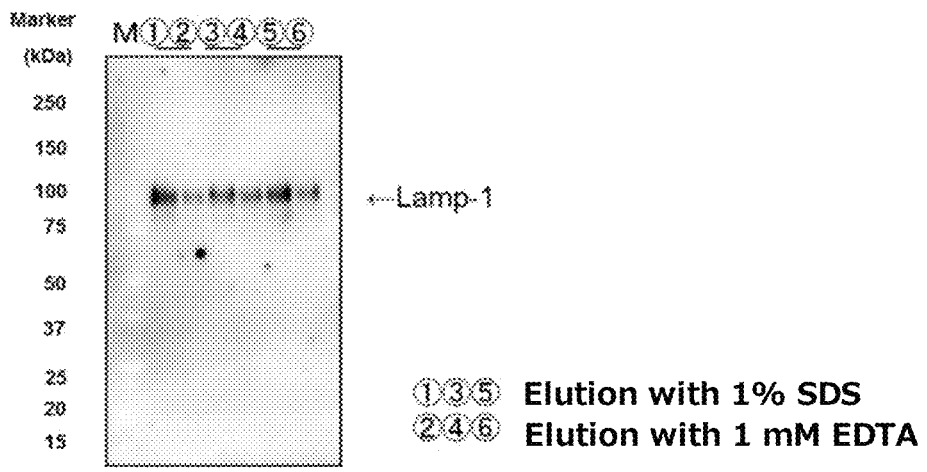
FIG. 8 is an electropherogram for confirming whether the extracellular membrane vesicles were obtained or not, by Western blotting, in Examples 28 to 33.

The results of Western blotting obtained are shown each in FIG. 8. In FIG. 8, each lane is as follows:

Lane 1: Results of Example 28 (the results of the case of obtaining the extracellular membrane vesicles by the method for bringing into contacted the carrier with the mTim-4 protein, further bringing into contacted with the calcium ion-containing cell culture supernatant sample, and using the 1% SDS aqueous solution as the eluent);

Lane 2: Results of Example 29 (the results of the case of obtaining the extracellular membrane vesicles by the method for bringing into contacted the carrier with the mTim-4 protein, further bringing into contacted with the calcium ion-containing cell culture supernatant sample, and using the 1 mM EDTA aqueous solution was used as an eluent);

Lane 3: Results of Example 30 (the results of the case of obtaining the extracellular membrane vesicles by the method for bringing into contacted the mTim-4 protein and the calcium ion-containing cell culture supernatant sample, further bringing into contacted with the carrier, and using the 1% SDS aqueous solution was used as an eluent);

Lane 4: Results of Example 31 (the results of the case of obtaining the extracellular membrane vesicles by the method for bringing into the mTim-4 protein with the calcium ion-containing cell culture supernatant sample, further bringing into contacted with the carrier, and using the 1 mM EDTA aqueous solution was used as an eluent);

Lane 5: Results of Example 32 (the results of the case of obtaining the extracellular membrane vesicles by the method for bringing into contacted the carrier, the calcium ion-containing cell culture supernatant sample, and the mTim-4 protein at the same time, and using the 1% SDS aqueous solution as the eluent), Lane 6: Results of Example 33 (the results of the case of obtaining the extracellular membrane vesicles by the method for bringing into contacted the carrier, the calcium ion-containing cell culture supernatant sample, and the mTim-4 protein at the same time, and using the 1 mM EDTA aqueous solution as the eluent).

As shown in FIG. 8, a band of Lamp-1, which is an exosome marker, was obtained at the vicinity of 100 kDa in any case of Examples 28 to 33 (Examples 28 to 33: the lanes 1 to 6).

In addition, from the results of Examples 28 to 33, it has been revealed that the step for forming the complex of the Tim-4 protein bound to the carrier and the extracellular membrane vesicles in the sample (complex formation step) may be any step, as long as the complex of the mTim-4 protein bound to the carrier and the extracellular membrane vesicles in the sample is accordingly formed, regardless of the order of contact among the Tim-4 protein pertaining to the present invention, the carrier pertaining to the present invention, and the extracellular membrane vesicles in the sample.

Examples 34 to 35, Comparative Examples 10 to 13. Comparison Between Obtaining Methods of the Present Invention and Conventional Method As described below, the extracellular membrane vesicles were obtained by the obtaining method of the present invention by elution with SDS (Example 34), by the obtaining method of the present invention by elution with EDTA (Example 35), by the anti-CD 63 antibody immobilization method (Comparative Examples 10 to 11), and by Exosome-Human CD63 Isolation/Detection (Comparative Examples 12 to 13).

<Immobilization of Tim-4 Protein on Carrier>

The solution (15 μL) containing the 10 μg/μL Dynabeads M-270 Streptavidin (produced by Thermo Fisher Scientific Inc.) (containing $1 \times 10^7$ particles of the Dynabeads M-270

Streptavidin) was dispensed into the 1.5 mL tube (manufactured by BM Equipment Co., Ltd), and subjected to the washing operation.

Subsequently, 200 μL of the PBS solution containing 0.25 μg of the SH-group biotin-labeled FLAG tag fusion type mouse-derived Tim-4 protein, prepared by the same method as in Examples 11 to 12, was added in its entirety to the 1.5 mL tube containing the Dynabeads M-270 Streptavidin after the washing operation, and subjected to a reaction under refrigeration for 1 hour to obtain the PBS solution containing the mTim-4 carrier.

<Preparation of Anti-CD63 Antibody (H5C6)-Immobilized Carrier>

The solution (50 μL) containing the 30 μg/μL Dynabeads M-270 Carboxylic Acid (produced by Thermo Fisher Scientific, Inc.) (containing $1 \times 10^8$ particles of the Dynabeads M-270 Carboxylic Acid) was dispensed into the 1.5 mL tube (manufactured by BM Equipment Co., Ltd), and subjected to the washing operation using the reaction buffer (0.1 M MES, pH 5.0).

On the other hand, 30 g (60 μL) of the anti-CD63 antibody (H5C6) (produced by BD Pharmingen) was diluted with 490 μL of the reaction buffer (0.1 M MES, pH 5.0) to obtain a reaction buffer-diluted anti-CD 63 antibody solution.

Subsequently, 550 μL of the reaction buffer-diluted anti-CD 63 antibody solution was added to the 1.5 mL tube containing the Dynabeads M-270 Carboxylic Acid, after the washing operation, and mixed with inversion at room temperature for 30 minutes. Thereafter, further 50 μL of 3 mg/mL WSC (produced by Dojindo Molecular Technologies, Inc.) was added and mixed with inversion at room temperature for 4 hours, and after the washing operation with TBS-T, dilution was carried out with 50 μL PBS to obtain the PBS solution containing the anti-CD63 antibody (H5C6) carrier.

In this way, two kinds of the carriers shown in the following Table 14 were obtained.

TABLE 14

|  | 1 | 2 |
|---|---|---|
| Protein or antibody to be immobilized on carrier | Biotin-labeled (SH-group) FLAG tag fusion type mouse-derived Tim-4 protein | Anti-CD63 antibody (H5C6) |
| Carrier | Dynabeads M-270 Streptavidin | Dynabeads M-270 Carboxylic Acid |

<Obtaining of Extracellular Membrane Vesicles by Obtaining Method of the Present Invention>

The resulting mTim-4 carrier-containing PBS solution (200 μL) above (containing $1 \times 10^7$ particles of the mTim-4 carriers) was subjected to the washing operation three times with 500 μL of PBS, and then 50 μL of the calcium ion-containing culture supernatant sample, prepared by the same method as in Examples 1 to 8, was added to the mTim-4 carrier in a pellet state, and subjected to a reaction at 8° C. for 3 hours.

Thereafter, the mTim-4 carrier after the reaction was subjected to the washing operation three times with 500 μL of TBS-T containing 2 mM $CaCl_2$. At the third time of washing, each 250 μL of the mTim-4 carrier was dispensed into the two 1.5 mL tubes. Each 20 μL of the 1% SDS aqueous solution or the 1 mM EDTA aqueous solution was added, as the eluent, to each 0.3 mg of the mTim-4 carrier in a pellet state, and they were mixed using a vortex mixer at room temperature for each 10 seconds and spun down. Each of the 1.5 mL tubes was loaded on a magnet stand, and the mTim-4 carrier was collected on the tube wall using magnetic force to recover the supernatant (eluate).

<Obtaining of Extracellular Membrane Vesicles by Anti-CD 63 Antibody Immobilization Method>

The extracellular membrane vesicles in the calcium ion-containing culture supernatant sample was obtained in the same method as in the <Obtaining of extracellular membrane vesicles by obtaining method of the present invention>, except for using "5 μL of the anti-CD63 antibody (H5C6) carrier-containing PBS solution (containing $1 \times 10^7$ particles of the carrier)", instead of "200 μL of the mTim-4 carrier-containing PBS solution", and by eluting the extracellular membrane vesicles with the 1% SDS aqueous solution or the 1 mM EDTA aqueous solution to recover the supernatant (eluate).

<Obtaining of Extracellular Membrane Vesicles by Exosome-Human CD 63 Isolation/Detection>

The extracellular membrane vesicles in the calcium ion-containing culture supernatant sample was obtained by the same method as in the <Obtaining of extracellular membrane vesicles by obtaining method of the present invention>, except for using "1 mL of the Exosome-Human CD 63 Isolation/Detection (produced by Thermo Fisher Scientific Inc.) (containing $1 \times 10^7$ particles of the carrier)", instead of "200 μL of the mTim-4 carrier-containing PBS solution", and by eluting the extracellular membrane vesicles with the 1% SDS aqueous solution or the 1 mM EDTA aqueous solution to recover the supernatant (eluate).

It should be noted that, the types of the carriers, and the eluents used to obtain the extracellular membrane vesicles from the carrier, used in each Example and Comparative Example, and the lane numbers in Western blotting to be described later are shown in the following Table 15.

TABLE 15

Figure 9:
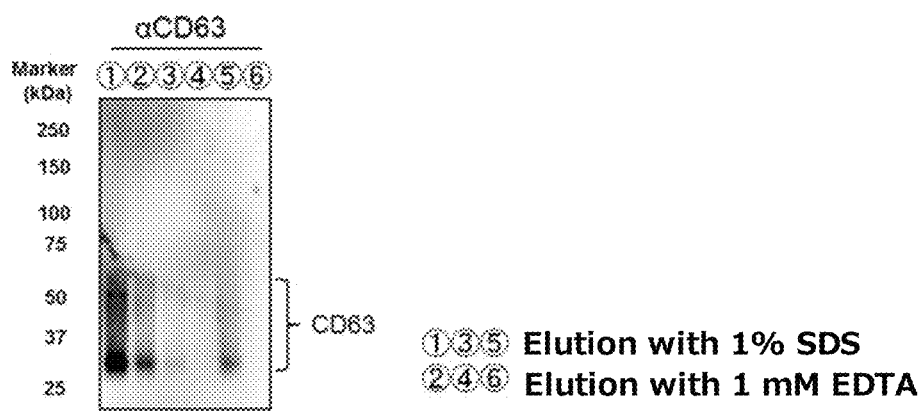
FIG. 9 is an electropherogram for confirming whether the extracellular membrane vesicles were obtained or not, by Western blotting, in Examples 34 to 35, and Comparative Examples 10 to 13.

|  | Example 34 | Example 35 | Comparative Example 10 | Comparative Example 11 | Comparative Example 12 | Comparative Example 13 |
|---|---|---|---|---|---|---|
| Method | Obtaining method of the present invention | | Anti-CD63 antibody method | | Exosome-Human CD63 Isolation/Detection | |
| Protein or antibody to be immobilized to carrier | FLAG tag fusion type mouse-derived Tim-4 protein (Biotin-labeled SH-group) | | Anti-CD63 antibody (H5C6) | | Anti-CD63 antibody | |
| Carrier | Dynabeads M-270 Streptavidin | | Dynabeads M-270 Carboxylic Acid | | — | |
| Eluent | 1% SDS | 1 mM EDTA | 1% SDS | 1 mM EDTA | 1% SDS | 1 mM EDTA |
| Lane number in FIG. 9 | 1 | 2 | 3 | 4 | 5 | 6 |

<Western Blotting>

Western blotting was carried out by the same method as in "(7) Western blotting" of Examples 1 to 8, except for using "7.5 µL of each supernatant (eluate) obtained in Examples 34 to 35 and Comparative Examples 10 to 13", instead of "7.5 µL of each supernatant (eluate) obtained in Examples 1 to 8".

<Results>

The results of Western blotting obtained are shown in FIG. 9. In FIG. 9, each lane is as follows:

Lane 1: Result of Example 34 (the results of the case where the extracellular membrane vesicles were obtained by the obtaining method of the present invention, and the 1% SDS aqueous solution was used as the eluent);

Lane 2: Result of Example 35 (the results of the case where the extracellular membrane vesicles were obtained by the obtaining method of the present invention, and the 1 mM EDTA aqueous solution was used as the eluent);

Lane 3: Results of Comparative Example 10 (the results of the case where the extracellular membrane vesicles were obtained by the anti-CD63 antibody method, and the 1% SDS aqueous solution was used as the eluent);

Lane 4: Results of Comparative Example 11 (the results of the case where the extracellular membrane vesicles were obtained by the anti-CD63 antibody method, and the 1 mM EDTA aqueous solution was used as the eluent);

Lane 5: Result of Comparative Example 12 (the results of the case where the extracellular membrane vesicles were obtained by Exosome-Human CD63 Isolation/Detection, and the 1% SDS aqueous solution was used as the eluent);

Lane 6: Result of Comparative Example 13 (the results of the case where the extracellular membrane vesicles were obtained by Exosome-Human CD63 Isolation/Detection, and the 1 mM EDTA aqueous solution was used as the eluent).

As shown in FIG. 9, a band of CD63, which is one of exosome markers, was observed at the vicinity of 25 to 60 kDa in Examples 34 to 35, wherein obtaining of the extracellular membrane vesicles was carried out by the obtaining method of the present invention (Examples 34 to 35: lanes 1 to 2).

On the other hand, as shown in FIG. 9, the band of CD63 was observed only slightly at the vicinity of 25 to 60 kDa (Comparative Examples 10 to 13: the lanes 3 to 6), in Comparative Examples 10 to 11 wherein obtaining of the extracellular membrane vesicles was carried out by the anti-CD63 antibody method, and in Comparative Examples 12 to 13 wherein obtaining of the extracellular membrane vesicles was carried out by the Exosome-Human CD63 Isolation/Detection.

From the above, it has been revealed that more extracellular membrane vesicles can be recovered, according to the obtaining method of the present invention, as compared with the method for obtaining the extracellular membrane vesicles by affinity of the surface antigen protein and the antibody, using the antibody against the surface antigen protein of the extracellular membrane vesicles in, such as the anti-CD63 antibody method, or Exosome-Human CD63 Isolation/Detection, or the like.

Examples 36 to 38. Obtaining of Residual Extracellular Membrane Vesicles from the Ultracentrifugal Separation-Treated Sample by Obtaining Method of the Present Invention As described below, the obtaining method of the present invention was carried out for the sample from which the extracellular membrane vesicles had been removed and obtained by the ultracentrifugal separation method which is a conventional method (hereinafter it may be abbreviated as ultracentrifugal separation treatment, in some cases).

<(1) Removal of Extracellular Membrane Vesicles by Ultracentrifugal Separation Method>

FBS (15 mL, produced by Corning Inc.) was subjected to centrifugal separation treatment (10,000×G, for 20 minutes) to separate impurities, and the supernatant was transferred to a new tube to obtain the centrifugal separation treated FBS. Next, each 5 mL of the resulting centrifugal separation treated FBS was subjected to ultracentrifugal separation treatment (110,000×G, overnight) or ultracentrifugal separation treatment (450,000×G, overnight), and the supernatant was transferred to a new tube to obtain each 5 mL of the ultracentrifugal separation-treated (110,000×G) FBS and ultracentrifugal separation treated (450,000×G) FBS.

<(2) Washing of Beads>

The PBS solution (180 µL) containing the 10 µg/µL Dynabeads MyOne Streptavidin C1 (produced by Thermo Fisher Scientific Inc.) (containing 1.8 mg of the Dynabeads MyOne Streptavidin C1) was dispensed into each of three tubes. Next, each 1500 µL of PBS was added to the tube, and after stirring, each tube was loaded on a magnet stand, the Dynabeads MyOne Streptavidin C1 was collected on the tube wall by using magnetic force, and the solution in the tube was discarded with a pipette (hereinafter it may be abbreviated as the washing operation, in some cases).

<(3) Immobilization of Fc Tag Fusion Type Mouse-Derived Tim-4 Protein on Beads>

The PBS solution (1500 µL) containing 3 µg of the SH-group biotin-labeled Fc tag fusion type mouse-derived Tim-4 protein was each added to 1.8 mg of the pellet-like Dynabeads MyOne Streptavidin C1 after the washing operation, and subjected to a reaction at 8° C. for 10 minutes to obtain each 1500 µL of the PBS solution containing the carrier on which the SH-group biotin-labeled Fc tag fusion type mTim-4 protein was bound (mTim-4 carrier).

<(4) Obtaining of Extracellular Membrane Vesicles by Obtaining Method of the Present Invention>

The resulting mTim-4 carrier (1.8 mg) was subjected to the washing operation each three times with 1500 µL of PBS to obtain the mTim-4 carrier in a pellet state. Thereafter, each 5 mL of the centrifugal separation treated FBS, the ultracentrifugal separation treated FBS (110,000×G) and the ultracentrifugal separation treated FBS (450,000×G) was dispensed into three 15 mL centrifuge tubes (manufactured by Corning Inc.), then 1.8 mg of the mTim-4 carrier in a pellet state was added and subjected to a reaction at 8° C. for 2 hours. After the reaction, the 15 mL centrifuge tubes were loaded on a magnet stand, and the mTim-4 carrier was collected on the tube wall using magnetic force, and each supernatant (each FBS) was recovered in each of new 15 mL centrifuge tubes. The pellet-like mTim-4 carrier remained in the centrifuge tube was each subjected to the washing operation with 3 mL of TBS-T containing 2 mM $CaCl_2$ (Tris buffer, 0.0005% Tween 20, 2 mM $CaCl_2$), and then each 1 mL of TBS-T containing 2 mM $CaCl_2$ was added to the mTim-4 carrier in a pellet state and suspended, and the entire amount of the suspension was transferred to the 1.5 mL tube, followed by subjecting to the washing operation each twice.

Each 50 µL of the TBS solution containing 1 mM EDTA, as the eluent, was added to 1.8 mg of the pellet-like mTim-4 carrier, and they were mixed at room temperature for 10 seconds using a vortex mixer and spun down. Each of the 1.5 mL tubes was loaded on a magnet stand, and the mTim-4 carrier was collected on the tube wall using magnetic force to recover the eluate. The TBS solution (50 µL) containing 1 mM EDTA was added again to recover the eluate in the same method using the mTim-4 carrier used above.

Thereafter, the beads, used when the eluate was recovered twice, were again added to each supernatant (each FBS) recovered in the 15-mL centrifuge tube, and the operation for recovering the extracellular membrane vesicles in each supernatant (each FBS) was repeated further twice by the same method as described above to obtain each eluate.

<(5) Western Blotting>

The resulting each eluate (100 μL) was ultrafiltrated with the VIVASPIN 500 (MVCO 10,000) (manufactured by Sartorius AG), so as to attain 30 μL. Five μL of the 4×sample buffer solution (produced by Wako Pure Chemical Industries, Ltd.) was added to each 15 μL of the ultrafiltrated eluate, and incubated at 98° C. for 5 minutes to obtain each sample for Western blotting. Each 20 μL of the sample for Western blotting was loaded on the Super Sep Ace 5-20% gel (produced by Wako Pure Chemical Industries Ltd.), and subjected to electrophoresis at 25 mA for 65 minutes. The resulting electrophoresis gel was transcribed onto the PVDF membrane (produced by Millipore Corporation) at 1 mA/cm$^2$ for 60 minutes using the semi-dry blotter and the discontinuous buffer (Anode buffer 1: 0.3 M Tris/20% methanol, Anode buffer 2: 0.025 M Tris/20% methanol, Cathode buffer: 0.025 M Tris/0.04 M aminocaproic acid/20% methanol). The 3% skimmed milk, diluted with PBS-T (PBS buffer, 0.1% Tween 20), was added to the post-transcription PVDF membrane, and subjected to a reaction at room temperature for 1 hour for blocking, and 2 mL of the anti-bovine CD9 antibody (produced by Novus Biologicals LLC, hereinafter it may be abbreviated as "the anti-bovine CD9 antibody", in some cases), diluted 1000-fold with PBS-T, was added and subjected to a reaction at room temperature for 1 hour. The PVDF membrane, after the reaction, was washed three times with PBS-T, and the secondary antibody {anti-mouse IgG (H+L), rabbit, IgG fraction, peroxidase-conjugated antibody} (produced by Wako Pure Chemical Industries Ltd.), diluted 10,000-fold with PBS-T, was subjected to a reaction at room temperature for 1 hour. After washing 5 times with PBS-T, the ImmunoStar Basic (produced by Wako Pure Chemical Industries, Ltd.) was added to a membrane, which had been subjected to a reaction with the anti-bovine CD9 antibody, and the ImmunoStar Zeta (produced by Wako Pure Chemical Industries, Ltd.) was added to a membrane, which had been subjected to a reaction with the anti-Flotillin-2 antibody, and a luminescent signal was detected using the LAS-4000 (manufactured by GE Healthcare). It should be noted that, the anti-bovine CD9 antibody and the anti-Flotillin-2 antibody are the antibodies recognizing CD9 and Flotillin-2, which are marker proteins of exosome, respectively.

<(6) Measurement of Average Particle Number and Average Particle Size>

Each 100 μL of the resulting eluate was treated with a centrifugal filter (0.45 μm, PVDF) (manufactured by Millipore Corporation), and diluted 5-fold with water, and then particles contained in the diluted solution were measured three times using a NanoSight LM 10 (manufactured by NanoSight Ltd.), according to a manual of the NanoSight, and the average particle number (Particles) and the average particle size (Mean Size) were examined.

It should be noted that, the method for treating the samples, and the method for obtaining the extracellular membrane vesicles remaining in the sample, used in each Example, are shown in the following Table 16.

TABLE 16

Figure 10:
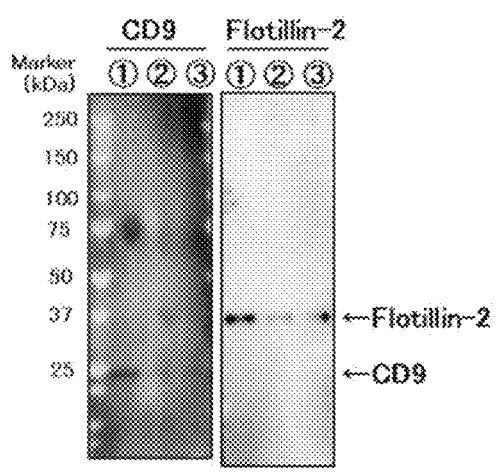
FIG. 10 is an electropherogram for confirming whether the extracellular membrane vesicles were obtained or not, by Western blotting, in Examples 36 to 38.

| | | Example 36 | Example 37 | Example 38 |
|---|---|---|---|---|
| Treatment method of sample | Ultracentrifugal separation method (gravity in ultracentrifugal separation method) | — | ◯ (110000 × g) | ◯ (450000 × g) |
| | + | | | |
| Obtaining of extracellular membrane vesicles remaining in a sample by the method of the present invention | Obtaining method of the present invention | ◯ | ◯ | ◯ |
| Lane number in FIG. 10 | | 1 | 2 | 3 |

<Results>

The results of Western blotting obtained, and the measurement results of average particle number and average particle size by the NanoSight are shown in FIG. 10 and Table 17, respectively. In FIG. 10, each lane shows the following result:

Lane 1: Result of Example 36 (the results of the case where the sample was centrifugal separation treated and obtaining of the extracellular membrane vesicles was carried out by the obtaining method of the present invention);

Lane 2: Results of Example 37 (the results of the case where obtaining of the extracellular membrane vesicles was carried out by the obtaining method of the present invention, after subjecting the sample to centrifugal separation treatment and ultracentrifugal separation treatment at 110,000× G);

Lane 3: Results of Example 38 (the results of the case where obtaining of the extracellular membrane vesicles was carried out by the obtaining method of the present invention, after subjecting the sample to centrifugal separation treatment and ultracentrifugal separation treatment at 450,000× G).

From FIG. 10, it has been revealed that bands of CD9 and Flotillin-2 which are the exosome markers were confirmed, and the extracellular membrane vesicles contained in the sample could not be removed (obtained) completely by the ultracentrifugal separation treatment, and a large quantity of the extracellular membrane vesicles remained in the sample, also in the case where obtaining of the extracellular membrane vesicles was carried out by the obtaining method of the present invention, after subjecting the sample to centrifugal separation treatment, and ultracentrifugal separation treatment at 110,000×G or at 450,000×G (Examples 37 to 38), (Examples 37 to 38: Lanes 2 to 3). Furthermore, it has been revealed that the extracellular membrane vesicles remained in the sample, which were not removed (obtained) completely by these ultracentrifugal separation methods, can be obtained (removed) by the obtaining method of the present invention (Examples 37 to 38: Lanes 2 to 3).

From Table 17, it was confirmed that size (particle size) of the extracellular membrane vesicles obtained was almost the same between the case where obtaining of the extracellular membrane vesicles was carried out by the obtaining method of the present invention, after subjecting the sample to centrifugal separation treatment and ultracentrifugal separation treatment at 110,000×G or at 450,000×G (Examples 37 to 38), and the case where obtaining of the extracellular membrane vesicles was carried out by the obtaining method of the present invention, after subjecting the sample to centrifugal separation treatment (Example 36). Thus, it has been revealed that the extracellular membrane vesicles remaining in the sample, which could not be removed completely by the ultracentrifugal separation method, were not fragmented and was present as particles.

TABLE 17

|  |  | Particles | Mean size (nm) |
|---|---|---|---|
| Example 36 | ① Untreated | $2.04 \times 10^9$ | 155 |
| Example 37 | ② 110,000 × g | $1.36 \times 10^9$ | 162 |
| Example 38 | ③ 450,000 × g | $1.20 \times 10^9$ | 159 |

Examples 39 to 40. Obtaining of Remaining Extracellular Membrane Vesicles by Obtaining Method of the Present Invention from Sample after Treatment by Total Exosome Isolation (Polymer Precipitation)

As described below, the obtaining method of the present invention was carried out for the sample, from which the extracellular membrane vesicles contained had been removed (obtained) by Total Exosome Isolation (polymer precipitation), which is a conventional method (hereinafter it may be abbreviated as "the polymer precipitation treatment", in some cases).

<(1) Removal of Extracellular Membrane Vesicles by Total Exosome Isolation (Polymer Precipitation) Method>

FBS (10 mL, produced by Corning Inc.) was subjected to centrifugal separation treatment (10,000×G, for 20 minutes) to separate impurities and obtain the centrifugal separation treated FBS. Subsequently, 1 mL of the Total Exosome Isolation (from serum) (produced by Thermo Fisher Scientific Inc.) was added to 5 mL of the resulting centrifugal separation treated FBS, and allowed to stand under refrigeration for 30 minutes, and centrifugal separation treated (10,000×G, for 20 minutes), then the supernatant was recovered to obtain 6 mL of FBS treated with the Total Exosome Isolation.

<(2) Washing of Beads>

The PBS solution (180 μL) containing the 10 μg/μL Dynabeads MyOne Streptavidin C1 (produced by Thermo Fisher Scientific Inc.) (containing 1.8 mg of the Dynabeads MyOne Streptavidin C1) was dispensed into each of the two tubes. Next, 1500 μL of PBS was added to each of the tubes, and after stirring, each tube was loaded on a magnet stand, the Dynabeads MyOne Streptavidin C1 was collected on the tube wall by using magnetic force, and the solution in the tube was discarded with a pipette (hereinafter it may be abbreviated as the washing operation, in some cases).

<(3) Immobilization of Fc Tag Fusion Type Mouse-Derived Tim-4 Protein on Beads>

The PBS solution (1500 μL) containing 3 μg of the SH-group biotin-labeled Fc tag fusion type mouse-derived Tim-4 protein, prepared by the same method as in Examples 5 to 8, was added to 1.8 mg of the Dynabeads MyOne Streptavidin C1, in a pellet state, after the washing operation, and subjected to a reaction at 8° C. for 10 minutes to obtain each 1500 μL of the PBS solution containing the carrier on which the SH-group biotin-labeled Fc tag fusion type mouse-derived Tim-4 protein was bound (the mTim-4 carrier).

<(4) Obtaining of Extracellular Membrane Vesicles by Obtaining Method of the Present Invention>

The resulting mTim-4 carrier (1.8 mg) was washed each three times with 1500 μL of PBS to obtain the mTim-4 carrier in a pellet state. Thereafter, each 1.8 mg of the mTim-4 carrier in a pellet state was added to 5 mL of the centrifugal separation-treated FBS or 6 mL of the Total Exosome Isolation-treated FBS which had been dispensed into 15 mL centrifuge tubes (produced by Corning Inc.), and subjected to a reaction at 8° C. for 2 hours.

After the reaction, each of the 15 mL centrifuge tubes were loaded on a magnet stand, and the mouse-derived Tim-4 carrier was collected on the tube wall by magnetic force to recover each supernatant (each FBS) in new 15 mL centrifuge tubes. The pellet-like mTim-4 carrier remained in the centrifuge tubes was subjected to the washing operation each with 3 mL of TBS-T containing 2 mM $CaCl_2$ (Tris buffer, 0.0005% Tween 20, 2 mM $CaCl_2$), and then each 1 mL of TBS-T containing 2 mM $CaCl_2$ was added to the pellet-like mTim-4 carrier and suspended, and after the entire amount of the suspension was transferred to the 1.5 mL tube, the washing operation was each carried out twice.

The TBS solution (50 μL) containing 1 mM EDTA, as the eluent, was added to each 1.8 mg of the mTim-4 carrier in a pellet state, and then they were mixed using a vortex mixer at room temperature for 10 seconds and spun down. Each 1.5 mL tube was loaded on a magnet stand, and the mTim-4 carrier was collected on the tube wall using magnetic force to recover the eluate. The TBS solution (50 μL) containing 1 mM EDTA was added again to recover the eluate in the same method using the mTim-4 carrier used above.

Thereafter, the mTim-4 carrier (beads) used in recovering the eluate twice was added again to each supernatant (each FBS) recovered in the 15 mL-centrifuge tube, and by the same method as described above, the procedure of recovering the extracellular membrane vesicles in each supernatant (each FBS) was repeated further twice to obtain each eluate.

<(5) Western Blotting>

Each 300 μL of the resulting eluate was ultrafiltrated with the VIVASPIN 500 (MVCO 10,000) (produced by Sartorius AG), so as to attain 30 μL. Each 10 μL of the 4× sample buffer (produced by Wako Pure Chemical Industries, Ltd.) was added to 30 μL of each ultrafiltrated eluate, and incubated at 98° C. for 5 minutes to obtain each sample for Western blotting. Each 20 μL of the sample for Western blotting was loaded at each 2 places on the Super Sep Ace 5-20% gel (produced by Wako Pure Chemical Industries, Ltd.) and subjected to electrophoresis at 25 mA for 65 minutes. The resulting electrophoresis gel was transcribed onto the PVDF membrane (produced by Millipore Corporation) at 1 mA/$cm^2$ for 60 minutes using the semi-dry blotter and the discontinuous buffer (Anode buffer 1: 0.3 M Tris/20% methanol, Anode buffer 2: 0.025 M Tris/20% methanol, Cathode buffer: 0.025 M Tris/0.04 M aminocaproic acid/20% methanol). The 3% skimmed milk, diluted with PBS-T (PBS buffer, 0.1% Tween 20), was added to the post-transcription PVDF membrane, and subjected to a reaction at room temperature for 1 hour for blocking, and 2 mL of the anti-bovine CD9 antibody (produced by Novus Biologicals LLC, hereinafter it may be abbreviated as "the anti-bovine CD9 antibody", in some cases), diluted 1000-fold with PBS-T, or the anti-human Flotillin-2 antibody (produced by BD Biosciences, hereinafter it may be abbreviated as "the anti-human Flotillin-2 antibody", in some cases), diluted 250-fold with PBS-T, was added and subjected to a reaction at room temperature for 1 hour. After the reaction, the PVDF membrane was washed three times with PBS-T, and the secondary antibody {anti-mouse IgG (H+L), rabbit, IgG fraction, peroxidase-conjugated antibody} (produced by Wako Pure Chemical Industries Ltd.), diluted 10,000-fold with PBS-T, was subjected to a reaction at room temperature for 1 hour. After washing 5 times with PBS-T, the ImmunoStar Basic (produced by Wako Pure Chemical Industries, Ltd.) was added to a membrane, which had been subjected to a reaction with the anti-bovine CD9 antibody, and the ImmunoStar Zeta (produced by Wako Pure Chemical Industries, Ltd.) was added to a membrane, which had been subjected to a reaction with the anti-Flotillin-2 antibody, and a luminescent signal was detected using the LAS-4000 (manufactured by GE Healthcare). It should be noted that, the anti-bovine CD9 antibody is an antibody against CD9 which is one of the marker proteins of exosome, and the anti-human Flotillin-2 antibody is an antibody against Flotillin-2 which is one of the marker proteins of exosome.

It should be noted that, the method for treating the sample, and the methods of obtaining the extracellular membrane vesicles remaining in the sample, used in each Example, and the lane number in Western blotting are shown in the following Table 18.

TABLE 18

Figure 11:
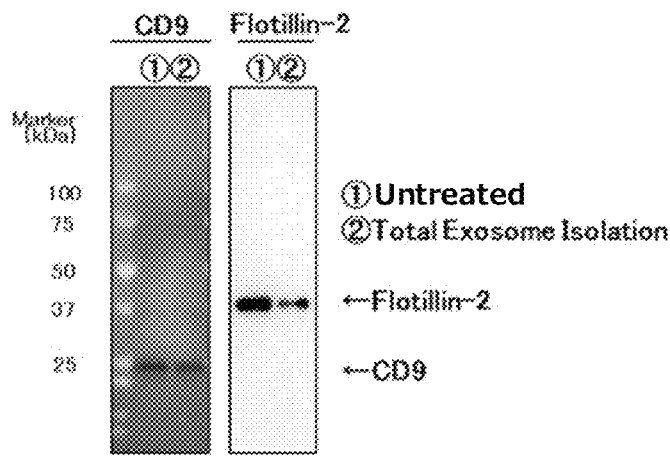
FIG. 11 is an electropherogram for confirming whether the extracellular membrane vesicles were obtained or not, by Western blotting, in Examples 39 to 40.

|  |  | Example 39 | Example 40 |
|---|---|---|---|
| Treatment method of sample | Total Exosome Isolation (PEG precipitation) method + | — | ○ |
| Obtaining of extracellular membrane vesicles remaining in a sample by the method of the present invention | Obtaining method of the present invention | ○ | ○ |
| Lane number in FIG. 11 |  | 1 | 2 |

<Results>

The results of Western blotting obtained are shown in FIG. 11. In FIG. 11, each lane represents the following result.

Lane 1: Results of Example 39 (the results of the case where obtaining of the extracellular membrane vesicles was carried out by the obtaining method of the present invention, after subjecting the sample to centrifugal separation treatment);

Lane 2: Results of Example 40 (the results of the case where obtaining of the extracellular membrane vesicles was carried out by the obtaining method of the present invention, after subjecting the sample to centrifugal separation treatment and polymer precipitation treatment).

From FIG. 11, it has been revealed that also in the case where obtaining of the extracellular membrane vesicles were carried out by the obtaining method of the present invention, after subjecting the sample to centrifugal separation treatment, and the polymer precipitation (Example 40), the extracellular membrane vesicles contained in the sample could not be removed (obtained) completely by the Total Exosome Isolation (polymer precipitation) method, and a large quantity of the extracellular membrane vesicles remained in the sample, from the fact that bands of CD9 and Flotillin-2, which are the exosome markers, were confirmed (Example 40: Lane 2).

Furthermore, it has been revealed that the extracellular membrane vesicles remained in the sample that were not removed (obtained) completely by the Total Exosome Isolation (polymer precipitation) method can be obtained by the obtaining method of the present invention (Example 40: Lane 2).

Examples 41 to 47. Obtaining (Removal) of Extracellular Membrane Vesicles from Sample by Removing Method of the Present Invention and/or Conventional Method (Ultracentrifugation Method, Total Exosome Isolation (Polymer Precipitation) Method)

As described below, the extracellular membrane vesicles were obtained (removed) from the sample by the removing method of the present invention and/or the conventional method (ultracentrifugation method, Total Exosome Isolation (polymer precipitation) method).

<(1) Removal of Extracellular Membrane Vesicles by Ultracentrifugal Separation Method>

FBS (28 mL, produced by Corning Inc.) was subjected to centrifugal separation treatment (10,000×G, for 20 minutes) to separate impurities and obtain centrifugal separation treated FBS (hereinafter it may be abbreviated as "the removed sample-1", in some cases). Subsequently, 12 mL of the resulting centrifugal separation treated FBS ("the removed sample-1") was subjected to ultracentrifugal separation treatment (110,000×G, overnight) to obtain ultracentrifugal separation treated FBS (110,000×G) (hereinafter it may be abbreviated as "the removed sample-2", in some cases).

<(2) Removal of Extracellular Membrane Vesicles by Total Exosome Isolation (Polymer Precipitation) Method>

Subsequently, 1.6 mL of Total Exosome Isolation (from serum) (produced by Thermo Fisher Scientific Inc.) was added to 8 mL of the centrifugal separation treated FBS ("the removed sample-1"), and allowed to stand under refrigeration for 30 minutes, and centrifugal separation treated (10,000×G, for 20 minutes), then each supernatant was recovered to obtain 9.6 mL of Total Exosome Isolation treated FBS (hereinafter it may be abbreviated as "the removed sample-3", in some cases).

In addition, 0.8 mL of Total Exosome Isolation was added to 4 mL of the ultracentrifugal separation treated (110,000×G) FBS ("the removed Sample-2"), and allowed to stand under refrigeration for 30 minutes, and centrifugal separation treated (10,000×G, 20 minutes) to recover each supernatant and obtain 4.8 mL of ultracentrifugal separation treated (110,000×G)/Total Exosome Isolation treated FBS (hereinafter it may be abbreviated as "the removed sample-4", in some cases).

<(3) Washing of Beads>

The PBS solution (240 μL) containing the 10 μg/μL Dynabeads MyOne Streptavidin C1 (produced by Thermo Fisher Scientific Inc.) (containing 2.4 mg of the Dynabeads MyOne Streptavidin C1) was dispensed into each of three tubes. Next, 2000 μL of PBS was added to each of the tubes, and after stirring, each tube was loaded on a magnet stand, the Dynabeads MyOne Streptavidin C1 was collected on the tube wall using magnetic force, and the solution in the tube was discarded with a pipette (hereinafter it may be abbreviated as "the washing operation", in some cases).

the following Table 19 was added to 0.6 mg of the mTim-4 carrier in a pellet state, in each addition amount to the mouse-derived Tim-4 carrier of the removed sample, and each was subjected to a reaction at 8° C. for 3 hours.

TABLE 19

|  |  | Example 41 | Example 42 | Example 43 | Example 44 | Example 45 | Example 46 | Example 47 |
|---|---|---|---|---|---|---|---|---|
| Name of sample obtained in each Example | | Removed sample-5 | Removed sample-6 | Removed sample-4 | Removed sample-2 | Removed sample-3 | Removed sample-7 | Removed sample-1 |
| Treatment method of sample | Centrifugal separation treatment | ○ | ○ | ○ | ○ | ○ | ○ | ○ |
| | Ultracentrifugal separation Method (gravity in ultracentrifugation method) | ○ (110,000 × g) | — | ○ (110,000 × g) | ○ (110,000 × g) | — | — | — |
| | Total Exosome Isolation (PEG precipitation) method | — | ○ | ○ | — | ○ | — | — |
| | Removing method of the present invention | ○ | ○ | — | — | — | ○ | — |
| Addition amount of removed sample to mouse-derived Tim-4 carrier | | 1 mL | 1.2 mL | 1.2 mL | 1 mL | 1.2 mL | 1 mL | 1 mL |

<(4) Immobilization of Fc Tag Fusion Type Mouse-Derived Tim-4 Protein on Beads>

The PBS solution (2000 μL) containing 4 μg of the SH-group biotin-labeled Fc tag fusion type mouse-derived Tim-4 protein was added to each 2.4 mg of the Dynabeads MyOne Streptavidin C1 in a pellet state, after the washing operation, and subjected to a reaction at 8° C. for 10 minutes to obtain each 2000 μL of the PBS solution containing the carrier on which the SH-group biotin-labeled Fc tag fusion type mouse-derived Tim-4 protein was bound (the mTim-4 carrier).

<(5) Removal of Extracellular Membrane Vesicles>

The resulting 2.4 mg of the mTim-4 carrier was subjected to the washing operation three times with each 2000 μL of PBS to obtain the mTim-4 carrier in a pellet state.

Thereafter, each 4 mL of centrifugal separation treated FBS ("the removed sample-1"), 4 mL of ultracentrifugal separation treated (110,000×G) FBS ("the removed sample-2"), or 4.8 mL of Total Exosome Isolation treated FBS ("the removed sample-3") was dispensed into each tube and subjected to a reaction at 8° C. for 1 hour. After the reaction, each of the tubes was loaded on a magnet stand, and the mTim-4 carrier was collected on the tube wall using magnetic force to recover supernatant (each FBS) in a new tube.

The mTim-4 carrier in a pellet state remaining in the tube was subjected to the washing operation three times with each 4 mL of TBS-T (Tris buffer, 0.0005% Tween 20), and then each supernatant (each FBS) was added again, and each of the operations from the reaction to washing was repeated five times in total. After the fifth time reaction, each supernatant (each FBS) was transferred to a new tube and centrifugal separation treated (10,000×G, for 20 minutes), then the supernatant was recovered to obtain 4 mL of ultracentrifugal separation treated (110,000×G)/Tim-4 treated FBS (hereinafter it may be abbreviated as "the removed sample-5", in some cases), 4.8 mL of Total Exosome Isolation treated/Tim-4 treated FBS (hereinafter it may be abbreviated as "the removed sample-6", in some cases), and 4 mL of the Tim-4 treated FBS (hereinafter it may be abbreviated as "the removed sample-7", in some cases).

<(6) Obtaining of Extracellular Membrane Vesicles by Obtaining Method of the Present Invention>

Seven 0.6 mg mTim-4 carriers were newly prepared by the same way as the above method, and each was subjected to the washing operation. The removed sample described in After the reaction, each 1.5 mL tube was loaded on a magnet stand, and the mTim-4 carrier was collected on the tube wall by magnetic force, and each supernatant (each FBS) was recovered to obtain the mTim-4 carrier in a pellet state.

The resulting mTim-4 carrier in a pellet state was subjected to the washing operation three times with each 1 mL of TBS-T containing 2 mM $CaCl_2$ (Tris buffer, 0.0005% Tween 20, 2 mM $CaCl_2$), and then each 50 μL of the TBS solution containing 1 mM EDTA, as the eluent, was added to each 0.6 mg of the mTim-4 carrier in a pellet state, and they were mixed using a vortex mixer at room temperature for 10 seconds, and spun down. Each 1.5 mL tube was loaded on a magnet stand, and the mTim-4 carrier was collected on the tube wall using magnetic force to recover each eluate. The TBS solution (50 μL) containing 1 mM EDTA was added again to recover each eluate in the same method.

<(7) Western Blotting>

In the resulting eluate, 100 μL was ultrafiltrated, so as to attain 30 μL with the VIVASPIN 500 (MVCO 10,000) (produced by Sartorius AG). To each 30 μL of the ultrafiltrated eluate, 10 μL of the 4× sample buffer (produced by Wako Pure Chemical Industries, Ltd.) was added and incubated at 98° C. for 5 minutes to obtain each sample for Western blotting. The sample for Western blotting (each 20 μL) was loaded, by two places, on the Super Sep Ace 5-20% gel (produced by Wako Pure Chemical Industries, Ltd.), and subjected to electrophoresis at 25 mA for 65 minutes. The resulting electrophoresis gel was transcribed onto the PVDF membrane (produced by Millipore Corporation) under 1 $mA/cm^2$ for 60 minutes using the semi-dry blotter and the discontinuous buffer (Anode buffer 1: 0.3 M Tris/20% methanol, Anode buffer 2: 0.025 M Tris/20% methanol, Cathode buffer: 0.025 M Tris/0.04 M aminocaproic acid/20% methanol). To the PVDF membrane after transcription, the 3% skimmed milk diluted with PBS-T (the PBS buffer, 0.1% Tween 20) was added and subjected to a reaction at room temperature for 1 hour for blocking, and 2 mL of the anti-bovine CD9 antibody (produced by Novus Biologicals LLC, hereinafter it may be abbreviated as "the anti-bovine CD9 antibody", in some cases) diluted 1000-fold with PBS-T, or the anti-human Flotillin-2 antibody (produced by BD Biosciences, hereinafter it may be abbreviated as "the anti-human Flotillin-2 antibody", in some cases), diluted 250-fold with PBS-T, was subjected to a reaction at room temperature for 1 hour. After the reaction, the PVDF membrane was washed three times with PBS-T, and the secondary antibody {anti-mouse IgG (H+L), rabbit, IgG fraction, peroxidase-conjugated antibody} (produced by Wako Pure Chemical Industries Ltd.), diluted 10,000-fold with PBS-T, was subjected to a reaction at room temperature for 1 hour. After washing five times with PBS-T, the ImmunoStar Basic (produced by Wako Pure Chemical Industries, Ltd.) was added to the membrane after being subjected to a reaction with the anti-bovine CD9 antibody, and the ImmunoStar Zeta (produced by Wako Pure Chemical Industries, Ltd.) was added to the membrane after being subjected to a reaction with the anti-Flotillin-2 antibody, and a luminescent signal was detected using the LAS-4000 (manufactured by GE Healthcare). It should be noted that the anti-bovine CD9 antibody is an antibody against CD9, which is one of the marker proteins of exosome, and the anti-human Flotillin-2 antibody is an antibody against Flotillin-2, which is one of the marker proteins of exosome.

It should be noted that, the method for treating the sample, the method for obtaining (removing) the extracellular membrane vesicles remaining in the sample, used in each Example, and the lane numbers in Western blotting to be described later are shown in the following Table 20.

Lane 4: Results of Example 44 (the results of the case where obtaining of the extracellular membrane vesicles was carried out by the obtaining method of the present invention, after subjecting the sample to centrifugal separation treatment, and ultracentrifugal separation treatment);

Lane 5: Results of Example 45 (the results of the case where obtaining of the extracellular membrane vesicles was carried out by the obtaining method of the present invention, after subjecting the sample to centrifugal separation treatment, and polymer precipitation treatment);

Lane 6: Results of Example 46 (the results of the case where obtaining of the extracellular membrane vesicles was carried out by the obtaining method of the present invention, after subjecting the sample to centrifugal separation treatment, and treatment with the removing method of the present invention);

Lane 7: Results of Example 47 (the results of the case where obtaining of the extracellular membrane vesicles was carried out by the obtaining method of the present invention, after subjecting the sample to centrifugal separation treatment).

Figure 12:
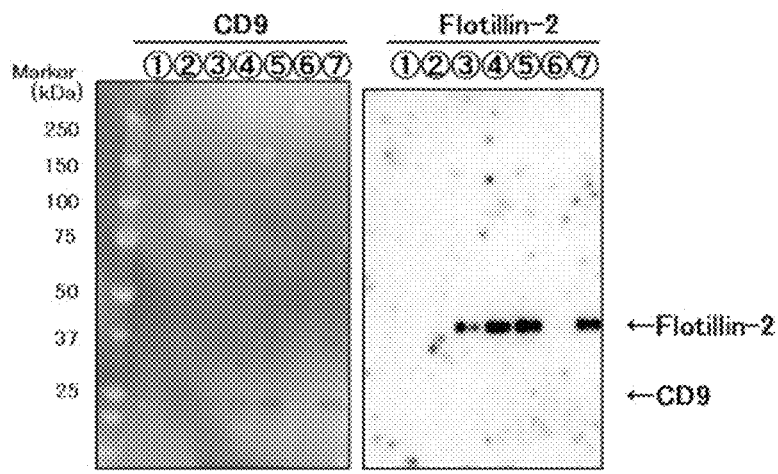
FIG. 12 is an electropherogram for confirming whether the extracellular membrane vesicles were obtained (removed) or not, by Western blotting, in Examples 41 to 47.

From FIG. 12, it has been revealed that the extracellular membrane vesicles contained in the sample cannot be removed completely, and a large quantity of the extracellular membrane vesicles remain in the sample, from the fact that

TABLE 20

| | | Example 41 | Example 42 | Example 43 | Example 44 | Example 45 | Example 46 | Example 47 |
|---|---|---|---|---|---|---|---|---|
| Name of sample obtained in each Example | | Removed sample-5 | Removed sample-6 | Removed sample-4 | Removed sample-2 | Removed sample-3 | Removed sample-7 | Removed sample-1 |
| Treatment method of sample | Centrifugal separation treatment | ○ | ○ | ○ | ○ | ○ | ○ | ○ |
| | Ultracentrifugal separation method (gravity in ultracentrifugation method) | ○ (110,000 × g) | — | ○ (110,000 × g) | ○ (110,000 × g) | — | — | — |
| | Total Exosome Isolation (PEG precipitation) method | — | ○ | ○ | — | ○ | — | — |
| | Removing method of the present invention | ○ | ○ | — | — | — | ○ | — |
| Addition amount of removed sample to mouse-derived Tim-4 carrier | | 1 mL | 1.2 mL | 1.2 mL | 1 mL | 1.2 mL | 1 mL | 1 mL |
| Obtaining of extracellular membrane vesicles remaining in the sample by the obtaining method of the present invention | | ○ | ○+ | ○ | ○ | ○ | ○ | ○ |
| Lane number in FIG. 12 | | 1 | 2 | 3 | 4 | 5 | 6 | 7 |

<Results>

The results of Western blotting obtained are shown in FIG. 12. In FIG. 12, each lane shows the following result.

Lane 1: Results of Example 41 (the results of the case where obtaining of the extracellular membrane vesicles was carried out by the obtaining method of the present invention, after subjecting the sample to centrifugal separation treatment, ultracentrifugal separation treatment, and further treatment with the removing method of the present invention);

Lane 2: Results of Example 42 (the results of the case where obtaining of the extracellular membrane vesicles was carried out by the obtaining method of the present invention, after subjecting the sample to centrifugal separation treatment, polymer precipitation treatment, and further treatment with the removing method of the present invention);

Lane 3: Results of Example 43 (the results of the case where obtaining of the extracellular membrane vesicles was carried out by the obtaining method of the present invention, after subjecting the sample to centrifugal separation treatment, ultracentrifugal separation treatment, and further polymer precipitation treatment);

the bands of exosome markers CD9 and Flotillin-2 are observed, in the ultracentrifugation method and Total Exosome Isolation (polymer precipitation) method, which are the conventional methods (Examples 44 to 45: lanes 4 to 5). In addition, it has been revealed that the extracellular membrane vesicles contained in the sample cannot be removed sufficiently, and resulted in to remain, from the fact that the bands of CD9 and Flotillin-2 are observed, even if these conventional methods are combined (Example 43: lane 3). On the other hand, it has been revealed that the extracellular membrane vesicles in the sample, which cannot be removed only by the conventional methods, can be removed (obtained) by combining the ultracentrifugation method or Total Exosome Isolation (polymer precipitation) method, which are the conventional methods, with the removing method of the present invention, from the fact that the bands of CD9 and Flotillin-2 are not confirmed (Examples 41 to 42: lanes 1-2). Furthermore, it has been revealed that the extracellular membrane vesicles in the sample can be removed sufficiently, even with the method of the present invention alone (Example 46: lane 6). In addition, it has been suggested that the viruses can also be removed similarly as the extracellular membrane vesicles, according to the removing (obtaining) method of the present invention.

Examples 48 to 55. Reutilization of Tim Carrier of the Present Invention in Removing Method of the Present Invention The removing method of the present invention was repeated using the Tim carrier of the present invention as follows.
<(1) Preparation of Sample>
One mL of FBS (produced by Corning Inc.) was subjected to centrifugal separation treatment (10,000×G, for 20 minutes) to separate impurities to obtain 1 mL of the centrifugal separation treated FBS.
<(2) Washing of Beads>
The PBS solution (60 µL) containing the 10 µg/µL Dynabeads MyOne Streptavidin C1 (produced by Thermo Fisher Scientific Inc.) (containing 0.6 mg of the Dynabeads MyOne Streptavidin C1) was dispensed into the 1.5 mL tube (manufactured by BM Equipment Co., Ltd.). Next, 500 µL of PBS was added to each 1.5 mL tube, and after stirring, the 1.5 mL tube was loaded on a magnet stand, the Dynabeads MyOne Streptavidin C1 was collected on the tube wall using magnetic force, and the solution in the 1.5 mL tube was discarded with a pipette (hereinafter it may be abbreviated as the washing operation, in some cases).
<(3) Immobilization of Fc Tag Fusion Type Mouse-Derived Tim-4 Protein on Beads>
The PBS solution (500 µL) containing 1 µg of the SH-group biotin-labeled Fc tag fusion type mouse-derived Tim-4 protein was added to 0.6 mg of the Dynabeads MyOne Streptavidin C1, in a pellet state, after the washing operation, and subjected to a reaction at 8° C. for 10 minutes to obtain 500 µL of the PBS solution containing the carrier on which the SH-group biotin-labeled Fc tag fusion type mouse-derived Tim-4 protein was bound (the mTim-4 carrier).
<(4) Removal of Extracellular Membrane Vesicles by Removing Method of the Present Invention>
The 1.5 mL tube was loaded on a magnet stand and the mTim-4 carrier was collected on the tube wall using magnetic force, and the solution in the 1.5 mL tube was discarded with a pipette, and then the mTim-4 carrier was subjected to the washing operation three times with each 500 µL of PBS to obtain the mTim-4 carrier in a pellet state. Thereafter, 1 mL of the centrifugal separation treated FBS was added to the mTim-4 carrier in a pellet state, and subjected to a reaction at 8° C. for 1 hour.
After the reaction, the 1.5 mL tube was loaded on a magnet stand, the mTim-4 carrier was collected on the tube wall using magnetic force to recover the supernatant (FBS) in a new 1.5 mL tube (referred to as supernatant-1). The mTim-4 carrier in a pellet state was subjected to the washing operation three times with 500 µL of TBS-T containing 2 mM $CaCl_2$ (Tris buffer, 0.0005% Tween 20, 2 mM $CaCl_2$).

The TBS solution (50 µL) containing 1 mM EDTA as the eluent was added to 0.6 mg of each mTim-4 carrier in a pellet state, and then they were mixed using a vortex mixer at room temperature for 10 seconds, and spun down. The 1.5 mL tube was loaded on a magnet stand, and the mTim-4 carrier was collected to the tube wall using a magnetic force to recover the eluate (referred to as the eluate-1). The TBS solution (50 µL) containing 1 mM EDTA was added again to the mTim-4 carrier to recover the eluate by the same method (referred to as eluate-2). The resulting eluate-1 and eluate-2 were mixed to obtain a removed sample-8.

The supernatant-1 was added again to the mTim-4 carrier after the elution operation (after the elution operation to obtain the eluate-2) and the operation of recovering the extracellular membrane vesicles in the supernatant-1 was repeated eight times in total to obtain each eluate.

The resulting removed samples and the lane numbers in Western blotting to be described later are as shown in the following Table 21.

TABLE 21

Figure 13:
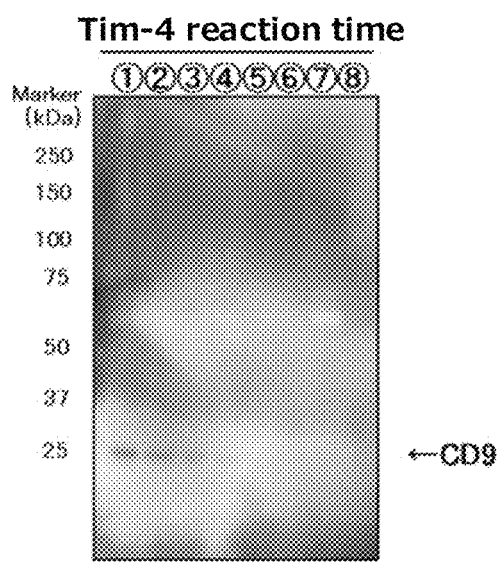
FIG. 13 is an electropherogram for confirming whether the extracellular membrane vesicles were obtained (removed) or not, by Western blotting, in Examples 48 to 55.

| | Example 48 | Example 49 | Example 50 | Example 51 | Example 52 | Example 53 | Example 54 | Example 55 |
|---|---|---|---|---|---|---|---|---|
| Name of sample | Removed sample 8 | Removed sample 9 | Removed sample 10 | Removed sample 11 | Removed sample 12 | Removed sample 13 | Removed sample 14 | Removed sample 15 |
| Mouse-derived Tim-4 carrier and number of times sample reutilized | 0 (unused) | 1 | 2 | 3 | 4 | 5 | 6 | 7 |
| Lane numbers in FIG. 13 | 1 | 2 | 3 | 4 | 5 | 6 | 7 | 8 |

<(5) Western Blotting>
Each 100 µL of the resulting eluate was ultrafiltrated, so as to attain 30 µL with the VIVASPIN 500 (MVCO 10,000) (manufactured by Sartorius AG). To each 15 µL of the ultrafiltrated eluate, 5 µL of the 4× sample buffer (produced by Wako Pure Chemical Industries, Ltd.) was added and incubated at 98° C. for 5 minutes to obtain each sample for Western blotting. Each 20 µL of the sample for Western blotting was loaded on the Super Sep Ace 5-20% gel (produced by Wako Pure Chemical Industries, Ltd.) and subjected to electrophoresis at 25 mA for 65 minutes. The resulting electrophoresis gel was transcribed onto the PVDF membrane (produced by Millipore Corporation) at 1 $mA/cm^2$ for 60 minutes using the semi-dry blotter and the discontinuous buffer (Anode buffer 1: 0.3 M Tris/20% methanol, Anode buffer 2: 0.025 M Tris/20% methanol, Cathode buffer: 0.025 M Tris/0.04 M aminocaproic acid/20% methanol). The 3% skimmed milk, diluted with PBS-T (PBS buffer, 0.1% Tween 20), was added to the post-transcription PVDF membrane, and subjected to a reaction at room temperature for 1 hour for blocking, and 2 mL of the anti-bovine CD9 antibody (produced by Novus Biologicals LLC, hereinafter it may be abbreviated as "the anti-bovine CD9 antibody", in some cases), diluted 1,000-fold with PBS-T, was subjected to a reaction at room temperature for 1 hour. The PVDF membrane after the reaction was washed three times with PBS-T, and the secondary antibody {anti-mouse IgG (H+L), rabbit, IgG fraction, peroxidase-conjugated antibody} (produced by Wako Pure Chemical Industries Ltd.), diluted 10,000-fold with PBS-T, was subjected to a reaction at room temperature for 1 hour. After washing five times with PBS-T, the ImmunoStar Zeta (produced by Wako Pure Chemical Industries, Ltd.) was added, and a luminescent signal was detected using the LAS-4000 (manufactured by GE Healthcare). It should be noted that, the anti-bovine CD9 antibody is an antibody against CD9, which is one of the marker proteins of exosome.

<Results>

The results of Western blotting obtained are shown in FIG. 13. In FIG. 13, each lane shows the following result.

Lane 1: Results of Example 48 (the results of the case where the extracellular membrane vesicles in the sample were removed by the obtaining/removing method of the present invention using the unused Tim-4 carrier of the present invention);

Lane 2: Results of Example 49 (the results of the case where the extracellular membrane vesicles in the sample used once were removed by the obtaining/removing method of the present invention using the Tim-4 carrier of the present invention used once);

Lane 3: Results of Example 50 (the results of the case where the extracellular membrane vesicles in the sample used twice were removed by the obtaining/removing method of the present invention using the Tim-4 carrier of the present invention used twice);

Lane 4: Results of Example 51 (the results of the case where the extracellular membrane vesicles in the sample used 3 times were removed by the obtaining/removing method of the present invention using the Tim-4 carrier of the present invention used 3 times);

Lane 5: Results of Example 52 (the results of the case where the extracellular membrane vesicles in the sample used 4 times were removed by the obtaining/removing method of the present invention using the Tim-4 carrier of the present invention used 4 times);

Lane 6: Results of Example 53 (the results of the case where the extracellular membrane vesicles in the sample used 5 times were removed by the obtaining/removing method of the present invention using the Tim-4 carrier of the present invention used 5 times);

Lane 7: Results of Example 54 (the results of the case where the extracellular membrane vesicles in the sample used 6 times were removed by the obtaining/removing method of the present invention using the Tim-4 carrier of the present invention used 6 times);

Lane 8: Results of Example 55 (the results of the case where the extracellular membrane vesicles in the sample used 7 times were removed by the obtaining/removing method of the present invention using the Tim-4 carrier of the present invention used 7 times).

From FIG. 13, it has been revealed that the extracellular membrane vesicles can be removed more reliably, by utilizing the Tim-4 carrier of the present invention repeatedly, from the fact that when the removal operation is carried out by repeatedly using the Tim-4 carrier of the present invention, amount of exosome recovered from the sample decreases. In addition, it has been revealed that the Tim-4 carrier of the present invention is reusable, by separating the extracellular membrane vesicles from the complex of the Tim-4 protein bound to the carrier and the extracellular membrane vesicle in the sample, using EDTA, which is the calcium ion chelating agent.

Examples 56 to 67, Comparative Examples 14 to 15. Obtaining of Extracellular Membrane Vesicles by Carrier on which Tim Family Protein is Immobilized As described below, obtaining of the extracellular membrane vesicles pertaining to the present invention was carried out by using the carrier in which the Tim-1 protein, the Tim-3 protein, or the Tim-4 protein, which is the Tim family, was each immobilized on the beads.

<(1) Preparation of Calcium Ion-Containing Culture Supernatant (Stock Solution)>

The human chronic myelogenous leukemia cell strain K562, $1\times10^7$ cells, secreting the extracellular membrane vesicles, was cultured for three days under condition at 37° C. and 5% $CO_2$, using 80 mL of the X-VIVO15 medium (produced by Lonza AG), then the cells were precipitated by centrifugal separation treatment (300×G, for 5 minutes) to remove the supernatant. The precipitated cells were suspended in 60 mL of the X-VIVO 15 medium containing 10 μM monensin sodium (produced by MP Biomedicals Co., Ltd) and cultured for 24 hours under condition at 37° C. and 5% $CO_2$.

Thereafter, the culture solution was subjected to centrifugal separation treatment (300×G, for 5 minutes) to recover the culture supernatant. The recovered culture supernatant (60 mL) was further subjected to centrifugal separation treatment three times (the first time: 300×G, for 3 minutes, the second time: 1,200×G, for 20 minutes, the third time: 10,000×G, for 20 minutes) to separate impurities to obtain the supernatant (hereinafter it may be abbreviated as "the culture supernatant (stock solution)", in some cases).

In addition, $CaCl_2$ was added to the resulting culture supernatant stock solution, so as to attain the final concentration of 2 mM to obtain a sample of K562 cell culture supernatant concentrated solution containing 2 mM $CaCl_2$ (hereinafter it may be abbreviated as "the calcium ion-containing culture supernatant (stock solution)", in some cases).

<(2) Washing of Beads>

The PBS-T solution (20 μL) containing the 30 μg/μL Dynabeads Protein G (produced by Thermo Fisher Scientific Inc.) (containing 0.6 mg of the Dynabeads Protein G) was dispensed into seven 1.5 mL tubes (manufactured by BM Equipment Co., Ltd.), and each subjected to the washing operation.

<(3) Immobilization of Fc Tag Fusion Type Tim Protein on Beads>

Each 200 μL of the TBS solution containing 1 μg of the Fc tag fusion type mouse-derived Tim-1 protein, the Fc tag fusion type mouse-derived Tim-3 protein, the Fc tag fusion type mouse-derived Tim-4 protein, the Fc tag fusion type human-derived Tim-1 protein, the Fc tag fusion type human-derived Tim-3 protein, or the Fc tag fusion type human-derived Tim-4 protein (all produced by Wako Pure Chemical Industries, Ltd.) was added to the 1.5 mL tubes containing 0.6 mg of Dynabeads Protein G respectively, and subjected to a reaction at 8° C. for 1 hour to obtain each of the carrier on which the Fc tag fusion type mTim-1 protein was bound, the carrier on which the Fc tag fusion type mTim-3 protein was bound, the carrier on which the Fc tag fusion type mTim-4 protein-bound carrier, the carrier on which the Fc tag fusion type hTim-1 protein was bound, the carrier on which the Fc tag fusion type hTim-3 protein was bound, and the carrier on which the Fc tag fusion type hTim-4 protein was bound. It should be noted that, the resulting these six types of carriers are shown in the following Table 22. They may be abbreviated collectively as "the Tim protein-bound carrier", in some cases.

TABLE 22

|  | | 1 | 2 | 3 | 4 | 5 | 6 |
|---|---|---|---|---|---|---|---|
| Tim protein-bound carrier | Carrier | Dynabeads Protein G beads | | | | | |
|  | Fc tag fusion type Tim protein | Human-derived Tim-1 | Mouse-derived Tim-1 | Human-derived Tim-3 | Mouse-derived Tim-3 | Human-derived Tim-4 | Mouse-derived Tim-4 |

<(4) Obtaining of Extracellular Membrane Vesicles by Method of the Present Invention>

The resulting 6 types of the Tim protein-bound carriers above were each subjected to the washing operation three times with 500 μL of TBS-T (Tris buffer, 0.1% Tween 20) and twice with 500 μL of TBS to obtain the Tim protein-bound carriers in a pellet state. Subsequently, 1 mL of the calcium ion-containing culture supernatant (stock solution) prepared in the (1) was added to each of the Tim protein-bound carriers in a pellet state, and the Dynabeads Protein G which had been subjected to only the washing operation (hereinafter it may be abbreviated as "the Tim protein non-bound carrier", in some cases), and each subjected to a reaction at 8° C. for 3 hours.

Thereafter, the Tim protein-bound carrier or the Tim protein non-bound carrier, after the reaction, was subjected to the washing operation three times with each 500 μL of the calcium ion-containing TBS-T (Tris buffer, 0.0005% Tween 20, 2 mM $CaCl_2$). At the third time of the washing operation, 500 μL of the $CaCl_2$-containing TBS-T solution containing the Tim protein-bound carrier or the Tim protein non-bound carrier was dispensed into each of the two 1.5 mL tubes, by each 250 μL aliquot, and after the tube was loaded on a magnetic stand, the washing solution was removed.

50 μL of 1% SDS aqueous solution or the TBS solution (25 μL) containing 1 mM EDTA, as the eluent, was added to each of 0.3 mg of the pellet-like Tim protein-bound carrier, or the Tim protein non-bound carrier, and they were mixed using a vortex mixer at room temperature for 10 seconds and spun down. The TBS solution (25 μL) containing 1 mM EDTA was added again to the tube to which EDTA had been added and the same operation was carried out to obtain each supernatant (eluate).

<(5) Western Blotting>

The 4×sample buffer (3.75 μL, produced by Wako Pure Chemical Industries, Ltd.) was added to 11.25 μL of the resulting each supernatant (each eluate) in the (4), and incubated at 95° C. for 3 minutes to obtain each sample for Western blotting. Each 15 μL of the sample for Western blotting was loaded on the Super Sep Ace 5-20% gel (produced by Wako Pure Chemical Industries, Ltd.), and subjected to electrophoresis at 30 mA for 60 minutes. The resulting electrophoresis gel was transcribed onto the PVDF membrane (produced by Millipore Corporation) at 1 mA/cm² for 60 minutes using the semi-dry blotter and the discontinuous buffer (Anode buffer 1: 0.3 M Tris/20% methanol, Anode buffer 2: 0.025 M Tris/20% methanol, Cathode buffer: 0.025 M Tris/0.04 M aminocaproic acid/20% methanol). The five % skimmed milk, diluted with TBS-T (TBS buffer, 0.1% Tween 20), was added to the transcribed PVDF membrane and subjected to a reaction at room temperature for 1 hour for blocking, and then 2 mL of the anti-human Lamp-1 antibody (produced by BD Biosciences), diluted 250-fold with PBS-T, or the 250-fold diluted anti-human Flotillin-2 antibody (produced by BD Biosciences) were subjected to a reaction at room temperature for 1 hour. The PVDF membrane after the reaction was washed three times with TBS-T, and subjected to a reaction with the secondary antibody {anti-mouse IgG (H+L), rabbit, IgG fraction, peroxidase-conjugated antibody} (produced by Wako Pure Chemical Industries Ltd.), diluted 5,000-fold with PBS-T, at room temperature for 1 hour. After washing five times with TBS-T, the ImunoStar Zeta (produced by Wako Pure Chemical Industries, Ltd.) was added to the PVDF membrane, after subjected to a reaction with each antibody, and a luminescent signal was detected using the LAS-4000 (manufactured by GE Healthcare).

It should be noted that the types of Tim proteins, the carrier and the eluents used for obtaining the extracellular membrane vesicles from the Tim protein-bound (non-bound) carrier, used in each Example and Comparative Example, are shown in the following Table 23.

TABLE 23

Figure 14:
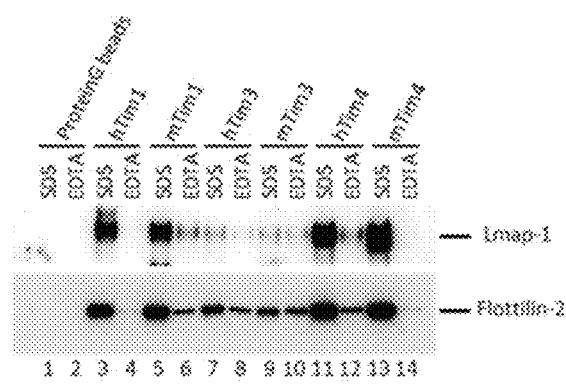
FIG. 14 is an electropherogram for confirming whether the extracellular membrane vesicles were obtained or not, by Western blotting, in Examples 56 to 67, and Comparative Examples 14 to 15.

|  |  | Comparative Example | | Example | | | | | | | | | | | | |
|---|---|---|---|---|---|---|---|---|---|---|---|---|---|---|---|---|
|  |  | 14 | 15 | 56 | 57 | 58 | 59 | 60 | 61 | 62 | 63 | 64 | 65 | 66 | 67 |
| Tim protein-(non-)bound carrier | Carrier | — | — | Dynabeads Protein G beads | | | | | | | | | | | | |
|  | Fc tag fusion type Tim protein | — | — | Human-derived Tim-1 | Human-derived Tim-1 | Mouse-derived Tim-1 | Mouse-derived Tim-1 | Human-derived Tim-3 | Human-derived Tim-3 | Mouse-derived Tim-3 | Mouse-derived Tim-3 | Human-derived Tim-4 | Human-derived Tim-4 | Mouse-derived Tim-4 | Mouse-derived Tim-4 |
|  | Eluent | 1% SDS | 1 mM EDTA | 1% SDS | 1 mM EDTA | 1% SDS | 1 mM EDTA | 1% SDS | 1 mM EDTA | 1% SDS | 1 mM EDTA | 1% SDS | 1 mM EDTA | 1% SDS | 1 mM EDTA |
|  | Lane numbers in FIG. 14 | 1 | 2 | 3 | 4 | 5 | 6 | 7 | 8 | 9 | 10 | 11 | 12 | 13 | 14 |

<Results>

The results of Western blotting obtained are shown in FIG. 14. In FIG. 14, each lane is as follows.

Lane 1: Results of Comparative Example 14 (the results of the case where the carrier of only the magnetic beads of the Dynabeads protein G was used, and the 1% SDS aqueous solution was used as the eluent);

Lane 2: Results of Comparative Example 15 (the results of the case where the carrier of only the magnetic beads of the Dynabeads protein G was used and the TBS solution containing 1 mM EDTA was used as the eluent);

Lane 3: Results of Example 56 (the results of the case of using the carrier in which the human-derived Tim-1 protein was bound to the Dynabeads protein G, and using the 1% SDS aqueous solution as the eluent);

Lane 4: Results of Example 57 (the results of the case of using the carrier in which the human-derived Tim-1 protein was bound to the Dynabeads protein G, and using the TBS solution containing 1 mM EDTA as the eluent);

Lane 5: Results of Example 58 (the results of the case of using the carrier in which the mouse-derived Tim-1 protein was bound to the Dynabeads protein G, and using the 1% SDS aqueous solution as the eluent);

Lane 6: Result of Example 59 (the results in a case of using the carrier in which the mouse-derived Tim-1 protein was bound to the Dynabeads protein G, and using the TBS solution containing 1 mM EDTA as the eluent);

Lane 7: Results of Example 60 (the results of the case of using the carrier on which the human-derived Tim-3 protein was bound to the Dynabeads protein G, and using the 1% SDS aqueous solution as the eluent);

Lane 8: Results of Example 61 (the results of the case of using the carrier in which the human-derived Tim-3 protein was bound to the Dynabeads protein G, and using the TBS solution containing 1 mM EDTA as the eluent);

Lane 9: Results of Example 62 (the results of the case of using the carrier in which the mouse-derived Tim-3 protein was bound to the Dynabeads protein G, and using the 1% SDS aqueous solution as the eluent); Lane 10: Results of Example 63 (the results of the case of using the carrier in which the mouse-derived Tim-3 protein was bound to the Dynabeads protein G, and using the TBS solution containing 1 mM EDTA as the eluent);

Lane 11: Results of Example 64 (the results of the case of using the carrier in which the human-derived Tim-4 protein was bound to the Dynabeads protein G, and using the 1% SDS aqueous solution as the eluent);

Lane 12: Results of Example 65 (the results of the case of using the carrier in which the human-derived Tim-4 protein was bound to the Dynabeads protein G, and using the TBS solution containing 1 mM EDTA as the eluent);

Lane 13: Results of Example 66 (the results of the case of using the carrier in which the mouse-derived Tim-4 protein was bound to the Dynabeads protein G, and using the 1% SDS aqueous solution as the eluent);

Lane 14: Results of Example 67 (the results in a case of using the carrier in which the mouse-derived Tim-4 protein was bound to the Dynabeads protein G, and using the TBS solution containing 1 mM EDTA as the eluent).

From FIG. 14, it has been revealed the extracellular membrane vesicles can be obtained by using the carrier on which the Tim-1 protein, the Tim-3 protein or the Tim-4 protein is bound (the Tim protein-bound carrier), regardless of the origin of the protein or the elution method, from the fact that a band of Lamp-1 or Flotillin-2, which is exosome marker protein, was observed in lanes 3 to 14.

In addition, it has been revealed that, in the case of eluting with SDS, more extracellular membrane vesicles can be obtained in the order of the Tim-4 protein-bound carrier>the Tim-1 protein-bound carrier>the Tim-3 protein-bound carrier.

Examples 68 to 79. Obtaining of Extracellular Membrane Vesicles by Carrier on which Tim Protein is Immobilized Obtaining of the extracellular membrane vesicles pertaining to the present invention was carried out, using the carriers on which each of the biotin-labeled Tim-1 protein, the biotin-labeled Tim-3 protein or the biotin-labeled Tim-4 protein was immobilized.

<(1) Preparation of Culture Supernatant Sample>

The calcium ion-containing culture supernatant (stock solution) was obtained by the same method as in "(1) preparation of calcium ion-containing culture supernatant (stock solution)" in Examples 50 to 67, and Comparative Examples 14 to 15.

<(2) Biotin Labeling of SH-Group of Fc Tag Fusion Type Tim-1 Protein>

For 200 μL of the PBS solution containing the Fc tag fusion type mouse-derived Tim-1 protein (produced by Wako Pure Chemical Industries, Ltd.) (containing 20 μg of the Fc tag fusion type mouse-derived Tim-1 protein), the SH-group of the Fc tag fusion type mouse-derived Tim-1 protein was labeled with biotin using the Biotin Labeling Kit-SH (produced by Dojindo Molecular Technologies, Inc.), according to a protocol attached to the kit to obtain 200 μL of the PBS solution containing the SH-group biotin-labeled Fc tag fusion type mouse-derived Tim-1 protein.

<(3) Biotin Labeling of SH-Group of Fc Tag Fusion Type Tim-3 Protein>

For 200 μL of the PBS solution containing the Fc tag fusion type mouse-derived Tim-3 protein (produced by Wako Pure Chemical Industries, Ltd.) (containing 20 μg of the Fc tag fusion type mouse-derived Tim-3 protein), the SH-group of the Fc tag fusion type mouse-derived Tim-3 protein was labeled with biotin using the Biotin Labeling Kit-SH (produced by Dojindo Molecular Technologies, Inc.), according to a protocol attached to the kit to obtain 200 μL of the PBS solution containing the SH-group biotin-labeled Fc tag fusion type mouse-derived Tim-3 protein.

<(4) Biotin Labeling of SH-Group of Fc Tag Fusion Type Tim-4 Protein>

For 100 μL of the PBS solution containing the Fc tag fusion type mouse-derived Tim-4 protein (produced by Wako Pure Chemical Industries, Ltd.) (containing 10 μg of the Fc tag fusion type mouse-derived Tim-4 protein), the SH-group of the Fc tag fusion type mouse-derived Tim-4 protein was labeled with biotin using the Biotin Labeling Kit-SH (produced by Dojindo Molecular Technologies, Inc.), according to a protocol attached to the kit to obtain 100 μL of the PBS solution containing the SH-group biotin-labeled Fc tag fusion type mouse-derived Tim-4 protein.

<(5) Dilution of Tag-Fused Tim Protein>

The PBS solution (10 μL) containing the Fc tag fusion type mTim-1 protein (produced by Wako Pure Chemical Industries, Ltd.) (containing 1 μg of the Fc tag fusion type mTim-1 protein) was mixed with 190 μL of TBS to obtain 200 μL of a solution containing 1 μg of the biotin-unlabeled Fc tag fusion type mTim-1 protein.

The TBS solution (11.5 μL) containing the SH-group biotin-labeled Fc tag fusion type mTim-1 protein prepared in the (2) (containing 1 μg of the SH-group biotin-labeled Fc tag fusion type mTim-1 protein) was mixed with 188.5 μL of TBS to obtain 200 μL of a solution containing 1 μg of the biotin-labeled Fc tag fusion type mTim-1 protein.

The PBS solution (10 μL) containing the Fc tag fusion type mTim-3 protein (produced by Wako Pure Chemical Industries, Ltd.) (containing 1 μg of the Fc tag fusion type mTim-3 protein) was mixed with 190 μL of TBS to obtain 200 μL of a solution containing 1 μg of the biotin-unlabeled Fc tag fusion type mTim-3 protein.

The TBS solution (9.0 μL) containing the SH-group biotin-labeled Fc tag fusion type mTim-3 protein prepared in the (3) (containing 1 μg of the SH-group biotin-labeled Fc tag fusion type mTim-3 protein) was mixed with 191.0 μL of TBS to obtain 200 μL of a solution containing 1 μg of the biotin-labeled Fc tag fusion type mTim-3 protein.

The PBS solution (10 µL) containing the Fc tag fusion type mTim-4 protein (produced by Wako Pure Chemical Industries, Ltd.) (containing 1 µg of the Fc tag fusion type mTim-4 protein) was mixed with 190 µL of TBS to obtain 200 µL of a solution containing 1 µg of the biotin-unlabeled Fc tag fusion type mTim-4 protein.

The TBS solution (10 µL) containing the SH-group biotin-labeled Fc tag fusion type mTim-4 protein prepared in the (4) (containing 1 µg of the SH-group biotin-labeled Fc tag fusion type mTim-4 protein) was mixed with 190 µL of TBS to obtain 200 µL of a solution containing 1 µg of the biotin-labeled Fc tag fusion type mTim-4 protein.

<(6) Washing of Beads>

The PBS-T solution (20 µL) containing 30 µg/µL of the Dynabeads Protein G (produced by Thermo Fisher Scientific Inc.) (containing 0.6 mg of the Dynabeads Protein G) was transferred into six 1.5 mL tubes (manufactured by BM Equipment Co., Ltd.), and each subjected to the washing operation.

In addition, 60 µL of PBS solution containing the 10 µg/µL Dynabeads M-270 Streptavidin C1 (produced by Thermo Fisher Scientific Inc.) (containing 0.6 mg of the Dynabeads M-270 Streptavidin C1) was dispensed into each of the 1.5 mL tubes (manufactured by BM Equipment Co., Ltd.), and the washing operation was carried out by the same method as above using 500 µL of TBS.

<(7) Immobilization of Fc Tag Fusion Type Tim Protein on Beads>

The solution (200 µL) containing 1 µg of the SH-group biotin-unlabeled Fc tag fusion type mTim-1 protein, 200 µL of the solution containing 1 µg of the SH-group biotin-unlabeled Fc tag fusion type mTim-3 protein, or 200 µL of the solution containing 1 µg of the SH-group biotin-unlabeled Fc tag fusion type mTim-4 protein was each added to six 1.5 mL tubes containing the 0.6 mg of pellet-like Dynabeads Protein G, after the washing operation, and subjected to a reaction at 8° C. for 1 hour to obtain each of the carrier on which the SH-group biotin-unlabeled Fc tag fusion type mTim-1 protein was bound (it may be abbreviated as "the biotin-unlabeled Fc tag fusion type mTim-1 carrier", in some cases), the carrier on which the SH-group biotin-unlabeled Fc tag fusion type mTim-3 protein was bound (it may be abbreviated as "the biotin-unlabeled Fc tag fusion type mTim-3 carrier", in some cases), and the carrier on which the SH-group biotin-unlabeled Fc tag fusion type mTim-4 protein was bound (it may be abbreviated as "the biotin-unlabeled Fc tag fusion type mTim-4 carrier", in some cases).

In addition, 200 µL of the solution containing 1 µg of the SH-group biotin-labeled Fc tag fusion type mTim-1 protein, 200 µL of a solution containing 1 µg of the SH-group biotin-labeled Fc tag fusion type mTim-3 protein, or 200 µL of a solution containing 1 µg of the SH-group biotin-labeled Fc tag fusion type mTim-4 protein was added to the 1.5 mL tube containing 0.6 mg of the pellet-like Dynabeads M270 Streptavidin C1, after the washing operation, to bind on the beads by the same method as above to prepare each of the carrier on which the SH-group biotin-labeled Fc tag fusion type mTim-1 protein was bound (it may be abbreviated as "the biotin-labeled Fc tag fusion type mTim-1 carrier", in some cases), the carrier on which the SH-group biotin-labeled Fc tag fusion type mTim-3 protein was bound (it may be abbreviated as "the biotin-labeled Fc tag fusion type mTim-3 carrier", in some cases), and the carrier on which the SH-group biotin-labeled Fc tag fusion type mTim-4 protein was bound (it may be abbreviated as "the biotin-labeled Fc tag fusion type mTim-4 carrier", in some cases).

It should be noted that, the resulting these six types of the carriers may be abbreviated collectively as "the Tim protein-bound carrier" in some cases.

<(8) Obtaining of Extracellular Membrane Vesicles by Obtaining Method of the Present Invention>

The resulting these Tim protein-bound carriers above were subjected to the washing operation three times with 500 µL of TBS-T (Tris buffer, 0.1% Tween 20), and twice with 500 µL of TBS to obtain the Tim protein-bound carrier in a pellet state. Subsequently, 1 mL of the calcium ion-containing culture supernatant (stock solution) was added to each of the resulting six pellet-like Tim protein-bound carriers, and each subjected to a reaction at 8° C. for 3 hours. After that, the Tim protein-bound carriers after the reaction were subjected to the washing operation 3 times with each 500 µL of the calcium ion-containing TBS-T (Tris buffer, 0.0005% Tween 20, 2 mM $CaCl_2$). At the third time of the washing operation, 500 µL of the $CaCl_2$-containing TBS-T solution containing the Tim protein-bound carrier was dispensed into each of the two 1.5 mL tubes in an amount of each 250 µL, and the tubes were loaded on a magnetic stand, and then the washing solution was removed.

50 µL of 1% SDS aqueous solution or 25 µL of the TBS solution containing 1 mM EDTA, as the eluent, was added to each 0.3 mg of the 6 types of the Tim protein-bound carriers in a pellet state, and they were mixed using a vortex mixer at room temperature for 10 seconds, and spun down. To the tube to which EDTA had been added, 25 µL of the TBS solution containing 1 mM EDTA was added again, and the same operation was carried out to obtain the eluate.

It should be noted that the types of Tim proteins, the carriers, and the Tim protein-(un) bound carriers, used in each Example, are shown in the following Table 24.

TABLE 24

| | | Example | | | | | | | | | | | |
|---|---|---|---|---|---|---|---|---|---|---|---|---|---|
| | | 68 | 69 | 70 | 71 | 72 | 73 | 74 | 75 | 76 | 77 | 78 | 79 |
| Tim protein-bound carrier | Carrier | Dynabeads Protein G beads | | Streptavidin beads | | Dynabeads Protein G beads | | Streptavidin beads | | Dynabeads Protein G beads | | Streptavidin beads | |
| | Fc tag fusion type Tim protein | Biotin-unlabeled mouse-derived Tim-1 | | SH-group biotin-labeled mouse-derived Tim-1 | | Biotin-unlabeled mouse-derived Tim-3 | | SH-group biotin-labeled mouse-derived Tim-3 | | Biotin-unlabeled mouse-derived Tim-4 | | SH-group biotin-labeled mouse-derived Tim-4 | |

<(9) Western Blotting>

Western blotting was carried out by the same method as in "(5) Western blotting" in Examples 56 to 67, except for using 11.25 µL of the resulting each eluate in the (6), instead of "11.25 µL of the resulting each eluate in (4)", in <(5) Western blotting> of Examples 56 to 67, and using, as the secondary antibody, {anti-mouse IgG (H+L), donkey, IgG fraction, peroxidase-conjugated antibody}(produced by Jackson Immuno Research Inc.), diluted 30,000-fold with TBS-T, instead of "the secondary antibody {anti-mouse IgG (H+L), rabbit, IgG fraction, peroxidase-conjugated antibody}(produced by Wako Pure Chemical Industries, Ltd.).

It should be noted that the types of Tim proteins, carriers, and the eluents used for obtaining the extracellular membrane vesicles from the Tim protein-bound (non-bound) carrier, used in each Example, and the lane numbers in Western blotting are shown in the following Table 25.

TABLE 25

Figure 15:
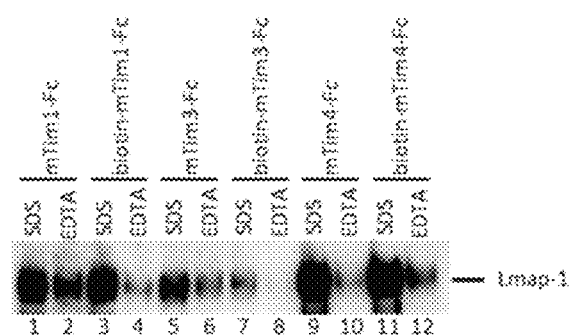
FIG. 15 is an electropherogram for confirming whether the extracellular membrane vesicles were obtained or not, by Western blotting, in Examples 68 to 79.

|  |  | Example |  |  |  |  |  |  |  |  |  |  |  |
|---|---|---|---|---|---|---|---|---|---|---|---|---|---|
|  |  | 68 | 69 | 70 | 71 | 72 | 73 | 74 | 75 | 76 | 77 | 78 | 79 |
| Tim protein-bound carrier | Carrier | Dynabeads Protein G beads | | Streptavidin beads | | Dynabeads Protein G beads | | Streptavidin beads | | Dynabeads Protein G beads | | Streptavidin beads | |
|  | Fc tag fusion type Tim protein | Biotin-unlabeled mouse-derived Tim-1 | | SH-group biotin-labeled mouse-derived Tim-1 | | Biotin-unlabeled mouse-derived Tim-3 | | SH-group biotin-labeled mouse-derived Tim-3 | | Biotin-unlabeled mouse-derived Tim-4 | | SH-group biotin-labeled mouse-derived Tim-4 | |
|  | Eluent | 1% SDS | 1 mM EDTA | 1% SDS | 1 mM EDTA | 1% SDS | 1 mM EDTA | 1% SDS | 1 mM EDTA | 1% SDS | 1 mM EDTA | 1% SDS | 1 mM EDTA |
| Lane numbers in FIG. 15 |  | 1 | 2 | 3 | 4 | 5 | 6 | 7 | 8 | 9 | 10 | 11 | 12 |

<Results>

The results of Western blotting obtained are shown in FIG. 15. In FIG. 15, each lane is the result of the following.

Lane 1: Results of Example 68 (the results of the case of using the carrier in which the SH-group biotin-unlabeled Fc tag fusion type mTim-1 protein was bound on the Dynabeads protein G, and using the 1% SDS aqueous solution as the eluent);

Lane 2: Results of Example 69 (the results of the case of using a carrier in which the SH-group biotin-unlabeled Fc tag fusion type mTim-1 protein was bound on the Dynabeads protein G, and using the TBS solution containing 1 mM EDTA as the eluent);

Lane 3: Results of Example 70 (the results of the case of using a carrier in which the SH-group biotin-labeled Fc tag fusion type mTim-1 protein was bound on the Dynabeads M270 Streptavidin, and using the 1% SDS aqueous solution as the eluent);

Lane 4: Results of Example 71 (the results of the case of using a carrier in which the SH-group biotin-labeled Fc tag fusion type mTim-1 protein was bound on the Dynabeads M270 Streptavidin, and using the TBS solution containing 1 mM EDTA as the eluent);

Lane 5: Results of Example 72 (the results of the case of using a carrier in which the SH-group biotin-unlabeled Fc tag fusion type mTim-3 protein was bound on the Dynabeads protein G, and using the 1% SDS aqueous solution as the eluent);

Lane 6: Results of Example 73 (the results of the case of using a carrier in which the SH-group biotin-unlabeled Fc tag fusion type mTim-3 protein was bound on the Dynabeads protein G, and using the TBS solution containing 1 mM EDTA as the eluent);

Lane 7: Results of Example 74 (the results of the case of using a carrier in which the SH-group biotin-labeled Fc tag fusion type mTim-3 protein was bound on the Dynabeads M270 Streptavidin, and using the 1% SDS aqueous solution as the eluent);

Lane 8: Results of Example 75 (the results of the case of using a carrier in which the SH-group biotin-labeled Fc tag fusion type mTim-3 protein was bound on the Dynabeads M270 Streptavidin, and using the TBS solution containing 1 mM EDTA as the eluent);

Lane 9: Results of Example 76 (the results of the case of using a carrier in which the SH-group biotin-unlabeled Fc tag fusion type mTim-4 protein was bound on the Dynabeads protein G, and using the 1% SDS aqueous solution as the eluent);

Lane 10: Results of Example 77 (the results of the case of using a carrier in which the SH-group biotin-unlabeled Fc tag fusion type mTim-4 protein was bound on the Dynabeads protein G, and using the TBS solution containing 1 mM EDTA as the eluent);

Lane 11: Results of Example 78 (the results of the case of using a carrier in which the SH-group biotin-labeled Fc tag fusion type mTim-4 protein was bound on the Dynabeads M270 Streptavidin, and using the 1% SDS aqueous solution as the eluent);

Lane 12: Results of Example 79 (the results of the case of using a carrier in which the SH-group biotin-labeled Fc tag fusion type mTim-4 protein was bound on the Dynabeads M270 Streptavidin, and using the TBS solution containing 1 mM EDTA as the eluent).

From FIG. 15, it has been revealed that the extracellular membrane vesicles can be obtained, by using the carrier on which the Tim-1, the Tim-3, or the Tim-4 was bound (the Tim protein-bound carrier), from the fact that a band of Lamp-1, which is a marker protein of exosome, was observed in any of the lanes 1 to 12.

In addition, it has been revealed that more extracellular membrane vesicles can be obtained in the order of the Tim-4 protein-bound carrier>the Tim-1 protein-bound carrier>the Tim-3 protein-bound carrier. It has been revealed that when eluting with the calcium chelating agent, more extracellular membrane vesicles can be obtained by immobilization on the beads (carriers) via the SH group of the Tim4 protein, as compared with immobilizing via the tag (lanes 9 to 12).

Examples 80 to 83, Comparative Examples 16 to 19. Obtaining of Extracellular Membrane Vesicles by Carrier on which Tim Family Protein was Immobilized Obtaining of the extracellular membrane vesicles pertaining to the present invention was carried out using the carrier in which the Tim-1 protein, the Tim-2 protein, or the Tim-4 protein was immobilized, as the Tim family protein, on the beads.

<(1) Preparation of Calcium Ion-Containing Culture Supernatant Sample> may be abbreviated as "the 6×His tag fusion type mTim-2 protein-bound carrier"), and the carrier on which the Tim-4 protein was bound (it may be abbreviated as "the 6×His tag fusion type mTim-4 protein-bound carrier", in some cases).

It should be noted that the resulting 6×His fusion type mTim-1 protein-bound carrier, and the 6×His fusion type mTim-4 protein-bound carrier may be abbreviated collectively as "the Tim protein-bound carrier" in some cases.

The types of the Tim proteins, the carrier and the Tim family protein-(non-)bound carriers, used in each Example, are shown in the following Table 26.

TABLE 26

|  |  | Comparative Example 16 | Comparative Example 17 | Example 80 | Example 81 | Comparative Example 18 | Comparative Example 19 | Example 82 | Example 83 |
|---|---|---|---|---|---|---|---|---|---|
| Tim family protein-(non-)bound carrier | Carrier Tim family protein | — | — | Anti-6×His tag antibody-bound Dynabeads Protein G carrier | | | | | |
|  |  |  |  | 6×His tag fusion type mouse-derived Tm-1 protein | 6×His tag fusion type mouse-derived Tm-1 protein | 6×His tag fusion Type mouse-derived Tm-2 protein | 6×His tag fusion Type mouse-derived Tm-2 protein | 6×His tag fusion type mouse-derived Tm-4 protein | 6×His tag fusion type mouse-derived Tm-4 protein |

The calcium ion-containing culture supernatant sample was obtained by the same method as in "(1) Preparation of culture supernatant sample" of Examples 1 to 8.

<(2) Washing of Beads>

The PBS-T solution (20 μL) containing the 30 μg/μL Dynabeads Protein G (produced by Thermo Fisher Scientific Inc.) (containing 4.8 mg of the Dynabeads Protein G) was dispensed into each of the four 1.5 mL tubes (manufactured by BM Equipment Co., Ltd.), and each was subjected to the washing operation.

<(3) Immobilization of 6×His Tag Fusion Type Tim Family Protein on Beads>

The TBS solution (100 μL) containing 4 μg of the anti-6×His antibody (clone No. 28 to 75, produced by Wako Pure Chemical Industries, Ltd.) was added to each of the four 1.5 mL tubes containing 0.6 mg of the Dynabeads Protein G, in a pellet state, after the washing operation, and subjected to a reaction at 8° C. for 30 minutes to obtain 100 μL of the TBS solution containing the carrier on which the anti-6×His antibody was bound. These carriers on which the anti-6×His antibody was bound were subjected to the washing operation three times with each 250 μL of TBS-T (Tris buffer, 0.1% Tween 20), and then subjected to the washing operation twice with each 250 μL of TBS.

Next, 100 μL of the TBS solution containing 1 μg of the 6×His tag fusion type mouse-derived Tim-1 protein (produced by R & D Systems Inc.), 100 μL of the TBS solution containing 1 μg of the 6×His tag fusion type mouse-derived Tim-2 protein (produced by R & D Systems Inc.), or 100 μL of the TBS solution containing 1 μg of the 6×His tag fusion type mouse-derived Tim-4 protein (produced by R & D Systems Inc.) was each added to the anti-6×His antibody-bound Dynabeads Protein G carrier after the washing operation and subjected to a reaction at 8° C. for 1 hour to obtain each of the carrier on which the Tim-1 protein was bound via the anti-6×His antibody (it may be abbreviated as "the 6×His tag fusion type mTim-1 protein-bound carrier", in some cases), the carrier on which the Tim-2 protein was bound (it <(4) Obtaining of Extracellular Membrane Vesicles by Obtaining Method of the Present Invention>

The resulting anti-6×His antibody-bound Dynabeads Protein G carrier, the 6×His tag fusion type mTim-1 protein-bound carrier, the 6×His tag fusion type mTim-2 protein-bound carrier, the 6×His tag fusion type mTim-2 protein-bound carrier in the (3) were each subjected to the washing operation three times with 250 μL of TBS-T (Tris buffer, 0.1% Tween 20) and twice with 250 μL of TBS to obtain each carrier in a pellet state. Thereafter, 200 μL of the calcium ion-containing culture supernatant sample was added to each carrier in a pellet state, and subjected to a reaction at 8° C. for 3 hours. Each carrier after the reaction was subjected to the washing operation three times with 500 μL of the calcium ion-containing TBS-T (Tris buffer, 0.0005% Tween 20, 2 mM $CaCl_2$). At the third time of the washing operation, 500 μL of the $CaCl_2$-containing TBS-T solution containing each carrier was dispensed into two 1.5 mL tubes in an amount of each 250 μL, and after loading the tube on a magnetic stand, the washing solution was removed.

50 μL of the 1% SDS aqueous solution or 25 μL of the TBS solution containing 1 mM EDTA, as the eluent, was added to each 0.3 mg of the carrier in a pellet state, and they were mixed using a vortex mixer at room temperature for 10 seconds, and spun down. To the tube to which EDTA had been added, 25 μL of the TBS solution containing 1 mM EDTA was added again, and the same operation was carried out to obtain the eluate.

<(5) Western Blotting>

Western blotting was carried out by the same method as in "(7) Western blotting" in Examples 68 to 79, except for using 11.25 μL of the resulting each eluate in the (4).

It should be noted that the types of the Tim family proteins, the carrier, and the eluents used for obtaining the extracellular membrane vesicles from the Tim protein-bound (non-bound) carrier, used in each Example, and the lane numbers in Western blotting are shown in the following Table 27.

TABLE 27

Figure 16:
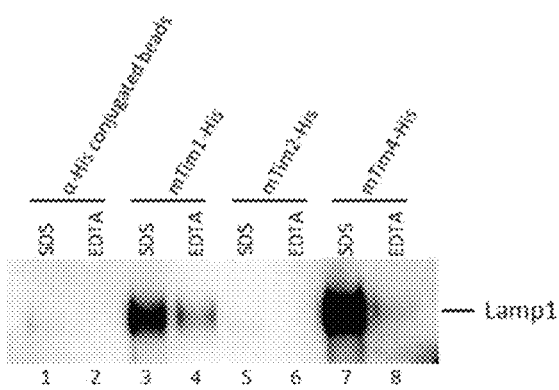
FIG. 16 is an electropherogram for confirming whether the extracellular membrane vesicles were obtained or not, by Western blotting, in Examples 80 to 83, and Comparative Examples 16 to 19.

| | | Comparative Example 16 | Comparative Example 17 | Example 80 | Example 81 | Comparative Example 18 | Comparative Example 19 | Example 82 | Example 83 |
|---|---|---|---|---|---|---|---|---|---|
| Tim family protein-(non-)bound carrier | Carrier | — | — | Anti-6xHis tag antibody-bound Dynabeads Protein G carrier | | | | | |
| | Tim family protein | | | 6xHis tag fusion type mouse-derived Tm-1 protein | | 6xHis tag fusion Type mouse-derived Tm-2 protein | | 6xHis tag fusion type mouse-derived Tm-4 protein | |
| Eluent | | 1% SDS | 1 mM EDTA | 1% SDS | 1 mM EDTA | 1% SDS | 1 mM EDTA | 1% SDS | 1 mM EDTA |
| Lane numbers in FIG. 16 | | 1 | 2 | 3 | 4 | 5 | 6 | 7 | 8 |

<Results>

The results of Western blotting obtained are shown in FIG. 16. In FIG. 16, each lane shows the following result.

Lane 1: Results of Comparative Example 16 (the results of the case of using the carrier in which the anti-6xHis antibody was bound on the Dynabeads protein G, and using the 1% SDS aqueous solution as the eluent);

Lane 2: Results of Comparative Example 17 (the results of the case of using the carrier in which the anti-6xHis antibody was bound to the Dynabeads protein G, and using the TBS solution containing 1 mM EDTA as the eluent);

Lane 3: Results of Example 80 (the results of the case of using the carrier in which the 6xHis tag fusion type mTim-1 protein was bound on the Dynabeads protein G via the anti-6xHis antibody, and using the 1% SDS aqueous solution as the eluent);

Lane 4: Results of Example 81 (the results of the case of using the carrier in which the 6xHis tag fusion type mTim-1 protein was bound on the Dynabeads protein G via the anti-6xHis antibody, and using the TBS solution containing 1 mM EDTA as the eluent);

Lane 5: Results of Comparative Example 18 (the results of the case of using the carrier in which the 6xHis tag fusion type mTim-2 protein was bound on the Dynabeads protein G via the anti-6xHis antibody, and using the 1% SDS aqueous solution as the eluent);

Lane 6: Results of Comparative Example 19 (the results of the case of using the carrier in which the 6xHis tag fusion type mTim-2 protein was bound on the Dynabeads protein G via the anti-6xHis antibody, and using the TBS solution containing 1 mM EDTA as the eluent);

Lane 7: Results of Example 82 (the results of the case of using the carrier in which the 6xHis tag fusion type mTim-4 protein was bound on the Dynabeads protein G via the anti-6xHis antibody, and using the 1% SDS aqueous solution as the eluent);

Lane 8: Result of Example 83 (the results of the case of using the carrier in which the 6xHis tag fusion type mTim-4 protein was bound on the Dynabeads protein G via the anti-6xHis antibody, and using the TBS solution containing 1 mM EDTA as the eluent).

From FIG. 16, in the case of binding the 6xHis tag fusion type Tim-2 protein, a band of Lamp-1, which is a marker protein of exosome, was not observed in any of the elution methods (lanes 5 to 6). On the other hand, in the case of the carrier on which the 6xHis tag fusion type Tim-1 protein or the 6xHis tag fusion type Tim-4 protein was bound, the band of anti-Lamp-1, which is a marker protein of exosome, was observed in any of the elution methods (lanes 3 to 4, lanes 7 to 8). From these results, it has been revealed that the extracellular membrane vesicles cannot be obtained, using the carrier on which the Tim-2 protein was immobilized.

In addition, it has been revealed that, when eluting by SDS, more extracellular membrane vesicles can be obtained in the order of the carrier on which the Tim-4 protein is bound>carrier on which the Tim-1 protein is bound.

Examples 84 to 95, Comparative Examples 20 to 21. Obtaining of Viruses by Carrier on which Tim Protein is Immobilized As described below, obtaining of the viruses pertaining to the present invention was carried out using the carrier on which the Tim-1 protein, the Tim-3 protein, or the Tim-4 protein, as Tim protein, was each immobilized on the beads.

<(1) Preparation of Co-Transfection Cell Culture Supernatant>

A PSFM-J1 medium (produced by Wako Pure Chemical Industries, Ltd.) containing about 2 µg of mouse IL23 expression vector DNA, 90 ng of Linear AcNPV DNA, and 3 µL of TransiT-Insect (produced by Mirus Bio LLC) was added to $1.0 \times 10^6$ cells of Sf9 cell seeded in a 25 cm² flask. After culturing for 7 days at 28° C., the culture supernatant (co-transfection solution) was recovered.

<(2) Preparation of Baculovirus-Containing Insect Cell Culture Supernatant Sample>

Sf9 cells diluted with the PSFM-J 1 medium, so as to attain $1.5 \times 10^6$ cells/mL (50 mL), were prepared. The co-transfection solution of 1/200 volume of the culture solution was added thereto, and cultured at 27° C. under shaking at 130 rpm. After 72 hours, the cell culture solution was recovered, and subjected to centrifugal separation at 3,000× G, for 30 minutes at 4° C., to fractionate into precipitate and supernatant. The resulting supernatant was used as a recombinant baculovirus solution expressing mouse IL-23 (hereinafter it may be abbreviated as "the baculovirus solution", in some cases).

In addition, $CaCl_2$ was added to the resulting baculovirus solution, so as to attain the final concentration of 2 mM to obtain the baculovirus solution containing 2 mM $CaCl_2$ (hereinafter it may be abbreviated as "the calcium ion-containing baculovirus solution", in some cases).

<(3) Washing of Beads>

Washing of the beads was carried out by the same method as in "(2) Washing of beads" of Examples 56 to 67 and Comparative Examples 14 to 15.

<(4) Immobilization of Fc Tag Fusion Type Tim Protein on Beads>

As shown in the following Table 28, 6 types of the Tim protein-bound carriers were obtained by the same method as in "(3) Immobilization of Fc tag fusion type Tim protein on beads" of Examples 56 to 67 and Comparative Examples 14 to 15.

TABLE 28

| | 1 | 2 | 3 | 4 | 5 | 6 |
|---|---|---|---|---|---|---|
| Tim protein-bound carrier | Carrier | Dynabeads Protein G beads | | | | |
| | Fc tag fusion type Tim protein | Human-derived Tim-1 | Mouse-derived Tim-1 | Human-derived Tim-3 | Mouse-derived Tim-3 | Human-derived Tim-4 | Mouse-derived Tim-4 |

<(5) Obtaining of Baculovirus by Method of the Present Invention>

Each eluate was obtained by carrying out similarly as in "(4) Obtaining of extracellular membrane vesicles by method of the present invention" in Examples 56 to 67 and Comparative Examples 14 to 15, except for using "1 mL of the calcium ion-containing baculovirus solution prepared in the (2)", instead of "1 mL of the calcium ion-containing culture supernatant".

<(6) Western Blotting>

Western blotting was carried out by the same method as in "(5) Western blotting" of Examples 56 to 67 and Comparative Examples 14 to 15, except for using "the anti-baculovirus gp64 antibody (produced by Novus Biologicals LLC), diluted 500-fold with TBS-T", instead of "2 mL of the anti-human Lamp-1 antibody, or diluted 250-fold with TBS-T (produced by BD Biosciences), and 2 mL of the 250-fold diluted anti-human Flotillin-2 antibody (produced by BD Biosciences)".

It should be noted that the types of Tim proteins, carrier, and the eluents used for obtaining the extracellular membrane vesicles from the Tim protein-bound (non-bound) carrier, used in each Example and Comparative Example, and the lane numbers in Western blotting are shown in the following Table 29.

Lane 5: Results of Example 86 (the results of the case of using the carrier in which the mTim-1 protein was bound on the Dynabeads protein G, and using the 1% SDS aqueous solution as the eluent);

Lane 6: Results of Example 87 (the results of the case of using the carrier in which the mTim-1 protein was bound on the Dynabeads protein G, and using the TBS solution containing 1 mM EDTA as the eluent);

Lane 7: Results of Example 88 (the results of the case of using the carrier in which the hTim-3 protein was bound on the Dynabeads protein G, and using the 1% SDS aqueous solution as the eluent);

Lane 8: Results of Example 89 (the results of the case of using the carrier in which the hTim-3 protein was bound on the Dynabeads protein G, and using the TBS solution containing 1 mM EDTA as the eluent);

Lane 9: Results of Example 90 (the results of the case of using the carrier in which the mTim-3 protein was bound on the Dynabeads protein G, and using the 1% SDS aqueous solution as the eluent);

Lane 10: Results of Example 91 (the results of the case of using the carrier in which the mTim-3 protein was bound on

TABLE 29

Figure 17:
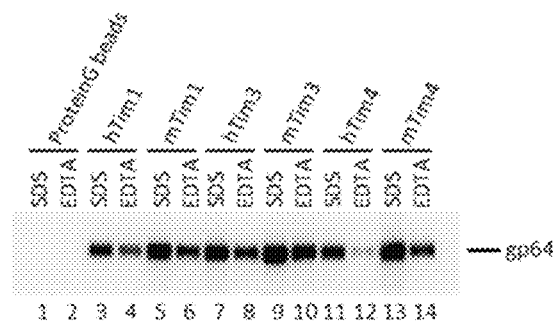
FIG. 17 is an electropherogram for confirming whether the extracellular membrane vesicles were obtained or not, by Western blotting, in Examples 84 to 95, and Comparative Examples 20 to 21.

| | | Comparative Example | | Example | | | | | | | | | | | | |
|---|---|---|---|---|---|---|---|---|---|---|---|---|---|---|---|---|
| | | 20 | 21 | 84 | 85 | 86 | 87 | 88 | 89 | 90 | 91 | 92 | 93 | 94 | 95 |
| Tim protein-(non-)bound carrier | Carrier | — | | Dynabeads Protein G beads | | | | | | | | | | | |
| | Fc tag fusion type Tim protein | | | Human-Derived Tim-1 (hTim-1) | | Mouse-derived Tim-1 (mTim-1) | | Human-Derived Tim-3 (hTim-3) | | Mouse-derived Tim-3 (mTim-3) | | Human-Derived Tim-4 (hTim-4) | | Mouse-derived Tim-4 (mTim-4) | |
| | Eluent | 1% SDS | 1 mM EDTA | 1% SDS | 1 mM EDTA | 1% SDS | 1 mM EDTA | 1% SDS | 1 mM EDTA | 1% SDS | 1 mM EDTA | 1% SDS | 1 mM EDTA | 1% SDS | 1 mM EDTA |
| | Lane numbers in FIG. 17 | 1 | 2 | 3 | 4 | 5 | 6 | 7 | 8 | 9 | 10 | 11 | 12 | 13 | 14 |

<Results>

The results of Western blotting obtained are shown in FIG. 17. In FIG. 17, each lane shows the following result.

Lane 1: Results of Comparative Example 20 (the results of the case where only the magnetic beads carrier of the Dynabeads protein G was used, and the 1% SDS aqueous solution was used as the eluent);

Lane 2: Results of Comparative Example 21 (the results of the case where only the magnetic beads carrier of the Dynabeads protein G was used, and the TBS solution containing 1 mM EDTA was used as the eluent);

Lane 3: Results of Example 84 (the results of the case of using the carrier in which the hTim-1 protein was bound on the Dynabeads protein G, and using the 1% SDS aqueous solution as the eluent);

Lane 4: Results of Example 85 (the results of the case of using the carrier in which the hTim-1 protein was bound on the Dynabeads protein G, and using the TBS solution containing 1 mM EDTA as the eluent);

Lane 11: Results of Example 92 (the results of the case of using the carrier in which the hTim-4 protein was bound on the Dynabeads protein G, and using the 1% SDS aqueous solution as the eluent);

Lane 12: Results of Example 93 (the results of the case of using the carrier in which the hTim-4 protein was bound to the Dynabeads protein G, and using the TBS solution containing 1 mM EDTA as the eluent);

Lane 13: Results of Example 94 (the results of the case of using the carrier in which the mTim-4 protein was bound on the Dynabeads protein G, and using the 1% SDS aqueous solution as the eluent);

Lane 14: Results of Example 95 (the results of the case of using the carrier in which the mTim-4 protein was bound on the Dynabeads protein G, and using the TBS solution containing 1 mM EDTA as the eluent).

From FIG. 17, it has been revealed that the baculovirus can be obtained by using the carrier on which the Tim-1 protein, the Tim-3 protein or the Tim-4 protein is bound (the Tim protein-bound carrier), regardless of the origin of the Tim protein and the elution method, from the fact that a band of baculovirus marker protein gp64 was observed in the lanes 3 to 14.

In addition, it has been revealed that, when eluting by SDS, more viruses can be obtained in the order of the carrier on which the Tim3 protein is bound and the carrier on which the Tim-4 protein is bound in the same level, next the carrier on which the Tim-1 protein is bound.

It has been revealed that, when eluting using the calcium ion chelating agent, more viruses can be obtained in the order of the carrier on which the Tim-3 protein is bound, followed by the carrier on which the Tim-1 protein is bound, and the carrier to which the Tim-4 protein is bound.

dispensed into four 1.5 mL tubes (produced by BM Equipment Co., Ltd.), and each was subjected to the washing operation.

<(4) Immobilization of 6×His Tag Fusion Type Tim Family Protein on Beads>

The carrier on which the 6×His tag fusion type mTim-1 protein is bound, the carrier on which the 6×His tag fusion type mTim-2 protein is bound, and the carrier on which the 6×His tag fusion type mTim-4 protein is bound were each obtained by carrying out similarly as in "(3) Immobilization of 6×His tag fusion type Tim family protein on beads" of Examples 80 to 83 and Comparative Examples 16 to 19.

The types of the Tim family proteins, the carrier and the Tim family protein-(non-)bound carrier, used in each Example, are shown in the following Table 30.

TABLE 30

| | | Comparative Example 22 | Comparative Example 23 | Example 96 | Example 97 | Comparative Example 24 | Comparative Example 25 | Example 98 | Example 99 |
|---|---|---|---|---|---|---|---|---|---|
| Tim family protein-bound carrier | Carrier | | | Anti-6×His tag antibody-bound Dynabeads Protein G carrier | | | | | |
| | Tim family protein | — | — | 6×His tag fusion type mouse-derived Tim-1 protein | 6×His tag fusion Type mouse-derived Tim-2 protein | | | 6×His tag fusion type mouse-derived Tim-4 protein | |

Examples 96 to 99, Comparative Examples 22-25. Obtaining of Viruses by Carrier on which Tim Family Protein is Immobilized As described below, obtaining of the viruses pertaining to the present invention was carried out using the carrier in which each of the Tim-1 protein, the Tim-2 protein, or the Tim-4 protein, as the Tim family protein, was immobilized on the beads.

<(1) Preparation of Co-Transfection Cell Culture Supernatant>

Preparation of the co-transfected cell culture supernatant was carried out similarly as in "(1) Preparation of co-transfection cell culture supernatant" of Examples 84 to 95 and Comparative Examples 20 to 21.

<(2) Preparation of Calcium Ion-Containing and Baculovirus-Containing Insect Cell Culture Supernatant Sample>

The calcium ion-containing baculovirus solution was obtained by the same method as in "(2) Preparation of baculovirus-containing insect cell culture supernatant sample" of Examples 84 to 95 and Comparative Examples 20 to 21.

<(3) Washing of Beads>

The PBS-T solution (20 μL) containing the 30 μg/μL Dynabeads Protein G (produced by Thermo Fisher Scientific Inc.) (containing 4.8 mg of the Dynabeads Protein G) was <(5) Obtaining of Baculovirus by Obtaining Method of the Present Invention>

An eluate was obtained by carrying out the same method as in "(4) Obtaining of extracellular membrane vesicles by obtaining method of the present invention" of Examples 80 to 83 and Comparative Examples 16 to 19, except for using "200 μL of the calcium ion-containing baculovirus solution" prepared in the (2), instead of "200 μL of the calcium ion-containing cell culture supernatant sample".

<(6) Western Blotting>

Western blotting was carried out by the same method as in "(5) Western blotting" in Examples 80 to 83 and Comparative Examples 16 to 19, except for "adding 1 μL of the 4× sample buffer (produced by Wako Pure Chemical Industries, Ltd.) to 3 μL of the resulting each eluate obtained by the (5) Obtaining of baculovirus by obtaining method of the present invention", instead of "3.75 μL of the 4× sample buffer (produced by Wako Pure Chemical Industries, Ltd.) to 11.25 μL of the resulting each eluate", using "4 μL of each sample for Western blotting", instead of "15 μL of each sample for Western blotting", and using "the anti-baculovirus gp64 antibody" instead of "the anti-Lamp-1 antibody".

It should be noted that the types of Tim family proteins, carrier and the eluents used to obtain the extracellular membrane vesicles from the Tim family protein-(non-) bound carriers, used in each Example, and the lane numbers in Western blotting are shown in the following Table 31.

TABLE 31

| | | Comparative Example 22 | Comparative Example 23 | Example 96 | Example 97 | Comparative Example 24 | Comparative Example 25 | Example 98 | Example 99 |
|---|---|---|---|---|---|---|---|---|---|
| Tim family protein-bound carrier | Carrier | | | Anti-6×His tag antibody-bound Dynabeads Protein G carrier | | | | | |
| | Tim protein | — | — | 6×His tag fusion type mouse-derived Tim-1 protein | 6×His tag fusion Type mouse-derived Tim-2 protein | | | 6×His tag fusion type mouse-derived Tim-4 protein | |

TABLE 31-continued

Figure 18:
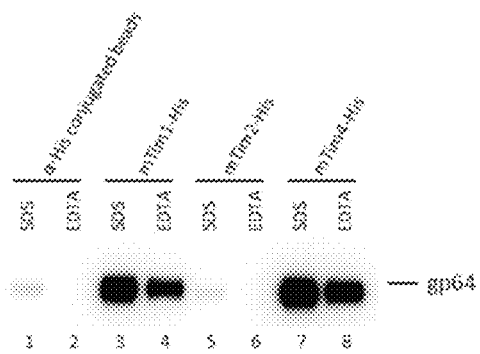
FIG. 18 is an electropherogram for confirming whether the extracellular membrane vesicles were obtained or not, by Western blotting, in Examples 96 to 99, and Comparative Examples 22 to 25.

|  | Comparative Example 22 | Comparative Example 23 | Example 96 | Example 97 | Comparative Example 24 | Comparative Example 25 | Example 98 | Example 99 |
|---|---|---|---|---|---|---|---|---|
| Eluent | 1% SDS | 1 mM EDTA | 1% SDS | 1 mM EDTA | 1% SDS | 1 mM EDTA | 1% SDS | 1 mM EDTA |
| Lane numbers in FIG. 18 | 1 | 2 | 3 | 4 | 5 | 6 | 7 | 8 |

<Results>

The results of Western blotting obtained are shown in FIG. 18. In FIG. 18, each lane shows the following result.

Lane 1: Results of Comparative Example 22 (the results of the case of using the carrier in which the anti-6×His tag antibody was bound on the Dynabeads protein G, and using the 1% SDS aqueous solution as the eluent);

Lane 2: Results of Comparative Example 23 (the results of the case of using the carrier in which the anti-6×His tag antibody was bound on the Dynabeads protein G, and using the TBS solution containing 1 mM EDTA as the eluent);

Lane 3: Results of Example 96 (the results of the case of using a carrier in which the 6×His tag fusion type mTim-1 protein was bound on the Dynabeads protein G via the anti-6×His tag antibody, and using the 1% SDS aqueous solution as the eluent);

Lane 4: Result of Example 97 (the results of the case of using the carrier in which the 6×His tag fusion type mTim-1 protein was bound on the Dynabeads protein G via the anti-6×His tag antibody, and using the TBS solution containing 1 mM EDTA as the eluent);

Lane 5: Result of Comparative Example 24 (the results of the case of using the carrier in which the 6×His tag fusion type mTim-2 protein was bound on the Dynabeads protein G via the anti-6×His tag antibody, and using the 1% SDS aqueous solution as the eluent);

Lane 6: the result of Comparative Example 25 (the results of the case of using the carrier in which the 6×His tag fusion type mTim-2 protein was bound on the Dynabeads protein G via the anti-6×His tag antibody, and using the TBS solution containing 1 mM EDTA as the eluent);

Lane 7: Results of Example 98 (the results of the case of using the carrier in which the 6×His tag fusion type mTim-4 protein was bound on the Dynabeads protein G via the anti-6×His tag antibody, and using the 1% SDS aqueous solution as the eluent);

Lane 8: Results of Example 99 (the results of the case of using the carrier in which the 6×His tag fusion type mTim-4 protein was bound on the Dynabeads protein G via the anti-6×His tag antibody, and using the TBS solution containing 1 mM EDTA as the eluent).

From FIG. 18, when the Tim-2 protein was bound, no gp64 band of baculovirus marker protein was observed by any of the elution methods (lanes 5 to 6). On the other hand, the gp64 band was observed in any of the elution methods for the carrier on which the Tim-1 protein or the Tim-4 protein was bound (lanes 3 to 4, lanes 7 to 8).

From this result, it has been revealed that it was impossible to obtain the baculovirus with the carrier on which the Tim-2 protein was immobilized.

Examples 100 to 105, Comparative Examples 26 to 33. Comparison of Sensitivity in Detection of Extracellular Membrane Vesicles by ELISA Using PS Protein As described below, the extracellular membrane vesicles derived from the K562 cell culture supernatant was detected by carrying out sandwich ELISA using a plate (well) on which an antibody against the PS protein or an exosome surface marker protein (hereinafter it may be abbreviated as "the marker protein", in some cases) is immobilized, and using the HRP-labeled anti-CD63 antibody, as a detection antibody.

<(1) Preparation of Culture Supernatant (Stock Solution)>

The human chronic myelogenous leukemia cell strain K562, $1×10^7$ cells, secreting the extracellular membrane vesicles, was cultured using 80 mL of the X-VIVO 15 medium (produced by Lonza AG) for 3 days under condition at 37° C. and 5% $CO_2$. Then the cells were precipitated by centrifugal separation treatment (300×G, for 5 minutes) to remove the supernatant. The precipitated cells were suspended in 60 mL of the X-VIVO 15 medium containing 10 μM monensin sodium (produced by MP Biomedicals Co., Ltd) and cultured for 24 hours under condition at 37° C. and 5% $CO_2$.

Thereafter, the culture solution was subjected to centrifugal separation treatment (300×G, for 5 minutes) to recover the culture supernatant. The recovered culture supernatant (60 mL) was further subjected to centrifugal separation treatment three times (the first time: 300×G, for 3 minutes, the second time: 1,200×G, for 20 minutes, the third time: 10,000×G, for 20 minutes) to separate impurities and obtain a supernatant (hereinafter it may be abbreviated as "the culture supernatant (stock solution)", in some cases).

<(2) Preparation of Dilution Series of Ultracentrifugation Precipitate Fraction of Calcium Ion-Containing K562 Cell Culture Supernatant>

The resulting culture supernatant stock solution (10 mL) in the (1) was subjected to centrifugal separation treatment (10,000×G, for 20 minutes) to separate impurities, and the supernatant was transferred to a new tube to obtain 10 mL of a centrifugal separation treated K562 cell culture supernatant. Next, 10 mL of the resulting centrifugal separation treated K562 cell culture supernatant was subjected to ultracentrifugal separation treatment (110,000×G, for 70 minutes), the supernatant was removed, and then 10 mL of TBS was added to the precipitate and suspended. The suspension was subjected to ultracentrifugal separation treatment (110,000×G, for 70 minutes), supernatant was removed, and then 200 μL of TBS was added to the precipitate, and suspended to obtain an ultracentrifugation precipitate fraction of K562 cell culture supernatant. Protein concentration of the ultracentrifugation precipitate fraction of K562 cell culture supernatant was measured using a Protein Assay BCA Kit (produced by Wako Pure Chemical Industries, Ltd.), according to a protocol attached to the kit. The dilution series of the ultracentrifugation precipitate fraction of the calcium ion-containing K562 cell culture supernatant was prepared by dilution with TBS containing 2 mM $CaCl_2$, so as to attain a protein concentration of each 125, 250, 500, 1000, and 2000 ng/mL.

<(3) Preparation of HRP-Labeled Anti-CD63 Mouse Monoclonal Antibody>

The anti-CD63 mouse monoclonal antibody H5C6 (100 μL, 50 μg) (produced by BD Biosciences) was labeled with HRP using a Peroxidase Labeling Kit-NH$_2$ (manufactured by Dojindo Molecular Technologies, Inc.), according to a protocol attached to the kit to obtain 200 μL of the HRP-labeled anti-CD63 mouse monoclonal antibody. Glycerol (200 μL) was added to and mixed with the resulting labeled antibody, and stored at −20° C. as the HRP-labeled anti-CD63 mouse monoclonal antibody stock solution. The HRP-labeled anti-CD63 mouse monoclonal antibody stock solution was diluted 2,000-fold with the 2 mM CaCl$_2$-containing TBS to prepare a diluted solution of the HRP-labeled anti-CD63 mouse monoclonal antibody.

<(4) Preparation of Immobilizing Solutions of PS Protein and Anti-Marker Protein Antibody>

Immobilizing solutions of various PS proteins and the anti-marker protein antibodies were prepared as follows. The anti-CD9 mouse monoclonal antibody M-L 13 (16 μL, 8 μg) (produced by BD Biosciences) and 784 μL of a 50 mM MOPS (pH 7.5) solution were mixed to prepare 800 μL of the anti-CD9 antibody immobilizing solution. The anti-CD 63 mouse monoclonal antibody H5C6 (16 μL, 8 μg) (produced by BD Biosciences) and 784 μL of the 50 mM MOPS (pH 7.5) solution were mixed to prepare 800 μL of the anti-CD 63 antibody immobilizing solution. The anti-CD81 mouse monoclonal antibody JS-81 (16 μL, 8 μg) (produced by BD Biosciences) and 784 μL of the 50 mM MOPS (pH 7.5) solution were mixed to prepare 800 μL of the anti-CD81 antibody immobilizing solution. The His tag fusion type mouse MFG-E8 protein (80 μL, 8 μg) (produced by R & D Systems Inc.) and 720 μL of the 50 mM MOPS (pH 7.5) solution were mixed to prepare 800 μL of the mMFG-E8 immobilizing solution. The His tag fusion type human MFG-E8 protein (80 μL, 8 μg) (produced by R & D Systems Inc.) and 720 μL of the 50 mM MOPS (pH 7.5) solution were mixed to prepare 800 μL of the hMFG-E8 immobilizing solution. The His tag fusion type human Annexin V protein (40 μL, 8 μg) (produced by Creative BioMart) and 760 μL of the 50 mM MOPS (pH 7.5) solution were mixed to prepare 800 μL of the hAnnexin V immobilizing solution. The Fc tag fusion type mouse Tim-1 protein (32 μL, 8 μg) (produced by Wako Pure Chemical Industries, Ltd.) and 768 μL of the 50 mM MOPS (pH 7.5) solution were mixed to prepare 800 μL of the mTim-1 immobilizing solution. The His tag fusion type mouse Tim-2 protein (80 μL, 8 μg) (produced by R & D Systems Inc.) and 720 μL of the 50 mM MOPS (pH 7.5) solution were mixed to prepare 800 μL of the mTim-2 immobilizing solution. The Fc tag fusion type mouse Tim-3 protein (32 μL, 8 μg) (produced by Wako Pure Chemical Industries, Ltd.) and 768 μL of the 50 mM MOPS (pH 7.5) solution were mixed to prepare 800 μL of the mTim-3 immobilizing solution. The Fc tag fusion type mTim-4 protein (32 μL, 8 μg) (produced by Wako Pure Chemical Industries, Ltd.) and 768 μL of the 50 mM MOPS (pH 7.5) solution were mixed to prepare 800 μL of the mTim-4 immobilizing solution. The Fc tag fusion type human Tim-1 protein (32 μL, 8 μg) (produced by Wako Pure Chemical Industries, Ltd.) and 768 μL of the 50 mM MOPS (pH 7.5) solution were mixed to prepare 800 μL of the hTim-1 immobilizing solution. The Fc tag fusion type human Tim-3 protein (32 μL, 8 μg) (produced by Wako Pure Chemical Industries, Ltd.) and 768 μL of the 50 mM MOPS (pH 7.5) solution were mixed to prepare 800 μL of the hTim-3 immobilizing solution. The Fc tag fusion type human Tim-4 protein (32 μL, 8 μg) (produced by Wako Pure Chemical Industries, Ltd.) and 768 μL of the 50 mM MOPS (pH 7.5) solution were mixed to prepare 800 μL of the hTim-4 immobilizing solution.

<(5) ELISA Measurement>

The PS protein immobilizing solution or the anti-marker protein antibody immobilizing solution was dispensed into six wells, by 100 μL per well for one type of a protein, to an Immuno-plate Maxisorp C96 (manufactured by Nunc A/S), and allowed to stand at 8° C. overnight. After removing the dispensed solution, a blocking solution (TBS containing 25% Block Ace) was added to each well in each amount of 300 μL, and subjected to a reaction at room temperature for 1 hour, while mixing at 500 rpm using a plate mixer. After the blocking solution was removed, for the wells on which the resulting PS protein or anti-marker protein antibody was immobilized, each 100 μL of the dilution series of the calcium ion-containing K562 cell culture supernatant ultracentrifugation precipitate fraction, having each a protein concentration of 125, 250, 500, 1000, or 2000 ng/mL, was added to each of 5 wells, and 100 μL of TBS containing 2 mM CaCl$_2$ was each added, as a blank, to 1 well, and the mixture was subjected to a reaction at room temperature for 1 hour, while mixing at 500 rpm using the plate mixer. After washing three times with 300 μL of TBS-T containing 2 mM CaCl$_2$, 100 μL of the diluted HRP-labeled anti-CD63 mouse monoclonal antibody solution was added to each well, and the mixture was subjected to a reaction at room temperature for 1 hour, while mixing at 500 rpm using the plate mixer. After washing five times with 300 μL of TBS-T containing 2 mM CaCl$_2$, 100 μL of the TMB solution (produced by Wako Pure Chemical Industries, Ltd.) was added to each well, and subjected to a standing reaction at room temperature for 30 minutes. After stopping the reaction by the addition of 100 μL of 1 M HCl, absorbance at 450 nm was measured with a microplate reader Tecan Ultra (produced by Tecan Ltd.).

It should be noted that the proteins immobilized on the plate and possibility of detection (results), in each Example and Comparative Example, are shown in the following Table 32.

TABLE 32

Figure 19:
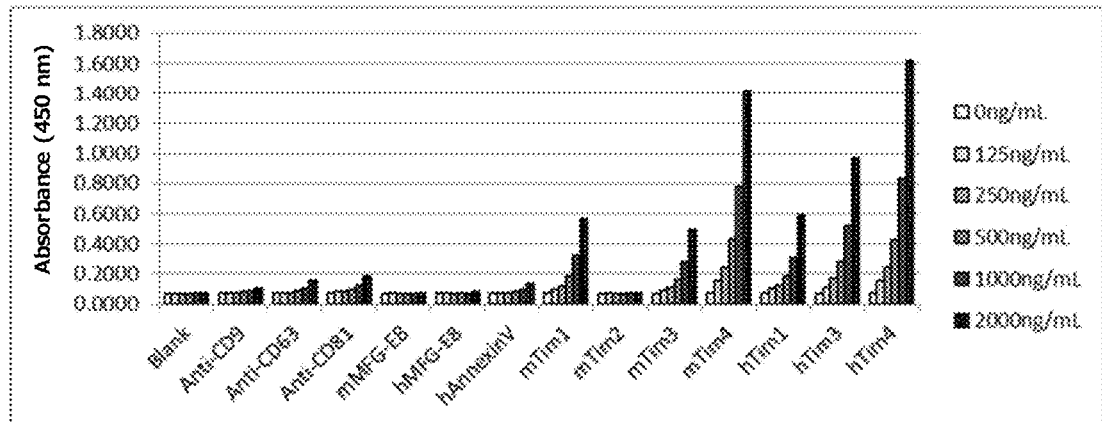
FIG. 19 is detection result of the extracellular membrane vesicles by an ELISA method, in Examples 100 to 105, and Comparative Examples 26 to 33.

|  | Comparative Example 26 | Comparative Example 27 | Comparative Example 28 | Comparative Example 29 | Comparative Example 30 | Comparative Example 31 | Comparative Example 32 |
|---|---|---|---|---|---|---|---|
| Protein immobilized on a plate | — | Anti-CD9 | Anti-CD63 | Anti-CD81 | His tag fusion type mouse-derived MFG-E8 | His tag fusion type human-derived MFG-E8 | His tag fusion type human-derived hAnnexin V |
| Capability of detection | X | Δ | Δ | Δ | Δ | Δ | Δ |
| Name of lanes in FIG. 19 | Blank | Anti-CD9 | Anti-CD63 | Anti-CD81 | mMFG-E8 | hMFG-E8 | hAnnexin V |

TABLE 32-continued

|  | Example 100 | Comparative Example 33 | Example 101 | Example 102 | Example 103 | Example 104 | Example 105 |
| --- | --- | --- | --- | --- | --- | --- | --- |
| Protein immobilized on a plate | Fc tag fusion type mouse-derived Tim-1 protein | Fc tag fusion type mouse-derived Tim-2 protein | Fc tag fusion type mouse-derived Tim-3 protein | Fc tag fusion type mouse-derived Tim-4 protein | Fc tag fusion type human-derived Tim-1 protein | Fc tag fusion type human-derived Tim-3 protein | Fc tag fusion type human-derived Tim-4 protein |
| Capability of detection | ○ | Δ | ○ | ◎ | ○ | ○ | ◎ |
| Name of lanes in FIG. 19 | mTim-1 | mTim-2 | mTim-3 | mTim-4 | hTim-1 | hTim-3 | hTim-4 |

<Results>

The results of the ELISA measurement obtained are shown in FIG. 19. FIG. 19 shows each of detection signals (absorbance at 450 nm) derived from the HRP-labeled anti-CD63 mouse monoclonal antibody bound to exosomes contained in each protein concentration dilution series of the calcium ion-containing K562 cell culture supernatant ultracentrifugation precipitate fraction in the wells on which the PS protein or the anti-marker protein antibody was immobilized. The horizontal axis shows the type of the PS protein or the anti-marker protein antibody immobilized on the well, and in the detection results for the wells on which the same PS protein or the like was immobilized, protein concentration in the calcium ion-containing K562 cell culture supernatant ultracentrifugation precipitate fraction used is 0, 125, 250, 500, 1000, 2000 ng/mL in the order from the left. In addition, the vertical axis shows the detection signal derived from the HRP-labeled anti-CD63 mouse monoclonal antibody bound to the exosome contained in each protein concentration dilution series of the K562 cell culture supernatant ultracentrifugation precipitate fraction.

In the wells, on which each of the Tim-1 protein, the Tim-3 protein, or the Tim-4 protein was immobilized, the extracellular membrane vesicles are detectable in higher sensitivity (Examples 100 to 105), as compared with the wells on which the anti-CD9 antibody, the anti-CD63 antibody or the anti-CD81 antibody, which is the anti-marker protein antibody, was each immobilized, the wells on which the MFG-E8 or the Annexin V, which is a PS protein, was each immobilized, and the well on which the Tim-2 protein, which is the Tim family protein, was immobilized (Comparative Examples 27 to 33). That is, it has been revealed that the detection method of the present invention, using the Tim protein pertaining to the present invention, is capable of detecting the extracellular membrane vesicles in higher sensitivity, as compared with the conventional methods. In particular, it has been revealed that the extracellular membrane vesicles can be detected in particularly high sensitivity by using the Tim-4 protein among the Tim proteins.

Examples 106 to 109. Comparison of Sensitivity in Detection of Extracellular Membrane Vesicles by ELISA by Difference in Tim Protein Immobilization Method As described below, detection sensitivity of the extracellular membrane vesicles was compared in the case where the Tim-1 protein or the Tim-4 protein was each immobilized directly on a plate, with the case where the SH-group biotin-labeled Tim-1 protein or the SH-group biotin-labeled Tim-4 protein was each immobilized on the plate via streptavidin.

<(1) Preparation of Ultracentrifugation Precipitate Fractions of K562 Cell Culture Supernatant>

The dilution series of the ultracentrifugation precipitate fractions of the calcium ion-containing K562 cell culture supernatant was prepared by the same method as in "(2) Preparation of ultracentrifugation precipitate fraction of calcium ion-containing K562 cell culture supernatant" of Examples 100 to 105 and Comparative Examples 26 to 33, except for "diluting the ultracentrifugation precipitate fraction of the calcium ion-containing K562 cell culture supernatant with TBS containing 2 mM $CaCl_2$, so as to attain a protein concentration of each 500, 1000 ng/mL", instead of "diluting the ultracentrifugation precipitate fraction of the calcium ion-containing K562 cell culture supernatant with TBS containing 2 mM $CaCl_2$, so as to attain a protein concentration of each 125, 250, 500, 1000, 2000 ng/m L".

<(2) Preparation of HRP-Labeled Anti-CD63 Mouse Monoclonal Antibody>

The diluted solution of the HRP-labeled anti-CD63 mouse monoclonal antibody was prepared by the same method as in "(3) Preparation of HRP-labeled anti-CD63 mouse monoclonal antibody" of Examples 100 to 105 and Comparative Examples 26 to 33.

<(3) Preparation of Biotin-Labeling and Immobilizing Solution of Tim-1 Protein and Tim-4 Protein>

The Fc tag fusion type mouse-derived Tim-1 protein 40 µL, (10 µg) (produced by Wako Pure Chemical Industries, Ltd.), and 40 µL (10 µg) of the Fc tag fusion type mouse-derived Tim-4 protein (produced by Wako Pure Chemical Industries Ltd.) were each labeled with biotin using the Biotin Labeling Kit-SH (produced by Dojindo Molecular Technologies, Inc.), according to a protocol attached to the kit to obtain the SH-group biotin-labeled Fc tag fusion type mTim-1 protein, and the SH-group biotin-labeled Fc tag fusion type mTim-4. Protein concentrations of the SH-group biotin-labeled Fc tag fusion type mTim-1 protein, and the SH-group biotin-labeled Fc tag fusion type mTim-4 protein were each measured using the Protein Assay BCA Kit (produced by Wako Pure Chemical Industries, Ltd.), according to a protocol attached to the kit. The SH-group biotin-labeled Fc tag fusion type mTim-1 protein solution and the SH-group biotin-labeled Fc tag fusion type mTim-4 protein solution were each prepared by diluting these with TBS, so as to attain a protein concentration of 5 µg/mL.

The Fc tag fusion type mouse-derived Tim-1 protein (produced by Wako Pure Chemical Industries, Ltd.), or the Fc tag fusion type mouse-derived Tim-4 protein (8 µL, (2 µg) (produced by Wako Pure Chemical Industries Ltd.), and 392 µL of the 50 mM MOPS (pH 7.5) solution were mixed to prepare each of 400 µL of the mTim-1 protein immobilizing solution or the mTim-4 protein immobilizing solution.

In addition, 2 µL (10 µg) of streptavidin (produced by Wako Pure Chemical Industries, Ltd.), and 998 µL of the 50 mM MOPS (pH 7.5) solution were mixed to prepare 1000 µL of the streptavidin immobilizing solution.

<(4) Immobilization>

Each of the protein immobilizing solutions was added to three wells by each 100 µL (0.5 µg) per well of the Immuno-plate Maxisorp C96 (manufactured by Nunc A/S), and the plate was allowed to stand at 8° C. overnight. After removal of the added solution, a blocking solution (TBS containing 25% Block Ace) was added to each well each 300 µL, and the mixture was subjected to a reaction at room temperature for 1 hour, while mixing at 500 rpm using the plate mixer.

In addition, the streptavidin immobilizing solution was added to six wells by each 100 µL (0.5 µg) per well of the Immuno-plate Maxisorp C96 (produced by Nunc A/S), and the plate was allowed to stand at 8° C. overnight. After removal of the added solution, the blocking solution (TBS containing 25% Block Ace) was added to each well each 300 µL, and the mixture was subjected to a reaction at room temperature for 1 hour while mixing at 500 rpm using the plate mixer. After removal of the blocking solution, the SH-group biotin-labeled Fc tag fusion type mTim-1 protein solution and the SH-group biotin-labeled Fc tag fusion type mTim-4 protein solution were added to 3 wells by each 100 µL (0.5 µg) per well, and the mixture was subjected to a reaction at room temperature for 1 hour, while mixing at 500 rpm using the plate mixer.

<(5) ELISA Measurement>

The ELISA measurement was carried out by the same method as in Examples 100 to 105 and Comparable Examples 26 to 33, except for each adding "each 100 µL of the calcium ion-containing dilution series of the ultracentrifugation precipitate fraction of the K562 cell culture supernatant, having a protein concentration of 500 or 1000 ng/mL, to each well of two wells on which each protein was immobilized," instead of each adding "for the wells on which the resulting PS protein or anti-marker protein antibody was immobilized, each 100 µL of the dilution series of the calcium ion-containing K562 cell culture supernatant ultracentrifugation precipitate fraction, having each a protein concentration of 125, 250, 500, 1000, or 2000 ng/mL, was added to each of 5 wells".

It should be noted that the proteins immobilized on the plate, the methods for immobilizing the protein on the plate, and possibility of detection (result), in each Example and Comparative Example, are shown in the following Table 33. Possibility of detection in Table 33 is each comparison between Examples 106 and 107, and between Examples 108 and 109.

Figure 20:
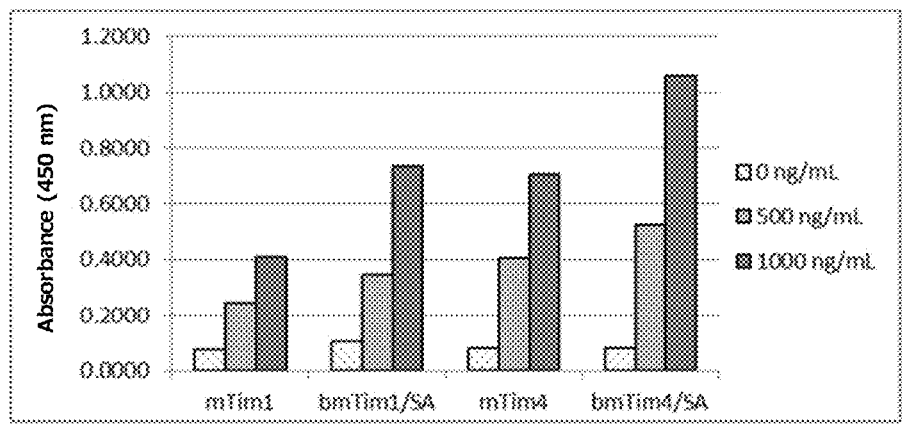
FIG. 20 is detection result of the extracellular membrane vesicles by the ELISA method, in Examples 106 to 109.

The results of the ELISA measurement obtained are shown in FIG. 20. FIG. 20 shows detection signals (absorbance at 450 nm) derived from the HRP-labeled anti-CD63 mouse monoclonal antibody bound to exosomes contained in each protein concentration dilution series of the ultracentrifugation precipitate fraction of the calcium ion-containing K562 cell culture supernatant, in the wells on which the mTim-1 protein was directly immobilized on a plate, the wells on which the mTim-4 protein was directly immobilized on a plate, the wells on which the mTim-1 protein was immobilized by biotin-streptavidin binding, and the wells on which the mTim-4 protein was immobilized by biotin-streptavidin binding.

The horizontal axis shows the type of the Tim proteins immobilized on the well. In addition, the vertical axis shows detection signal derived from the HRP-labeled anti-CD63 mouse monoclonal antibody bound to the exosome contained in each protein concentration dilution series of the ultracentrifugation precipitate fraction of the calcium ion-containing K562 cell culture supernatant.

From FIG. 20, it has been revealed that the extracellular membrane vesicles in the sample can be detected, according to ELISA using the Tim-1 protein or the Tim-4 protein, irrespective of the immobilization method of the Tim protein on the plate (Examples 106 to 109). In particular, the extracellular membrane vesicles can be detected in higher sensitivity in the wells on which the Tim protein was immobilized via streptavidin (Example 107, wherein the plate and the Tim protein were bound by binding of biotin of the SH-group of the mTim-1 and streptavidin, and Example 109, wherein the plate and the Tim protein were bound by binding of biotin of the SH-group of the mTim-4 and streptavidin), as compared with the wells in which the Tim protein was immobilized directly on the plate (Example 106, wherein the mTim-1 was immobilized directly to the plate, and Example 108, wherein the mTim-4 was immobilized directly on the plate).

Therefore, it has been revealed that, as the binding form between the Tim protein and a solid phase, such a case is more preferable where the plate and the Tim protein are bound by binding of biotin of the SH-group of the Tim protein and streptavidin.

Examples 110 to 115. Comparative Example 34 to 39. Comparison of Sensitivity in Detection of Viruses by ELISA Using PS Protein As described below, baculovirus in the baculovirus-containing insect cell culture supernatant sample was detected by carrying out a sandwich ELISA using a plate on which various PS proteins or the antibody against baculovirus surface marker protein gp64 was immobilized, and using the HRP-labeled anti-gp64 antibody as a detection antibody.

TABLE 33

|  | Example 106 | Example 107 | Example 108 | Example 109 |
|---|---|---|---|---|
| Immobilized protein | Fc tag fusion type mouse-derived Tim-1 protein | SH-group biotin-labeled Fc tag fusion type mouse-derived Tim-1 protein | Fc tag fusion type mouse-derived Tim-4 protein | SH-group biotin-labeled Fc tag fusion type mouse-derived Tim-4 protein |
| Immobilization method | Direct immobilization | Biotin-streptavidin binding | Direct immobilization | Biotin-streptavidin binding |
| Possibility of detection | ○ | ◉ | ○ | ◉ |
| Name of lane in FIG. 20 | mTim-1 | bmTim-1/SA | mTim-4 | bmTim-4/SA |

<(1) Preparation of Co-Transfection Cell Culture Supernatant>

Co-transfection cell culture supernatant was prepared by the same method as in "(1) Preparation of co-transfection cell culture supernatant" of Examples 84 to 95 and Comparative Examples 20 to 21.

<(2) Preparation of Calcium Ion-Containing and Baculovirus-Containing Insect Cell Culture Supernatant Sample>

The calcium ion-containing baculovirus solution was obtained similarly as in "(2) Preparation of baculovirus-containing insect cell culture supernatant sample" of Examples 84 to 95 and Comparative Examples 20 to 21.

<(3) Preparation of Dilution Series of Baculovirus-Containing Insect Cell Culture Supernatant Sample>

The baculovirus-containing insect cell culture supernatant sample (50 µL) and 4950 µL of the PSFM-J1 medium were mixed to prepare a 100-fold diluted solution, then 2.0 mL of the 100-fold diluted solution and 2.0 mL of the PSFM-J1 medium were mixed to prepare 4.0 mL of the 200-fold diluted solution, then 2.0 mL of the 200-fold diluted solution and 2.0 mL of the PSFM-J1 medium were mixed to prepare 4.0 mL of a 400-fold diluted solution, and then 2.0 mL of the 400-fold diluted solution and 2.0 mL of the PSFM-J1 medium were mixed to prepare 4.0 mL of a 800-fold diluted solution.

<(4) Preparation of HRP-Labeled Anti-Gp64 Mouse Monoclonal Antibody>

The anti-gp64 mouse monoclonal antibody AcV1 200 µL, (100 µg) (produced by Novus Biologacals LLC) was labeled with HRP using the Peroxidase Labeling Kit-NH$_2$ (produced by Dojindo Molecular Technologies, Inc.), according to a protocol attached to the kit to obtain 200 µL of the HRP-labeled anti-gp64 mouse monoclonal antibody solution. The HRP-labeled anti-gp64 mouse monoclonal antibody solution was diluted 1,000-fold with TBS containing 2 mM CaCl$_2$ to prepare a diluted solution of the HRP-labeled anti-gp64 mouse monoclonal antibody.

<(5) Preparation of Immobilizing Solutions of PS Protein and Anti-Gp64 Antibody>

As described below, the immobilizing solutions of various PS proteins and marker proteins were prepared. The anti-gp64 mouse monoclonal antibody AcV1 (12 µL, 6 µg) (produced by Novus Biologicals LLC) and 588 µL of the 50 mM MOPS (pH 7.5) solution were mixed to prepare 600 µL of the anti-gp64 antibody immobilizing solution. The His tag fusion type mouse-derived MFG-E8 protein (60 µL, 6 µg) (produced by R & D Systems Inc.) and 540 µL of the 50 mM MOPS (pH 7.5) solution were mixed to prepare 600 µL of the mMFG-E8 immobilizing solution. The His tag fusion type human-derived MFG-E8 protein (60 µL, 6 µg) (produced by R & D Systems Inc.) and 540 µL of the 50 mM MOPS (pH 7.5) solution were mixed to prepare 600 µL of the hMFG-E8 immobilizing solution. The His tag fusion type human-derived Annexin V protein (30 µL, 6 µg) (produced by Creative BioMart) and 570 µL of the 50 mM MOPS (pH 7.5) solution were mixed to prepare 600 µL of the hAnnexin V immobilizing solution. The Fc tag fusion type mouse-derived Tim-1 protein (24 µL, 6 µg) (produced by Wako Pure Chemical Industries, Ltd.) and 576 µL of the 50 mM MOPS (pH 7.5) solution were mixed to prepare 600 µL of the mTim-1 immobilizing solution. The His tag fusion type mouse-derived Tim-2 protein (60 µL, 6 µg) (produced by R & D Systems Inc.) and 540 µL of the 50 mM MOPS (pH 7.5) solution were mixed to prepare 600 µL of the mTim-2 immobilizing solution. The Fc tag fusion type mouse-derived Tim-3 protein (24 µL, 6 µg) (produced by Wako Pure Chemical Industries, Ltd.) and 576 µL of the 50 mM MOPS (pH 7.5) solution were mixed to prepare 600 µL of the mTim-3 immobilizing solution. The Fc tag fusion type mouse-derived Tim-4 protein (24 µL, 6 µg) (produced by Wako Pure Chemical Industries, Ltd.) and 576 µL of the 50 mM MOPS (pH 7.5) solution were mixed to prepare 600 µL of mTim-4 immobilizing solution. The Fc tag fusion type human-derived Tim-1 protein (24 µL, 6 µg) (produced by Wako Pure Chemical Industries, Ltd.) and 576 µL of the 50 mM MOPS (pH 7.5) solution were mixed to prepare 600 µL of the hTim-1 immobilizing solution. The Fc tag fusion type human-derived Tim-3 protein (24 µL, 6 µg) (produced by Wako Pure Chemical Industries, Ltd.) and 576 µL of the 50 mM MOPS (pH 7.5) solution were mixed to prepare 600 µL of the hTim-3 immobilizing solution. The Fc tag fusion type human-derived Tim-4 protein (24 µL, 6 µg) (produced by Wako Pure Chemical Industries, Ltd.) and 576 µL of the 50 mM MOPS (pH 7.5) solution were mixed to prepare 600 µL of the hTim-4 immobilizing solution.

<(6) ELISA Measurement>

The PS protein immobilizing solution or anti-gp64 antibody immobilizing solution was dispensed into the Immuno-plate Maxisorp C96 (produced by Nunc A/S), each five wells for one type of a protein, by 100 µL per well, and allowed to stand at 8° C. overnight. After removing the dispensed solution, each 300 µL of a blocking solution (TBS containing 25% Block Ace) was added to each well, and subjected to a reaction at room temperature for 1 hour, while mixing at 500 rpm using the plate mixer. After removal of the blocking solution, for the resulting wells on which the PS protein or the anti-gp64 antibody was immobilized, each 100 µL of the calcium ion-containing and baculovirus-containing insect cell culture supernatant sample dilution series (100-fold diluted, 200-fold diluted, 400-fold diluted, 800-fold diluted) prepared in (3) was added to each well of 4 wells, and 100 µL of the PMSF-J1 medium as a blank was added to 1 well, and the mixture was subjected to a reaction at room temperature for 1 hour, while mixing at 500 rpm using the plate mixer. After washing three times with 300 µL of the 2 mM CaCl$_2$-containing TBS-T, 100 µL of the HRP-labeled anti-gp64 mouse monoclonal antibody diluted solution was added to each well, and the mixture was subjected to a reaction at room temperature for 1 hour, while mixing at 500 rpm using the plate mixer. After washing five times with 300 µL of the 2 mM CaCl$_2$-containing TBS-T, 100 µL of the TMB solution (produced by Wako Pure Chemical Industries, Ltd.) was added to each well, and subjected to a standing reaction at room temperature for 30 minutes. After stopping the reaction by the addition of 100 µL of 1 M HCl, absorbance at 450 nm was measured with the microplate reader Tecan Ultra (produced by Tecan Ltd.).

It should be noted that proteins immobilized on the plate, and possibility of detection (results), in each Example and Comparative Example, are shown in the following Table 34.

TABLE 34

Figure 21:
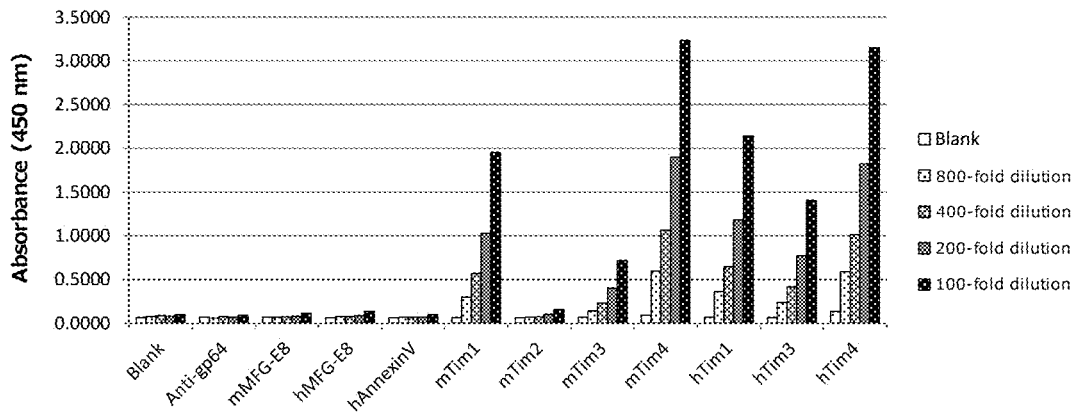
FIG. 21 is detection result of the extracellular membrane vesicles by the ELISA method, in Examples 110 to 115, and Comparative Examples 34 to 39.

|  | Comparative Example 34 | Comparative Example 35 | Comparative Example 36 | Comparative Example 37 | Comparative Example 38 | Example 110 |
|---|---|---|---|---|---|---|
| Protein immobilized on a plate | — | Anti-gp64 antibody | His tag fusion type mouse-derived MFG-E8 | His tag fusion type human-derived MFG-E8 | His tag fusion type human-derived Annexin V | Fc tag fusion type mouse-derived Tim-1 protein |
| Capability of detection | X | Δ | Δ | Δ | Δ | ◯ |
| Name of lanes in FIG. 21 | Blank | Anti-gp64 | mMFG-E8 | hMFG-E8 | hAnnexin V | mTim-1 |

|  | Comparative Example 39 | Example 111 | Example 112 | Example 113 | Example 114 | Example 115 |
|---|---|---|---|---|---|---|
| Protein immobilized on a plate | His tag fusion type mouse-derived Tim-2 protein | Fc tag fusion type mouse-derived Tim-3 protein | Fc tag fusion type mouse-derived Tim-4 protein | Fc tag fusion type human-derived Tim-1 protein | Fc tag fusion type human-derived Tim-3 protein | Fc tag fusion type human-derived Tim-4 protein |
| Capability of detection | Δ | ◯ | ◎ | ◯ | ◯ | ◎ |
| Name of lanes in FIG. 21 | mTim-2 | mTim-3 | mTim-4 | hTim-1 | hTim-3 | hTim-4 |

<Results>

The results of the ELISA measurement obtained are shown in FIG. 21. FIG. 21 shows detection signal (absorbance at 450 nm) derived from the HRP-labeled anti-gp64 mouse monoclonal antibody bound to exosomes contained in each dilution series of the calcium ion-containing and baculovirus-containing insect cell culture supernatant in the wells, on which various PS proteins or the anti-gp64 antibody was immobilized. The horizontal axis shows the types of the PS proteins or the anti-marker protein antibody immobilized on the well, and the detection results for the wells, on which the same PS protein or the like was immobilized, were shown in the order from left, blank, 800-fold dilution, 400-fold dilution, 200-fold dilution, and 100-fold dilution, in the dilution series of the calcium ion-containing and baculovirus-containing insect cells culture supernatant sample used. In addition, the vertical axis shows detection signal (absorbance at 450 nm) derived from the HRP-labeled anti-gp64 mouse monoclonal antibody.

In the wells, on which the Tim-1 protein, the Tim-3 protein, or the Tim-4 protein was each immobilized, viruses were detectable in higher sensitivity (Examples 110 to 115), as compared with the wells, on which the anti-gp64 antibody which is an antibody against a surface marker protein of baculovirus was immobilized, the wells on which the PS protein MFG-E8, or the Annexin V was immobilized was immobilized, and the well, on which the Tim family Tim-2 protein was immobilized (Comparative Example 34 to 39). That is, it has been revealed that the detection method of the present invention using the Tim protein pertaining to the present invention is capable of detecting viruses in higher sensitivity, as compared with the conventional methods. In particular, it has been revealed that the viruses can be detected in particularly higher sensitivity by using the Tim-4 protein among the Tim proteins.

Examples 116 to 119. Obtaining of Viruses by Carrier on which Tim Protein is Immobilized Obtaining of the viruses pertaining to the present invention was carried out using the carrier on which the biotin-labeled Tim-4 protein was immobilized.

<(1) Preparation of Co-Transfection Cell Culture Supernatant>

The co-transfection cell culture supernatant was prepared similarly as in "(1) Preparation of co-transfection cell culture supernatant" of Examples 84 to 95 and Comparative Examples 20 to 21.

<(2) Preparation of Calcium Ion-Containing and Baculovirus-Containing Insect Cell Culture Supernatant Sample>

The calcium ion-containing and baculovirus-containing insect cell culture supernatant sample was obtained by carrying out similarly as in "(2) Preparation of baculovirus-containing insect cell culture supernatant sample" of Examples 84 to 95 and Comparative Examples 20 to 21.

<(3) Preparation of Diluted Solution of Baculovirus-Containing Insect Cell Culture Supernatant Sample>

The calcium ion-containing and baculovirus-containing insect cell culture supernatant sample (100 µL) was mixed with 800 µL of the PSFM-J1 medium to prepare 900 µL of a nine-fold diluted solution.

<(4) Biotin Labeling of SH-Group of Tim-4 Protein>

For 100 µL of the PBS solution containing the Fc tag fusion type mouse-derived Tim-4 protein (produced by Wako Pure Chemical Industries, Ltd.) (containing 10 µg of the Fc tag fusion type mouse-derived Tim-4 protein), the SH-group of the Fc tag fusion type mouse-derived Tim-4 protein was labeled with biotin using the Biotin Labeling Kit-SH (produced by Dojindo Molecular Technologies, Inc.), according to a protocol attached to the kit to obtain 100 µL of the PBS solution containing the SH-group biotin-labeled Fc tag fusion type mTim-4 protein.

<(5) Dilution of Tag Fused Tim Protein>

The PBS solution (5 µL) containing the Fc tag fusion type mTim-4 protein (produced by Wako Pure Chemical Industries, Ltd.) (containing 0.5 µg of the Fc tag fusion type mouse-derived Tim-4 protein) was mixed with 95 µL of TBS to obtain 100 µL of a solution containing 0.5 µg of the biotin-unlabeled Fc tag fusion type mTim-4 protein.

The PBS solution (5 µL) containing the SH-group biotin-labeled Fc tag fusion type mTim-4 protein prepared in the (4) (containing 0.5 µg of the SH-group biotin-labeled Fc tag fusion type mTim-4 protein) was mixed with 95 µL of TBS to obtain 100 µL of a solution containing 1 µg of the biotin-labeled Fc tag fusion type mTim-4 protein.

<(6) Washing of Beads>

The PBS-T solution containing 30 µg/µL Dynabeads Protein G (5 µL) (produced by Thermo Fisher Scientific Inc.) (containing 0.3 mg of the Dynabeads Protein G) was transferred to a 1.5 mL tube (manufactured by BM Equipment Co., Ltd.), and after washing twice with 500 µL of TBS-T (TBS, 0.0005% Tween 20), the tube was loaded on a magnetic stand, and the washing solution was removed.

In addition, 30 µL of the PBS solution containing a MagCapture Tamavidin 2-REV (produced by Wako Pure Chemical Industries, Ltd.) (containing 0.3 mg of the beads) was transferred to the 1.5 mL tube (manufactured by BM Equipment Co., Ltd.), and after washing twice with 500 µL of TBS-T (TBS, 0.0005% Tween 20), the tube was loaded on a magnetic stand to remove the washing solution.

<(7) Immobilization of Tim Protein on Beads>

A solution (100 µL) containing 0.5 µg of the SH-group biotin-unlabeled Fc tag fusion type mTim-4 protein was added to the 1.5 mL tube containing 0.3 mg of the Dynabeads Protein G, in a pellet state, after the washing operation, and subjected to a reaction at 8° C. for 1 hour, under 1200 rpm using a thermomixer to obtain the carrier on which the SH-group biotin-unlabeled Fc tag fusion type mTim-4 was bound (it may be abbreviated as "the biotin-unlabeled Fc tag fusion type mTim-4 carrier", in some cases).

In addition, 100 µL of a solution containing 0.5 µg of the SH-group biotin-labeled Fc tag fusion type mTim-4 protein was added to the 1.5 mL tube containing 0.3 mg of the MagCapture Tamavidin 2-REV after the washing operation, and allowed to bind on the beads similarly as above to obtain the carrier on which the SH-group biotin-labeled Fc tag fusion type mTim-4 was bound (it may be abbreviated as "the biotin-labeled Fc tag fusion type mTim-4 carrier", in some cases).

It should be noted that, the resulting these two types of carriers may be abbreviated collectively as "the Tim protein-bound carrier" in some cases.

<(8) Obtaining of Baculovirus by Obtaining Method of the Present Invention>

The resulting these Tim protein-bound carriers above were subjected to the washing operation three times with 250 µL of TBS-T (TBS, 0.0005% Tween 20) to obtain the Tim protein-bound carrier in a pellet state. Subsequently, 100 µL of the diluted solution of the calcium ion-containing and baculovirus-containing insect cell culture supernatant prepared in the (3) was added to each of the resulting two kinds of Tim protein-bound carriers, in pellet state, and the mixture was subjected to a reaction at 8° C., for 12 hours under 1200 rpm using a thermomixer. Thereafter, the Tim protein-bound carrier after the reaction was subjected to the washing operation three times with each 250 µL of the calcium ion-containing TBS-T (Tris buffer, 0.0005% Tween 20, 2 mM $CaCl_2$). At the third time of the washing operation, 250 µL of the $CaCl_2$-containing TBS-T solution containing the Tim protein-bound carrier was each dispensed into two 1.5 mL tubes by 125 µL, and the tubes were loaded on a magnetic stand and then the washing solution was removed.

The 1% SDS aqueous solution (50 µL) or 25 µL of the TBS solution containing 1 mM EDTA, each as the eluent, was added to 0.15 mg of two kinds of the Tim protein-bound carriers, in a pellet state, and then they were mixed using a vortex mixer for 10 seconds and spun down. The TBS solution containing 1 mM EDTA (25 µL) was added again to the tube to which EDTA had been added, and the same operation was carried out to obtain the eluate.

It should be noted that the types of Tim proteins, carriers, and the Tim protein-(non) bound carriers, used in each Example, are shown in the following Table 35.

TABLE 35

| | | Example | | | |
|---|---|---|---|---|---|
| | | 116 | 117 | 118 | 119 |
| Tim protein-bound carrier | Carrier | Dynabeads protein G | Dynabeads protein G | MagCapture Tamavidin REV-2 | MagCapture Tamavidin REV-2 |
| | Tim protein | Biotin-unlabeled mouse-derived Tim-4 protein | Biotin-unlabeled mouse-derived Tim-4 protein | SH-group biotin-labeled Fc tag fusion type mouse-derived Tim-4 protein | SH-group biotin-labeled Fc tag fusion type mouse-derived Tim-4 protein |

<(9) Western Blotting>

Western blotting was carried out by the same method as in "(5) Western blotting" of Examples 80 to 83 and Comparative Examples 16 to 19, except for "adding 15 µL of the 4×sample buffer (produced by Wako Pure Chemical Industries, Ltd.) to each 15 µL of the eluate obtained in the (8) "Obtaining of baculovirus by obtaining method of the present invention", instead of "adding 3.75 µL of the 4× sample buffer (produced by Wako Pure Chemical Industries, Ltd.) to each 11.25 µL of the resulting eluate", and using "the anti-baculovirus gp64 antibody" instead of "the anti-Lamp-1 antibody".

It should be noted that the types of Tim proteins, carriers, and the eluents used for obtaining viruses from the Tim protein-bound carriers, used in each Example, and the lane numbers in Western blotting are shown in the following Table 36.

TABLE 36

| | | Example | | | |
|---|---|---|---|---|---|
| | | 116 | 117 | 118 | 119 |
| Tim protein-bound carrier | Carrier | Dynabeads protein G | Dynabeads protein G | MagCapture Tamavidin REV-2 | MagCapture Tamavidin REV-2 |

TABLE 36-continued

Figure 22:
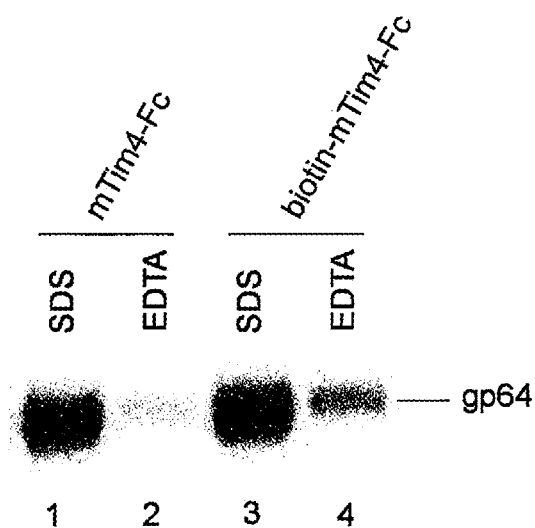
FIG. 22 is an electropherogram for confirming whether the extracellular membrane vesicles were obtained or not, by Western blotting, in Examples 116 to 119.

|  | Example | | | |
|---|---|---|---|---|
|  | 116 | 117 | 118 | 119 |
| Tim protein | Biotin-unlabeled mouse-derived Tim-4 protein | Biotin-unlabeled mouse-derived Tim-4 protein | SH-group biotin-labeled Fc tag fusion type mouse-derived Tim-4 protein | SH-group biotin-labeled Fc tag fusion type mouse-derived Tim-4 protein |
| Eluent | 1% SDS | 1 mM EDTA | 1% SDS | 1 mM EDTA |
| Lane numbers in FIG. 22 | 1 | 2 | 3 | 4 |

<Results>

The results of Western blotting obtained are shown in FIG. 22. In FIG. 22, each lane is the result of the following:

Lane 1: Results of Example 116 (the results of the case of using the carrier in which the SH-group biotin-unlabeled Fc tag fusion type mTim-4 protein was bound on the Dynabeads protein G, and using the 1% SDS aqueous solution as the eluent);

Lane 2: Results of Example 117 (the results of the case of using the carrier in which the SH-group biotin-unlabeled Fc tag fusion type mTim-4 protein was bound on the Dynabeads protein G, and using the TBS solution containing 1 mM EDTA as the eluent);

Lane 3: Results of Example 118 (the results of the case of using the carrier in which the SH-group biotin-labeled Fc tag fusion type mTim-4 protein was bound on the MagCapture Tamavidin REV-2, and using the 1% SDS aqueous solution as the eluent);

Lane 4: Results of Example 119 (the results of the case of using the carrier in which the SH-group biotin-labeled Fc tag fusion type mTim-4 protein was bound on the MagCapture Tamavidin REV-2, and using the TBS solution containing 1 mM EDTA as the eluent).

From FIG. 22, it has been revealed that the viruses cannot be obtained by using the carrier on which the SH-group biotin-unlabeled or labeled Tim-4 protein was bound, from the fact that a band of gp64, which is a marker protein of baculovirus, was observed in any cases of the lanes 1 to 4.

In addition, it has been revealed that more viruses can be obtained in immobilization on beads (carrier) via the SH-group of the Tim protein than immobilization via the tag, in the case where the elution is carried out with the calcium chelating agent, from comparison between lane 2 and lane 4

Examples 120 to 121, Comparative Examples 40 to 41. Comparison of Detection Sensitivity of Extracellular Membrane Vesicles by Flow Cytometer As described below, the extracellular membrane vesicles derived from the K562 cell culture supernatant was detected by the flow cytometer, using the carrier on which the Tim-4 protein or the antibody against CD63 of a surface marker protein of exosome was immobilized, and the PE-labeled anti-CD63 antibody as the detection antibody.

<(1) Preparation of Calcium Ion-Containing Culture Supernatant (Stock Solution)>

The human chronic myelogenous leukemia cell strain K562, $1 \times 10^7$ cells, secreting the extracellular membrane vesicles, was cultured for 3 days under condition at 37° C. and 5% $CO_2$, using 80 mL of the X-VIVO 15 medium (produced by Lonza AG). Then the cells were precipitated by centrifugal separation treatment (300×G, for 5 minutes) to remove the supernatant. The precipitated cells were suspended in 60 mL of the X-VIVO 15 medium containing 10 μM monensin sodium (produced by MP Biomedicals Co., Ltd) and cultured for 24 hours under condition at 37° C. and 5% $CO_2$.

Thereafter, the culture solution was subjected to centrifugal separation treatment (300×G, for 5 minutes) to recover the culture supernatant. The recovered culture supernatant (60 mL) was further subjected to centrifugal separation treatment three times (the first time: 300×G, for 3 minutes, the second time: 1,200×G, for 20 minutes, the third time: 10,000×G, for 20 minutes) to separate impurities and obtain a supernatant (hereinafter it may be abbreviated as "the culture supernatant (stock solution)", in some cases).

In addition, $CaCl_2$ was added to the resulting culture supernatant stock solution, so as to attain the final concentration of 2 mM, to obtain the 2 mM $CaCl_2$-containing K562 cell culture supernatant concentrated solution sample (hereinafter it may be abbreviated as "the calcium ion-containing culture supernatant (stock solution)", in some cases).

<(2) Preparation of Diluted Solution of Culture Supernatant Sample>

The resulting calcium ion-containing culture supernatant (stock solution) (500 μL), and 500 μL of the X-VIVO 15 medium were mixed to prepare 1.0 mL of a 2-fold diluted solution, then 200 μL of the 2-fold diluted solution and 800 μL of the X-VIVO 15 medium were mixed to prepare 1.0 mL of a 10-fold diluted solution to obtain each of the 2-fold diluted calcium ion-containing culture supernatant solution (stock solution) and the 10-fold diluted calcium ion-containing culture supernatant solution (stock solution).

<(3) Biotin Labeling of SH-Group of Tim-4 Protein>

For 100 μL of the PBS solution containing the Fc tag fusion type mouse-derived Tim-4 protein (produced by Wako Pure Chemical Industries, Ltd.) (containing 10 μg of the Fc tag fusion type mouse-derived Tim-4 protein), the SH-group of the Fc tag fusion type mouse-derived Tim-4 protein was labeled with biotin, using the Biotin Labeling Kit-SH (produced by Dojindo Molecular Technologies, Inc.), according to a protocol attached to the kit to obtain 100 μL of the PBS solution containing the SH-group biotin-labeled Fc tag fusion type mouse-derived Tim-4 protein.

<(5) Washing of Beads>

An Exosome-Streptavidin Isolation/Detection Reagent (20 μL) (containing the Dynabeads Streptavidin 4.5 μm, $1 \times 10^7$/mL) (produced by Thermo Fisher Scientific Inc.) was dispensed into each of two 1.5 mL tubes (manufactured by BM Equipment Co., Ltd.), and the washing operation was carried out using 200 μL of TBS.

An Exosome-Human CD63 Isolation/Detection Reagent (20 μL) (containing the Dynabeads Anti-CD63 antibody immobilized, 4.5 μm, $1 \times 10^7$/mL) (produced by Thermo Fisher Scientific Inc.) was dispensed into each of two 1.5 mL tubes (manufactured by BM Equipment Co., Ltd.), and the washing operation was carried out using 200 μL of TBS.

<(6) Immobilization of Tim-4 Protein on Beads>

A solution (100 μL) containing 0.1 μg of the SH-group biotin-labeled Fc tag fusion type mTim-4 protein was added to two 1.5 mL tubes containing the Dynabeads Streptavidin, in a pellet state, after the washing operation, and subjected to a reaction at 8° C. for 30 minutes under 1200 rpm using a thermomixer to obtain a solution containing the carrier on which the SH-group biotin-labeled Fc tag fusion type mTim-4 (it may be abbreviated as "the biotin-labeled Fc tag fusion type mTim-4 carrier", in some cases) was bound, (the solution may be abbreviated as "the solution containing biotin-labeled Fc tag fusion type mTim-4 carrier", in some cases).

<(7) Reaction with Extracellular Membrane Vesicles>

The resulting solution (100 μL) containing the biotin-labeled Fc tag fusion type mTim-4 carrier above was loaded on a magnetic stand, and then the solution in the solution containing the biotin-labeled Fc tag fusion type mTim-4 carrier was removed. The biotin-labeled Fc tag fusion type mTim-4 carrier, in a pellet state, and the Exosome-Human CD63 Isolation/Detection Reagent, in a pellet state, after the washing operation, were washed twice with 200 μL of TBS containing 0.1% BSA to obtain carriers, in a pellet state. Subsequently, 100 μL of the 2-fold diluted solution of the calcium ion-containing culture supernatant (stock solution), and the 10-fold diluted solution of the culture supernatant (stock solution) prepared in the (2) were each added to each of the resulting pellet-like carriers and subjected to a reaction at 8° C. for 12 hours under 1,200 rpm using a thermomixer. After that, the carrier after the reaction was subjected to the washing operation once with each 300 μL of TBS containing the calcium ion-the 0.1% BSA (TBS, 0.1% BSA, 2 mM $CaCl_2$), and once with 400 μL of TBS containing the calcium ion-0.1% BSA, and each carrier, in a pellet state, after the washing operation, was suspended in 300 μL of TBS containing the calcium ion-the 0.1% BSA (TBS, 0.1% BSA, 2 mM $CaCl_2$) to obtain two types of suspension of the carriers described in the following Table 37.

TABLE 37

| | 1 | 2 |
|---|---|---|
| Carrier | Dynabeads Streptavidin | Exosome-Human CD63 Isolation/Detection Reagent |
| Tim protein | SH-group biotin-labeled Fc tag fusion type mouse-derived Tim-4 protein | — |

<(8) Detection by PE-Labeled Anti-CD63 Antibody>

The resulting suspension of two types of the carriers in the (7) was each dispensed into two 1.5 mL tubes in each amount of 100 μL, and pelletized by magnetic separation, and then each 20 μL of the PE-labeled anti-CD63 mouse monoclonal antibody H5C6 (produced by BD Biosciences), or the PE-labeled control mouse IgG (produced by BD Biosciences) was added and subjected to a reaction 25° C. for 1 hour under 1000 rpm using a thermomixer. Thereafter, the washing operation was carried out twice with each 300 μL of TBS containing the calcium ion, and the 0.1% BSA (TBS, 0.1% BSA, 2 mM $CaCl_2$), and then the carriers were suspended in 500 μL of TBS containing the calcium ion, and the 0.1% BSA (TBS, 0.1% BSA, 2 mM $CaCl_2$). Thereafter, the filtrate filtered through a Falcon Cell Strainer (produced by Corning Inc.) was recovered, and measurement and analysis were carried out with a flow cytometer Gallios (manufactured by Beckman Coulter, Inc.). It should be noted that laser wavelength at the time of measurement was 488 nm, and detection wavelength was 575 nm.

It should be noted that the types of Tim proteins, carriers and the samples, used in each Example, are shown in the following Table 38.

TABLE 38

| | Example 120 | Example 121 | Comparative Example 40 | Comparative Example 41 |
|---|---|---|---|---|
| Carrier | Dynabeads Streptavidin | Dynabeads Streptavidin | Exosome-Human CD63 Isolation/Detection Reagent | Exosome-Human CD63 Isolation/Detection Reagent |
| Tim protein | SH-group biotin-labeled Fc tag fusion type mouse-derived Tim-4 protein | SH-group biotin-labeled Fc tag fusion type mouse-derived Tim-4 protein | — | — |
| Sample | 2-fold diluted calcium ion-containing culture supernatant (stock solution) | 10-fold diluted calcium ion-containing culture supernatant (stock solution) | 2-fold diluted calcium ion-containing culture supernatant (stock solution) | 10-fold diluted calcium ion-containing culture supernatant (stock solution) |

<Results>

Figure 23:
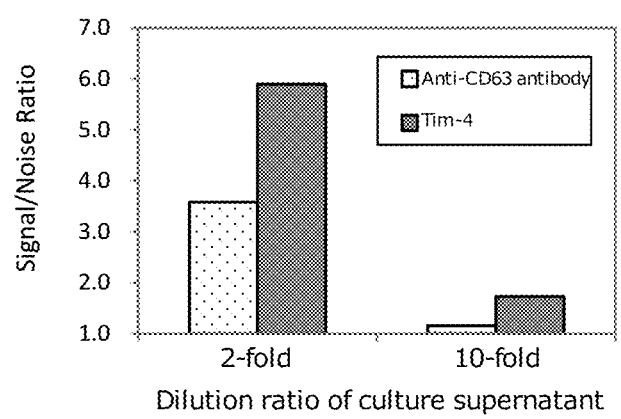
FIG. 23 is detection result of the extracellular membrane vesicles by a flow cytometry method, in Examples 120 to 121, and Comparative Examples 40 to 41.

The results of the flow cytometer measurement are shown in FIG. 23. FIG. 23 shows ratio of a signal detected exosomes captured using the biotin-labeled Fc tag fusion type mTim-4 carrier and the anti-CD63 antibody carrier from the calcium ion-containing culture supernatant (stock solution), diluted at each magnification by the PE-labeled anti-CD63 mouse monoclonal antibody, and a noise detected the same by the PE-labeled control mouse IgG (Signal/Noise ratio). The horizontal axis shows dilution magnification of the calcium ion-containing culture supernatant (stock solution) used, and the vertical axis shows ratio of the signal detected by the PE-labeled anti-CD63 mouse monoclonal antibody and the noise detected by the PE-labeled control mouse IgG.

From FIG. 23, it has been revealed that the extracellular membrane vesicles can be detected by using the carrier on which the Tim protein pertaining to the present invention is bound. In addition, it has been shown that the flow cytometer measurement can be carried out in higher Signal/Noise ratio (detection sensitivity) by using the carrier on which the Tim-4 is immobilized, as compared with using the carrier on which the anti-CD63 antibody is immobilized. That is, it has been revealed that the extracellular membrane vesicles can be detected in higher sensitivity by performing the flow cytometric analysis using the Tim carrier pertaining to the present invention, as compared with the conventional method.

Examples 122 to 123, Comparative Example 42 to 43. Obtaining of Viruses by Carrier on which Tim Protein is Immobilized Obtaining of the viruses pertaining to the present invention was carried out using the carrier on which the Tim protein was immobilized.

<(1) Biotin Labeling of SH-Group in Fc Tag Fusion Type mTim-4 Protein>

The SH-group of the Fc tag fusion type mouse-derived Tim-4 protein in 100 μL of the PBS solution containing the Fc tag fusion type mouse-derived Tim-4 protein (produced by Wako Pure Chemical Industries, Ltd.) (containing 10 μg of the Fc tag fusion type mouse-derived Tim-4 protein) was labeled with biotin using the Biotin Labeling Kit-SH (produced by Dojindo Molecular Technologies, Inc.), according to a protocol attached to the kit to obtain 100 μL of the PBS solution containing the SH-group biotin-labeled Fc tag fusion type mTim-4 protein.

<(2) Dilution of SH-Group Biotin-Labeled Fc Tag Fusion Type mTim-4 Protein>

The SH-group biotin-labeled Fc tag fusion type mTim-4 protein-containing TBS solution (10 μL) prepared in the (1) (containing 1 μg of the SH-group biotin-labeled Fc tag fusion type mTim-4 protein) was mixed with 190 μL of TBS to obtain 200 μL of a solution containing 1 μg of the SH-group biotin-labeled Fc tag fusion type mTim-4 protein.

<(3) Washing of Beads>

The PBS solution (60 μL) containing the MagCapture Tamavidin 2-REV (produced by Wako Pure Chemical Industries, Ltd.) (containing 0.6 mg of the MagCapture Tamavidin 2-REV) was transferred to two 1.5 mL tubes (manufactured by BM Equipment Co., Ltd.), and after washing each twice with 500 μL of TBS-T (TBS, 0.0005% Tween 20), the tube was loaded on a magnetic stand to remove the washing solution.

<(4) Immobilization of SH-Group Biotin-Labeled Fc Tag Fusion Type mTim-4 Protein on Beads>

The solution (200 μL) containing 1 μg of the SH-group biotin-labeled Fc tag fusion type mTim-4 protein, or 200 μL of TBS was added to the two 1.5 mL tubes containing 0.6 mg of the MagCapture Tamavidin 2-REV, after the washing operation, and each was subjected to a reaction at 8° C. for 1 hour at 1200 rpm using a thermomixer to obtain the carrier on which the SH-group biotin-labeled Fc tag fusion type mTim-4 was bound (it may be abbreviated as "the biotin-labeled Fc tag fusion type mTim-4-bound carrier", in some cases), and the carrier on which SH-group biotin-unlabeled Fc tag fusion type mTim-4 was bound (it may be abbreviated as "the biotin-labeled Fc tag fusion type mTim-4-non-bound carrier", in some cases). It should be noted that, the Tim protein-bound carrier and the Tim protein-non-bound carrier may be abbreviated collectively as "the Tim protein-(non-)bound carrier" in some cases.

<(5) Obtaining of Influenza Virus by Obtaining Method of the Present Invention>

The resulting 2 types of the Tim protein-(non-)bound carriers above were subjected to the washing operation three times with each 500 μL of TBS-T (Tris buffer, 0.0005% Tween 20). An influenza A virus solution (60 μL) (H1N1 A/WS/33 strain) (ATCC Code: VR-825), containing the calcium ion added with calcium chloride at the final concentration of 2 mM, was added to each of the two types of the Tim protein-(non-)bound carriers after the washing operation, and subjected to a reaction at 8° C. for 2 hours at 1200 rpm using a thermomixer. The two types of the Tim protein-(non-bound-)carriers after the reaction were subjected to the washing operation three times with each 500 μL of the calcium ion-containing TBS-T (Tris buffer, 0.0005% Tween 20, 2 mM $CaCl_2$). After the third time of the washing operation, 500 μL of the calcium ion-containing TBS-T (Tris buffer, 0.0005% Tween 20, 2 mM $CaCl_2$) was added to each of the two types of the Tim protein-(non-)bound carriers and suspended to obtain each 500 μL of suspension. The suspension was dispensed by 250 μL into each of the two 1.5 mL tubes, and after the tubes were loaded on a magnetic stand, the washing solution was removed to obtain each Tim protein-(non-)bound carrier in a pellet state.

It should be noted that the types of the carriers and the Tim protein, used in each Example and Comparative Example, are shown in the following Table 39.

TABLE 39

| | Comparative Example 42 | Comparative Example 43 | Example 122 | Example 123 |
|---|---|---|---|---|
| Carrier | MagCapture Tamavidin2-REV | MagCapture Tamavidin2-REV | MagCapture Tamavidin2-REV | MagCapture Tamavidin2-REV |
| Tim protein | — | — | Biotin-labeled Fc tag fusion type Tim-4 protein | Biotin-labeled Fc tag fusion type Tim-4 protein |

Among the four 1.5 ml tubes containing the resulting 0.3 mg of the Tim protein-(non-)bound carrier in a pellet state, for one 1.5 mL tube containing the Tim protein-bound carrier, and one 1.5 mL tube containing the Tim protein-non-bound carrier, each 20 μL of the 1% SDS aqueous solution was added as the eluent, then they were mixed using a vortex mixer at room temperature for 10 seconds, and spun down to obtain each eluate.

In addition, among the four 1.5 ml tubes containing 0.3 mg of the Tim protein-(non-)bound carrier in the pellet state, for one 1.5 mL tube containing the Tim protein-bound carrier and one 1.5 mL tube containing the Tim protein-non-bound carrier, each 10 μL of the TBS solution containing 50 mM EDTA as the eluent was added, and they were mixed using a vortex mixer at room temperature for 10 seconds, and spun down. The TBS solution containing 50 mM EDTA was again added to each of the tubes after spun down, and they were mixed using a vortex mixer at room temperature for 10 seconds, and spun down to obtain each eluate.

The TBS solution (2.2 μL) containing 10% β-propiolactone was added to each 20 μL of the resulting four types of the eluates, and they were mixed using a vortex mixer and left to stand on ice for 3 hours to obtain four types of 22.2 μL of β-propiolacton-treated eluates.

<(6) Western Blotting>

The TBS solution (3.3 μL) containing 10% β-propiolactone was added to 30 μL of the calcium ion-containing influenza A virus solution (H1N1 A/WS/33 strain) (ATCC Code: VR-825) and they were mixed using a vortex mixer. Then, 11.1 μL of the 4×sample buffer (produced by Wako Pure Chemical Industries, Ltd.) was added to the solution which had been left to stand on ice for 3 hours, and incubated at 95° C. for 3 minutes to obtain an input sample for Western blotting (44.4 μL in total). In addition, 7.4 μL of the 4× sample buffer (produced by Wako Pure Chemical Industries, Ltd.) was added to each 22.2 μL of the 4 types of the eluates treated with β-propiolactone, and incubated at 95° C. for 3 minutes to obtain each of the eluate samples for Western blotting (29.6 μL in total). The input sample (20 μL) for Western blotting and each 20 μL of the eluate sample for Western blotting were loaded on the Super Sep Ace 5-20% gel (produced by Wako Pure Chemical Industries, Ltd.), and subjected to electrophoresis at 30 mA for 60 minutes. The resulting electrophoresis gel was transcribed onto the PVDF membrane (produced by Millipore Corporation) at 1.2 mA/cm$^2$ for 60 minutes using the semi-dry blotter and the discontinuous buffer (Anode buffer 1: 0.3 M Tris/20% methanol, Anode buffer 2: 0.025 M Tris/20% methanol, Cathode buffer: 0.025 M Tris/0.04 M aminocaproic acid/ 20% methanol). The 5% skimmed milk, diluted with TBS-T (TBS buffer, 0.1% Tween 20), was added to the post-transcription PVDF membrane, and subjected to a reaction at room temperature for 1 hour for blocking, and then subjected to a reaction at room temperature for 1 hour, with 2 mL of the anti-influenza A virus Nucleoprotein antibody C43 (produced by Abcam plc), diluted 300-fold with TBS-T. The PVDF membrane after the reaction was washed three times with TBS-T, and reacted with the secondary antibody {anti-mouse IgG (H+L), donkey, IgG fraction, peroxidase-conjugated antibody} (produced by Jackson Immuno Research Laboratories, Inc.), diluted 30,000-fold with TBS-T at room temperature for 1 hour. After washing 5 times with TBS-T, the ImmunoStar Zeta (produced by Wako Pure Chemical Industries, Ltd.) was added to the PVDF membrane after being subjected to a reaction with each antibody, and a luminescent signal was detected using the LAS-4000 (manufactured by GE Healthcare).

It should be noted that the types of carriers, Tim protein, and the eluents for elution from the carrier, used in each Example, are shown in the following Table 40.

TABLE 40

Figure 24:
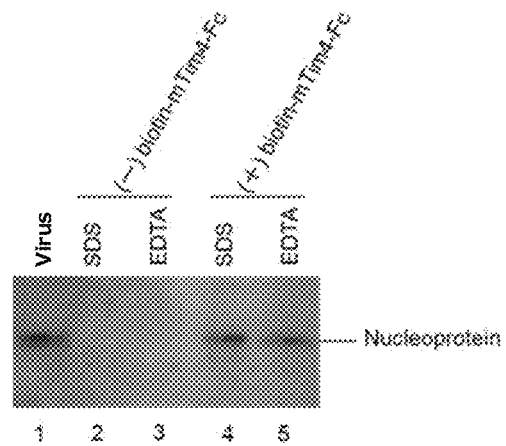
FIG. 24 is an electropherogram for confirming whether the extracellular membrane vesicles were obtained or not, by Western blotting, in Examples 122 to 123, and Comparative Examples 42 to 43

|  | Comparative Example 42 | Comparative Example 43 | Example 122 | Example 123 |
|---|---|---|---|---|
| Carrier | MagCapture Tamavidin2-REV | MagCapture Tamavidin2-REV | MagCapture Tamavidin2-REV | MagCapture Tamavidin2-REV |
| Tim protein | — | — | Biotin-labeled Fc tag fusion type Tim-4 protein | Biotin-labeled Fc tag fusion type Tim-4 protein |
| Eluent | 1% SDS | 1 mM EDTA | 1% SDS | 1 mM EDTA |
| Lane numbers in FIG. 24 | 2 | 3 | 4 | 5 |

<Results>

The results of Western blotting obtained are shown in FIG. 24. In FIG. 24, each lane is the result of the following.

Lane 1: Results of electrophoresis of influenza A virus;

Lane 2: Results of Comparative Example 42 (the results of the case of using the biotin-labeled Fc tag fusion type mTim-4-non-bound carrier, and using the 1% SDS solution as the eluent);

Lane 3: Results of Comparative Example 43 (the results of the case of using the biotin-labeled Fc tag fusion type mTim-4-non-bound carrier, and using the TBS solution containing 50 mM EDTA as the eluent);

Lane 4: Results of Example 122 (the results of the case of using the biotin-labeled Fc tag fusion type mTim-4-bound carrier, and using the 1% SDS solution as the eluent);

Lane 5: Results of Example 123 (the results of the case of using the biotin-labeled Fc tag fusion type mTim-4-bound carrier, and using the TBS solution containing 50 mM EDTA as the eluent).

From FIG. 24, it has been revealed that the influenza virus can be obtained by using the carrier on which the Tim protein was bound, from the fact that no band of the Nucleoprotein, which is a marker protein of influenza A virus, was observed in any of the cases in lanes 2 to 3 (in the case where the biotin-labeled Fc tag fusion type mTim-4-non-bound carrier was used), whereas the band of the Nucleoprotein, which is a marker protein of influenza A virus, was observed in any of the cases in the lanes 4 to 5 (in the case where the biotin-labeled Fc tag fusion type mTim-4-bound carrier was used).

In addition, it has been revealed that the influenza virus can be obtained efficiently by using the carrier on which the Tim protein is bound, from comparison between the lane 1 (the result of electrophoresis of the influenza A virus) and the lanes 4 to 5 (results of using the biotin-labeled Fc tag fusion type mTim-4-bound carrier).

Examples 124 to 125, Comparative Examples 44 to 45. Obtaining of Viruses by Carrier on which Tim Protein is Immobilized Obtaining of the viruses pertaining to the present invention was carried out using the carrier on which the Tim protein was immobilized.

<(1) Preparation of RS Virus-Containing HEp-2 Cell Culture Supernatant Sample>

A 10% FBS-containing D-MEM high glucose medium (20 mL) (produced by Wako Pure Chemical Industries, Ltd.) containing 1.5×10$^6$ cells of the HEp-2 cells was added to a 75 cm$^2$ flask and cultured for 4 days under condition at 37° C. and 5% CO$_2$. The supernatant was removed from the culture solution after the culture, and 5 mL of the E-MEM medium containing 2% FBS and 5.3×10$^5$ TCID$_{50}$/mL RS virus (ATCC, Code: VR-26) was added, and allowed to stand for 1 hour under condition at 36° C. and 5% CO$_2$. Additional 20 mL of the E-MEM medium containing 2% FBS was added and cultured for 3 days under condition at 36° C. and 5% CO$_2$. The supernatant was removed from the culture solution after the culture, and 20 mL of the E-MEM medium containing 2% FBS was added to culture the cells for 2 days under condition at 36° C. and 5% CO$_2$. Thereafter, the cells were released from the flask by pipetting, recovered together with the culture supernatant into a 50 mL centrifuge tube, and centrifuged at 1,500 rpm for 10 minutes to recover only the culture supernatant. Calcium chloride was added to the resulting culture supernatant, so as to attain the final concentration of 2 mM, and used it as "the calcium-containing RS virus solution".

<(2) Biotin Labeling of SH-Group in Fc Tag Fusion Type mTim-4 Protein>

The PBS solution (100 μL) containing the SH-group biotin-labeled Fc tag fusion type mTim-4 protein was obtained by carrying out the same method as in <(1) Biotin labeling of SH-group in Fc tag fusion type mTim-4 protein> of Examples 122 to 123 and Comparative Example 42 to 43.

<(3) Dilution of SH-Group Biotin-Labeled Fc Tag Fusion Type mTim-4 Protein>

The solution (200 μL) containing 1 μg of the SH-group biotin-labeled Fc tag fusion type mTim-4 protein was obtained by carrying out the same method as in <(2) Dilution of SH-group biotin-labeled Fc tag fusion type mTim-4 protein> of Examples 122 to 123 and Comparative Examples 42 to 43.

<(4) Washing of Beads>

The MagCapture Tamavidin 2-REV, after carrying out the washing operation, was obtained by carrying out the same method as in <(3) Washing of beads> of Examples 122 to 123 and Comparative Examples 42 to 43.

<(5) Immobilization of SH-Group Biotin-Labeled Fc Tag Fusion Type mTim-4 Protein on Beads>

The biotin-labeled Fc tag fusion type mTim-4 protein-bound carrier, and the biotin-labeled Fc tag fusion type mTim-4 protein-(non)-bound carrier were each obtained by carrying out the same method as in <(4) Immobilization of SH-group biotin-labeled Fc tag fusion type mTim-4 protein on beads> of Examples 122 to 123 and Comparative Examples 42 to 43.

It should be noted that the biotin-labeled Fc tag fusion type mTim-4 protein-bound carrier and the biotin-labeled Fc tag fusion type mTim-4 protein-non-bound carrier may be abbreviated collectively as "the Tim protein-non-bound carrier", in some cases.

<(6) Obtaining of RS Virus by Obtaining Method of the Present Invention>

Each 22.2 µL of the β-propiolacton-treated eluate was obtained by carrying out the same method as in <(5) Obtaining of influenza virus by obtaining method of the present invention> of Examples 122 to 123 and Comparative Examples 42 to 43, except for using "120 µL of the calcium ion-containing RS virus solution prepared in the (1)", instead of "60 µL of the influenza A virus solution (H1N1 A/WS/33 strain) (ATCC Code: VR-825) containing the calcium ion added with calcium chloride at the final concentration of 2 mM".

It should be noted that the types of carriers and the Tim protein, used in each Example, are shown in the following Table 41.

TABLE 41

|  | Comparative Example 44 | Comparative Example 45 | Example 124 | Example 125 |
|---|---|---|---|---|
| Carrier | MagCapture Tamavidin2-REV | MagCapture Tamavidin2-REV | MagCapture Tamavidin2-REV | MagCapture Tamavidin2-REV |
| Tim protein | — | — | Biotin-labeled Fc tag fusion type Tim-4 protein | Biotin-labeled Fc tag fusion type Tim-4 protein |

<(7) Western Blotting>

Western blotting was carried out by the same method as in <(6) Western blotting> of Examples 122 to 123 and Comparative Examples 42 to 43, except for using "30 µL of the calcium ion-containing RS virus solution" instead of "30 µL of the calcium ion-containing influenza A virus solution (H1N1 A/WS/33 strain) (ATCC Code: VR-825)", and using "2 mL of the anti-RS virus F protein antibody 2F7 (produced by Abcam plc), diluted 500-fold with TBS-T", instead of "2 mL of the anti-influenza A virus nucleoprotein antibody C43 (produced by Abcam plc), diluted 300-fold with TBS-T", and a luminescent signal was detected It should be noted that the types of the carriers, the Tim protein, and the eluents from the carriers, used in each Example, are shown in the following Table 42.

TABLE 42

Figure 25:
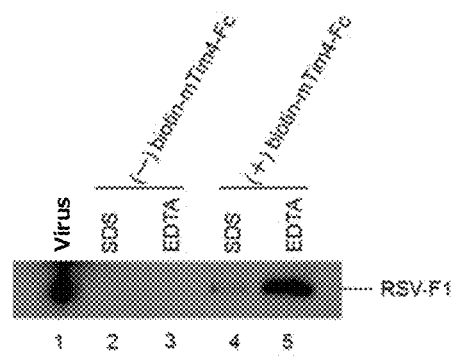
FIG. 25 is an electropherogram for confirming whether the extracellular membrane vesicles were obtained or not, by Western blotting, in Examples 124 to 125, and Comparative Examples 44 to 45.

|  | Comparative Example 44 | Comparative Example 45 | Example 124 | Example 125 |
|---|---|---|---|---|
| Carrier | MagCapture Tamavidin2-REV | MagCapture Tamavidin2-REV | MagCapture Tamavidin2-REV | MagCapture Tamavidin2-REV |
| Tim protein | — | — | Biotin-labeled Fc tag fusion type Tim-4 protein | Biotin-labeled Fc tag fusion type Tim-4 protein |
| Eluent | 1% SDS | 1 mM EDTA | 1% SDS | 1 mM EDTA |
| Lane numbers in FIG. 25 | 2 | 3 | 4 | 5 |

<Results>

The results of Western blotting obtained are shown in FIG. 25. In FIG. 25, each lane is the result of the following.

Lane 1: Results of electrophoresis of the RS virus;

Lane 2: Results of Comparative Example 44 (the results of the case of using the biotin-labeled Fc tag fusion type mTim-4-non-bound carrier, and using the 1% SDS solution as the eluent);

Lane 3: Results of Comparative Example 45 (the results of the case of using the biotin-labeled Fc tag fusion type mTim-4-non-bound carrier, and using the TBS solution containing 50 mM EDTA as the eluent);

Lane 4: Results of Example 124 (the results of the case of using the biotin-labeled Fc tag fusion type mTim-4-bound carrier, and using the 1% SDS solution as the eluent);

Lane 5: Results of Example 125 (the results of the case of using the biotin-labeled Fc tag fusion type mTim-4-bound carrier, and using the TBS solution containing 50 mM EDTA as the eluent).

From in FIG. 25, it has been revealed that the RS virus can be obtained by using the carrier on which the Tim protein is bound, from the fact that no band of the F protein, which is a marker protein of the RS virus, was observed in any of the cases in the lanes 2 to 3 (in the case where the biotin-labeled Fc tag fusion type mTim-4-non-bound carrier was used), whereas a band of the F protein, which is a marker protein of RS virus, was observed in any of the cases in the lanes 4 to 5 (in the case where the biotin-labeled Fc tag fusion type mTim-4-bound carrier was used).

In addition, it has been revealed that the RS virus can be obtained efficiently by using the carrier on which the Tim protein is bound, from comparison between the lane 1 (the result of electrophoresis of the RS virus) and the lanes 4 to 5 (result of using the biotin-labeled Fc tag fusion type mTim-4-bound carrier).

INDUSTRIAL APPLICABILITY

The Tim protein-bound carrier of the present invention, an obtaining method and a removing method for the extracellular membrane vesicle and virus using the carrier, and the kit comprising the carrier are capable of obtaining or removing the extracellular vesicle and virus present in the sample in higher purity or in a more intact state, as well as more easily and efficiently, as compared with conventional methods for obtaining the extracellular membrane vesicle and virus, and the kit comprising the antibody or the like to be used for the obtaining method.

The Tim protein-bound carrier of the present invention, and the obtaining method of the present invention are useful, since the extracellular membrane vesicle obtained by the obtaining method of the present invention are utilized as pharmaceuticals and the like, and the obtained virus are utilized as vaccines, or vectors, and the like.

The Tim protein-bound carrier of the present invention and the removing method of the present invention are the useful ones, since the samples from which the extracellular membrane vesicle or virus is removed by the removing method of the present invention are those prevented from contamination of biological extracellular membrane vesicle or enveloped virus, and are utilized for research, or the like, using the sample.

The Tim protein-bound carrier of the present invention, the detection method for the extracellular membrane vesicle and the virus using the carrier are capable of detecting the extracellular membrane vesicle and the virus in higher sensitivity, as compared with the conventional detecting methods for detecting the extracellular membrane vesicle and virus.

The Tim protein-bound carrier of the present invention and the detection method of the present invention are useful, because according to the detection method of the present invention, even in the case of detecting a trace amount of the extracellular membrane vesicle and virus in the specimen, it is possible to carry out the measurement as it is without concentration or purification of the specimen.

The invention claimed is:

1. A method for obtaining an extracellular membrane vesicle in the sample, comprising the following steps:
   (1) a step for forming a complex of Tim-4 protein bound to a carrier, and the extracellular membrane vesicle in a sample, in the presence of a calcium ion (complex formation step),
   (2) a step for separating the complex and the sample (complex separation step), and
   (3) a step for separating the extracellular membrane vesicle from the complex using a calcium ion chelating agent to obtain the extracellular membrane vesicle (obtaining step).

2. The method according to claim 1, wherein the complex formation step is a step for forming the complex of Tim-4 protein bound to the carrier, and the extracellular membrane vesicle in the sample, by contacting Tim-4 protein bound to the carrier and the extracellular membrane vesicle in the sample, in the presence of the calcium ion.

3. The method according to claim 1, wherein the complex formation step is a step for forming the complex of Tim-4 protein bound to the carrier, and the extracellular membrane vesicle in the sample, by contacting Tim-4 protein, the carrier and the extracellular membrane vesicle in the sample, in the presence of the calcium ion.

4. The method according to claim 1, wherein Tim-4 protein comprises an IgV domain.

5. The method according to claim 2, wherein Tim-4 protein comprises an IgV domain.

6. The method according to claim 3, wherein Tim-4 protein comprises an IgV domain.

7. The method according to claim 1, wherein the carrier binds to Tim-4 protein via a SH-group of the Tim-4 protein.

8. The method according to claim 2, wherein the carrier binds to Tim-4 protein via a SH-group of the Tim-4 protein.

9. The method according to claim 3, wherein the carrier binds to Tim-4 protein via a SH-group of the Tim-4 protein.

\* \* \* \* \*